(12) United States Patent
Bachmann et al.

(10) Patent No.: US 7,494,656 B2
(45) Date of Patent: *Feb. 24, 2009

(54) MOLECULAR ANTIGEN ARRAYS

(75) Inventors: Martin Bachmann, Seuzach (CH); Alain Tissot, Zurich (CH); Paul Pumpens, Riga (LV); Indulis Cielens, Riga (LV); Regina Renhofa, Riga (LV)

(73) Assignee: Cytos Biotechnology AG, Zurich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/601,687

(22) Filed: Nov. 20, 2006

(65) Prior Publication Data

US 2007/0128219 A1 Jun. 7, 2007

Related U.S. Application Data

(63) Continuation of application No. 10/617,876, filed on Jul. 14, 2003, now Pat. No. 7,138,252.

(60) Provisional application No. 60/396,126, filed on Jul. 17, 2002.

(51) Int. Cl.
*A61K 39/145* (2006.01)
*A61K 39/385* (2006.01)
*C12N 7/00* (2006.01)
*C12N 15/09* (2006.01)

(52) U.S. Cl. ............... 424/192.1; 424/193.1; 424/209.1; 424/210.1; 424/185.1; 435/235.1; 435/69.3

(58) Field of Classification Search ................ None
See application file for complete search history.

(56) References Cited

U.S. PATENT DOCUMENTS

| | | | |
|---|---|---|---|
| 4,722,840 A | 2/1988 | Valenzuela et al. | |
| 4,918,166 A | 4/1990 | Kingsman et al. | |
| 5,071,651 A | 12/1991 | Sabara et al. | |
| 5,143,726 A | 9/1992 | Thornton et al. | |
| 5,334,394 A | 8/1994 | Kossovsky et al. | |
| 5,374,426 A | 12/1994 | Sabara et al. | |
| 5,580,859 A | 12/1996 | Felgner et al. | |
| 5,698,424 A | 12/1997 | Mastico et al. | |
| 5,739,026 A | 4/1998 | Garoff et al. | |
| 5,766,602 A | 6/1998 | Xiong et al. | |
| 5,770,380 A | 6/1998 | Hamilton et al. | |
| 5,789,245 A | 8/1998 | Dubensky, Jr. et al. | |
| 5,792,462 A | 8/1998 | Johnston et al. | |
| 5,814,482 A | 9/1998 | Dubensky, Jr. et al. | |
| 5,871,747 A | 2/1999 | Gengoux-Sedlik et al. | |
| 5,928,647 A | 7/1999 | Rock | |
| 5,939,598 A | 8/1999 | Kucherlapati et al. | |
| 6,004,763 A | 12/1999 | Gengoux et al. | |
| 6,054,312 A | 4/2000 | Larocca et al. | |
| 6,231,864 B1 | 5/2001 | Birkett | |
| 6,380,364 B1 | 4/2002 | Mueller et al. | |
| 6,932,971 B2 * | 8/2005 | Bachmann et al. | 424/193.1 |
| 7,094,409 B2 * | 8/2006 | Bachmann et al. | 424/196.11 |
| 7,115,266 B2 * | 10/2006 | Bachmann | 424/185.1 |
| 7,128,911 B2 * | 10/2006 | Bachmann et al. | 424/185.1 |
| 7,138,252 B2 * | 11/2006 | Bachmann et al. | 435/69.1 |
| 7,279,165 B2 * | 10/2007 | Bachmann et al. | 424/193.1 |
| 2002/0064533 A1 | 5/2002 | Murray | |
| 2002/0081295 A1 | 6/2002 | Schiller et al. | |
| 2003/0157479 A1 | 8/2003 | Bachmann et al. | |
| 2003/0175290 A1 | 9/2003 | Renner et al. | |
| 2003/0175711 A1 | 9/2003 | Renner et al. | |

FOREIGN PATENT DOCUMENTS

| | | |
|---|---|---|
| EP | 0 259 149 B1 | 12/1993 |
| EP | 0 385 610 B1 | 3/1994 |
| EP | 0 465 081 B1 | 4/1994 |
| EP | 0 283 505 B1 | 7/1994 |
| EP | 0 425 082 B1 | 4/1995 |
| WO | WO 92/11291 A1 | 7/1992 |
| WO | WO 94/06472 A1 | 3/1994 |
| WO | WO 94/15585 A1 | 7/1994 |
| WO | WO 96/05293 A1 | 2/1996 |
| WO | WO 96/30523 A2 | 10/1996 |
| WO | WO 97/31948 A1 | 9/1997 |

(Continued)

OTHER PUBLICATIONS

Abraham, J.M., et al., "An invertible element of DNA controls phase variation of type 1 fimbriae of *Escherichia coli*," *Proc. Natl. Acad. Sci. USA* 82:5724-5727, National Academy Press (1985).

(Continued)

*Primary Examiner*—Mary E Mosher
(74) *Attorney, Agent, or Firm*—Sterne, Kessler, Goldstein & Fox PLLC

(57) ABSTRACT

The present invention provides a composition comprising an AP205 virus like particle (VLP) and an antigen. The invention also provides a process for producing an antigen or antigenic determinant bound to AP205 VLP. AP205 VLP bound to an antigen is useful in the production of compositions for inducing immune responses that are useful for the prevention or treatment of diseases, disorders or conditions including infectious diseases, allergies, cancer, drug addiction, poisoning and to efficiently induce self-specific immune responses, in particular antibody responses.

51 Claims, 11 Drawing Sheets

FOREIGN PATENT DOCUMENTS

| | | |
|---|---|---|
| WO | WO 98/15631 A1 | 4/1998 |
| WO | WO 99/07839 A2 | 2/1999 |
| WO | WO 99/07839 A3 | 2/1999 |
| WO | WO 99/28478 A1 | 6/1999 |
| WO | WO 99/40934 A1 | 8/1999 |
| WO | WO 99/57289 A2 | 11/1999 |
| WO | WO 99/57289 A3 | 11/1999 |
| WO | WO 99/67293 A1 | 12/1999 |
| WO | WO 00/23955 A1 | 4/2000 |
| WO | WO 00/32227 A2 | 6/2000 |
| WO | WO 00/50461 A1 | 8/2000 |
| WO | WO 00/59928 A1 | 10/2000 |
| WO | WO 01/62284 A2 | 8/2001 |
| WO | WO 01/85208 A2 | 11/2001 |
| WO | WO 02/056905 A1 | 7/2002 |
| WO | WO 03/024481 A2 | 3/2003 |

OTHER PUBLICATIONS

Abraham, S.N., et al., "Glycerol-Induced Unraveling of the Tight Helical Conformation of *Escherichia coli* Type 1 Fimbriae," *J. Bacteriol.* 174:5145-5148, American Society for Microbiology (1992).

Adhin, M.R., et al., "Nucleotide Sequence from the ssRNA Bacteriophage JP34 Resolves the Discrepancy between Serological and Biophysical Classification," *Virology* 170:238-242, Academic Press, Inc. (1989).

Aguzzi, A., "Prion diseases, blood and the immune system: concerns and reality," *Haematologica* 85:3-10, II Pensiero Scientifico Editore (Jan. 2000).

Ansel, K.M., et al., "In Vivo-activated CD4 T Cells Upregulate CXC Cheomkine Receptor 5 and Reprogram Their Response to Lymphoid Chemokines," *J. Exp. Med.* 190:1123-1134, The Rockefeller University Press (1999).

Ansel, K.M., et al., "A chemokine-driven positive feedback loop organizes lymphoid follicles," *Nature* 406:309-314, Nature Publishing Group (Jul. 2000).

Antonysamy, M.A., et al., "Evidence for a Role of IL-17 in Organ Allograft Rejection: IL-17 Promotes the Functional Differentiation of Dendritic Cell Progenitors," *J. Immunol.* 162:577-584, The American Association of Immunologists (1999).

Arenberg, D.A., et al., "The murine CC chemokine, 6C-kine, inhibits tumor growth and angiogenesis in a human lung cancer SCID mouse model," *Cancer Immunol. Immunother.* 49:587-592, Springer-Verlag (Jan. 2001).

Arnon, R., et al., "A mimotope peptide-based vaccine against *Schistosoma mansoni*: synthesis and characterization," *Immunology* 101:555-562, Blackwell Science, Ltd. (Dec. 2000).

Bachmann, M.F., and Zinkernagel, R.M., "The influence of virus structure on antibody responses and virus serotype formation," *Immunol. Today* 17:553-558, Elsevier Science, Ltd. (1996).

Bachmann, M.F., and Zinkernagel, R.M., "Neutralizing Antiviral B Cell Responses," *Annu. Rev. Immunol.* 15:235-270, Annual Reviews, Inc. (1997).

Bachmann, M.F., et al., "TRANCE, a Tumor Necrosis Factor Family Member Critical for CD40 Ligand-independent T Helper Cell Activation," *J. Exp. Med.* 189:1025-1031, The Rockefeller University Press (1999).

Banerjee, R.R., and Lazar, M.A., "Dimerization of Resistin and Resistin-like Molecules Is Determined by a Single Cysteine," *J. Biol. Chem.* 276:25970-25973, The American Society for Biochemistry and Molecular Biology, Inc. (Jul. 2001).

Bard, F. et al., "Peripherally administered antibodies against amyloid β-peptide enter the central nervous system and reduce pathology in a mouse model of Alzheimer disease," *Nat. Med.* 6:916-919, Nature Publishing Company (Aug. 2000).

Bass, S., and Yang, M., "Expressing cloned genes in *Escherichia coli*," in *Protein Function: A Practical Approach*, 2nd ed., Creighton, T.E., ed., IRL Press, Oxford, Great Britain, pp. 29-55 (1997).

Bernhagen, J., et al., "Purification, Bioactivity, and Secondary Structure Analysis of Mouse and Human Macrophage Migration Inhibitory Factor (MIF)," *Biochemistry* 33:14144-14155, American Chemical Society (1994).

Biaselle, C.J., and Millar, D.B., "Studies on Triton X-100 detergent micelles," *Biophys. Chem.* 3:355-361, North-Holland Publishing Company (1975).

Bleul, C.C., et al., "The lymphocyte chemoattractant SDF-1 is a ligand for LESTR/fusin and blocks HIV-1 entry," *Nature* 382:829-833, Nature Publishing Group (1996).

Blomfield, I.C., et al., "Type 1 Fimbriation and *fimE* Mutants of *Escherichia coli* K-12," *J. Bacteriol.* 173:5298-5307, American Society for Microbiology (1991).

Blomfield, I.C., et al., "Integration host factor stimulates both FimB- and FimE-mediated site-specific DNA inversion that controls phase variation of type 1 fimbriae expression in *Escherichia coli*," *Mol. Microbiol.* 23:705-717, Blackwell Science, Ltd. (1997).

Boder, E.T., and Wittrup, K.D., "Yeast Surface Display for Directed Evolution of Protein Expression, Affinity, and Stability," *Methods Enzymol.* 328:430-444, Academic Press (Oct. 2000).

Bonci, A., et al., "Relatedness and Phylogeny Within the Family of Periplasmic Chaperones Involved in the Assembly of Pili or Capsule-Like Structures of Gram-Negative Bacteria," *J. Mol. Evol.* 44:299-309, Springer-Verlag (1997).

Brandner, S., et al., "A crucial role for B cells in neuroinvasive scrapie," *Transfus. Clin. Biol.* 6:17-23, Elsevier, Paris (1999).

Brinton, Jr., C.C., "The structure, function, synthesis and genetic control of bacterial pili and a molecular model for DNA and RNA transport in gram negative bacteria," *Trans. N.Y. Acad. Sci.* 27:1003-1054, New York Academy of Sciences (1965).

Brown, K.D., et al., "A family of small inducible proteins secreted by leukocytes are members of a new superfamily that includes leukocyte and fibroblast-derived inflammatory agents, growth factors, and indicators of various activation processes," *J. Immunol.* 142:679-687, The American Association of Immunologists (1989).

Brown, P.M., et al., "A Single-Step Purification of Biologically Active Recombinant Human Interleukin-5 from a Baculovirus Expression System," *Protein Expr. Purif.* 6:63-71, Academic Press, Inc. (1995).

Brown, K.L., et al., "Scrapie replication in lymphoid tissues depends on prion protein-expressing follicular dendritic cells," *Nat. Med.* 11:1308-1312, Nature Publishing Company (1999).

Bullitt, E., et al., "Development of pilus organelle subassemblies in vitro depends on chaperone uncapping of a beta zipper," *Proc. Natl. Acad. Sci. USA* 93:12890-12895, National Academy Press (1996).

Bullitt, E., and Makowski, L., "Bacterial Adhesion Pili Are Heterologous Assemblies of Similar Subunits," *Biophys. J.* 74:623-632, Biophysical Society (1998).

Burger, J.A., et al., "Blood-derived nurse-like cells protect chronic lymphocytic leukemia B cells from spontaneous apoptosis through stromal cell-derived factor-1," *Blood* 96:2655-2663, The American Society of Hematology (Oct. 2000).

Burghoff, R.L., et al., "Utilization of the Mouse Large Intestine To Select an *Escherichia coli* F-18 DNA Sequence That Enhances Colonizing Ability and Stimulates Synthesis of Type 1 Fimbriae," *Infect. Immun.* 61:1293-1300, American Society for Microbiology (1993).

Cannon-Carlson S., et al., "Expression, Purification, and Characterization of Recombinant Human Interleukin-13 from NS-O Cells," *Protein Expr. Purif.* 12:239-248, Academic Press (1998).

Chabaud, M., et al., "Enhancing Effect of IL-17 on IL-1-Induced IL-6 and Leukemia Inhibitory Factor Production by Rheumatoid Arthritis Synoviocytes and Its Regulation by Th2 Cytokines," *J. Immunol.* 161: 409-414, The American Association of Immunologists (1998).

Chabaud, M., et al., "Human Interleukin-17. A T Cell-Derived Proinflammatory Cytokine Produced by the Rheumatoid Synovium," *Arthritis Rheum.* 42:963-970, Wiley-Liss, Inc. (1999).

Chabaud, M., et al., "Contribution of Interleukin 17 to synovium matrix destruction in rheumatoid arthritis," *Cytokine* 12:1092-1099, Cell Press (Jul. 2000).

Clark, H.F, et al., "Comparative Characterization of a C-Type Virus-Producing Cell Line (VSW) and a Virus-Free Cell Line (VH2) From *Vipera russelli*," *J. Natl. Cancer Inst.* 51:645-657, Oxford University Press (1973).

Clark-Lewis, I., et al., "Chemical Synthesis, Purification, and Characterization of Two Inflammatory Proteins, Neutrophil Activating Peptide 1 (Interleukin-8) and Neutrophil Activating Peptide 2," *Biochemistry 30*:3128-3135, American Chemical Society (1991).

Coffman, R.L., et al., "Antibody to Interleukin-5 Inhibits Helminth-Induced Eosinophilia in Mice," *Science 245*:308-310, American Association for the Advancement of Science (1989).

Cohen, C., and Parry D.A.D, "α-Helical coiled coils-a widespread motif in proteins," *Trends Biochem. Sci. 11*:245-248, Elsevier Science Publishers B.V. (1986).

Corti, M., et al., "GM1-ganglioside-Triton X-100 mixed micelles: changes of micellar properties studied by laser-light scattering and enzymatic methods," *Chem. Phys. Lipids 28*:197-214, Elsevier/North-Holland Scientific Publishers, Ltd. (1981).

Coutelier, J.-P., et al., "IgG2a Restriction of murine antibodies elicited by viral infections," *J. Exp. Med. 165*:64-69, The Rockefeller University Press (1987).

Crump, M.P., et al., "Solution Structure of Eotaxin, a Chemokine That Selectively Recruits Eosinophils in Allergic Inflammation," *J. Biol. Chem. 273*:22471-22479, The American Society for Biochemistry and Molecular Biology, Inc. (1998).

Davis, N.L., et al., "In Vitro Synthesis of Infectious Venezuelan Equine Encephalitis Virus RNA from a cDNA Clone: Analysis of a Viable Deletion Mutant," *Virology 171*:189-204, Academic Press (1989).

Daugherty, P.S., et al., "Development of an optimized expression system for the screening of antibody libraries displayed on the *Escherichia coli* surface," *Protein Eng. 12*:613-621, Oxford University Press (1999).

Dealwis, C., et al., "Crystal structure of chemically synthesized [N33A] stromal cell-derived factor 1α, a potent ligand for the HIV-1 "fusin" coreceptor," *Proc. Natl. Acad. Sci. USA 95*:6941-6946, National Academy Sciences (Jun. 2001).

Dodson, K.W., et al., "Outer-membrane PapC molecular usher discriminately recognizes periplasmic chaperone-pilus subunit complexes," *Proc. Natl. Acad. Sci. USA 90*:3670-3674, National Academy Press (1993).

Dudler, J., et al., "Effect of interleukin 17 on proteoglycan degradation in murine knee joints," *Ann. Rheum. Dis. 59*:529-532, Bmj Publishing Group (Jul. 2000).

Eckhardt, S.G., et al., "Hepatitis B Virus Core Antigen Has Two Nuclear Localization Sequences in the Arginine-Rich Carboxyl Terminus," *J. Virol. 65*:575-582, American Society for Microbiology (1991).

Eisenmesser, E.Z., et al., "Expression, Purification, Refolding, and Characterization of Recombinant Human Interleukin-13: Utilization of Intracellular Processing," *Protein Expr. Purif. 20*:186-195, Academic Press (Nov. 2000).

Eisenmesser, E.Z., et al., "Solution Structure of Interleukin-13 and Insights into Receptor Engagement," *J. Mol. Biol. 310*:231-241, Academic Press (Jun. 2001).

Eisenstein, B.I., "Phase Variation of Type 1 Fimbriae in *Escherichia coli* Is Under Transcriptional Control," *Science 214*:337-339, American Association for the Advancement of Science (1981).

Elisseeva, E.L., et al., "NMR Studies of Active N-terminal Peptides of Stromal Cell-derived Factor-1," *J. Biol. Chem. 275*:26799-26805, The American Society for Biochemistry and Molecular Biology, Inc. (Sep. 2000).

Eshdat, Y., et al., "Dissociation and Reassembly of *Escherichia coli* Type 1 Pili," *J. Bacteriol. 148*:308-314, American Society for Microbiology (1981).

Ettinger, R., et al., "A Critical Role for Lymphotoxin-β Receptor in the Development of Diabetes in Nonobese Diabetic Mice," *J. Exp. Med. 193*:1333-1339, The Rockefeller University Press (Jun. 2001).

Fehr, T., et al., "Role of Repetitive Antigen Patterns for Induction of Antibodies Against Antibodies," *J Exp. Med. 185*:1785-1792, The Rockefeller University Press (1997).

Folkman, J., and Klagsbrun, M., "Angiogenic Factors," *Science 235*:442-447, American Association for the Advancement of Science (1987).

Folkman, J., "Angiogenesis in cancer, vascular, rheumatoid and other disease," *Nat. Med. 1*:27-31, Nature Publishing Company (1995).

Forssmann, U., et al., "Eotaxin-2, a Novel CC Chemokine that Is Selective for the Chemokine Receptor CCR3, and Acts Like Eotaxin on Human Eosinophil and Basophil Leukocytes," *J. Exp. Med. 185*:2171-2176, The Rockefeller University Press (1997).

Fossiez, F., et al., "T Cell Interleukin-17 Induces Stromal Cells to Produce Proinflammatory and Hematopoietic Cytokines," *J. Exp. Med. 183*:2593-2603, The Rockefeller University Press (1996).

Fossiez F., et al., "Interleukin-17," *Intern. Rev. Immunol. 16*:541-551, Harwood Academic Publishers (1998).

Fujiwara, K., et al., "Novel preparation method of immunogen for hydrophobic hapten, enzyme immunoassay for daunomycin and adriamycin," *J. Immunol. Methods 45*:195-203, Elsevier/North-Holland Biomedical Press (1981).

Gally, D.L., et al., "Environmental Regulation of the *fim* Switch Controlling Type 1 Fimbrial Phase Variation in *Escherichia coli* K-12: Effects of Temperature and Media," *J. Bacteriol. 175*:6186-6193, American Society for Microbiology (1993).

Gally, D. L., et al., "Interaction of FimB and FimE with the *fim* switch that controls the phase variation of type 1 fimbriate in *Escherichia coli* K-12," *Mol. Microbiol. 21*:725-738, Blackwell Science, Ltd. (1996).

Gherardi, E. et al., "A single-step procedure for cloning and selection of antibody-secreting hybridomas," *J. Immunol. Methods 126*: 61-68, Elsevier (1990).

Golmohammadi, R., et al., "The crystal structure of bacteriophage Qβ at 3.5Å resolution," *Structure 4*:543-554, Current Biology, Ltd. (1996).

Gunn, M.D., et al., "A B-cell-homing chemokine made in lymphoid follicles activates Burkitt's lymphoma receptor-1," *Nature 391*:799-803, Nature Publishing Group (1998).

Hanes, J., et al., "Picomolar affinity antibodies from a fully synthetic naive library selected and evolved by ribosome display," *Nat. Biotechnol. 18*:1287-1292, Nature Publishing Company (Dec. 2000).

Hanson, M.S., et al., "Purification of the *Escherichia coli* Type 1 Pilin and Minor Pilus Proteins and Partial Characterization of the Adhesin Protein," *J. Bacteriol. 170*:3350-3358, American Society for Microbiology (1988).

Hanson, M.S., and Brinton, Jr., C.C., "Identification and characterization of *E. coli* type-1 pilus tip adhesion protein," *Nature 332*:265-268, Nature Publishing Group (1988).

Harrison, J.L., et al., "Screening of Phage Antibody Libraries," *Methods Enzymol. 267*:83-109, Macmillan Publishers, Ltd. (1996).

Haslam, D.B., et al., "The amino-terminal domain of the P-pilus adhesin determines receptor specificity," *Mol. Microbiol. 14*:399-409, Blackwell Scientific Publications (1994).

Hedrick, J.A., and Zlotnik, A., "Identification and Characterization of a Novel β Chemokine Containing Six Conserved Cysteines," *J. Immunol. 159*: 1589-1593, The American Association of Immunologists (1997).

Heveker, N., et al., Dissociation of the signalling and antiviral properties of SDF-1-derived small peptides, *Curr. Biol. 8*:369-376, Current Biology. Ltd. (1998).

Hirel, P.-H., et al., "Extent of N-terminal methionine excision from *Escherichia coli* proteins is governed by the side-chain length of the penultimate amino acid," *Proc. Natl. Acad. Sci. USA 86*:8247-8251, National Academy Press (1989).

Holmes, W.D., et al., "Solution Studies of Recombinant Human Stromal-Cell-Derived Factor-1," *Prot. Expr. Purif. 21*:367-377, Academic Press (Apr. 2001).

Holmgren, A., et al., "Conserved immunoglobulin-like features in a family of periplasmic pilus chaperones in bacteria," *EMBO J. 11*:1617-1622, Oxford University Press (1992).

Holmgren, A., and Bränden, C.-I., "Crystal structure of chaperone protein PapD reveals an immunoglobulin fold," *Nature 342*:248-251, Nature Publishing Group (1989).

Hultgren, S.J., et al., "The PapG adhesin of uropathogenic *Escherichia coli* contains separate regions for receptor binding and for the incorporation into pilus," *Proc. Natl. Acad. Sci. USA 86*:4357-4361, National Academy Press (1989).

Hultgren, S.J., et al., "PapD and superfamily of periplasmic immunoglobulin-like pilus chaperones," *Adv. Prot. Chem. 44*:99-123, Academic Press, Inc. (1993).

Hultgren, S.J., et al., "Pilus and Nonpilus Bacterial Adhesins: Assembly and Function in Cell Recognition," *Cell* 73:887-901, Cell Press (1993).

Hultgren, S.J., et al., "Bacterial Adhesins and Their Assembly," in *Escherichia coli and Salmonella*, Neidhardt, F.C., et al., eds., ASM Press, Washington, D.C. pp. 2730-2756 (1996).

Humbles, A.A., et al., "Kinetics of Eotaxin Generation and Its Relationship to Eosinophil Accumulation in Allergic Airways Disease: Analysis in a Guinea Pig Model In Vivo," *J. Exp. Med.* 186:601-612, The Rockefeller University Press (1997).

Hung, D.L., et al., "Molecular basis of two subfamilies of immunoglobulin-like chaperones," *EMBO J.* 15:3792-3805, Oxford University Press (1996).

Hung, D.L. and Hultgren, S.J., "Pilus Biogenesis via the Chaperone/Usher Pathway: An Integration of Structure and Function," *J. Struct. Biol.* 124:201-220, Academic Press (1998).

Ikeda, T., et al., "Determination of Three Isoforms of the Receptor Activator of Nuclear Factor-κB Ligand and Their Differential Expression in Bone and Thymus," *Endocrinology* 142:1419-1426, The Endocrine Society (Apr. 2001).

Ingley, E., et al., "Production and purification of recombinant human interleukin-5 from yeast and baculovirus expression systems," *Eur. J. Biochem.* 196:623-629, Blackwell Science, Ltd. (1991).

Jacob-Dubuisson, F., et al., "PapD chaperone function in pilus biogenesis depends on oxidant and chaperone-like activities of DsbA," *Proc. Natl. Acad. Sci. USA* 91:11552-11556, National Academy Press (1994).

Jacob-Dubuisson, F., et al., "Initiation of assembly and association of the structural elements of a bacterial pilus depend on two specialized tip proteins," *EMBO J.* 12:837-847, Oxford University Press (1993).

Jacob-Dubuisson, F., et al., "Chaperone-assisted Self-assembly of Pili Independent of Cellular Energy," *J. Biol. Chem.* 269:12447-12455, The American Society for Biochemistry and Molecular Biology, Inc. (1994).

Jiang, X., et al., "Norwalk Virus Genome Cloning and Characterization," *Science* 250:1580-1583, American Association for the Advancement of Science (1990).

Jones, C.H., et al., "FimC is a periplasmic PapD-like chaperone that directs assembly of type 1 pili in bacteria," *Proc. Natl. Acad. Sci. USA* 90:8397-8401, National Academy Press (1993).

Jones, C.H., et al., "FimH adhesin of type 1 pili is assembled into a fibrillar tip structure in the Enterobacteriaceae," *Proc. Natl. Acad. Sci. USA* 92:2081-2085, National Academy Press (1995).

Josien, R., et al., "TRANCE, a Tumor Necrosis Factor Family Member, Enhances the Longevity and Adjuvant Properties of Dendritic Cells In Vivo," *J. Exp. Med.* 191: 495-501, The Rockefeller University Press (Feb. 2000).

Jovanovic, D.V., et al., "IL-17 Stimulates the Production and Expression of Proinflammatory Cytokines, IL-β and TNF-α, by Human Macrophages," *J. Immunol.* 160:3513-3521, The American Association of Immunologists (1998).

Kapp, U., et al., "Interleukin 13 Is Secreted by and Stimulates the Growth of Hodgkin and Reed-Sternberg Cells," *J. Exp. Med.* 189:1939-1945, The Rockefeller University Press (1999).

Kastelein, R.A. et al., "Effect of the sequence upstream from the ribosome-binding site on the yield of protein from the cloned gene for phage MS2 coat protein," *Gene* 23:245-254, Elsevier (1983).

Kim, K.J., et al., "Inhibition of vascular endothelial growth factor-induced angiogenesis suppresses tumour growth in vivo," *Nature* 362:841-844, Nature Publishing Group (1993).

Kim, K.-H., et al., "A Cysteine-rich Adipose Tissue-specific Secretory Factor Inhibits Adipocyte Differentiation," *J. Biol. Chem.* 276:11252-11256, The American Society for Biochemistry and Molecular Biology, Inc. (Apr. 2001).

Klemm, P., "The *fimA* gene encoding the type-1 fimbrial subunit of *Escherichia coli*. Nucleotide sequence and primary structure of the protein," *Euro. J. Biochem.* 143:395-399, Blackwell Science, Ltd. (1984).

Klemm, P., and Christiansen, G., "Three *fim* genes required for the regulation of length and mediation of adhesion of *Escherichia coli* type 1 fimbriae," Mol. Gen. Genet. 208:439-445, Springer-Verlag (1987).

Klemm, P., et al., "The major subunit of *Escherichia coli* type 1 fimbriate is not required for D-mannose-specific adhesion," *Mol. Microbiol.* 4:553-559, Blackwell Scientific Publications (1990).

Klemm, P., and Christiansen, G., "The *fimD* gene required for cell surface localization of *Escherichia coli* type 1 fimbriae," *Mol. Gen. Genet.* 220:334-338, Springer-Verlag (1990).

Klemm, P., "FimC, a chaperone-like periplasmic protein of *Escherichia coli* involved in biogenesis of type 1 fimbriae," *Res. Microbiol.* 143:831-838, Institut Pasteur/Elsevier (1992).

Klemm, P., and Krogfelt, K.A., "Type 1 Fimbriae of *Escherichia coli*," in *Fimbriae*. Klemm, P., ed., CRC Press, Inc., Boca Raton, FL., pp. 9-26 (1994).

Kodama, S., et al., "Characterization of recombinant murine interleukin 5 expressed in Chinese hamster ovary cells," *Glycobiology* 2:419-427, Oxford University Press (1992).

Kodama, S., et al., "Carbohydrate Structures of Human Interleukin 5 Expressed in Chinese Hamster Ovary Cells," *J. Biochem.* (Tokyo) 110:693-701, Japanese Biochemical Society (1991).

Kopf, M., et al., "IL-5 Deficient Mice Have a Developmental Defect in CD5+ B-1 Cells and Lack Eosinophilia but have Normal Antibody and Cytotoxic T Cell Responses," *Immunity* 4:15-24, Cell Press (1996).

Koschel, M., et al., "Extensive Mutagenesis of the Hepatitis B Virus Core Gene and Mapping of Mutations That Allow Capsid Formation," *J. Virol* 73:2153-2160, American Society for Microbiology (1999).

Koths, K., "Structure-Function Studies on Human Macrophage Colony-Stimulating Factor (M-CSF)," *Mol. Reprod. Dev.* 46:31-38, Wiley-Liss, Inc. (1997).

Kozlovska, T.M., et al., "Recombinant RNA phage Qβ capsid particles synthesized and self-assembled in *Escherichia coli*," *Gene* 137:133-137, Elsevier Science Publishers B.V. (1993).

Kozlovskaya, T.M., et al., "Formation of capsid-like structures as a result of the expression of a cloned envelope protein gene from RNA-containing bacteriophage fr," *Dokl. Akad. Nauk. SSSR* 287: 452-455, Erivan Akademiia Nauk Armianskoi Ssr (1986).

Kozlovskaya, T.M., et al., "Formation of capsid-like structures as a result of the expression of a cloned envelope protein gene from RNA-containing bacteriophage fr," STNEasy, Accession No. 1986:219892, CAplus English abstract (1986) (Document AT37).

Krogfelt, K.A., et al., "Direct Evidence that the FimH Protein Is the Mannose-Specific Adhesin of *Escherichia coli* Type 1 Fimbriae," *Infect. Immun.* 58:1995-1998, American Society for Microbiology (1990).

Kuehn, M.J., et al., "Structural Basis of Pilus Subunit Recognition by the PapD Chaperone," *Science* 262:1234-1241, American Association for the Advancement of Science (1993).

Kunimoto, D.Y, et al., "High-level production of murine interleukin-5 (IL-5) utilizing recombinant baculovirus expression. Purification of the rIL-5 and its use in assessing the biologic role of IL-5 glycosylation," *Cytokine* 3:224-230, W.B. Saunders Company (1991).

Landschulz, W.H., et al., "The Leucine Zipper: A Hypothetical Structure Common to a New Class of DNA Binding Proteins," *Science* 240:1759-1764, American Association for the Advancement of Science (1988).

Leake, C.J., et al., "Cytopathic Effect and Plaque Formation by Arboviruses in a Continuous Cell Line (XTC-2) from the Toad *Xenopus laevis*," *J. gen. Virol.* 35:335-339, Cambridge University Press (1977).

Lee, K.H., et al., "Two-Dimensional Electrophoresis of Proteins as a Tool in the Metabolic Engineering of Cell Cycle Regulation," *Biotech. Bioeng.* 50:336-340, John Wiley & Sons, Inc. (1996).

Leech, M., et al., "Involvement of macrophage migration inhibitory factor in the evolution of rat adjuvant arthritis," *Arthritis Rheum.* 41:910-917, Arthritis Foundation (1998).

Leech, M., et al. "Regulation of macrophage migration inhibitory factor by endogenous glucocorticoid in rat adjuvant-induced arthritis," *Arthritis Rheum.* 43:827-833, Arthritis Foundation (Apr. 2000).

Liljeström, P., and Garoff, H., "A new generation of animal cell expression vectors based on the semliki forest virus replicon," *Bio/technology* 9:1356-1361, Nature Publishing Company (1991).

Liljeström, P., "Alphavirus expression systems," *Curr. Opin. Biotechnol.* 5:495-500, Current Biology, Ltd. (1994).

Lim, F., et al., "The RNA-binding Site of Bacteriophage Qβ Coat Protein," *J. Biol. Chem.* 271:31839-31845, The American Society for Biochemisty and Molecular Biology, Inc. (1996).

Lin, E.Y., et al., "Colony-stimulating Factor 1 Promotes Progression of Mammary Tumors to Malignancy," *J. Exp. Med.* 193:727-739, The Rockefeller University Press (Mar. 2001).

Lindberg, F., et al., "PapD, a Periplasmic Transport Protein in P-Pilus Biogenesis," *J. Bacteriol.* 171:6052-6058, American Society for Microbiology (1989).

Lo-Man, R., et al., "A recombinant virus-like particle system derived from parvovirus as an efficient antigen carrier to elicit a polarized Th1 immune response without adjuvant," *Eur. J. Immunol.* 28:1401-1407, Wiley-VCH Verlag GmbH (1998).

López, O., et al., "Direct formation of mixed micelles in the solubilization of phospholipid liposomes by Triton X-100," *FEBS Lett.* 426:314-318, Elsevier (1998).

Lowe, M.A., et al., "Immunoelectron Microscopic Analysis of Elongation of Type 1 Fimbriae in *Escherichia coli*," *J. Bacteriol.* 169:157-163, American Society for Microbiology (1987).

Lu, D., et al., "Identification of the Residues in the Extracellular Region of KDR Important for Interaction with Vascular Endothelial Growth Factor and Neutralizing Anti-KDR Antibodies," *J. Biol. Chem.* 275:14321-14330, The American Society for Biochemistry and Molecular Biology, Inc. (May 2000).

Lum, L., et al., "Evidence for a Role of a Tumor Necrosis Factor-α(TNF-α)-converting Enzyme-like Protease in Shedding of TRANCE, a TNF Family Member Involved in Osteoclastogenesis and Dendritic Cell Survival," *J. Biol. Chem.* 274:13613-13618, The American Society for Biochemistry and Molecular Biology, Inc. (1999).

Lundstrom, K., "Alphaviruses as expression vectors," *Curr. Opin. Biotechnol.* 8:578-582, Current Biology, Ltd. (1997).

Luther, S.A., et al., "BLC Expression in Pancreatic Islets Causes B Cell Recruitment and Lymphotoxin-Dependent Lymphoid Neogenesis," *Immunity* 12:471-481, Cell Press (May 2000).

Mackay, J.L., and Browning, J.L., "Turning off follicular dendritic cells," *Nature* 395:26-27, Macmillan Magazines, Ltd. (1998).

Martiny-Baron, G., and Marmé, D., "VEGF-mediated angiogenesis: a new target for cancer therapy," *Curr. Opin. Biotechnol.* 6:675-680, Current Biology, Ltd. (1995).

Matsui, S.M., et al., "The Isolation and Characterization of a Norwalk Virus-Specific cDNA," *J. Clin. Invest.* 87:1456-1461, The American Society for Clinical Investigation, Inc. (1991).

Matsumoto, M., et al., "Role of Lymphotoxin and the Type 1 TNF Receptor in the Formation of Germinal Centers," *Science* 271:1289-1291, American Association for the Advancement of Science (1996).

Matthews, W., et al., "A receptor tyrosine kinase cDNA isolated from a population of enriched primitive hematopoietic cells and exhibiting close genetic linkage to c-*kit*," *Proc. Natl. Acad. Sci. USA* 88:9026-9030, National Academy Press (1991).

Matusevicius, D., et al., "Interleukin-17 mRNA expression in blood and CSF mononuclear cells is augmented in multiple sclerosis," *Mult. Scler.* 5:101-104, Stockton Press (1999).

Mayer, K.L., and Stone, M.J., "NMR Solution Structure and Receptor Peptide Binding of the CC Chemokine Eotaxin-2," *Biochemistry* 39:8382-8395, American Chemical Society (Jul. 2000).

McClain, M.S., et al., "Roles of *fimB* and *fimE* in Site-Specific DNA Inversion Associated with Phase Variation of Type 1 Fimbriae in *Escherichia coli*," *J. Bacteriol.* 173:5308-5314, American Society for Microbiology (1991).

McPherson, P.S., "Regulatory Role of SH3 Domain-mediated Protein-Protein Interactions in Synaptic Vesicle Endocytosis," *Cell Signal* 11:229-238, Elsevier Science, Inc. (1999).

Mikulowska, A., et al., "Macrophage Migration Inhibitory Factor Is Involved in the Pathogensis of Collagen Type II-Induced Arthritis in Mice," *J. Immunol.* 158:5514-5517, The American Association of Immunologists (1997).

Millauer, B., et al., "Glioblastoma growth inhibited in vivo by a dominant-negative Flk-1 mutant," *Nature* 367:576-579, Nature Publishing Group (1994).

Min, H., et al., "Osteoprotegerin Reverses Osteoporosis by Inhibiting Endosteal Osteoclasts and Prevents Vascular Calcification by Blocking a Process Resembling Osteoclastogenesis," *J. Exp. Med.* 192:463-474, The Rockefeller University Press (Aug. 2000).

Mitchell, D.L., et al., "Purification and characterization of recombinant murine interleukin-5 glycoprotein, from a Baculovirus expression system," *Biochem. Soc. Trans.* 21:332S, Portland Press (1993).

Montrasio, F. et al., "Impaired Prion Replication in Spleens of Mice Lacking Follicular Dendritic Cells," *Science* 288:1257-1259, American Association for the Advancement of Science (May 2000).

Morein, B., et al., "Iscom, a novel structure for antigenic presentation of membrane proteins from enveloped viruses," *Nature* 308:457-460, Nature Publishing Group (1984).

Moriya, C., et al., "Large quantity production with extreme convenience of human SDF-1α and SDF-1β by a Sendai virus vector," *FEBS Lett.* 425:102-111, Amsterdam Elsevier Science B.V. (1998).

Müller, A., et al., "Involvement of chemokine receptors in breast cancer metastasis," *Nature* 410:50-56, Nature Publishing Group (Mar. 2001).

Murphy, Jr., K.P., et al., "Expression of Human Interleukin-17 in *Pichia pastoris*: Purification and Characterization," *Protein Expr. Purif.* 12:208-214, Academic Press (1998).

Nagira, M., et al., "Molecular Cloning of a Novel Human CC Chemokine Secondary Lymphoid-Tissue Chemokine That Is a Potent Chemoattractant for Lymphocytes and Mapped to Chromosome 9p13," *J. Biol. Chem.* 272:19518-19524, The American Society for Biochemistry and Molecular Biology, Inc. (1997).

Nanki, T., et al., "Stromal Cell-Derived Factor-1-CXC Chemokine Receptor 4 Interactions Play a Central Role in CD4[+] T Cell Accumulation in Rheumatoid Arthritis Synovium," *J. Immunol.* 165:6590-6598, The American Association of Immunologists (Dec. 2000).

Naureckiene, S., and Uhlin., B.E., "In vitro analysis of mRNA processing by Rnase E in the pap operon of *Escherichia coli*," *Mol. Microbiol.* 21:55-68, Blackwell Science, Ltd. (1996).

Neirynck, S., et al., "A universal influenza A vaccine based on the extracellular domain of the M2 protein," *Nat. Med.* 5:1157-1163, Nature Publishing Company (1999).

Newman, J.V., et al., "Stimulation of *Escherichia coli* F-18Col[−] Type-1 fimbriae synthesis by *leuX*," *FEMS Microbiol. Lett.* 122:281-287, Elsevier (1994).

Ni, C.-Z., et al., "Crystal structure of the coat protein from the GA bacteriophage: Model of the unassembled dimer," *Protein Sci.* 5:2485-2493, Cambridge University Press (1996).

Nilsson, P., et al., "Mutations Affecting mRNA Processing and Fimbrial Biogenesis in the *Escherichia coli pap* Operon," *J. Bacteriol.* 178:683-690, American Society for Microbiology (1996).

Oberlin, E., et al., "The CXC chemokine SDF-1 is the ligand for LESTR/fusin and prevents infection by T-cell-line-adapted HIV-1," *Nature* 382:833-835, Nature Publishing Group (1996).

Ohnishi, Y., et al., "Crystal Structure of Recombinant Native SDF-1α with Additional Mutagenesis Studies: An Attempt at a More Comprehensive Interpretation of Accumulated Structure-Activity Relationship Data," *J. Interferon Cytokine Res.* 20:691-700, Mary Ann Liebert, Inc. (Aug. 2000).

Olszewska, W., et al., "Protection against Measles Virus-Induced Encephalitis by Anti-mimotope Antibodies: The Role of Antibody Affinity," *Virology* 272:98-105, Academic Press (Jun. 2000).

Orndorff, P.E., and Falkow, S., "Identification and Characterization of a Gene Product That Regulates Type 1 Piliation in *Escherichia coli*," *J. Bacteriol.* 160:61-66, American Society for Microbiology (1984).

Orndorff, P.E., and Falkow, S., "Nucleotide Sequence of *pilA*, the Gene Encoding the Structural Component of Type 1 Pili in *Escherichia coli*," *J. Bacteriol.* 162:454-457, American Society for Microbiology (1985).

O'Shea, E.K., et al., "Evidence That the Leucine Zipper Is a Coiled Coil," *Science* 243:538-542, American Association for the Advancement of Science (1989).

O'Shea, E.K., et al., "Mechanism of Specificity in the Fos-Jun Oncoprotein Heterodimer," *Cell* 68:699-708, Cell Press (1992).

Pandit, J., et al., "Three-dimensional Structure of Dimeric Human Recombinant Macrophage Colony-Stimulating Factor," *Science* 258:1358-1362, American Association for the Advancement of Science (1992).

Pierrot, C., et al., "Expression of Rat Interleukin-5 and Generation of Neutralizing Antiserum: a Comparative Study of Rat IL-5 Produced in *Escherichia coli* and Insect Cells," *Biochem. Biophys. Res. Commun.* 253:756-760, Academic Press (1998).

Pierson-Mullany, L.K., et al. "Characterization of polyclonal allergen-specific IgE responses by affinity distributions," *Mol. Immunol.* 37:613-620, Elsevier Science, Ltd. (Aug. 2000).

Piossek, C., et al., "Vascular Endothelial Growth Factor (VEGF) Receptor II-derived Peptides Inhibit VEGF," *J. Biol. Chem.* 274:5612-5619, The American Society for Biochemistry and Molecular Biology, Inc. (1999).

Presta, L.G., et al., "Humanization of an Anti-Vascualr Endothelial Growth Factor Monoclonal Antibody for the Therapy of Solid Tumors and Other Disorders," *Cancer Res.* 57:4593-4599, The American Association for Cancer Research (1997).

Priano, C., et al., "A Complete Plasmid-based Complementation System for RNA Coliphage Qβ: Three Proteins of Bacteriophages Qβ (Group III) and SP (Group IV) can be Interchanged," *J. Mol. Biol.* 249:283-297, Academic Press, Ltd. (1995).

Proudfoot, A.E.I., et al., "Preparation and characterization of human interleukin-5 expressed in recombinant *Escherichia coli,*" *Biochem. J.* 270:357-361, Portland Press, Ltd. (1990).

Renner, W.A., et al., "Recombinant Cyclin E Expression Activates Proliferation and Obviates Surface Attachment of Chinese Hamster Ovary (CHO) Cells in Protein-Free Medium," *Biotech. Bioeng.* 47:476-482, Joney Wlley & Sons, Inc. (1995).

Risau, W., "Mechanisms of angiogenesis," *Nature* 386:671-674, Nature Publishing Group (1997).

Ritter, A., et al., "The Pai-associated *leuX* specific $tRNA_5^{Leu}$ affects type 1 fimbriation in pathogenic *Escherichia coli* by control of FimB recombinase expression," *Mol. Microbiol.* 25:871-882, Blackwell Science, Ltd. (1997).

Roesch, P.L., and Blomfield, I.C., "Leucine alters the interaction of the leucine-responsive regulatory protein (Lrp) with the *fim* switch to stimulate site-specific recombination in *Escherichia coli,*" *Mol. Microbiol.* 27:751-761, Blackwell Science, Ltd. (1998).

Roher, A.E., et al., "Isolation and Chemical Characterization of Alzheimer's Disease Paired Helical Filament Cytoskeletons: Differentiation from Amyloid Plaque Core Protein," *J. Cell Biol.* 107:2703-2716, The Rockefeller University Press (1988).

Roher, A.E., et al., "Morphological and Biochemical Analyses of Amyloid Plaque Core Proteins Purified from Alzheimer Disease Brain Tissue," *J. Neurochem.* 61: 1916-1926, Raven Press, Ltd. (1993).

Romagnani, S., "The Th1/Th2 paradigm," *Immunol. Today* 18:263-266, Elsevier Science, Ltd. (1997).

Rothenberg, M.E., et al., "Targeted Disruption of the Chemokine Eotaxin Partially Reduces Antigen-induced Tissue Eosinophilia," *J. Exp. Med.* 185:785-790, The Rockefeller University Press (1997).

Rusconi, S., et al., "In vitro inhibition of HIV-1 by Met-SDF-1β alone or in combination with antiretroviral drugs," *Antivir. Ther.* 5:199-204, International Medical Press (Sep. 2000).

Russell, P.W., and Orndorff, P.E., "Lesions in Two *Escherichia coli* Type 1 Pilus Genes Alter Pilus Number and Length without Affecting Receptor Binding," *J. Bacteriol.* 174:5923-5935, American Society for Microbiology (1992).

Santos, L., et al., "Role of macrophage migration inhibitory factor (MIF) in murine antigen-induced arthritis: interaction with glucocorticoids," *Clin. Exp. Immunol.* 123:309-314, Blackwell Science (Feb. 2001).

Saulino, E.T., et al., "Ramifications of kinetic partitioning on usher-mediated pilus biogenesis," *EMBO J.* 17:2177-2185, Oxford University Press (1998).

Schenk, D., et al., "Immunization with amyloid-β attenuates Alzheimer-disease-like pathology in the PDAPP mouse," *Nature* 400:173-177, Nature Publishing Group (1999).

Schlesinger, S., "Alphaviruses—vectors for the expression of heterologous genes," *Trends Biotechnol.* 11:18-22, Elsevier Science Publishers, Ltd. (1993).

Selkoe, D.J., "Translating cell biology into therapeutic advances in Alzheimer's disease," *Nature* 399:A23-A31, Nature Publishing Group (1999).

Slonim, L.N., et al., "Interactive surface in the PapD chaperone cleft is conserved in pilus chaperone superfamily and essential in subunit recognition and assembly," *EMBO J.* 11:4747-4756, Oxford University Press (1992).

Smyth, C.J., et al., "Fimbrial adhesins: similarities and variations in structure and biogenesis," *FEMS Immun. Med. Microbiol.* 16:127-139, Elsevier (1996).

Soto, H., et al., "The CC chemokine 6Ckine binds the CXC chemokine receptor CXCR3," *Proc. Natl. Acad. Sci. USA* 95:8205-8210, National Academy Press (1998).

Soto, G.E., et al., "Periplasmic chaperone recognition motif of subunits mediates quaternary interactions in the pilus," *EMBO J.* 17:6155-6167, Oxford University Press (1998).

Soto, G.E., and Hultgren, S.J., "Bacterial Adhesins: Common Themes and Variations in Architecture and Assembly," *J. Bacteriol.* 181:1059-1071, American Society for Microbiology (1999).

Steppan, C.M., et al., "The hormone resistin links obesity to diabetes," *Nature* 409:307-312, Nature Publishing Group (Jan. 2001).

Stollar, V., "Togaviruses in Cultured Arthropod Cells," in *The Togaviruses. Biology, Structure, Replication*, Schlesinger, R.W., ed., Academic Press, Inc. New York, N.Y., pp. 583-621 (1980).

Strauss, J., and Strauss, E.G., "The Alphaviruses: Gene Expression, Replication, and Evolution," *Microbiol. Rev.* 58:491-562, American Society for Microbiology (1994).

Striker, R.T., et al., "Stable Fiber-forming and Nonfiber-forming Chaperone-Subunit Complexes in Pilus Biogenesis," *J. Biol. Chem.* 269:12233-12239, The American Society for Biochemistry and Molecular Biology, Inc. (1994).

Sturchler-Pierrat, C., et al., "Two amyloid precursor protein transgenic mouse models with Alzheimer disease-like pathology," *Proc. Natl. Acad. Sci. USA* 94:13287-13292, National Academy Press (1997).

Sun, H.-W., et al., "Crystal structure at the 2.6-Å resolution of human macrophage migration inhibitory factor," *Proc. Natl. Acad. Sci. USA* 93:5191-5196, National Academy Press (1996).

Tang, J.-L., et al., "Interleukin-17 antagonism inhibits acute but not chronic vascular rejection," *Transplantation* 72:348-350, Lippincott Williams & Wilkens (Jul. 2001).

Tanimori, H., et al., "Enzyme immunoassay of neocarzinostatin using β-galactosidase as label," *J. Pharm. Dyn.* 4:812-819, Pharmaceutical Society of Japan (1981).

Teixeira, M.M., et al., "Chemokine-induced Eosinophil Recruitment. Evidence of a Role for Endogenous Eotaxin in an In Vivo Allergy Model in Mouse Skin," *J. Clin. Invest.* 100:1657-1666, The American Society for Clinical Investigation, Inc. (1997).

Tewari, R., et al., "Neutrophil Activation by Nascent FimH Subunits of Type 1 Fimbriae Purified from the Periplasm of *Escherichia coli,*" *J. Biol. Chem.* 268:3009-3015, The American Society for Biochemistry and Molecular Biology, Inc. (1993).

Teunissen, M.B.M., et al., "Interleukin-17 and Interferon-γ Synergize in the Enhancement of Proinflammatory Cytokine Production by Human Keratinocytes," *J. Invest. Dermatol.* 111:645-649, The Society for Investigative Dermatology, Inc. (1998).

Thanassi, D.G., et al., "The PapC usher forms an oligomeric channel: Implications for pilus biogenesis across the outer membrane," *Proc. Natl. Acad. Sci. USA* 95:3146-3151, National Academy Press (1998).

De Togni, P., et al., "Abnormal Development of Peripheral Lymphoid Organs in Mice Deficient in Lymphotoxin," *Science* 264:703-707, American Association for the Advancement of Science (1994).

Topchieva, I., and Karezin, K., "Self-Assembled Supramolecular Micellar Structures Based on Non-ionic Surfactants and Cyclodextrins," *J. Colloid Interface Sci.* 213:29-35, Academic Press (1999).

Tworney, T., et al., "Structure and immunogenicity of experimental foot-and-mouth disease and poliomyelitis vaccines," *Vaccine* 13:1603-1610, Elsevier Science, Ltd. (1995).

Ulrich, R., et al., "Core particles of hepatitis B virus as carrier for foreign epitopes," *Adv. Virus Res.* 50:141-182, Academic Press (1998).

Vicari, A.P., et al., "Antitumor Effects of the Mouse Chemokine 6Ckine/SLC Through Angiostatic and Immunological Mechanisms," *J. Immunol.* 165:1992-2000, The American Association of Immunologists (Aug. 2000).

Visintin, M. et al., "Selection of antibodies for intracellular function using a two-hybrid in vivo system," *Proc. Natl. Acad. Sci. USA* 96:11723-11728, National Academy Press (1999).

Walse, B., et al., "Transferred nuclear Overhauser effect spectroscopy study of a peptide from the PapG pilus subunit bound by the *Escherichia coli* PapD chaperone," *FEBS Lett.* 412:115-120, Elsevier Science B.V. (1997).

Warnes, A., et al., "Expression of the measles virus nucleoprotein gene in *Escherichia coli* and assembly of nucleocapsid-like structures," *Gene* 160:173-178, Elsevier Science B.V. (1995).

Watson, E., et al., "Structure determination of the intact major sialylated oligosaccharide chains of recombinant human erythropoietin expressed in Chinese hamster ovary cells," *Glycobiology* 4:227-237, Oxford niversity Press (1994).

Wei, Y.Q., et al., "Immunotherapy of tumors with xenogeneic endothelial cells as a vaccine," *Nat. Med.* 6:1160-1166, Nature Publishing Company (Oct. 2000).

Witherell, G.W., and Uhlenbeck, O.C., "Specific RNA Binding by Qβ Coat Protein," *Biochemistry* 28:71-76, American Chemical Society (1989).

Wong, C.K., et al., "Elevation of proinflammatory cytosine (IL-18, IL-17, IL-12) and Th2 cytokine (IL-4) concentrations in patients with systemic lupus erythematosus," *Lupus* 9:589-593, Macmillan Publishers Ltd. (2000).

Wu, Q., et al. "Reversal of Spontaneous Autoimmune Insulitis in Nonobese Diabetic Mice by Soluble Lymphotoxin Receptor," *J. Exp. Med.* 193:1327-1332, The Rockefeller University Press (Jun. 2001).

Wuttke, M., et al., "Structural Characterization of Human Recombinant and Bone-derived Bone Sialoprotein," *J. Biol. Chem.* 276:36839-36848, The American Society for Biochemistry and Molecular Biology, Inc. (2001).

Wynne, S.A., et al., "The Crystal Structure of the Human Hepatitis B Virus Capsid," *Mol. Cell* 3:771-780, Cell Press (1999).

Xiong, C., et al., "Sindbis Virus: An Efficient, Broad Host Range Vector for Gene Expression in Animal Cells," *Science* 243:1188-1191, American Association for the Advancement of Science (1989).

Yao, Z., et al., "Human IL-17: A Novel Cytokine Derived from T Cells," *J. Immunol.* 155:5483-5486, The American Association of Immunologists (1995).

Yao, Z., et al., "Molecular characterization of the human interleukin (IL)-17 receptor," *Cytokine* 9:794-800, Academic Press, Ltd. (1997).

Yone, K., et al., "Epitopic Regions for Antibodies against Tumor Necrosis Factor α," *J. Biol. Chem.* 270:19509-19515, The American Society for Biochemistry and Molecular Biology, Inc. (1995).

Yuan, T-T., et al., "Subtype-Independent Immature Secretion and Subtype-Dependent Replication Deficiency of a Highly Frequent, Naturally Occurring Mutation of Human Hepatitis B Virus Core Antigen," *J. Virol.* 73:10122-10128, American Society for Microbiology (1999).

Zang, M., et al., "Production of Recombinant Proteins in Chinese Hamster Overy Cells Using A Protein-Free Cell Culture Medium," *Bio/Technology* 13:389-392, Nature Publishing Company (1995).

Zhou, S., and Standring, D.N., "Cys Residues of the Hepatitis B Virus Capsid Protein Are Not Essential for the Assembly of Viral Core Particles but Can Influence Their Stability," *J. Virol.* 66:5393-5398, American Society for Microbiology (1992).

Zimmermann, N., et al., "Murine Eotaxin-2: A Constitutive Eosinophil Chemokine Induced by Allergen Challenge and IL-4 Overexpression," *J. Immunol.* 165:5839-5846, The American Association of Immunologists (Nov. 2000).

Ziolkowska, M., et al., "High Levels of IL-17 in Rheumatoid Arthritis Patients: IL-15 Triggers In Vitro IL-17 Production Via Cyclosporin A-Sensitive Mechanism," *J. Immunol.* 164:2832-2838, The American Association of Immunologists (Mar. 2000).

Zuercher, A.W., et al., "Oral anti-IgE immunization with epitope-displaying phage," *Eur. J. Immunol.* 30:128-135, Wiley-Vch Verlag GmbH (Jan. 2000).

Fehr, T., et al., "T cell-independent type I antibody response against B cell epitopes expressed repetitively on recombinant virus particles," *Proc. Natl. Acad. Sci. USA* 95:9477-9481, National Academy Press (1998).

Frenkel, D., et al., "Generation of auto-antibodies towards Alzheimer's disease vaccination," *Vaccine* 19:2615-2619, Elsevier Science, Ltd. (Mar. 2001).

International Search Report for International Application No. PCT/IB02/00166 mailed on Oct. 29, 2002. European Patent Office, Netherlands (2002).

International Search Report for International Application No. PCT/IB02/00168 mailed on Nov. 4, 2002. European Patent Office, Netherlands (2002).

Kozlovska, T.M., et al., "RNA Phage Qβ Coat Protein as a Carrier for Foreign Epitopes," *Intervirology* 39:9-15, S. Karger AG (1996).

Kratz, P.A., et al., "Native display of complete foreign protein domains on the surface of hepatitis B virus capsids," *Proc. Natl. Acad. Sci. USA* 96:1915-1920, National Academy of Sciences (1999).

Nieland, J.D., et al., "Chimeric Papillomavirus Virus-like Particles Induce a Murine Self-Antigen-Specific Protective and Therapeutic Antitumor Immune Response," *J. Cell. Biochem.* 73:145-152, Wiley-Liss, Inc. (1999).

Slepushkin, V.A., et al., "Protection of mice against influenza A virus challenge by vaccination with baculovirus-expressed M2 protein," *Vaccine* 13:1399-1402, Elsevier Science Ltd. (1995).

Vasiljeva, I., et al., "Mosaic Qβ coats as a new presentation model," *FEBS Lett.* 431:7-11, Federation of European Biochemical Societies (1998).

International Search Report for International Application No. PCT/IB 02/00166, mailed Jan. 31, 2003. European Patent Office, Netherlands (2002).

Baba, T.W., et al., "Pathogenicity of Live, Attenuated SIV After Mucosal Infection of Neonatal Macaques," *Science* 267:1820-1825, American Association for the Advancement of Science (1995).

Bachmann, M.F., et al., "Dendritic cells process exogenous viral proteins and virus-like particles for class I presentation to CD8+ cytotoxic T lymphocytes," *Eur. J. Immunol.* 26:2595-2600, VCH Verlagsgesellschaft mbH (1996).

Boorsma, M., et al., "A temperature-regulated replicon-based DNA expression system," *Nat. Biotechnol.* 18:429-432, Nature America, Inc. (Apr. 2000).

Borisova, G., et al., "Hybrid Hepatitis B Virus Nucleocapsid Bearing an Immunodominant Region from Hepatitis B Virus Surface Antigen," *J. Virol.* 67:3696-3701, American Society for Microbiology (1993).

Cesareni, G., "Peptide display on filamentous phage capsids: A new powerful tool to study protein-ligand interaction," *FEBS Lett.* 307:66-70, Elsevier Science Publishers B.V. (1992).

Connor, R.I., et al., "Immunological and Virological Analyses of Persons Infected by Human Immunodeficiency Virus Type 1 while Participating in Trials of Recombinant gp120 Subunit Vaccines," *J. Virol.* 72:1552-1576, American Society for Microbiology (1998).

Crameri, R. and Suter, M., "Display of biologically active proteins on the surface of filamentous phages: a cDNA cloning system for selection of functional gene products linked to the genetic information responsible for their production," *Gene* 137:69-75, Elsevier Science Publishers B.V. (1993).

Daniel, M.D., et al., "Protective Effects of a Live Attenuated SIV Vaccine with a Deletion in the *nef*Gene," *Science* 258:1938-1941, American Association for the Advancement of Science (1992).

de la Cruz, V.F., et al., "Immunogenicity and Epitope Mapping of Foreign Sequences via Genetically Engineered Filamentous Phage," *J. Biol. Chem.* 263:4318-4322, The American Society for Biochemistry and Molecular Biology, Inc. (1988).

Donnelly, J.J., et al., "DNA Vaccines," *Annu. Rev. Immunol.* 15:617-648, Annual Reviews, Inc. (1997).

Ebina, S., et al., "Chemical Modification of Bovine Pancreatic Trypsin Inhibitor for Single Site Coupling of Immunogenic Peptides for NMR Conformational Analysis," *J. Biol. Chem.* 264:7882-7888, The American Society for Biochemistry and Molecular Biology, Inc. (1989).

Esposito, G., et al., "Conformational study of a short *Pertussis* toxin T cell epitope incorporated in a multiple antigen peptide template by CD and two-dimensional NMR: Analysis of the structural effects on the activity of synthetic immunogens," *Eur. J. Biochem. 217*:171-187, Blackwell Science Ltd. on behalf of the Federation of European Biochemical Societies (1993).

Förster, E., et al., "Natural and recombinant enzymatically active or inactive bee venom phospholipase $A_2$ has the same potency to release histamine from basophils in patients with Hymenoptera allergy," *J. Allergy Clin. Immunol. 95*:1229-1235, Mosby-Year Book, Inc. (1995).

Frolov, I., et al., "Alphavirus-based expression vectors: Strategies and applications," *Proc. Natl. Acad. Sci. USA 93*:11371-11377, National Academy Press (1996).

Gilbert, S.C., et al., "A protein particle vaccine containing multiple malaria epitopes," *Nat. Biotechnol. 15*:1280-1284, Nature America Publishing (1997).

Greenstone, H.L., et al., "Chimeric paillomavirus virus-like particles elicit antitumor immunity against the E7 oncoprotein in an HPV16 tumor model," *Proc. Natl. Acad. Sci. USA 95*:1800-1805, National Academy Press (1998).

Hahn, C.S., et al., "Infectious Sindbis virus transient expression vectors for studying antigen processing and presentation," *Proc. Natl. Acad. Sci. USA 89*:2679-2683, National Academy Press (1992).

Harding, C.V., and Song, R., "Phagocytic Processing of Exogenous Particulate Antigens by Macrophages for Presentation by Class I MHC Molecules," *J. Immunol. 153*:4925-4933, The American Association of Immunologists (1994).

Hilleman, M.R., "Six decades of vaccine development—a personal history," *Nat. Med. Vaccine Suppl. 4*:507-514 (May 1998).

Hui, E. K-W. et al., "Hepatitis B viral core proteins with an N-terminal extension can assemble into core-like particles but cannot be enveloped," *J. Gen. Virol. 80*:2647-2659, Society for General Microbiology (1999).

Iannolo, G., et al., "Construction, Exploitation and Evolution of a New Peptide Library Displayed at High Density by Fusion to the Major Coat Protein of Filamentous Phage," *Biol. Chem. 378*:517-521, Walter de Gruyter & Co. (1997).

Iannolo, G., et al., "Modifying FIlamentous Phage Capsid: Limits in the Size of the Major Capsid Protein," *J. Mol. Biol. 248*:835-844, Academic Press, Ltd. (1995).

Ikram, H., and Prince, A.M., "A method for coupling the Hepatitis B surface antigen to aldehyde-fixed erythrocytes for use in passive hemagglutination," *J. Virol. Methods 2*:269-275, Elsevier/North-Holland Biomedical Press (1981).

Kovacsovics-Bankowski, M., et al., "Efficient major histocompatibility complex class I presentation of exogenous antigen upon phagocytosis by macrophages," *Proc. Natl. Acad. Sci. USA 90*:4942-4946, National Academy Press (1993).

Lo, K. K-W., et al., "Surface-modified mutants of cytochrome P450cam: enzymatic properties and electrochemistry," *FEBS Lett. 451*:342-346, Elsevier Science B.V. on behalf of the Federation of European Biochemical Societies (1999).

Minenkova, O.O., et al., "Design of specific immunogens using filamentous phage as the carrier," *Gene 128*:85-88, Elsevier Science Publishers B.V. (1993).

Neurath, A.R., et al., "Hepatitis B Virus surface antigen (HBsAg) as carrier for synthetic peptides having an attached hydrophobic tail," *Mol. Immunol. 26*:53-62, Pergamon Press (1989).

Perham, R.N., et al., "Engineering a peptide epitope display system on filamentous bacteriophage," *FEMS Microbiol. Rev. 17*:25-31, Elsevier Science Publishers on behalf of the Federation of European Microbiological Societies (1995).

Petrenko, V.A., et al., "A library of organic landscapes on filamentous phage," *Protein Engin. 9*:797-801, Oxford University Press (1996).

Pumpens, P. and Grens, E., "Hepatitis B core particles as a universal display model: a structure-function basis for development," *FEBS Lett. 442*:1-6, Elsevier Science B.V. on behalf of the Federation of European Biochemical Societies (1999).

Quash, G., et al., "The preparation of latex particles with covalently bound polyamines IgG and measles agglutinins and their use in visual agglutination tests," *J. Immunol. Methods 22*:165-174, Elsevier/North-Holland Biomedical Press (1978).

Raychaudhuri, S., and Rock, K.L., "Full mobilizing host defense: Building better vaccines," *Nat. Biotechnol. 16*:1025-1031, Nature America, Inc. (1998).

Redfield, R.R., et al., "Disseminated vaccinia in a military recruit with Human Immunodeficiency Virus (HIV) disease," *N. Eng. J. Med. 316*:673-676, Massachusetts Medical Society (1987).

Rudolf, M.P., et al., Molecular Basis for Nonanaphylactogenicty of a Monoclonal Anti-IgE Antibody, *J. Immunol. 165*:813-819, The American Association of Immunologists (2000).

Sedlik, C., et al., "Recombinant parvovirus-like particles as an antigen carrier: A novel nonreplicative exogenous antigen to elicit protective antiviral cytotoxic T cells," *Proc. Natl. Acad. Sci. USA 94*:7503-7508, National Academy Press (1997).

Shen, L., et al., "Recombinant Virus Vaccine-Induced SIV-Specific $CD8^+$ Cytotoxic T Lymphocytes," *Science 252*:440-443, American Association for the Advancement of Science (1991).

Tanimori, H., et al., "Enzyme Immunoassay of Neocarzinostatin Using β-Galactosidase as Label," *J. Pharm. Dyn. 4*:812-819, Pharmaceutical Society of Japan (1981).

Townsend, A., and Bodmer, H., "Antigen recognition by class I-restricted T lymphocytes," *Ann. Rev. Immunol. 7*:601-624, Annual Reviews, Inc. (1989).

VanCott, T.C., et al., "Antibodies with Specificity to Native gp120 and Neutralization Activity against Primary Human Immunodeficiency Virus Type 1 Isolates Elicited by Immunization with Oligomeric gp160," *J. Virol. 71*:4319-4330, American Society for Microbiology (1997).

Watkins, S.J., et al., "The 'adenobody' approach to viral targeting: specific and enhanced adenoviral gene delivery," *Gene Ther. 4*:1004-1012, Stockton Press (1997).

Willis, A.E., et al., "Immunological properties of foreign peptides in multiple display on a filamentous bacteriophage," *Gene 128*:79-83, Elsevier Science Publishers B.V. (1993).

Dialog File 351, Accession No. 9831660, Derwent WPI English language abstract for WO 94/06472 (Document AP3), Date not available.

International Preliminary Examination Report for International Application No. PCT/IB99/01925, European Patent Office, Munich (Aug. 2000) (not for publication).

International Search Report for International Application No. PCT/IB99/01925, European Patent Office, Netherlands (Jun. 2000) (not for publication).

NCBI Entrez, GenBank Report, Accession No. P03153, from Seeger, C., et al. (Jan. 1990).

NCBI Entrez, GenBank Report, Accession No. X59397, from Jordan, C.T., et al. (Nov. 1991).

NCBI Entrez, GenBank Report, Accession No. 711678A, from Shipolini, R.A., et al. (Jul. 1992).

NCBI Entrez, GenBank Report, Accession No. M27603, from Orndorff, P.E., and Falkow, S. (Apr. 1993).

NCBI Entrez, GenBank Report, Accession No. M20706, from Nassal M. (Apr. 1993).

NCBI Entrez, GenBank Report, Accession No. AAA37490, from Rouvier E. (Jul. 1993).

NCBI Entrez, GenBank Report, Accession No. M90520, from Kew, M.C., et al. (Aug. 1993).

NCBI Entrez, GenBank Report, Accession No. X00981, from Klemm, P. (Sep. 1993).

NCBI Entrez, GenBank Report, Accession No. VCBPQB, from Maita, T., and Konigsberg, W. (Dec. 1993).

NCBI Entrez, GenBank Report, Accession No. AAA16663, from Kozlovska, T.M., et al. (Mar. 1994).

NCBI Entrez, GenBank Report, Accession No. X02514, from Yanisch-Perron, C., et al. (May 1994).

NCBI Entrez, GenBank Report, Accession No. X85256, from Lai, M.E., et al. (Apr. 1995).

NCBI Entrez, GenBank Report, Accession No. X85259, from Lai, M.E., et al., (Apr. 1995).

NCBI Entrez, GenBank Report, Accession No. X85260, from Lai, M.E., et al. (Apr. 1995).

NCBI Entrez, GenBank Report, Accession No. X85272, from Lai, M.E., et al. (Apr. 1995).

NCBI Entrez, GenBank Report, Accession No. X85275, from Lai, M.E., et al. (Apr. 1995).
NCBI Entrez, GenBank Report, Accession No. X85284, from Lai, M.E., et al. (Apr. 1995).
NCBI Entrez, GenBank Report, Accession No. X85285, from Lai, M.E., et al. (Apr. 1995).
NCBI Entrez, GenBank Report, Accession No. X85286, from Lai, M.E., et al. (Apr. 1995).
NCBI Entrez, GenBank Report, Accession No. X85287, from Lai, M.E., et al. (Apr. 1995).
NCBI Entrez, GenBank Report, Accession No. X85291, from Lai, M.E., et al. (Apr. 1995).
NCBI Entrez, GenBank Report, Accession No. X85293, from Lai, M.E., et al. (Apr. 1995).
NCBI Entrez, GenBank Report, Accession No. X85295, from Lai, M.E., et al. (Apr. 1995).
NCBI Entrez, GenBank Report, Accession No. X85296, from Lai, M.E., et al. (Apr. 1995).
NCBI Entrez, GenBank Report, Accession No. X85297, from Lai, M.E., et al. (Apr. 1995).
NCBI Entrez, GenBank Report, Accession No. X85298, from Lai, M.E., et al. (Apr. 1995).
NCBI Entrez, GenBank Report, Accession No. X85299, from Lai, M.E., et al. (Apr. 1995).
NCBI Entrez, GenBank Report, Accession No. X85301, from Lai, M.E., et al. (Apr. 1995).
NCBI Entrez, GenBank Report, Accession No. X85302, from Lai, M.E., et al. (Apr. 1995).
NCBI Entrez, GenBank Report, Accession No. X85303, from Lai, M.E., et al. (Apr. 1995).
NCBI Entrez, GenBank Report, Accession No. X85305, from Lai, M.E., et al. (Apr. 1995).
NCBI Entrez, GenBank Report, Accession No. X85307, from Lai, M.E., et al. (Apr. 1995).
NCBI Entrez, GenBank Report, Accession No. X85311, from Lai, M.E., et al. (Apr. 1995).
NCBI Entrez, GenBank Report, Accession No. X85314, from Lai, M.E., et al. (Apr. 1995).
NCBI Entrez, GenBank Report, Accession No. X85315, from Lai, M.E., et al. (Apr. 1995).
NCBI Entrez, GenBank Report, Accession No. X85316, from Lai, M.E., et al. (Apr. 1995).
NCBI Entrez, GenBank Report, Accession No. X85317, from Lai, M.E., et al. (Apr. 1995).
NCBI Entrez, GenBank Report, Accession No. X85319, from Lai, M.E., et al. (Apr. 1995).
NCBI Entrez, GenBank Report, Accession No. X80925, from Karayiannis, P. (Dec. 1995).
NCBI Entrez, GenBank Report, Accession No. AAC50341, from Yao, Z., et al. (Jan. 1996).
NCBI Entrez, GenBank Report, Accession No. X72702, from Preisler-Adams, S., et al. (Feb. 1996).
NCBI Entrez, GenBank Report, Accession No. VCBPR7, from Weber, K., et al. (Apr. 1996).
NCBI Entrez, GenBank Report, Accession No. 1604193A, from Gomez, F., et al. (Oct. 1996).
NCBI Entrez, GenBank Report, Accession No. B56338, from Hoffman, D.R. (May 1997).
NCBI Entrez, GenBank Report, Accession No. U95551, from Rao, B.S., et al. (Jun. 1997).
NCBI Entrez, GenBank Report, Accession No. S14764, from Vandermeers, A., et al. (Oct. 1997).
NCBI Entrez, GenBank Report, Accession No. P03611, from Weber, K., et al. (Nov. 1997).
NCBI Entrez, GenBank Report, Accession No. AAC14699, from Beekwilder, M.J., et al. (Apr. 1998).
NCBI Entrez, GenBank Report, Accession No. AAC14704, from Beekwilder, M.J., et al. (Apr. 1998).
NCBI Entrez, GenBank Report, Accession No. AF043593, from Gunther, S., et al. (May 1998).
NCBI Entrez, GenBank Report, Accession No. 1POC, from Scott, D.L., et al. (Sep. 1998).
NCBI Entrez, GenBank Report, Accession No. CAA30374, from Inokuchi, Y., et al. (Feb. 1999).
NCBI Entrez, GenBank Report, Accession No. X02496, from Bichko, V., et al. (Apr. 1999).
NCBI Entrez, GenBank Report, Accession No. MFIV62, from Cox, N.J., et al. (Jul. 1999).
NCBI Entrez, GenBank Report, Accession No. VCBPFR, from Wittmann-Liebold, B., et al. (Jul. 1999).
NCBI Entrez, GenBank Report, Accession No. A59055, from Hoffman, D.R., and Schmidt, J.O. (Aug. 1999).
NCBI Entrez, GenBank Report, Accession No. B59055, from Hoffman, D.R., and Schmidt, J.O. (Aug. 1999).
NCBI Entrez, GenBank Report, Accession No. AF051814, from Boyd, E.F., and Hartl, D.L. (Sep. 1999).
NCBI Entrez, GenBank Report, Accession No. AF051815, from Boyd, E.F., and Hartl, D.L. (Sep. 1999).
NCBI Entrez, GenBank Report, Accession No. AF110999, from Chang, S.F., et al. (Oct. 1999).
NCBI Entrez, GenBank Report, Accession No. AB033559, from Okamoto, H., et al. (Oct. 1999).
NCBI Entrez, GenBank Report, Accession No. AB010289, from Koseki, T., et al. (Dec. 1999).
NCBI Entrez, GenBank Report, Accession No. AJ132364, from Graupner, S., et al. (Apr. 2000).
NCBI Entrez, GenBank Report, Accession No. AF237482, from Johnson, J.R., et al. (May 2000).
NCBI Entrez, GenBank Report, Accession No. M32138, from Tong, S.P., et al. (Jul. 2000).
NCBI Entrez, GenBank Report, Accession No. AF229646, from Skerker, J.M., and Shapiro, L. (Aug. 2000).
NCBI Entrez, GenBank Report, Accession No. M95589, from Shi, H., et al. (Jan. 2001).
NCBI Entrez, GenBank Report, Accession No. VCBPM2, from Min Jou, W., et al. (Jan. 2001).
NCBI Entrez, GenBank Report, Accession No. AF323080, from Steppan, C.M., et al. (Jan. 2001).
NCBI Entrez, GenBank Report, Accession No. AF323081, from Steppan, C.M., et al. (Jan. 2001).
NCBI Entrez, GenBank Report, Accession No. U14003, from Plunkett, G., III, et al. (Jan. 2001).
NCBI Entrez, GenBank Report, Accession No. AF121239, from Hannoun, C., et al. (Feb. 2001).
NCBI Entrez, GenBank Report, Accession No. AF121240, from Hannoun, C., et al. (Feb. 2001).
NCBI Entrez, GenBank Report, Accession No. AF121242, from Hannoun, C., et al. (Feb. 2001).
NCBI Entrez, GenBank Report, Accession No. X59795, from Lai, M.E., et al. (Mar. 2001).
NCBI Entrez, GenBank Report, Accession No. X65257, from Lai, M.E., et al. (Mar. 2001).
NCBI Entrez, GenBank Report, Accession No. X65258, from Lai, M.E., et al. (Mar. 2001).
NCBI Entrez, GenBank Report, Accession No. AF151735, from Gerner, P., et al. (Apr. 2001).
NCBI Entrez, GenBank Report, Accession No. AJ000636, from Gousset, N., et al. (Nov. 2001).
NCBI Entrez, GenBank Report, Accession No. AAB59424, from Kenten, J.H., et al. (Feb. 2002).
NCBI Entrez, GenBank Report, Accession No. AAC06250, from Beekwilder, M.J., et al. (Mar. 2002).
NCBI Entrez, GenBank Report, Accession No. L09137, from Yanisch-Perron, C., et al. (May 2002).
NCBI Entrez, GenBank Report, Accession No. O09006, from Hromas, R., et al. (Jun. 2002).
NCBI Entrez, GenBank Report, Accession No. P40224, from Nagasawa, T., et al. (Jun. 2002).
NCBI Entrez, GenBank Report, Accession No. P34884, from Bernhagen, J., et al. (Jun. 2002).
NCBI Entrez, GenBank Report, Accession No. P06821, from Winter, G., et al. (Jun. 2002).
NCBI Entrez, GenBank Report, Accession No. P30904, from Sakai, M., et al. (Jun. 2002).

NCBI Entrez, GenBank Report, Accession No. NP_040754, from Inokuchi, Y., et al. (Jun. 2003).

NCBI Entrez, GenBank Report, Accession No. NP_061354, from Ishikawa, S., et al. (Sep. 2003).

NCBI Entrez, GenBank Report, Accession No. NP_031804, from Lenda, D.M., et al. (Sep. 2003).

NCBI Entrez, GenBank Report, Accession No. NP_006410, from Luther, S.A., et al. (Sep. 2003).

NCBI Entrez, GenBank Report, Accession No. NP_000748, from Yao, G.Q., et al. (Sep. 2003).

NCBI Entrez, GenBank Report, Accession No. P03069, from Hinnebusch, A.G., et al. (Sep. 2003).

NCBI Entrez, GenBank Report, Accession No. O00585, from Hromas, R., et al. (Sep. 2003).

NCBI Entrez, GenBank Report, Accession No. P14174, from Weiser, W.Y., et al. (Sep. 2003).

NCBI Entrez, GenBank Report, Accession No. P48061, from Spotila, L.D., et al. (Sep. 2003).

NCBI Entrez, GenBank Report, Accession No. P80003, from Vandermeers, A., et al. (Sep. 2003).

Swiss-Prot/TrEMBL, TN11_Mouse, Primary Accession No. O35235, entered in Swiss-Prot in Oct. 2001.

Swiss-Prot/TrEMBL, TN11_Human, Primary Accession No. O14788, entered in Swiss-Prot in Oct. 2001.

Co-pending U.S. Appl. No. 10/264,267, inventors Bachmann, M., filed Oct. 4, 2002 (Not Published).

Co-pending U.S. Appl. No. 10/289,456, inventors Bachmann et al., filed Nov. 7, 2002 (Not Published).

Co-pending U.S. Appl. No. 10/346,190, inventors Bachmann et al., filed Jan. 17, 2003 (Not Published).

Co-pending U.S. Appl. No. 10/622,064, inventors Bachmann et al., filed Jul. 18, 2003 (Not Published).

Co-pending U.S. Appl. No. 10/622,087, inventors Bachmann et al., filed Jul. 18, 2003 (Not Published).

Co-pending U.S. Appl. No. 10/622,124, inventors Bachmann et al., filed Jul. 18, 2003 (Not Published).

Chackerian B., et al., "Induction of autoantibodies to mouse CCR5 with recombinant papillomavirus particles," *Proc. Natl. Acad. Sci. USA* 96:2373-2378, National Academy Press (Mar. 1999).

Gardiner, S.M., et al., "Active immunization with angiotensin 1 peptide analogue vaccines selectively reduces the pressor effects of exogenous angiotensin I in conscious rats," *Br. J. Pharmacol.* 129:1178-1182 (Mar. 2000).

Hermanson, G.T., in *Bioconjugate Techniques*, Academic Press, San Diego, CA, pp. 1-296 (1996).

Jeannin, P., et al., "Immunogenicity and antigenicity of synthetic peptides derived from the mite allergen *Der p 1*," *Mol. Immunol.* 30:1511-1518, Pergamon Press, Ltd. (1993).

Klovins, J., "Nucleotide sequence of a ssRNA phage from *Acinebacter*: kinship to coliphages," *J. Gen. Virol.* 83:1523-1533, Society For General Microbiology (Jun. 2002).

Sutcliffe, J.G., et al., "Complete nucleotide sequence of the *Escherichia coli* Plasmid pBR322," *Cold Spring Harb. Symp. Quant. Biol.* 43:77-90, Cold Spring Harbor Laboratory Press (1979).

NCBI Entrez, GenBank Report, Accession No. AF334111, from Klovins, J., et al. (Feb. 2002).

Jegerlehner, A., et al., "A molecular assembly system that renders antigens of choice highly repetitive for induction of protective B cell responses," *Vaccine* 20:3104-3112, Elsevier Science, Ltd. (Aug. 2002).

*The Biology of Animal Viruses*, 2nd ed., Fenner, F., et al., eds., Academic Press, New York, NY, pp. 117-119(1974).

NCBI Entrez, PubMed Abstract, PMID: 2205968, Diallo, A., et al., "Morbillivirus group: genome organization and proteins," *Vet. Microbiol.* 23:155-163 (1990).

Lechner F. et al., "Virus-Like Particles as a Modular System for Novel Vaccines," *Intervirology* 45:212-217, S. Karger AG, Basel (Jul. 2002).

Brown, William L. et al., "RNA Bacteriophage Capsid-Mediated Drug Delivery and Epitope Presentation," *Intervirology* 45:371-380, S. Karger AG, Basel (Jul. 2002).

International Search Report for PCT/EP 03/07572, European Patent Office, The Netherlands (Dec. 2003).

Klovins, J. et al., "Nucleotide sequence of a ssRNA phage from *Acinetobacter* kinship to coliphages," Journal of General Virology 83:1523-1533, SGM (2002).

* cited by examiner

```
                                    Nhe I          Linker
  1  GAT CCA GCA GCT GGG CTC GAG GTG CTA GCG GGA GGG GGT GGA TGT GGG
      D   P   A   A   G   L   E   V   L   A   G   G   G   G   C   G Xa
      Factor Xa    ↓  Hind III          hu IgG1
 49  ATC GAA GGT CGC AAG CTT ACT CAC ACA TGC CCA CCG TGC CCA GCA CCT
      I   E   G   R   K   L   T   H   T   C   P   P   C   P   A   P 97  GAA GCC GAG GGG GCA CCG TCA GTC TTC CTC TTC CCC CCA AAA CCC AAG
      E   A   E   G   A   P   S   V   F   L   F   P   P   K   P   K 145  GAC ACC CTC ATG ATC TCC CGG ACC CCT GAG GTC ACA TGC GTG GTG GTG
      D   T   L   M   I   S   R   T   P   E   V   T   C   V   V   V 193  GAC GTG AGC CAC GAA GAC CCT GAG GTC AAG TTC AAC TGG TAC GTG GAC
      D   V   S   H   E   D   P   E   V   K   F   N   W   Y   V   D 241  GGC GTG GAG GTG CAT AAT GCC AAG ACA AAG CCG CGG GAG GAG CAG TAC
      G   V   E   V   H   N   A   K   T   K   P   R   E   E   Q   Y 289  AAC AGC ACG TAC CGT GTG GTC AGC GTC CTC ACC GTC CTG CAC CAG GAC
      N   S   T   Y   R   V   V   S   V   L   T   V   L   H   Q   D 337  TGG CTG AAT GGC AAG GAG TAC AAG TGC AAG GTC TCC AAC AAA GCC CTC
      W   L   N   G   K   E   Y   K   C   K   V   S   N   K   A   L 385  CCA GCC TCC ATC GAG AAA ACC ATC TCC AAA GCC AAA GGG CAG CCC CGA
      P   A   S   I   E   K   T   I   S   K   A   K   G   Q   P   R 433  GAA CCA CAG GTG TAC ACC CTG CCC CCA TCC CGG GAT GAG CTG ACC AAG
      E   P   Q   V   Y   T   L   P   P   S   R   D   E   L   T   K 481  AAC CAG GTC AGC CTG ACC TGC CTG GTC AAA GGC TTC TAT CCC AGC GAC
      N   Q   V   S   L   T   C   L   V   K   G   F   Y   P   S   D 529  ATC GCC GTG GAG TGG GAG AGC AAT GGG CAG CCG GAG AAC AAC TAC AAG
      I   A   V   E   W   E   S   N   G   Q   P   E   N   N   Y   K 577  ACC ACG CCT CCC GTG TTG GAC TCC GAC GGC TCC TTC TTC CTC TAC AGC
      T   T   P   P   V   L   D   S   D   G   S   F   F   L   Y   S 625  AAG CTC ACC GTG GAC AAG AGC AGG TGG CAG CAG GGG AAC GTC TTC TCA
      K   L   T   V   D   K   S   R   W   Q   Q   G   N   V   F   S 673  TGC TCC GTG ATG CAT GAG GCT CTG CAC AAC CAC TAC ACG CAG AAG AGC
      C   S   V   M   H   E   A   L   H   N   H   Y   T   Q   K   S

721  CTC TCC CTG TCT CCG GGT AAA TGA C
      L   S   L   S   P   G   K   -
```

FIG. 4A

```
                                    Nhe I              Linker
 1  GAT CCA GCA GCT GGG CTC GAG GTG CTA GCG GGA GGG GGT GGA TGT GGG
     D   P   A   A   G   L   E   V   L   A   G   G   G   G   C   G EK
    Enterokinase      ↓ Hind III                 hu IgG1
49  GAC GAT GAC GAC AAG CTT ACT CAC ACA TGC CCA CCG TGC CCA GCA CCT
     D   D   D   D   K   L   T   H   T   C   P   P   C   P   A   P
```

FIG. 4B

```
 1  ATG GAG ACA GAC ACA CTC CTG CTA TGG GTA CTG CTG CTC TGG GTT CCA
     M   E   T   D   T   L   L   L   W   V   L   L   L   W   V   P

Hind III                             Nhe I
49  GGT TCC ACT GGT GAC GCG GAT CCA GCA GCT GGG CTC GAG GTG CTA GCG
     G   S   T   G   D   A   D   P   A   A   G   L   E   V   L   A EK
           Linker              Enterokinase ↓ Hind III    hu IgG1
97  GGA GGG GGT GGA TGT GGG GAC GAT GAC GAC AAG CTT ACT CAC ACA TGC
     G   G   G   G   C   G   D   D   D   D   K   L   T   H   T
```

FIG. 4C

MOLECULAR ANTIGEN ARRAYS

CROSS REFERENCE TO RELATED APPLICATIONS

The present application is a continuation of U.S. application Ser. No. 10/617,876, filed Jul. 14, 2003, now U.S. Pat. No. 7,138,252, which claims the benefit of U.S. Provisional Application No. 60/396,126, filed Jul. 17, 2002, the disclosures of each of which are entirely incorporated herein by reference in their entireties.

BACKGROUND OF THE INVENTION

1. Field of the Invention

The present invention is in the fields of medicine, immunology, virology and molecular biology.

2. Related Art

Vaccination has provided one of the most effective ways of fighting infectious diseases and has led to the most significant benefits for public health in the last century. Early vaccination strategies used live, attenuated or inactivated pathogens as the immunogen. Safety concerns within the public and the authorities have fostered a search for more defined and safer vaccines.

This search stimulated a new direction of research, where individual antigens were isolated or recombinantly expressed and injected as immunogens. Examples of these include the development and use of subunit vaccines. Such vaccines, however, often require the addition of an adjuvant to generate a sufficient immune response against the antigen, as an isolated protein is typically not sufficiently immunogenic to generate a protective immune response. Although several strong adjuvants are known, such as complete Freund's adjuvant, they are generally toxic and cannot be used in humans. Great efforts are therefore being made in the search for new adjuvants.

Recently, research on the principles of discrimination by the immune system between self and foreign has revealed that the degree of organization and the repetitiveness of the antigens on the surfaces of viruses are a very strong signal for an antigen to be recognized as foreign (Bachmann & Zinkemagel, *Immunol. Today* 17:553-558 (1996)). This property of viral structures was made use of in the design of new vaccines based on virus-like particles (VLPs), which combined the immunogenicity of viral structures and the improved safety profile of non-replicable vaccines. In those vaccines, the antigen is either fused or chemically attached to virus-like particles, the chemical attachment being covalent or non-covalent. Thus, the immunogenic property of the viral structure is transferred to the antigen by linking the antigen to virus-like particles.

A variety of VLPs have been used for the attachment of antigens. For example, WO 00/32227 describes the use of Hepatitis B core antigen in the production of certain types of vaccines.

A new class of highly expressable and highly immunogenic VLPs has been disclosed in WO 02/056905, which is incorporated herein by reference in its entirety. These VLPs are composed of the coat protein of RNA bacteriophages. The coat proteins are expressed recombinantly in bacteria, and the VLP does not contain the phage RNA genome and therefore cannot replicate.

A new RNA bacteriophage, AP205, has been recently identified (Klovins, J., et al., *J. Gen. Virol.* 83: 1523-33 (2002).) The AP205 RNA phage (Taxonomy ID: 154784) is a single-stranded, positive-strand RNA (no DNA stage) virus, which belongs to the Leviviridae family, Levivirus genus, Unclassified Levivirus subgroup. The other members of this subgroup are RNA phages BO1, fr1, TW19, and PP7. Two described Levivirus subgroups include following RNA phages: fr, JP501, f2, M12, MS2, and R17 (subgroup I) and BZ13, JP34, TH1, GA, and KU1 (subgroup II). The AP205 genome is 4267 nucleotides (nt) in length. Full-length genomic sequence: accessions AF334111, NC_002700. The natural host of the AP205 phage is *Acinetobacter* spp. (Klovins, J., et al., *J. Gen. Virol.* 83: 1523-33 (2002)). The genome of the AP205 phage comprises three large open reading frames (ORFs), which code for the maturation, the coat and the replicase proteins. In addition, two additional small ORFs are present at the 5' terminus, preceding the maturation gene. The function of the proteins coded by these ORFs is unknown. It has been postulated that one of these ORFs might code for a lysis protein (Klovins, J., et al., *J. Gen. Virol.* 83: 1523-33 (2002)).

SUMMARY OF THE INVENTION

We have discovered that AP205 coat protein can be recombinantly expressed in bacteria using the vectors of the invention. We have also developed methods for purification of AP205 virus-like particles. Moreover, the AP205 coat proteins produced by the present method spontaneously formed capsids, as evidenced by Electron Microscopy (EM) and immunodiffusion, and therefore the coat protein alone together with RNA are sufficient for assembly of the capsid in *E. coli*. This rules out any role of the proteins coded by the two ORFs of unknown function. A surprising feature of the invention is that no sequence homology exists between the sequence of the AP205 coat protein and other RNA phage coat proteins from which the structure has been elucidated, yet the structural properties of the capsid formed by the AP205 coat protein and those formed by the coat protein of those RNA phages are nearly indistinguishable when seen in EM. We have discovered that AP205 VLPs are highly immunogenic, and can be linked with organic molecules to generate vaccine constructs displaying the organic molecules oriented in a repetitive manner. High titers were elicited against the so displayed organic molecules showing that bound organic molecules are accessible for interacting with antibody molecules and are immunogenic.

The present invention provides recombinantly expressed virus-like particles (VLPs), spontaneously assembled from at least one coat protein of bacteriophage AP205 recombinantly expressed in *E. coli*. In a related aspect, the invention provides assembly-competent mutant forms of AP205 VLPs, including AP205 coat protein with the substitution of proline at amino acid 5 to threonine (SEQ ID NO: 3). These VLPs, AP205 VLPs derived from natural sources (SEQ ID NO: 1), or AP205 viral particles, may be bound to at least one organic molecule to produce ordered repetitive arrays of the organic molecules. Organic molecules of the invention include antigens and antigen determinants, allergens, self antigens, haptens, cancer antigens and infectious disease antigens as well as small organic molecules such as drugs of abuse like nicotine and derivatives thereof. Immunisation of animals using antigen-AP205 VLP conjugates, or compositions comprising such conjugates as provided by the invention, induce a strong immune response against the displayed antigen. The VLP of the invention is thus useful for the attachment and display of molecules and in particular of antigens. Hence, the conjugates, compositions and methods of the invention are useful for the stimulation of an immune response against a variety of displayed antigens, and thus for the use in animals.

In a first aspect, the present invention provides for a virus-like particle comprising, alternatively or preferably consisting essentially of, or alternatively or preferably consisting of at least one protein selected from the group consisting of: (a) a protein having an amino acid sequence as set forth in SEQ ID NO: 1; (b) a protein having an amino acid sequence as set forth in SEQ ID NO:3; and (c) a mutein of said protein of (a) or (b). Preferably, said protein is recombinant. Thus, the invention provides for a capsid formed by at least one protein selected from the group consisting of: (a) a protein having an amino acid sequence as set forth in SEQ ID NO: 1; (b) a protein having an amino acid sequence as set forth in SEQ ID NO:3; and (c) a mutein of said protein of (a) or (b). In a preferred embodiment, said mutein has an amino acid sequence as set forth in SEQ ID NO:1 or as set forth in SEQ ID NO:3, wherein at least one amino acid residue, preferably three amino acid residues, more preferably two amino acid residues, and even more preferably one amino acid residue of SEQ ID NO: 1 or SEQ ID NO:3 is added, deleted or substituted, wherein preferably said at least one substitution is a conservative substitution. In a further preferred embodiment, said mutein has an amino acid sequence as set forth in SEQ ID NO:1 or as set forth in SEQ ID NO:3, wherein at least one cysteine residue, preferably two cysteine residues of SEQ ID NO: 1 or SEQ ID NO:3, is deleted or substituted, wherein preferably said at least one, preferably two, substitution is a conservative substitution. In a still further preferred embodiment, said mutein has an amino acid sequence as set forth in SEQ ID NO:1 or as set forth in SEQ ID NO:3, wherein at least one lysine residue, preferably three lysine residues, more preferably two lysine residues, and even more preferably one lysine of SEQ ID NO: 1 or SEQ ID NO:3 is added, deleted or substituted, wherein preferably said at least one substitution is a conservative substitution.

In a second aspect, the invention provides for a mutein having an amino acid sequence as set forth in SEQ ID NO:3. Alternatively, the invention provides for a mutein of the recombinant protein of SEQ ID NO: 1 or SEQ ID NO:3, wherein at least one amino acid residue, preferably three amino acid residues, more preferably two amino acid residues, and even more preferably one amino acid residue of SEQ ID NO: 1 or SEQ ID NO:3 is added, deleted or substituted, wherein preferably said at least one substitution is a conservative substitution.

In a still further aspect, the invention provides for a mutein of the recombinant protein of SEQ ID NO: 1 or SEQ ID NO:3, wherein at least one cysteine residue, preferably two cysteine residues of SEQ ID NO: 1 or SEQ ID NO:3, is deleted or substituted, wherein preferably said at least one, preferably two, substitution is a conservative substitution. Alternatively, the invention provides for a mutein of the recombinant protein of SEQ ID NO: 1 or SEQ ID NO:3, wherein at least one lysine residue, preferably three lysine residues, more preferably two lysine residues, and even more preferably one lysine of SEQ ID NO: 1 or SEQ ID NO:3 is added, deleted or substituted, wherein preferably said at least one substitution is a conservative substitution.

In another aspect, the invention provides for a vector for producing a AP205 virus like particle whose sequence is at least 80%, preferably at least 90%, more preferably at least 95%, and even more preferably 99% identical to that of SEQ ID NO:2 or SEQ ID NO: 4. Alternatively, the invention provides for a vector for the production of a recombinant protein comprising a polypeptide fused to a protein, wherein said protein is selected from the group consisting of: (a) a protein having an amino acid sequence as set forth in SEQ ID NO:1; (b) a protein having an amino acid sequence as set forth in SEQ ID NO:3; and (c) a mutein of said polypeptide of (a) or (b).

In a further aspect, the invention provides for a method of producing a AP205 virus-like particle comprising the steps of: (a) providing a nucleic acid comprising a nucleotide sequence being at least 80%, preferably at least 90%, more preferably at least 95%, and even more preferably 100% identical to that of SEQ ID NO:2 or SEQ ID NO: 4, or providing a vector comprising a nucleotide sequence being at least 80%, preferably at least 90%, more preferably at least 95%, and even more preferably 99% identical to that of SEQ ID NO:2 or SEQ ID NO: 4; (b) introducing said nucleic acid or said vector into a host cell; (c) expressing said nucleic acid or the sequence of said vector in said host cell to obtain a protein or a mutein capable of forming a AP205 virus-like particle. Preferably, said host cell is E.coli.

In still a further aspect, the invention provides for a method of producing a AP205 virus-like particle comprising the steps of: (a) providing a nucleic acid or a vector encoding at least one protein selected from the group consisting of: (i) a protein having an amino acid sequence as set forth in SEQ ID NO:1; (ii) a protein having an amino acid sequence as set forth in SEQ ID NO:3; and (iii) a mutein of said polypeptide of (i) or (ii); (b) introducing said nucleic acid or said vector into a host cell; (c) expressing said nucleic acid or the sequence of said vector in said host cell to obtain said protein or said mutein capable of forming a AP205 virus-like particle. Preferably, said host cell is E. coli. Preferred embodiments of the proteins and muteins indicated under (i) and (ii) have already been indicated above.

In a first embodiment, the invention provides a composition comprising one or more recombinant VLPs of RNA bacteriophage AP205 or mutants thereof. In a further embodiment, the invention provides compositions comprising one or more AP205 VLPs and one or more organic molecules, wherein the molecule is attached, linked, coupled or fused i.e. bound, to the AP205 VLPs. In another embodiment, the organic molecule is an antigen.

In certain other embodiments, the organic molecule is selected from the group consisting of: (a) an organic molecule suited to induce an immune response against cancer cells; (b) an organic molecule suited to induce an immune response against infectious diseases; (c) an organic molecule suited to induce an immune response against allergens; (d) an organic molecule suited to induce an improved response against self-antigens; (e) an organic molecule suited to induce an immune response in farm animals or pets; and (f) an organic molecule suited to induce a response against a drug, a hormone or a toxic compound and (g) fragments (e.g. an epitope or antigenic domain of any of the molecules set out in (a)-(f).

In another embodiment, the organic molecules are one or more antigens. In one such embodiment, the antigens are recombinant polypeptides. In another embodiment, the antigens are extracted from a natural source, such as pollen, bees, pathogens or tumors. In yet another embodiment, the antigen is selected from the group consisting of: (a) a polypeptide suited to induce an immune response against cancer cells; (b) a polypeptide suited to induce an immune response against infectious diseases; (c) a polypeptide suited to induce an immune response against allergens; (d) a polypeptide suited to induce an immune response against self-antigens; and (e) a polypeptide suited to induce an immune response in farm animals or pets.

In a particular embodiment, the antigen comprises an epitope of cytotoxic T-cells or helper T-cells. In a related embodiment the antigen comprises a B cell epitope.

In a related aspect, the invention provides methods for attaching, i.e. binding, organic molecules to the AP205 VLP. In certain embodiments, the organic molecules are bound in an oriented fashion to the AP205 VLP.

In another embodiment of the invention, the conjugates or compositions are used in methods of immunizating an animal by introducing it into an animal subcutaneously, intramuscularly, intranasally, intradermally, intravenously, transdermally, transmucosally, orally, or directly into a lymph node. In another embodiment, the composition is applied locally, near a tumor or local viral reservoir against which one would like to vaccinate.

The present invention also relates to a vaccine comprising an immunologically effective amount of the composition of the present invention together with a pharmaceutically acceptable diluent, carrier or excipient. In a futher embodiment, the vaccine further comprises at least one adjuvant, such as Alum or incomplete Freund's adjuvant. The invention also provides methods of immunizing and/or treating an animal comprising administering to the animal an immunologically effective amount of conjugates, compositions, or vaccines of the invention.

The AP205 VLPs conjuates or compositions can be used to vaccinate against tumors, viral diseases, self-molecules or non-peptide small molecules, for example. The vaccination can be for prophylactic or therapeutic purposes, or both. AP205 VLPs conjuates or compositions can be used to vaccinate against allergies in order to induce immune-deviation and/or antibody responses against the allergen, suitable for the treatment or prevention of allergies.

The invention further provides methods of treating or preventing diseases, physical disorders or conditions in an individual or a population of individuals, by the administration of compositions comprising or, alternatively, consisting essentially of, an AP205 VLP bound to an organic molecule. In a related aspect immune molecules and antibodies, respectively, such as antibodies, generated against such compositions may be used for treatment, prophalaxis or diagnosis of a disease, condition or disorder.

In another aspect of the invention, compositions comprising an AP205 VLP bound to an organic molecule are provided in the form of a kit. In another aspect of the invention, compositions comprising an immune molecule and antibody, respectively, isolated by the use of an AP205 VLP bound to an organic molecule are also provided in the form of a kit. Such kits are useful for a variety of purposes including but not limited to the detection of immune molecules and antibodies, respectively, reacting to organic molecules presented on the VLP, for detection of organic molecules, for the screening of immune molecules and antibodies, respectively, and/or for the diagnosis of conditions characterized by the presence or absence of the immune molecules and antibodies, respectively. In certain related embodiments, the kits of the invention may comprise one or more additional components such as buffers, carriers, excipients, adjuvants, detection reagents etc.

In another aspect, the invention also provides for vectors and host cells for the expression of the coat protein of RNA bacteriophage AP205 forming the virus-like particles.

Host cells include prokaryotes including *E. coli*; and eukaryotes including yeast, animals, cell lines, etc.

In another aspect, the invention provides methods for expressing the coat protein of RNA bacteriophage AP205 and the virus-like particles thereof. In another aspect, the invention provides methods for purifying and isolating virus-like particles of bacteriophage AP205.

Other embodiments of the present invention will be apparent to one of ordinary skill in light of what is known in the art, the following drawings and description of the invention, and the claims.

BRIEF DESCRIPTION OF THE DRAWINGS

FIG. 1D shows an electron micrograph picture of AP205 phage particles, while an electron micrograph picture of self assembled particles of recombinant AP205 VLP is shown in FIG. 1E.

FIG. 4A-4C shows partial sequences of the different eukaryotic expression vectors used. Only the modified sequences are shown. FIG. 4A: pCep-Xa-Fc*: the sequence is shown from the BamHI site onwards and different features are shown above the translated sequence (SEQ ID NO: 103 and SEQ ID NO: 104). The arrow indicates the cleavage site of the factor Xa protease. FIG. 4B: pCep-EK-Fc*: the sequence is shown from the BamHI site onwards and different features are shown above the translated sequence (SEQ ID NO: 105 and SEQ ID NO: 106). The arrow indicates the cleavage site of the enterokinase. The sequence downstream of the HindIII site is identical to the one shown in FIG. 4A. FIG. 4C: pCep-SP-EK-Fc*: the sequence is shown from the beginning of the signal peptide on and different features are shown above the translated sequence (SEQ ID NO: 107 and SEQ ID NO: 108). The signal peptide sequence which is cleaved of by the signal peptidase is shown in bold The arrow indicates the cleavage site of the enterokinase. The sequence downstream of the Hind III site is identical to the one shown in FIG. 4A.

FIG. 5A shows a schematic description of the MIF constructs, with added amino acid linker containing a cysteine residue. FIG. 5B shows an SDS-PAGE analysis of the purified MIF constructs, run under reducing conditions and stained with Coomassie-brillant blue. Loaded on the gels are the purified rat constructs rMIF-C1 (SEQ ID NO: 114), rMIF-C2 (SEQ ID NO: 115), and rMIF-C3 (SEQ ID NO: 117), described in FIG. 5A.

Molecular Marker. Lane 2: AP205 VLP. Lane 3: derivatized AP205 VLP. Lane 4: dialyzed, derivatized AP205 VLP. Lane 5: dialyzed, derivatized AP205 VLP. Lane 6: Coupling reaction of rMIF-C1 to AP205 VLP. The coupling product is indicated by an arrow in the figure. The molecular weights of the marker proteins are indicated on the left border of the gel.

Figure 7:
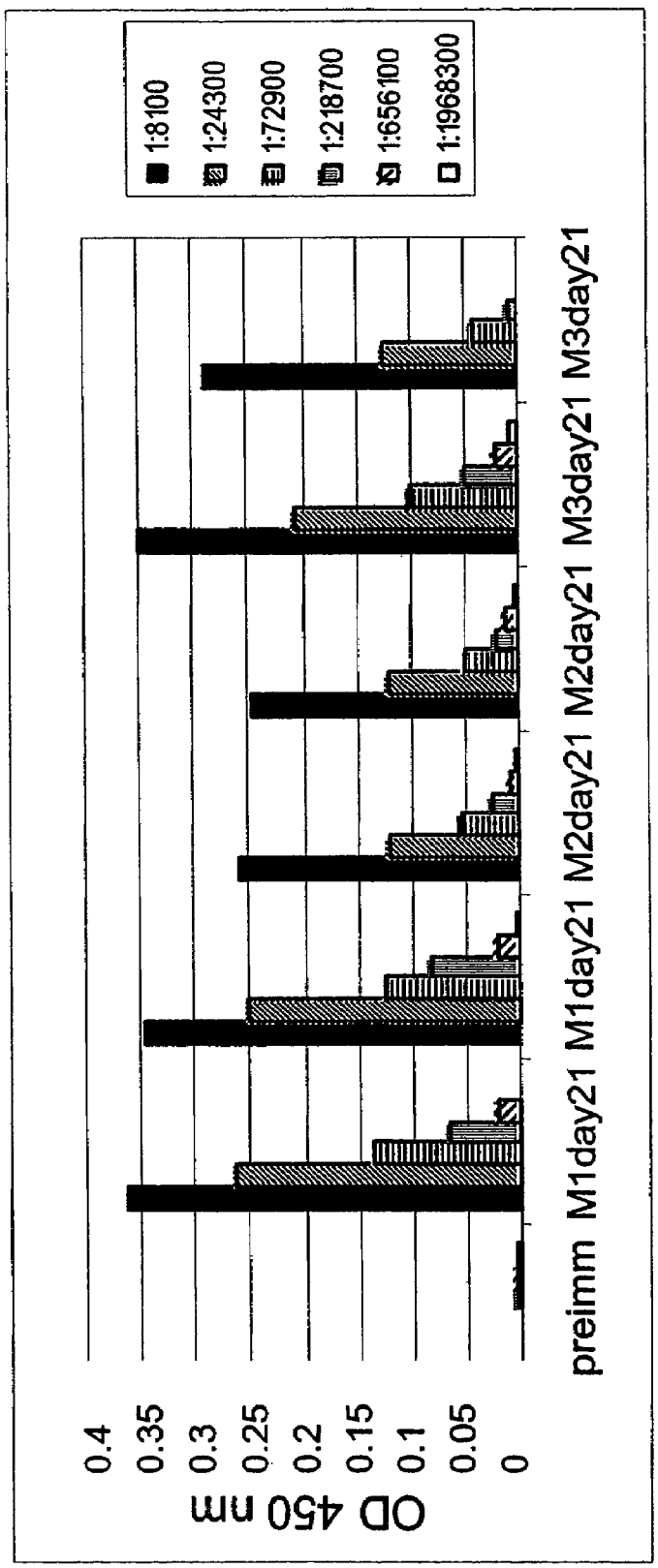

FIG. 7 shows the analysis by ELISA of the IgG response specific for rMIF-C1 in the sera of mice immunized with rMIF-C1 coupled to AP205 VLP.

Figure 8:
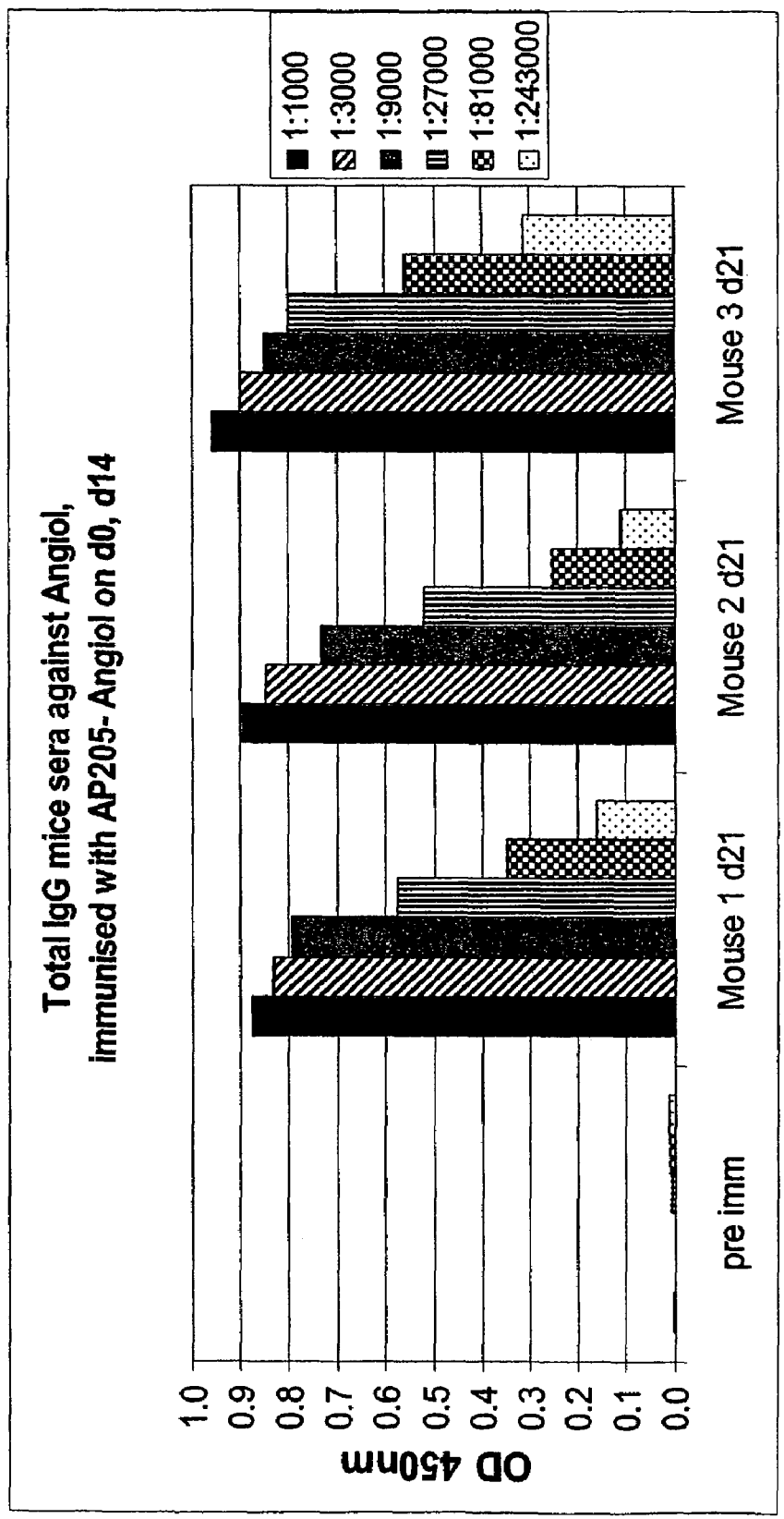

FIG. 8 shows an ELISA analysis of the IgG antibodies specific for Angio I peptide in the sera of the three mice (1-3) immunized on day 0 and 14 against the Angio I peptide coupled to AP205 VLP. Total IgG titers were determined in the day 21 sera.

DETAILED DESCRIPTION OF THE INVENTION

Definitions

The following definitions are summaries of concepts commonly understood by one of ordinary skill in the relevant art and are provided for the purposes of comprehension of the following disclosure but are not meant to be a limitation of the disclosure.

Amino acid linker: An "amino acid linker", or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occuring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1-C6 alkyl-, cycloalkyl(C5, C6), aryl or heteroaryl moiety. However, in addition to an amino acid linker, a linker comprising preferably a C1-C6 alkyl-, cycloalkyl-(C5, C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

Animal: As used herein, the term "animal" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

Antibody: As used herein, the term "antibody" refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or-more human immunoglobulins and that do not express endogenous immunoglobulins, as described, for example, in U.S. Pat. No. 5,939,598, the disclosure of which is incorporated herein by reference in its entirety.

Antigen: As used herein, the term "antigen" refers to a molecule capable of being bound by an antibody or a T cell receptor (TCR) if presented by MHC molecules. The term "antigen", as used herein, also encompasses T-cell epitopes. A T-cell epitope is recognized by a T-cell receptor in the context of a MHC class I, present on all cells of the body except erythrocytes, or class II, present on immune cells and in particular antigen presenting cells. This recognition event leads to activation of T-cells and subsequent effector mechanisms such as proliferation of the T-cells, cytokine secretion, perforin secretion etc. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a $T_H$ cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens. Antigens, as used herein, include but are not limited to allergens, self antigens, haptens, cancer antigens and infectious disease antigens as well as small organic molecules such as drugs of abuse (like nicotine) and fragments and derivatives thereof. Furthermore, antigens used for the present invention can be peptides, proteins, domains, carbohydrates, alkaloids, lipids or small molecules such as, for example, steroid hormones and fragments and derivatives thereof Antigenic determinant: As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant contains one or more epitopes. Allergens also serve as antigens in vertebrate animals.

Allergens: As used herein, the term "allergen" refers to antigens associated with allergies. An allergic response is characterized by the release of inflammatory factors, particularly histamine, leading to pathologic inflammation in an individual. Allergies are, typically, also associated with IgE antibodies directed against the allergens. The term "allergen", as used herein, also encompasses "allergen extracts" and "allergenic epitopes." Examples of allergens include, but are not limited to: pollens (e.g. grass, ragweed, birch and mountain cedar); house dust and dust mites; mammalian epidermal allergens and animal danders; mold and fungus; insect bodies and insect venom; feathers; food; and drugs (e.g., penicillin).

AP205 virus-like particle or AP205 VLP: As used herein, the terms "AP205 virus-like particle" or "AP205 VLP" refer to compositions and virus-like particles, respectively, comprising, or alternatively consisting essentially of, or alternatively and preferably consisting of at least one protein and coat protein, respectively, of the bacteriophage AP205, or a fragment or a mutein thereof, wherein said at least one coat protein, or fragment or mutein thereof, is typically and preferably able to assemble forming a virus-like particle. In alternative and preferred embodiments the terms "AP205 virus-like particle" or "AP205 VLP", as used herein, refer to compositions and virus-like particles, respectively, comprising, or alternatively consisting essentially of, or alternatively and preferably consisting of at least one protein and coat protein, respectively, of the bacteriophage AP205, or a mutein thereof, wherein said at least one coat protein of the bacteriophage AP205 or said mutein thereof is able to assemble forming a virus-like particle. In a very preferred embodiment of the present invention, the terms "AP205 virus-like particle" or "AP205 VLP" refer to compositions and virus-like particles, respectively, comprising, or alternatively consisting essentially of, or alternatively and preferably consisting of at least one coat protein of the bacteriophage AP205 having an amino acid sequence as set forth in SEQ ID NO:1, wherein typically and preferably said at least one coat protein is able to assemble to a virus-like particle and capsid, respectively. In a further alternative very preferred embodiment of the present invention, the terms "AP205 virus-like particle" or "AP205 VLP" refer to compositions comprising, or alternatively consisting essentially of, or alternatively and preferably consisting of at least one mutein of a coat protein of the bacteriophage AP205 having an amino acid sequence as set forth in SEQ ID NO:3, wherein said at least one mutein of said coat protein is able to assemble to a virus-like particle. In a further alternative very preferred embodiment of the present invention, the terms "AP205 virus-like particle" or "AP205 VLP" refer to compositions and virus-like particles, respectively, comprising, or alternatively consisting essentially of, or alternatively and preferably consisting of at least one mutein of a coat protein of the bacteriophage AP205 having an amino acid sequence as set forth in SEQ ID NO:1 or SEQ ID NO:3, wherein said at least one mutein of said protein is able to assemble to a virus-like particle. In a further alternative very preferred embodiment of the present invention, the terms "AP205 virus-like particle" or "AP205 VLP" refer to compositions and virus-like particles, respectively, comprising, or alternatively consisting essentially of, or alternatively and preferably consisting of at least one mutein having an amino acid sequence as set forth in SEQ ID NO:1 or as set forth in SEQ ID NO:3, wherein at least one amino acid residue, preferably three amino acid residues, more preferably two amino acid residues, and even more preferably one amino acid residue is added, deleted or substituted, wherein preferably said at least one substitution is a conservative substitution. In a still further alternative very preferred embodiment of the present invention, the terms "AP205 virus-like particle" or "AP205 VLP" refer to compositions and virus-like particles, respectively, comprising, or alternatively consisting essentially of, or alternatively and preferably consisting of at least one mutein having an amino acid sequence as set forth in SEQ ID NO:1 or as set forth in SEQ ID NO:3, wherein at least one cysteine residue, preferably three cysteine residues, more preferably two cysteine residues, and even more preferably one cysteine is deleted or substituted, wherein preferably said at least one substitution is a conservative substitution. In again another alternative very preferred embodiment of the present invention, the terms "AP205 virus-like particle" or "AP205 VLP" refer to compositions and virus-like particles, respectively, comprising, or alternatively consisting essentially of, or alternatively and preferably consisting of at least one mutein having an amino acid sequence as set forth in SEQ ID NO:1 or as set forth in SEQ ID NO:3, wherein at least one lysine residue, preferably three lysine residues, more preferably two lysine residues, and even more preferably one lysine is added, deleted or substituted, wherein preferably said at least one substitution is a conservative substitution. Further preferred embodiments of the AP205 VLP become apparent as this specification proceeds. The AP205 subunits composing the AP205 VLP may all be linked to other subunits within the particle by disulfide briges, or alternatively a majority of the AP205 VLP subunits are linked to other AP205 VLP subunits within the particle by disulfide bridges. In some embodiments, a minority or none of the AP205 VLP subunits are linked by disulfide bridges to other AP205 VLP subunits within the particle.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent.

Attachment Site, First: As used herein, the phrase "first attachment site" refers to an element of non-natural or natural origin, to which the second attachment site located on the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the core particle such as, preferably the virus-like particle. Multiple first attachment sites are present on the surface of the core and virus-like particle, respectively, typically in a repetitive configuration.

Attachment Site, Second: As used herein, the phrase "second attachment site" refers to an element associated with the antigen or antigenic determinant to which the first attachment site located on the surface of the core particle and virus-like particle, respectively, may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is of non-natural origin, i.e. not naturally occurring within the antigen or antigenic determinant, these antigen or antigenic constructs comprise an "amino acid linker".

Bound: As used herein, the term "bound" refers to binding or attachment that maybe covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled," "fused" and "attached."

Coat protein(s): As used herein, the term "coat protein(s)" refers to the protein(s) of a bacteriophage or an RNA-phage capable of being incorporated within the capsid assembly of the bacteriophage or the RNA-phage. The coat protein is also referred to as CP. In the current invention the term more usually refers to the coat protein(s) of the RNA-phage AP205.

Core particle: As used herein, the term "core particle" refers to a rigid structure with an inherent repetitive organization. A core particle as used herein may be the product of a synthetic process or the product of a biological process.

Disease, disorder, condition: As used herein, the terms "disease" or "disorder" refer to any adverse condition of an individual including tumors, cancer, allergies, addiction, autoimmunity, poisoning or impairment of optimal mental or bodily function. "Conditions" as used herein includes diseases and disorders but also refers to physiologic states. For example, fertility is a physiologic state but not a disease or disorder. Compositions of the invention suitable for preventing pregnancy by decreasing fertility would therefore be described as a treatment of a condition (fertility), but not a treatment of a disorder or disease. Other conditions are understood by those of ordinary skill in the art.

Epitope: As used herein, the term "epitope" refers to basic element or smallest unit of recognition by an individual antibody or T-cell receptor, and thus the particular domain, region or molecular structure to which the antibody or T-cell receptor binds. An antigen may consist of numerous epitopes while a hapten, typically, possesses few epitopes.

Immune response: As used herein, the term "immune response" refers to any action by the immune system of an individual that is directed against a molecule or compound, such as an antigen. In mammals, the immune response includes both the activities of cells and the production of soluble molecules such as cytokines and antibodies. The term thus includes a humoral immune response and/or cellular immune response leading to the activation or proliferation of B- and/or T-lymphocytes. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant.

Immune Deviation: As used herein, the term immune deviation refers to the stimulation of an immune response that is of a different nature to a preexisting immune response. For example, an individual possessing a $T_H2$ immune response against an allergen such that IgE antibodies are produced upon exposure to the allergen may be induced, by embodiments of the present invention, to produce a $T_H1$ immune response against the allergen. Such $T_H1$ response will counteract the allergy inducing $T_H2$ response and so alleviate allergic disease.

Immunotherapeutic: As used herein, the term "immunotherapeutic" refers to a composition for the treatment of diseases, disorders or conditions. More specifically, the term is used to refer to a method of treatment wherein a beneficial immune response is generated by vaccination.

Immunologically effective amount: As used herein, the term "Immunologically effective amount" refers to an amount of a composition sufficient to induce an immune response in an individual when introduced into that individual. The amount of a composition necessary to be immunologically effective varies according many factors including to the composition, the presence of other components in the composition (e.g. adjuvants), the antigen, the route of immunization, the individual, the prior immune or physiologic state etc.

Individual: As used herein, the term "individual" refers to multicellular organisms and includes both plants and animals. Preferred multicellular organisms are animals, more preferred are vertebrates, even more preferred are mammals, and most preferred are humans.

Low or undetectable: As used herein, the phrase "low or undetectable," when used in reference to gene expression level, refers to a level of expression which is either significantly lower than that seen when the gene is maximally induced (e.g., at least five fold lower) or is not readily detectable by the methods used in examples herein.

Mimotope: As used herein, the term "mimotope" refers to a substance which induces an immune response to an antigen or antigenic determinant. Generally, the term mimotope will be used with reference to a particular antigen. For example, a peptide which elicits the production of antibodies to a phospholipase $A_2$ ($PLA_2$) is a mimotope of the antigenic determinant to which the antibodies bind. A mimotope may or may not have substantial structural similarity to or share structural properties with an antigen or antigenic determinant to which it induces an immune response. Methods for generating and identifying mimotopes which induce immune responses to particular antigens or antigenic determinants are known in the art and are described elsewhere herein.

Mutein: As used herein, the term "mutein" refers to a protein or polypeptide differing by one or more amino acids from a given reference (e.g. natural, wild type, etc.) polypeptide, wherein such difference is caused by addition, substitution or deletion of at least one amino acid or a combination thereof. Preferred embodiments comprise mutations derived from substitution of at least one amino acid, preferably derived from conservative substitution of at least one amino acid. Conservative substitutions include isosteric substitutions, substitutions where the charged, polar, aromatic, aliphatic or hydrophobic nature of the amino acid is maintained. For example, substitution of a cysteine residue with a serine residue is a conservative substitution. In preferred embodiments of the present invention, the term "mutein" refers to a protein or polypeptide differing by three, preferably two and most preferably one amino acid from a given reference (e.g. natural, wild type, etc.) polypeptide, wherein such difference is caused by addition, substitution or deletion or a combination thereof. In further preferred embodiments of the present invention, the term "mutein" refers to a protein or polypeptide differing by three, preferably two and most preferably one amino acid from a given reference (e.g. natural, wild type, etc.) polypeptide, wherein such difference is derived from substitution of three, preferably two and most preferably one amino acid, preferably derived from conservative substitution of three, preferably two and most preferably one amino acid.

Natural origin: As used herein, the term "natural origin" means that the whole or parts thereof are not synthetic and exist or are produced in nature. Preferably, as used herein, the term "natural origin" means that the whole is not synthetic and exist or is produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 1 to 30 nanometers, preferably 5 to 15 nanometers.

Organic molecule: As used herein, the term "organic molecule" or "organic molecules" referring to the present invention include preferably antigens and antigen determinants, allergens, self antigens, haptens, cancer antigens and infectious disease antigens as well as small organic molecules such as drugs of abuse (like nicotine) and fragments and derivatives thereof.

Polypeptide: As used herein the term "polypeptide" refers to a polymer composed of amino acid residues, generally natural amino acid residues, linked together through peptide bonds. A polypeptide may not necessarily be limited in size, and include both proteins and peptides. A peptide is a polypeptide of a typical size of about five to about 50 amino acids, or any number amino acids within this general range. A peptide may, however, also be of longer length, for example up to 120-150 amino acids.

Protein: As used herein, the term protein refers to a polypeptide generally of a size of above about 5 or more, 10 or more 20 or more, 25 or more, 50 or more, 75 or more, 100 or more, 200 or more, 500 or more, 1000 or more, 2000 or more amino acids. Proteins generally have a defined three dimensional structure although they do not necessarily need to, and are often referred to as folded, as opposed to peptides and polypeptides which often do not possess a defined three-dimensional structure, but rather can adopt a large number of different conformations, and are referred to as unfolded. Peptides may, however, also have a defined three-dimensional structure.

Purified: As used herein, when the term "purified" is used in reference to a molecule, it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified. For example, even if niRNA is diluted with an aqueous solvent during oligo dT column chromatography, MRNA molecules are purified by this chromatography if naturally associated nucleic acids and other biological molecules do not bind to the column and are separated from the subject mRNA molecules. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

Receptor: As used herein, the term "receptor" refers to proteins or glycoproteins or fragments thereof capable of interacting with another molecule, called the ligand. The ligand may belong to any class of biochemical or chemical compounds. The receptor need not necessarily be a membrane-bound protein. Soluble protein, like e.g., maltose binding protein or retinol binding protein are receptors as well.

Residue: As used herein, the term "residue" is meant to mean a specific amino acid in a polypeptide backbone or side chain.

Recombinant host cell: As used herein, the term "recombinant host cell" refers to a host cell into which one ore more nucleic acid molecules of the invention have been introduced. Host cells include eukaryotes include e.g. mammalian, insect, plant, avian, yeast; and prokaryotic e.g. *E.coli, B.subtilis*, etc.

RNA-phage: As used herein, the term "RNA-phage" refers to RNA viruses infecting bacteria, more specifically to single-stranded positive-sense RNA viruses infecting bacteria.

Self antigen: As used herein, the tem "self antigen" refers to molecules or compounds capable of being encoded by the host's DNA. These include peptides, proteins, carbohydrates, nucleic acids, lipids and other biological molecules. More typically and preferably, the tem "self antigen" refers to polypeptides or proteins encoded by the host's DNA. Products generated by proteins or RNA encoded by the host's DNA are also defined as self. Proteins modified through post translational modifications and proteolytic processing or by alternative splicing of a self-gene product are also defined as self. Products generated by proteins or RNA encoded by the host's DNA are defined as self. In addition, proteins that result from a combination of two or several self-molecules or that represent a fraction of a self-molecule and proteins that have a high homology to self-molecules as defined above (>95%, preferably >97%, more preferably >99%) may also be considered self.

Vector: As used herein, the term "vector" refers to an agent (e.g., a plasmid or virus) used to transmit genetic material to a host cell. A vector may be composed of either DNA or RNA.

Virus-like particle (VLP): As used herein, the term "virus-like particle" refers to a structure resembling a virus particle. Moreover, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host.

This definition should, however, also encompass virus-like particles of bacteriophages, in which the aforementioned gene or genes are still present but inactive, and, therefore, also leading to non-replicative and noninfectious virus-like particles of a bacteriophage.

Virus particle: The term "virus particle" as used herein refers to the morphological form of a virus. In some virus types it comprises a genome surrounded by a protein capsid; others have additional structures (e.g., envelopes, tails, etc.).

One, a, or an: When the terms "one," "a," or "an" are used in this disclosure, they mean "at least one" or "one or more," unless otherwise indicated.

As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM inclusive).

Overview

We have discovered that recombinant AP205 coat proteins can be expressed in bacteria using the vectors of the invention and obtained in purified form. Recombinant AP205 coat proteins hereby spontaneously self-assemble within the bacteria into AP 205 virus-like particles. The invention provides for host cells and vectors suitable for expression of AP205 VLPs and also assembly competent variant forms of the AP205 coat protein. These expressed VLPs, AP205 VLPs derived from natural sources, or AP205 viral particles, maybe bound to organic molecules to produce ordered repetitive arrays of the organic molecules.

Organic molecules of the invention include antigens, allergens, self antigens, haptens, cancer antigens and infectious disease antigens. In one embodiment, the organic molecules are polypeptides or proteins.

Formation of conjugates of the invention, i.e. binding organic molecules to the VLP, is achieved by attachment, linkage, fusion or other binding, including covalent and non covalent bonds. In one embodiment, the VLP contains a first attachment site, the organic molecule contains a second attachment site. Association between the organic molecule occurs by linking the first and second attachment sites directly, or via a third molecule, typically and preferably via a cross-linker. Attachment sites may occur naturally, or may be introduced. In a preferred embodiment, the binding comprises at least one covalent bond, preferably comprises a peptide bond or alternatively and preferably comprises a non-peptide bond.

Immunization of animals with AP205 VLP conjugates, or with compositions comprising such conjugates as provided by the invention, induce a strong immune response against the displayed organic molecule. Hence, the conjugates and compositions of the invention are useful for the stimulation of an immune response against a variety of displayed antigens, and thus for the use in animals. The present invention also relates to a vaccine comprising an immunologically effective amount of the composition of one or more conjuagtes of the present invention together with a pharmaceutically acceptable diluent, carrier or excipient. The AP205 VLPs can be used to vaccinate against haptens, allergens, tumors, viral diseases, or self-molecules or non-peptidic small molecules, for example. The vaccination can be for prophylactic or therapeutic purposes, or both. In a related aspect immune molecules and antibodies, respectively, such as antibodies, generated against such compositions may be used for treatment, prophalaxis or diagnosis of a disease, condition or disorder. Such antibodies, and compositions of the invention are also useful as kits.

Cloning of the AP205 Bacteriophage Coat Protein

The AP205 genome consists of a maturation protein, a coat protein, a replicase and two open reading frames not present in related phages; a lysis gene and an open reading frame playing a role in the translation of the maturation gene (Klovins, J., et al., *J. Gen. Virol.* 83: 1523-33 (2002)). In one aspect of the invention the coat protein cDNA was isolated by reverse transcription of AP205 bacteriophage RNA followed by PCR, using known methods in the art. The cDNA of the coat protein including a ribosomal binding site upstream of the coat protein gene was cloned into vector pQb10 (Kozlovska, T. M., et al., *Gene* 137:133-37 (1993)). In another approach the cDNA of AP205 coat protein may be cloned in vector pQb185, replacing the bacteriophage Qβ coat protein gene, and thus downstream of the ribosomal binding site present in the vector. Both approaches lead to expression of the protein and formation of capsids. Thus, in the present invention, the coat protein may be expressed from vectors containing a ribosomal binding site which is not an AP205 ribosomal binding site, such as in the pQb185 vector.

Vectors pQb10 and pQb185 are vectors derived from pGEM vector, and expression of the cloned genes in these vectors is controlled by the trp promoter (Kozlovska, T. M. et al., *Gene* 137:133-37 (1993)). pAP283-58 (SEQ ID No. 2) comprises a putative AP205 ribosomal binding site in the following sequence, which is downstream of the XbaI site, and immediately upstream of the ATG start codon of the AP205 coat protein: tctagaATTTTCTGCGCACCCATC-CCGGGTGGCGCCCAAAGTGAGGAAAATCACatg (SEQ ID NO: 5). The vector pQb185 comprises a Shine Delagarno sequence downstream from the XbaI site and upstream of the start codon (tctagaTTAACCCAACGCGT AGGAG TCAGGCCatg (SEQ ID NO: 6), Shine Delagamo sequence underlined), which is also present in vector pAP281-32 (SEQ ID No. 4). Other vectors known to the Art include, e.g., pKK 223.3, pET vector family, pBR322 (Sutcliffe, J. G. *Cold Spring Harb. Symp. Quant. Biol.* 43 Pt 1: 77-90 (1979)), pUC 18, pUC19, which are all modified to comprise a suitable promoter and ribosomal binding sites if not present or not suitable for expression of the coat protein and subsequent formation of virus-like particles as would be recognized by one skilled in the art. Other vectors derived from the aforementioned vectors and other vectors suitable for expression of proteins in *E. coli* or other hosts known to one skilled in the art and in general any vector suitable for expression of proteins in *E. coli* or other hosts are suitable for practicing the invention, provided they allow expression of the coat protein and subsequent formation of virus-like particles. In one aspect of the present invention, vectors for expression of the gene of AP205 coat protein are transfected into *E. coli*. Suitable *E. coli* strains include, but are not limited to, *E. coli* K802, JM 109, RR1. Other *E. coli* strains are known to one of ordinary skill in the Art, and suitable combinations of vectors and strains can be identified by testing expression of the coat protein by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., *Gene* 137:133-37 (1993)).

AP205 coat proteins expressed from the vectors pAP283-58 and pAP281-32 maybe devoid of the initial Methionine amino-acid, due to processing in the cytoplasm of *E. coli*. The methionine-cleaved polypeptides, and hereby in particular the methionine-cleaved polypeptide of SEQ ID NO:1 and SEQ ID NO:3, as well as the uncleaved forms of the AP205 polypeptides leading to AP205 VLPs in accordance with the present invention, or mixtures thereof also leading to AP205 VLPs in accordance with the present invention are embodiments and within the scope of the invention.

AP205 Virus Like Particles

In one embodiment, the invention provides AP205 coat proteins that form capsids.

Such proteins are recombinantly expressed, or prepared from natural sources. Recombinant AP205 coat protein fragments able to assemble into a VLP are further embodiments of the invention. These fragments may be generated by deletion, either internally or at the termini of the coat protein. Insertions in the coat protein sequence or fusions to the coat protein sequence compatible with assembly into a VLP are further embodiments of the invention.

The outcome of insertions, deletions and fusions to the coat protein sequence and whether it is compatible with assembly into a VLP can be determined by electron microscopy.

The present invention provides methods of purification for the recombinant AP205 coat protein. The particles formed by the AP205 coat protein can be isolated in pure form by a combination of fractionation steps by precipitation and of purification steps by gel filtration.

Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety. In addition to gel filtration, other chromatographic steps such as ion exchange, hydrophobic interaction or affinity chromatography may also be used.

Expression of the recombinant AP205 coat protein leads to assembly into virus-like particles which, when analyzed by electron microscopy, have identical appearance and size as phage particles. It is a finding of the present invention, that the VLPs can be purified. This invention therefore provides a new VLP, which can be obtained in high amounts in a pure form.

AP205 VLPs self-assembled in *E. coli* have identical appearance and size as AP205 phage particles. As has been shown for other VLPs (Polyoma VP1 VLPs and Papilloma 1 VLPs, Chackerian B. et al., *PNAS* 96: 2373-2378 (1999)), manipulation of experimental conditions or fusion of epitopes to the VLP may lead to VLPs with a different state of assembly. For example, particles of lower triangulation number than the wt or major particle form may be obtained. Therefore, AP205 VLPs of smaller size than AP205 phage particles, or mixtures of AP205 VLPs of same size and smaller size than AP205 phage particles are also embodiments of the invention.

When analyzed in non-reducing PAGE, the AP205 VLP subunits runs at a higher apparent molecular weight than when analyzed by reducing PAGE, showing that the subunits are associated by disulfide bridges as described in Example 17 of WO03/024481.

In a further aspect, the present invention provides a vector containing an open reading frame suitable for the production of an AP205 virus like particle, said vector further comprising an additional nucleic acid such that the resulting vector is capable of producing a recombinant AP205 virus-like particle comprising amino acids encoded by said additional nucleic acid.

In another aspect, the present invention provides a vector containing an open reading frame suitable for the production of an AP205 virus like particle, said vector further comprising a restriction enzyme site suitable for the introduction of additional nucleic acid such that the resulting vector is capable of producing a recombinant virus-like particle comprising amino acids encoded by said additional nucleic acid.

Organic Molecules, Haptens and Antigens

Organic molecules used in the methods, conjugates and compositions of the present invention include any antigen, hapten, organic molecule, or fragment thereof. Molecules of the invention include haptens, organic molecules, and antigen fragments that are themselves (ie not bound to AP205 virus or virus like paticle) not capable of inducing an immune response in an animal. Organic molecule include for example: (a) organic molecule suited to induce an immune response against cancer cells; (b) organic molecules suited to induce an immune response against infectious diseases; (c) organic molecules suited to induce an immune response against allergens, (d) organic molecules suited to induce an immune response against self-antigens, (e) antigens or haptens suited to induce an immune response against drugs, hormones or toxins, particularly drugs of abuse and (f)fragments (e.g., a domain) of any of the organic molecule, antigens or haptens set out in (a)-(e).

Infectious Diseases

In one specific embodiment of the invention, the organic molecule, antigen or antigenic determinant is one that is useful for the prevention of infectious disease. Such treatment will be useful to treat a wide variety of infectious diseases affecting a wide range of hosts, e.g., human, cow, sheep, pig, dog, cat, other mammalian species and non-mammalian species as well. Such vaccines may be used prophylactically, to prevent an infection in an individual or population, or therapeutically, to mitigate an ongoing infection. Infectious diseases for which a vaccine is known or desired are well known to those skilled in the art, examples include infections of viral etiology such as HIV, influenza, Herpes, viral hepatitis, Epstein Barr, polio, viral encephalitis, measles, chicken pox, etc.; infections of bacterial etiology such as pneumonia, tuberculosis, syphilis, lyme disease, cholera, salmonellosis, meningitis, sepsis etc.; or infections of parasitic etiology such as malaria, trypanosomiasis, leishmaniasis, trichomoniasis, amoebiasis, etc. The antigens or antigenic determinants used in the conjugates, compositions and methods of the invention are known to those of ordinary skill in the relevant arts. Examples of antigens or antigenic determinants include the following: the HIV antigens gp140 and gp160; the influenza antigens hemagglutinin, M2 protein and neuraminidase, Hepatitis B surface antigen, and circumsporozoite protein of malaria.

In one such embodiment of the invention, the antigen or antigenic determinant is selected from the group consisting of: (a) a recombinant protein of HIV, (b) a recombinant protein of Influenza virus (e.g., an Influenza virus M2 protein or a fragment thereof), (c) a recombinant protein of Hepatitis C virus, (d) a recombinant protein of *Toxoplasma*, (e) a recombinant protein of *Plasmodium falciparum*, (f) a recombinant protein of *Plasmodium vivax*, (g) a recombinant protein of *Plasmodium ovale*, (h) a recombinant protein of *Plasmodium malariae*, (i) a recombinant protein of *Chlamydia*, and (j) a fragment of any of the proteins set out in (a)-(i).

In another embodiment, the invention is drawn to vaccine compositions comprising at least one antigen or antigenic determinant encoded by an Influenza viral nucleic acid, and the use of such vaccine compositions to elicit immune responses. In specific such embodiment, the Influenza antigen or antigenic determinant is an M2 protein (e.g., an M2 protein having the amino acids shown in GenBank Accession No. P06821 (SEQ ID NO. 127), PIR Accession No. MFIV62 (SEQ ID NO. 126), or fragment thereof (e.g., amino acids from about 2 to about 24). Portions of an M2 protein, as well as other proteins against which an immunological response is sought, suitable for use with the invention comprise peptides of any number of amino acids in length but will generally be at least 6 amino acids in length (e.g., peptides 6, 7, 8, 9, 10, 12, 15, 18, 20, 25, 30, 35, 40, 45, 50, 55, 60, 65, 70, 75, 80, 85, 90, 95, or 97 amino acids in length).

Hormones, Toxins and Drugs, Especially Drugs of Abuse

In an additional aspect, the invention provides compositions suitable for stimulating immune responses against haptens. These haptens include, but are not limited to, hormones, drugs and toxic compounds. Immune responses against a variety of drugs, hormones and toxic compounds are used to protect an individual at risk of exposure to such compounds, as therapy in an individual exposed to such compounds, or to prevent or treat addictions to such compounds Representative toxic compounds include, but are not limited to, the natural products of toxic plants, animals, and microorganisms. Such products include aflatoxin, ciguautera toxin, and tetrodotoxin. Other representative toxic compounds produced artificially, or as a result of metabolism include antibiotics (e.g. vancomycin), anticancer compounds (e.g. vinblastine) and chemical warfare agents (eg. Sarin, mustard gas, VX). One aspect of the invention includes the production of antibodies against toxic metabolites of commonly used pharmaceutical agents, such that an individual may continue to receive the beneficial effects of a pharmaceutical agent without side effects associated with toxic metabolites. Thus, in a preferred embodiment, the toxin is a metabolite generated in the body of an individual, wherein said metabolite is a metabolite of a pharmaceutical agent. In a further preferred embodiment, the toxin is a chemical warfare agent.

Organic molecules, antigens or antigenic determinants suitable for use in conjugates, compositions and methods of treatment of drug addiction, in particular recreational drug addiction, will be known to those of ordinary skill in the relevant arts. Representative examples of organic molecules, antigens or antigenic determinants include, for example, opioids and morphine derivatives such as codeine, fentanyl, heroin, morphine and opium; stimulants such as amphetamine, cocaine, MDMA (methylenedioxymethamphetamine), methamphetamine, methylphenidate, and nicotine; hallucinogens such as LSD, mescaline and psilocybin; cannabinoids such as hashish and marijuana, other addictive drugs or compounds; and derivatives, by-products, variants and complexes of such compounds.

Allergies and Cancer

In related embodiments, the invention provides compositions suitable for use as immunotherapeutics that may be used for the treatment or prevention of allergies or cancer.

Antigens or antigenic determinants suitable for use in conjugates, compositions and methods of treatment or prevention of allergies would be known to those of ordinary skill in the relevant art. Representative examples of such antigens or antigenic determinants include the following: bee venom phospholipase $A_2$, Bet v I (birch pollen allergen), 5 Dol m V (white-faced hornet venom allergen), Mellitin and Der p I (House dust mite allergen), gluten, gliadin, shellfish allergens, cockroach allergens, peanut and other nut allergens, ragweed and other pollen allergens, grevillea allergen, as well as fragments of each which can be used to elicit immunological responses. In a particular embodiment of the invention, the allergen is selected from the group consisting of (a) a recombinant protein of bee sting allergy, (b) a recombinant proteins of nut allergy, (c) recombinant proteins of food allergies, (d) recombinant proteins of asthma, (e) a recombinant protein of *Chlamydia*, and (f ) a fragment of any of the allergens of (a) through (e).

As noted above, a suitable antigen or antigenic determinant for use in the conjugates, compositions or methods of the present invention is Der p I. Der p I is a 25 kD protease found in house dust mite faecal particles and represents the major allergen of house dust mite. Accordingly, 80% of mite allergic patients have anti-Der p I IgE antibodies. In particular, the Der pI peptides p52-72 and p117-133 (SEQ ID NO: 64), among others, are known to comprise epitopes which are recognized by antibodies specific for the native Der p I. IgE antibodies raised in a polyclonal response to the whole antigen bind with high affinity to the peptide region 59-94 (L. Pierson-Mullany et al. (2000) Molecular Immunology). Other regions also bind IgE with high affinity. The peptide p117-133 contains a cysteine at its N-terminus representing the second attachment site in accordance with the invention. 3D modelling assigns peptides p52-72 and p117-133 to the surface of the whole protein (Jeannin, P. et al., Molecular Immunology 30:1511-1518 (1993)).However, other fragments of the Der p I protein may comprise B cell epitopes suitable for the present invention.

In a preferred embodiment of the inventive composition, the antigen or antigenic determinant is a Der p I peptide, and wherein said Der p I peptide with said second attachment site has an amino acid sequence selected from the group consisting of: a) CGNQSLDLAEQELVDCASQHGCH (SEQ ID NO: 97); and b) CQIYPPNANKIREALAQTHSA (SEQ ID NO: 64).

In additional embodiments, the invention provides vaccine compositions suitable for use in methods for preventing and/or attenuating allergic reactions, such as allergic reactions which lead to anaphylaxis. As disclosed elsewhere herein, allergic reactions may be characterized by the $T_H2$ responses against an antigen leading to the presence of IgE antibodies. Stimulation of $T_H1$ immune responses and the production of IgG antibodies may alleviate allergic disease. Thus, vaccine compositions of the invention include compositions which lead to the production of antibodies that prevent and/or attenuate allergic reactions. Thus, in certain embodiments, vaccine compositions of the invention include compositions which elicit an immunological response against an allergen. Examples of such allergens include phospholipases such as the phospholipase $A_2$ ($PLA_2$) proteins of *Apis mellifera* (GenBank Accession No. 443189, GenBank Accession No. 229378), *Apis dorsata* (GenBank Accession No. B59055), *Apis cerana* (GenBank Accession No. A59055), *Bombus pennsylvanicus* (GenBank Accession No. B56338), and *Heloderma suspectum* (GenBank Accession No. P80003; GenBank Accession No. S14764; GenBank Accession No. 226711).

Using the amino acid sequence of a $PLA_2$ protein of *Apis mellifera* (GenBank Accession No. 443189, GenBank Accession No. 229378) for illustration, peptides of at least about 60 amino acids in length, which represent any portion of the whole $PLA_2$ sequence, may also be used in compositions for preventing and/or attenuating allergic reactions. Examples of such peptides include peptides which comprise amino acids 1-60, amino acids 1-70, amino acids 10-70, amino acids 20-80, amino acids 30-90, amino acids 40-100, amino acids 47-99, amino acids 50-110, amino acids 60-120, amino acids 70-130, or amino acids 90-134, as well as corresponding portions of other PLA$_2$ proteins (e.g., PLA$_2$ proteins described above). Further examples of such peptides include peptides which comprise amino acids 1-10, amino acids 5-15, amino acids 10-20, amino acids 20-30, amino acids 30-40, amino acids 40-50, amino acids 50-60, amino acids 60-70, amino acids 70-80, amino acids 80-90, amino acids 90-100, amino acids 100-110, amino acids 110-120, or amino acids 120-130, as well corresponding portions of other PLA$_2$ proteins (e.g., PLA$_2$ proteins described above).

Portions of PLA$_2$, as well as portions of other proteins against which an immunological response is sought, suitable for use with the invention may comprise, or alternatively consist of, peptides which are generally at least 6 amino acids in length (e.g., peptides 6, 7, 8, 9, 10, 12, 15, 18, 20, 25, 30, 35, 40, 45, 50, 55, 60, 65, 70, 75, 80, 85, 90, 95, or 100 amino acids in length).

PLA$_2$ peptides (e.g., the full length PLA$_2$ proteins discussed above, as well as subportions of each) may also be coupled to any substance (e.g., an AP205 capsid protein or fragment thereof) which allows for the formation of ordered and repetitive antigen arrays.

The selection of antigens or antigenic determinants for compositions and methods of treatment for cancer would be known to those of ordinary skill in the relevant arts. In a particular embodiment of the invention, the antigen or antigenic determinant is selected from the group consisting of: (a) a recombinant protein of breast cancer cells; (b) a recombinant protein of kidney cancer cells; (c) a recombinant protein of prostate cancer cells; (d) a recombinant protein of skin cancer cells; (e) a recombinant protein of brain cancer cells; (f) a recombinant protein of leukemia cells; (g) a recombinant profiling; and (h) a fragment of any of the proteins set out in (a)-(g).

Representative examples of such types of antigens or antigenic determinants include the following: Her2 (breast cancer), GD2 (neuroblastoma), EGF-R (malignant glioblastoma), CEA (medullary thyroid cancer), and CD52 (leukemia), human melanoma protein gp100, human melanoma protein melan-A/MART-1, tyrosinase, NA17-A nt protein, MAGE-3 protein, p53 protein, and HPV 16 E7 protein, as well as fragments of each which can be used to elicit immunological responses. Further antigenic determinants useful for compositions and methods of treatment for cancer are molecules and antigenic determinants involved in angiogenesis. Angiogenesis, the formation of new blood vessels, plays an essential role in physiological and pathophysiological processes such as wound healing and solid tumor growth, respectively (Folkman, J. (1995) *Nat. Medicine* 1, 27-31; Folkman, J., and Klagsburn, M. (1987) *Science* 235,442-446; Martiny-Baron, G., and Marmé, D. (1995) *Curr. Opin. Biotechnol.* 6, 675-680; Risau, W. (1997) *Nature* 386, 671-674). Rapidly growing tumors initiate and depend on the formation of blood vessels to provide the required blood supply. Thus, it is believed that antiangiogenic agents are effective as anticancer therapeutics.

Among several putative angiogenic factors that have been identified, vascular endothelial growth factor (VEGF) is a potent endothelial cell specific mitogen and a primary stimulant of the vascularization of many solid tumors. Thus, blockage of VEGF action is a target for intervention in tumor-induced angiogenesis, as a means of blocking the endothelium rather than the tumor as a strategy to fight tumors (Millauer, B. et al. (1994) *Nature* 367, 576-579; Kim, J et al. (1993) *Nature* 362, 841-844).

An anti-VEGFR-II antibody (IMC-1C11) and an anti-VEGF antibody have been disclosed (Lu, D. et al. (2000) *J. Biol. Chem.* 275, 14321-14330; Presta, L. G, et al (1997) *Cancer Res.* 47, 4593-4599). The former neutralizing monoclonal anti-VEGFR-2 antibody recognizes an epitope that has been identified as putative VEGF/VEGFR-II binding site (Piossek, C. et al. (1999) *J Biol Chem.* 274, 5612-5619).

Thus, in one embodiment of the invention, the antigen or antigenic determinant used in conjugates, compositions or methods of the invention is a peptide derived from the VEGFR-II contact site. This provides a composition and a vaccine composition in accordance with the invention, which may have antiangiogenic properties useful for the treatment of cancer. Inhibition of tumor growth in mice using sera specific for VEGFR-2 has been demonstrated (Wei, Y Q et al. (2000) Nature Medicine 6, 1160-1166). Therefore, further antigenic determinants suitable for inventive compositions and antiangiogenic vaccine compositions in accordance with the invention comprise either the human VEGFR-II derived peptide with the amino acid sequence CTARTELNVGIDFN-WEYPSSKHQHKK (SEQ ID NO: 99), and/or the murine VEGFR-II derived peptide having the amino acid sequence CTARTELNVGLDFTWHSPPSKSHHKK (SEQ ID NO: 113), and/or the relevant extracellular globular domains 1-3 of the VEGFR-II.

Self-Antigens

In specific embodiments, the invention provides vaccine compositions suitable for use in methods for preventing and/or attenuating diseases or conditions which are caused or exacerbated by "self" gene products (e.g., tumor necrosis factors). It is usually difficult if not impossible to induce antibody responses to self-molecules by conventional vaccination. The present invention provides one way to improve the efficiency of vaccination by increasing the degree of repetitiveness of the antigen to be used for immunization, through binding of the antigen to the AP205 VLP.

Unlike isolated proteins, viruses induce prompt and efficient immune responses in the absence of any adjuvants both with and without T-cell help (Bachmann & Zinkernagel, *Ann. Rev. Immunol:* 15:235-270 (1997)). Although viruses often consist of few proteins, they are able to trigger much stronger immune responses than their isolated components. For B-cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann & Zinkernagel, *Immunol. Today* 17:553-558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann & Zinkemagel, *Ann. Rev. Immunol.* 15:235-270 (1997)). Viral structure is even linked to the generation of anti-antibodies in autoimmune disease and as a part of the natural response to pathogens (see Fehr, T., et al., *J Exp. Med.* 185:1785-1792 (1997)). Thus, antibodies presented by a highly organized viral surface are able to induce strong anti-antibody responses.

The immune system usually fails to produce antibodies against self-derived structures. For soluble antigens present at low concentrations, this is due to tolerance at the Th cell level. Under these conditions, coupling the self-antigen to a carrier that can deliver T help may break tolerance. For soluble proteins present at high concentrations or membrane-associated proteins at low concentration, B and $T_H$ cells may be tolerant. However, B cell tolerance may be reversible (anergy) and can be broken by administration of the antigen in a highly organized fashion coupled to a foreign carrier (Bachmann & Zinkemagel, *Ann. Rev. Immunol.* 15:235-270 (1997).

Thus, vaccine compositions of the invention include conjugates, compositions and methods which lead to the production of antibodies that prevent and/or attenuate diseases or conditions caused or exacerbated by "self" gene products. Examples of such diseases or conditions include graft versus host disease, IgE-mediated allergic reactions, anaphylaxis, adult respiratory distress syndrome, Crohn's disease, allergic asthma, acute lymphoblastic leukemia (ALL), diabetes, non-Hodgkin's lymphoma (NHL), Graves' disease, systemic lupus erythematosus (SLE), inflammatory autoimmune diseases, myasthenia gravis, immunoproliferative disease lymphadenopathy (IPL), angioimmunoproliferative lymphadenopathy (AIL), immunoblastive lymphadenopathy (IBL), rheumatoid arthritis, diabetes, multiple sclerosis, Alzheimer disease, osteoporosis, and autoimmune conditions associated with certain infections including rheumatic fever, scarlet fever, lyme disease, and infectious polyarthritis.

The selection of antigens or antigenic determinants for conjugates, compositions and methods of treatment for other diseases or conditions associated with self antigens would be also known to those of ordinary skills in the relevant art. Representative examples of such antigens or antigenic determinants are, for example, lymphotoxins (e.g. Lymphotoxin α (LT α), Lymphotoxin β (LT β)), and lymphotoxin receptors, Receptor activator of nuclear factor kB ligand (RANKL), vascular endothelial growth factor (VEGF), vascular endothelial growth factor receptor (VEGF-R), Interleukin-5, Interleukin-17, Interleukin-13, CCL21, CXCL12, SDF-1, MCP-1, Endoglin, Resistin, GHRH, LRHH, TRH, MIF, Eotaxin, Bradykinin, BLC, Tumor Necrosis Factor α and amyloid beta peptide ($A\beta_{1-42}$), as well as fragments of each which can be used to elicit immunological responses.

In one embodiment, the antigenic determinant is the amyloid beta peptide ($A\beta_{1-42}$) (DAEFRHDSGYEVHHQKLVF-FAEDVGSNKGAIIGL MVGGVVIA (SEQ ID NO: 7), or a fragment thereof. Aβ peptide has a central role in the neuropathology of Alzheimers disease.

Region specific, extracellular accumulation of Aβ peptide is accompanied by microgliosis, cytoskeletal changes, dystrophic neuritis and synaptic loss. These pathological alterations are thought to be linked to the cognitive decline that defines the disease.

In a mouse model of Alzheimer disease, transgenic animals engineered to produce $A\beta_{1-42}$ (PDAPP-mice), develop plaques and neuron damage in their brains. Recent work has shown immunization of young PDAPP-mice, using $A\beta_{1-42}$, resulted in inhibition of plaque formation and associated dystrophic neuritis (Schenk, D. et al., *Nature* 400:173-77 (1999)).

Furthermore immunization of older PDAPP mice that had already developed AD-like neuropathologies, reduced the extent and progression of the neuropathologies. In another study, peripherally administered antibodies raised against $A\beta_{1-42}$, were able to induce clearance of pre-existing amyloid (Bard, F. et al., *Nature Medicine* 6:916-19 (2000)). This study utilized either polyclonal antibodies raised against $A\beta_{1142}$, or monoclonal antibodies raised against synthetic fragments derived from different regions of Aβ. Thus induction of antibodies against Aβ using the conjugates, compositions and methods of the present invention can be considered as a potential therapeutic treatment for Alzheimer disease.

It is well established that the administration of purified proteins alone is usually not sufficient to elicit a strong immune response; isolated antigen generally must be given together with helper substances called adjuvants. Within these adjuvants, the administered antigen is protected against rapid degradation, and the adjuvant provides an extended release of a low level of antigen. In the present invention, Aβ peptide or fragments thereof are made immunogenic through binding to AP205 VLP and do not necessarily require an adjuvant.

As indicated, one of the key events in Alzheimer's Disease (AD) is the deposition of amyloid as insoluble fibrous masses (amyloidogenesis) resulting in extracellular neuritic plaques and deposits around the walls of cerebral blood vessels (for review see Selkoe, D. J. (1999) Nature. 399, A23-31). The major constituent of the neuritic plaques and congophilic angiopathy is amyloid β (Aβ), although these deposits also contain other proteins such as glycosaminoglycans and apolipoproteins. Aβ is proteolytically cleaved from a much larger glycoprotein known as Amyloid Precursor Proteins (APPs), which comprises isoforms of 695-770 amino acids with a single hydrophobic transmembrane region. Aβ forms a group of peptides up to 43 amino acids in length showing considerable amino- and carboxy-terminal heterogeneity (truncation) as well as modifications (Roher, A. E. et al (1988) J. Cell Biol. 107, 2703-2716. Roher, A. E. et al (1993) J. Neurochem. 61, 1916-1926). Prominent isoforms are Aβ1-40 and 1-42. It has a high propensity to form β-sheets aggregating into fibrils, which ultimately leads to the amyloid. Recent studies have demonstrated that a vaccination-induced reduction in brain amyloid deposits resulted in cognitive improvements (Schenk, D. et al. (1999) Nature. 400, 173-177). Hence, fragments of Aβ suitable for generating vaccines of the invention include, but are not limited to: Aβ1-15, Aβ1-27 and Aβ33-42. An amino acid linker is fused to the aminoacid sequence of Aβ or Aβ fragments to allow coupling to the AP205 VLP, as described elsewhere herein. Amino acid linkers suitable for fusion to the N-terminus of Aβ or Aβ fragments include but are not limited to the sequence CGG and CGHGNKS. Linkers suitable for fusion to the C-terminus of Aβ or Aβ fragments include but are not limited to the sequence GGC. In one embodiment, when a linker is fused to the C-terminus of Aβ or Aβ fragments, the C-terminal cysteine is amidated. The Aβ fragment 1-15 is fused to an amino acid linker and has the sequence: DAEFRHDSGYEVHHQGGC-NH2 (SEQ ID NO: 8), wherein the C.terminal cysteine is amidated, which is indicated by the C-terminal "NH2". The Aβ fragment 1-27 is fused to an amino acid linker and has the sequence: DAEFRHDSGYEVHHQKLVFFAEDVGSNGGC-NH2 (SEQ ID NO: 9). The Aβ fragment 33-42 is fused to an amino acid linker and has the sequence: CGHGNKSGLMVGGVVIA (SEQ ID NO: 10).

In one embodiment of the invention, the antigen or antigenic determinant comprises, or preferably is, an angiotensin peptide or a fragment thereof. The term "angiotensin peptide" as used herein, encompasses any peptide comprising the sequence, or any fragment thereof, of angiotensinogen, angiotensin I or angiotensin II. Angiotensin is associated with hypertension (Gardiner et al, *Br. J. Pharm.* 129: 1178 (2000)). Therefore, conjugates, compostion and methods of present invention suitable for reducing levels of angiotensin are suitable for the treatment of hypertension. In one embodiment, the conjugate or composition comprises at least one angiotensin peptide. The amino acid sequences of peptides in some embodiments are as follows: Angiotensinogen: DRVYIHPF-HLVIHN (SEQ ID NO: 11); Angiotensin I: DRVYIHPFHL (SEQ ID NO: 12); Angiotensin II: DRVYIHPF (SEQ ID NO:

13). Typically, one or more additional amino acids are added at the C- and/or at the N-terminus of the angiotensin peptide sequences. Those additional amino acids are, in particular, valuable for an oriented and ordered association to the AP205 virus-like particle. The sequence of the angiotensin peptides corresponds to the human sequence, which is identical to the murine sequence. Therefore, immunization of a human or a mouse with vaccines or compositions, respectively, comprising such angiotensin peptides as an antigen or antigenic determinant in accordance with the invention, is a vaccination against a self-antigen. In some embodiments, the angiotensin peptide with said second attachment site has an amino acid sequence selected from the group consisting of a) the amino acid sequence of CGGDRVYIHPF (SEQ ID NO: 14); b) the amino acid sequence of CGGDRVYIHPFHL (SEQ ID NO: 15); c) the amino acid sequence of DRVYIHPFHLGGC (SEQ ID NO: 16); and d) the amino acid sequence of CDRVYIHPFH (SEQ ID NO: 98).

In another embodiment of the invention, the antigenic determinant is RANKL (Receptor Activator of NFkB Ligand). RANKL is also known as TRANCE (TNF-related Activation Induced Cytokine), ODF (Osteoclast Differentiation Factor) or OPGL (Osteoprotegerin Ligand). The amino acid sequence of the extracellular part of human RANKL is shown in EMBL database deposit RANKL_human: TrEMBL:O14788. Sequences for the extracellular part of murine RANKL and an isoform are shown in EMBL database deposits RANKL_mouse: TrEMBL:O35235, and in RANKL_mouse splice forms:

TrEMBL:Q9JJK8 and TrEMBL:Q9JJK9, respectively.

It has been shown that RANKL is an essential factor in osteoclastogenesis. Inhibition of the interaction of RANKL with its receptor RANK can lead to a suppression of osteoclastogenesis and thus provide a means to stop excessive bone resorption as seen in osteoporosis and other conditions. The RANKL/RANK interaction was inhibited either by a RANK-Fc fusion protein or the soluble decoy receptor of RANKL, termed osteoprotegerin (OPG.)

In bone, RANKL is expressed on stromal cells or osteoblasts, while RANK is expressed on the osteoclast precursor. The interaction of RANK and RANKL is crucial for the development of osteoclast precursors to mature osteoclasts. The interaction can be blocked by OPG. OPG-deficient mice develop osteoporosis that can be rescued by injection of recombinant OPG, suggesting that OPG is able to reverse osteoporosis. Thus, inhibition of the RANK-RANKL interaction by providing suitable conjugates, compositions and methods of the invention (eg RANKL-AP205 VLP conjugates) are effective in reversing or preventing osteoporosis.

In addition, arterial calcification was observed in OPG knockout. mice which could be reversed by injection of OPG (Min et al., *J. Exp. Med.* 4: 463 (2000)). In an adjuvant-induced arthritis model OPG injection was able to prevent bone loss and cartilage destruction, but not inflammation (paw swelling). It is assumed that activated T cells lead to a RANKL-mediated increase of osteoclastogenesis and bone loss. OPG inhibits prostate cancer-induced osteoclastogenesis and prevents prostate tumor growth in the bone of mice. OPG diminishes advanced bone cancer pain in mice.

RANKL is a transmembrane protein of 245 aa belonging to the TNF-superfamily. Part of the extracellular region (178 aa) can be cleaved by a TACE-like protease (Lum et al., *J. Biol Chem.* 274:13613 (1999)). In addition splice variants lacking the transmembrane domain have been described (Ikeda et al., *Endocrinology* 142: 1419 (2001)). The cleaved extracellular portion contains the domain highly homologous to soluble TNF-α and forms homotrimers as seen for TNF-α. The C-terminus seems to be involved in the trimer contact site. One cysteine is present in this region of the sequence.

We have built a model for the 3-dimensional structure of the corresponding region of RANKL and found that the naturally present cysteine may not be accessible in the folded structure for interaction with a first attachment site on the carrier in accordance with the present invention. The N-terminus is one site suitable for attaching a second attachment site comprising an amino acid linker with an additional cysteine residue. A human-RANKL construct with an N terminal amino acid linker containing a cysteine residue fused to the extracellular part of RANKL is one embodiment of the invention. However, an amino-acid linker containing a cysteine residue as second attachment site and being fused at the C-terminus of the RANKL sequence or the extracellular part of RANKL leads to further embodiments of the invention.

Human-RANKL constructs are generated according to the teachings disclosed in herein and one of ordinary skill in the art is able to compare murine and human RANKL sequences in an amino acid sequence alignment to identify the part of the sequence of human-RANKL to be cloned in the vectors. Fragments containing amino acids 138-317 and corresponding to the C-terminal region of the extracellular domain of human RANKL, comprise one embodiment of the invention, and are modified for coupling to AP205 VLP as required according to the teachings of the present invention. The invention also embodies other suitable vectors used for expression in the suitable host described below. Additional human-RANKL constructs that are intended to be encompassed within the scope of the present invention include those comprising the part of the extracellular region (178 aa) or fragments thereof that can be shed by a TACE-like protease (Lum et al., *J. Biol Chem.* 274:13613 (1999)), or that comprise the sequence corresponding to the alternative splice variants lacking the transmembrane domain, as well as conservative fragments thereof. Human C-terminal fragments of RANKL comprising amino acids 165-317 are also embodiments of the invention. Fragments of RANKL which encompass the entire extracellular region (amino acids 71-317) and can be modified for coupling to AP205 VLP and as required according to the teaching of the present invention, are also within the scope of the invention.

RANKL has been expressed in different systems (e.g *E.coli*, insect cells, mammalian cells) and has been shown to be active. Therefore, several expression systems can be used for production of suitable RANKL antigens of the composition. In the case where expression of the protein is directed to the periplasm of *E. coli*, the signal peptide of RANKL, or of RANKL constructs consisting of the extracellular part of the protein, and both possibly modified to comprise a second attachment site in accordance with the invention, is replaced with a bacterial signal peptide. For expression of the protein in the cytoplasm of *E. coli*, RANKL constructs are devoid of signal peptide.

In one embodiment of the invention, the antigenic determinant is MIF or a fragment thereof. MIF is a cytokine that functions as an inhibitor of macrophage migration. It is also known as delayed early response protein 6 (DER6), glycosylation inhibiting factor or phenylpyruvate tautomerase.

MIF has been shown to be implicated in a wide range of conditions. MIF (MRNA and protein) is upregulated in delayed type hypersensitivity (DTH) reaction induced by tuberculin, and anti-MIF antibody inhibits this DTH reaction. MIF is also upregulated in renal allograft rejection. In a model for ocular autoimmune disease, experimental autoimmune uveoretinitis (EAU), anti-MIF treatment caused delay of EAU development. In patients, there is an increase in serum of MIF, which is also the case in Behcet's disease patients and patients suffering from iridocyclitis. Immunization against MIF may provide a way of treatment against rheumatoid arthritis. Thus conjugates, composites and methods of the invention suitable for immunizing againts MIF, or for reducing serum MIF, are useful in the treatment or prevention of those diseases, disorders and conditons associated with overproduction of MIF.

High serum MIF concentration has been found in atopic dermatitis patients. In skin lesions, MIF is diffusely expressed instead of being found in the basal cell layer in controls. MIF concentration is decreased after steroid treatment, consistent with a role of MIF in inflammation. MIF has also been found to contribute to the establishment of glomerulonephritis. Animals treated with anti-MIF antibody show significantly reduced glomerulonephritis. MIF is pituitary derived, secreted e.g. upon LPS stimulation, and potentiates endotoxemia. Accordingly, anti-MIF mAb inhibits endotoxemia and septic shock, while recombinant MIF markedly increases lethality of peritonitis. MIF is also a glucocorticoid-induced modulator of cytokine production, and promotes inflammation.

MIF is also produced by T-cells ($T_H2$), supports proliferation of T-cells, and anti-MIF-treatment reduces T-cell proliferation and IgG levels. There is an increased MIF concentration in the cerebrospinal fluid of multiple sclerosis and neuro-Behcet's disease patients. High MIF levels were also found in sera of patients with extended psoriasis. High MIF levels are found in sera of ulcerative colitis patients but not Crohn's disease patients.

High MIF levels have been found in sera of patients with bronchic asthma. MIF is also upregulated in synovial fluid of rheumatoid arthritis patients. Anti-MIF treatment was effectivly decreasing rheumatoid arthritis in mouse and rat models (Mikulowska et al., *J. Immunol.* 158:5514-7(1997); Leech et al., *Arthritis Rheum.* 41:910-7 (1998), Leech et al. *Arthritis Rheum.* 43:827-33 (2000), Santos et al., *Clin. Exp. Immunol* 123:309-14 (2001)). Thus, treatment directed at inhibiting MIF activity using a composition comprising MIF as an antigenic determinant are beneficial for the conditions mentioned above.

MIF from mouse, rat and human consists of 114 amino acid and contains three conserved cysteines, as shown in MIF_rat: SEQ ID NO: 120, MIF_mouse: SEQ ID NO: 121 and in MIF_human: SEQ ID NO: 119 SwissProt. Three subunits form a homotrimer that is not stabilized by disulfide bonds. The X-ray structure has been solved and shows three free cysteines (Sun et al., *PNAS* 93: 5191-96 (1996)), while some literature data claim the presence of a disulfide bond. Nonetheless, none of the cysteines are exposed enough for optimal interaction with a possible first attachment site present on the carrier. Thus, as the C-terminus of the protein is exposed in the trimer structure, an amino acid linker containing a cysteine residue is, in one aspect, added to the C-terminus of the protein, for generation of the second attachment site in this embodiment of the invention. There is only one amino acid change between mouse- and rat-MIF, and similarly a very high sequence homology (about 90% sequence identity) between human- and rat-MIF or human- and mouse-MIF. The invention embodies conjugates, compositions and methods comprising human- and mouse-MIF constructs associated to the AP205 VLP.

An amino acid linker containing a cysteine that is added at the N-terminus of the sequence of MIF leads to further embodiments of the present invention. MIF has been expressed in *E.coli*, purified and shown to be fully functional (Bernhagen et al., *Biochemistry* 33: 14144-14155 (1994)). Thus, MIF may be expressed in *E. coli* for generating the useful embodiments of the invention.

Tautomerase activity of MIF is inhibited if the start methionine is not cleaved from the construct. MIF constructs expressed in *E. coli* show tautomerase activity. Mutants of MIF where the start methionine is cleaved and where the proline residue right after the start methionine in the sequence is mutated to alanine also do not show tautomerase activity and represent further embodiments of the invention and are intended to be encompassed within the scope of the invention. In one specific embodiment, AP205 is conjugated to MIF mutants devoid of tautomerase activity.

In one embodiment of the invention, the antigen or antigenic determinant is Interleukin-17 (IL-17). Human IL-17 is a 32-kDa, disulfide-linked, homodimeric protein with variable glycosylation (Yao, Z. et al., *J. Immunol.* 155: 5483-5486 (1995); Fossiez, F. et al., *J. Exp. Med.* 183: 2593-2603 (1996)). The protein comprises 155 amino acids and includes an N-terminal secretion signal sequence of 19-23 residues. The amino acid sequence of IL-17 is similar only to a Herpesvirus protein (HSV13) and is not similarto other cytokines or known proteins. The amino acid sequence of human IL-17 is shown in GenBank ACCESSION #: AAC50341. The mouse protein sequence is shown in GenBank ACCESSION #: AAA37490. Of the large number of tissues and cell lines evaluated, the mRNA transcript encoding IL-17 has been detected only in activated T cells and phorbol 12-myristate 13-acetate/ionomycin-stimulated peripheral blood mononuclear cells (Yao, Z. et al., *J. Immunol.* 155: 5483-5486 (1995); Fossiez, F. et al., *J. Exp. Med.* 183: 2593-2603 (1996)). Both human and mouse sequences contain 6 cysteine residues.

The receptor for IL-17 is widely expressed in many tissues and cell types (Yao, Z. et al., *Cytokine* 9: 794-800 (1997)). Although the amino acid sequence of the human IL-17 receptor (866 aa) predicts a protein with a single trans-membrane domain and a long, 525 aa intracellular domain, the receptor sequence is unique and is not similar to that of any of the receptors from the cytokine/growth factor receptor family. This coupled with the lack of similarity of IL-17 itselfto other known proteins indicates that IL-17 and its receptor may be part of a novel family of signalling protein and receptors. Clinical studies indicate IL-17 may be involved in many inflammatory diseases. IL-17 is secreted by synovial T cells from rheumatoid arthritis patients and stimulates the production of inflammatory mediators (Chabaud, M. et al., *J. Immunol* 161: 409-414 (1998); Chabaud, M. et al., *Arthritis Rheum.* 42: 963-970 (1999)). High levels of IL-17 have been reported in patients with rheumatoid arthritis (Ziolkowska M. et al., *J Immunol.* 164:2832-8 (2000)).

Interleukin-17 has been shown to have an effect on proteoglycan degradation in murine knee joints (Dudler J. et al., *Ann Rheum Dis.* 59: 529-32 (2000)) and contribute to destruction of the synovium matrix (Chabaud M. et al., *Cytokine.* 12:1092-9 (2000)). There are relevant arthritis models in animals for testing the effect of immunizatioyn against IL-17 (Chabaud M. et al., *Cytokine.* 12:1092-9 (2000)). Elevated levels of IL-17 mRNA have been found in mononuclear cells from patients with multiple sclerosis (Matusevicius, D. et al., *Mult. Scler.* 5: 101-104 (1999)). Elevated serum levels of IL-17 are observed in patients suffering Systemic Lupus Erythematosus (Wong C. K. et al., *Lupus* 9: 589-93 (2000)). In addition, IL-17 mRNA levels are increased in T cells isolated from lesional psoriatic skin (Teunissen, M. B. et al., *J. Invest. Dermatol.* 111: 645-649 (1998)).

The involvement of IL-17 in rejection of kidney graft has also been demonstrated (Fossiez F. etal., *Int. Rev. Immunol.*

16:541-51 (1998)). Evidence for a role of IL-17 in organ allograft rejection has also been presented by Antonysamy et al. (*J. Immunol.* 162:577-84 (1999)) who showed IL-17 promotes the functional differentiation of dendritic cell progenitors. Their findings suggest a role for IL-17 in allogeneic T cell proliferation that may be mediated in part via a maturation-inducing effect on DCs. Furthermore the same group reports (Tang J. L. et al., *Transplantation* 72:348-50 (2001)) a role for IL-17 in the immunopathogenesis of acute vascular rejection where Interleukin-17 antagonism inhibits acute but not chronic vascular rejection. IL-17 appears to have potential as a novel target for therapeutic intervention in allograft rejection.

The anti-IL-17 monoclonal antibody mAb5 (Schering-Plough Research Institute) is able to completely inhibit the production of IL-6 from rheumatoid arthritis (RA) synovium supernatants following induction by 50 ng/ml of IL-17. An irrelevant mAb MX1 had no effect in this assay. mAb5 is a mouse IgG1 obtained after immunization with human rIL-17 (r=recombinant). A concentration of 1 µg/ml of mAb5 was able to completely inhibit the IL-6 production in the assay system (Chabaud, M. et al., *J. Immunol.* 161: 409-414 (1998)). Thus, immunization against IL-17 provides a way of treatment for the various conditions described above.

Thus, in one embodiment of the invention the composition comprises a linker containing a second attachment site fused to the C-terminus of recombinant IL-17. In further embodiments an amino acid linker containing a cysteine is fused to the N-terminus of the sequence corresponding to the sequence of the processed protein, or inserted at the N-terminus of the sequence of the mature form of the protein, C-terminally of the signal peptide. For eukaryotic expression systems, the signal peptide of the IL-17 gene, as it is the case for the other self-antigens indicated herein, may be replaced by another signal peptide, for example originating from a specific eukaryotic expression vector. For expression in bacteria, the signal peptide is replaced by a bacterial signal peptide for soluble expression in the periplasm. For expression in the cytoplasm, the construct is devoid of signal peptide. Constructs of human IL-17 devoid of signal peptide will, in some embodiments, comprise residues 24-155, 22-155, 21-155 or 20-155. Constructs of mouse IL-17 devoid of signal peptide will, in some embodiments, comprise residues 26-158, 25-158, 24-158 or 27-155. Human IL-17 may be expressed in CV 1/EBNA cells; recombinant hIL-17 has been shown to be secreted in both glycosylated and nonglycosylated forms (Yao, Z. et al., *J. Immunol.* 155: 5483-5486 (1995)). IL-17 can also be expressed as hIL-17/Fc fusion protein, with subsequent cleavage of the IL-17 protein from the fusion protein. IL-17 may also be expressed in the yeast *Pichia pastoris* (Murphy K.P. et. al., *Protein Expr Purif.* 12: 208-14 (1998)). Human IL-17 may also be expressed in *E. coli*. When expression of IL-17 in *E. coli* is directed to the periplasm, the signal peptide of IL-17 is replaced by a bacterial signal peptide. In one embodiment, IL-17 constructs are devoid of signal peptide for expression of the protein in the cytoplasm of *E. coli*, In another embodiment of the invention the antigenic determinant is Interleukin-13 (IL-13). IL-13 is a cytokine that is secreted by activated T lymphocytes and primarily impacts monocytes, macrophages, and B cells. The first 20 amino acids of the precursor protein correspond to the signal peptide, and are absent of the processed protein. The mouse sequence has also been described (Brown K. D. et al., *J. Immunol.* 142:679-687 (1989)). Depending on the expression host, the IL-13 construct will comprise the sequence of the precursor protein, e.g. for expression and secretion in eukaryotic hosts, or consist of the mature protein, e.g. for cytoplasmic expression in *E. coli*. For expression in the periplasm of *E. coli*, the signal peptide of IL-13 is replaced by a bacterial signal peptide.

IL-13 is a T helper 2-derived cytokine (like IL-4, IL-5) that has recently been implicated in allergic airway responses (asthma). Upregulation of IL-13 and IL-13 receptor has been found in many tumour types (e.g. Hodgkin lymphoma). Interleukin 13 is secreted by and stimulates the growth of Hodgkin and Reed-Stemberg cells (Kapp U. et al, *J Exp Med.* 189: 1939-46 (1999)). Thus, immunization against IL-13 provides a way of treating among others the conditions described above, such as Asthma or Hodgkins Lymphoma.

In one embodiment, the composition comprises an amino acid linker containing a cysteine residue and being fused to the N or C-terminus of the sequence of mature IL-13 to introduce a second attachment site within the protein. In other embodiments, an amino acid linker containing a cysteine is added to the N-terminus of the mature form of IL-13, since it is freely accessible according to the NMR structure of IL-13 (Eisenmesser, E. Z. et al., *J. Mol. Biol.* 310: 231 (2001)). In other embodiments, the amino acid linker containing a cysteine is fused to the N-terminus of the sequence corresponding to the sequence of the processed protein, or inserted at the N-terminus of the sequence of the mature form of the protein, C-terminally of the signal peptide. In other embodiments, an amino acid linker containing a cysteine residue is added to the C-terminus of the protein.

IL-13 may be expressed in *E.coli* (Eisenmesser E. Z. et al., *Protein Expr. Purif.* 20:186-95 (2000)), or in NS-0 cells (eukaryotic cell line) (Cannon-Carlson S. et al., *Protein Expr. Purif.* 12:239-48 (1998)).

In one embodiment of the invention, the antigenic determinant is Interleukin-5 (IL-5). IL-5 is a lineage-specific cytokine for eosinophilopoiesis and plays an important part in diseases associated with increased number of eosinophils, such as asthma.

The biological function of IL-5 has been shown in several studies (Coffinan R. L. et al., *Science* 245: 308-10 (1989); Kopf et al., *Immunity* 4:15-24 (1996)), which point to a beneficial effect of inhibiting IL-5 function in diseases mediated through eosinophils. Inhibition of the action of IL-5 provides thus a way of treatment against asthma and other diseases associated with eosinophils.

IL-5 forms a dimer, covalently linked by a disulfide bridge. A single chain (sc) construct has been reported wherein two monomers of IL-5 are linked by a peptide linker.

In one embodiment of the invention, a peptide linker containing a cysteine is added at the N-terminus of the sequence of the processed form of IL-5. Addition of a linker containing a cysteine is also envisaged at the N-terminus of the sequence of the processed form of a scIL-5. In other embodiments, the amino acid linker containing a cysteine is fused to the N-terminus of the sequence corresponding to the sequence of the processed protein, or inserted at the N-terminus of the sequence of the mature form of the protein, C-terminally of the signal peptide.

In other embodiments, a linker containing a cysteine is fused to the C-terminus of the sequence of IL-5, or to the C-terminus of a scIL-5 sequence.

A number of expression systems have been described for IL-5 and can be used in preparing the compositions of the invention. A bacterial expression system using *E.coli* has been described by Proudfoot et al., (*Biochem J.* 270:357-61 (1990)). In the case where IL-5 is expressed in the cytoplasm of *E. coli*, the IL-5 construct is devoid of a signal peptide. Insect cells may also be used for producing IL-5 constructs for making the compositions of the invention (Pierrot C. et al., *Biochem. Biophys. Res. Commun.* 253:756-60 (1998)).

Likewise, Baculovirus expression systems (sf9 cells; Ingley E. et al., *Eur. J. Biochem.* 196:623-9 (1991) and Brown P. M. et al., *Protein Expr. Purif.* 6: 63-71 (1995)) can also be used. Finally, mammalian expression systems have also been reported (CHO cells) and can be used in preparing these compositions of the invention (Kodama S et al., J. Biochem. (Tokyo) 110:693-701 (1991)).

Baculovirus expression systems (Mitchell et al., *Biochem. Soc. Trans.* 21:332S (1993); Kunimoto D Y et al., *Cytokine* 3:224-30.(1991)) and a mammalian cell expression system using CHO cells (Kodama S et al., *Glycobiology* 2:419-27 (1992)) have also been described for mouse IL-5.

The expression of murine IL-5 constructs wherein the IL-5 sequence is fused at its N-terminus to amino acid linkers containing a cysteine residue are suitable for coupling of IL-5 to AP205 VLP. Human constructs can be generated according to the teachings herein yield the proteins human C-IL-5-E, human C-IL-5-F and human C-IL-5-S suitable for coupling to AP205 VLP and leading to other embodiments of the invention.

In one embodiment of the invention, the antigenic determinant is CCL-21. CCL-21 is a chemokine of the CC subfamily that is also known as small inducable cytokine A21, as exodus-2, as SLD (secondary lymphocyte cytokine), as TCA4 (thymus-derived chemotactic agent 4) or 6Ckine.

CCL21 inhibits hemopoiesis and stimulates chemotaxis for thymocytes, activated T-cells and dendritic cells, but not for B cells, macrophages or neutrophils. It shows preferential activitiy towards naive T cells. It is also a potent mesangial cell chemoattractant. CCL21 binds to chemokine receptors CCR7 and to CXCR3 (depending on the species). It can trigger rapid integrin-dependent arrest of lymphocytes rolling under physiological shear and is highly expressed by high endothelial venules.

Murine CCL21 inhibited tumor growth and angiogenesis in a human lung cancer SCID mouse model (Arenberg et al., *Cancer Immunol. Immunother.* 49: 587-92 (2001)) and a colon carcinoma tumor model in mice (Vicari et al., *J. Immunol.* 165: 1992-2000 (2001)). The angiostatic activity of murine CCL21 was also detected in a rat corneal micropocket assay (Soto et al., *Proc. Natl. Acad. Sci. USA* 95: 8205-10 (1998).

It has been shown that chemokine receptors CCR7 and CXCR4 are upregulated in breast cancer cells and that CCL21 and CXCL12, the respective ligands, are highly expressed in organs representing the first destinations of breast cancer metastasis (Müller et al. (*Nature* 410: 50-6 (2001)). In vitro CCL21-mediated chemotaxis could be blocked by neutralizing anti-CCL21 antibodies as was CXCR4-mediated chemotaxis by the respective antibodies. Thus, immunization against CCL21 provides a way of treatment against metastatis spread in cancers, more specifically in breast cancer.

Secreted CCL21 consist of 110 or 111 aa in mice and humans, respectively. The respective sequences are shown in Swissprot: SY21_human and in Swissprot: SY21_mouse. In contrast to other CC cytokines does CCL21 contain two more cysteines within an extended region at the C-terminus. It is assumed that all cysteines are engaged in disulfide bonds.

In the following, constructs and expression systems are described for making compositions of the invention comprising the CCL21 antigenic determinant. In the NMR structure of the homologous protein eotaxin, both N- and C-terminus are exposed to the solvent. In some embodiments, an amino acid linker containing a cysteine residue as a second attachment site is added at the C-terminus of the protein. A fusion protein with alkaline phosphatase (at the C-terminus of CCL21) has been expressed and was shown to be functional, showing that fusions at the C-terminus of CCL21 are compatible with receptor binding. In specific embodiments, the amino acid linker containing a cysteine is fused to the N-terminus of the sequence corresponding to the sequence of the processed protein, or inserted at the N-terminus of the sequence of the mature form of the protein, C-terminally of the signal peptide.

Several expression systems have been described for production of CCL21 (e.g. Hedrick et al., *J Immunol.* 159: 1589-93 (1997)). For example, it may expressed in a baculovirus system (Nagira et al., *J. Biol. Chem.* 272: 19518-24 (1997)).

In a related embodiment, the antigenic determinant is Stromal derived factor-1 (SDF-1), now termed CXCL12. CXCL12 is a chemokine produced by bone marrow stromal cells and was originally identified as a stimulatory factor for pre-B cells.

As stated above, it has been shown that chemokine receptors CCR7 and CXCR4 are upregulated in breast cancer cells and that CCL21 and SDF-1, the respective ligands, are highly expressed in organs representing the first destinations of breast cancer metastasis (Müller et al. *Nature* 410: 50-6 (2001)). In vitro SDF-1/CXCR4-mediated chemotaxis could be inhibited by neutralizing anti-SDF-1 and anti-CXCR4 antibodies.

In a breast cancer metastasis model in SCID mice using the human MDA-MB-231 breast cancer cell line, a significant decrease in lung metastasis was observed when mice were treated with anti-CXCR4 antibodies. In the draining lymph nodes, a reduction of metastasis to the inguinal and axillary lymph nodes (38% instead of 100% metastasis in controls) was observed. Thus, immunization against CXCL12 provides a way of treatment against metastatis of cancers, more specifically of breast cancers.

The SDF-1/CXCR4 chemokine-receptor pair has been shown to increase the efficacy of homing of more primitive hematopoietic progenitor cells to be bone marrow. In addition, CXCR4 and SDF-1 are supposed to influence the distribution of chronic lymphocytic leukemia cells. These cells invariably infiltrate the bone marrow of patients and it was shown that their migration in the bone marrow was CXCR4 dependent. Chronic lymphocytic leukemia cells undergo apoptosis unless they are cocultured with stromal cells. SDF-1 blocking antibodies could inhibit this protective effect of stromal cells (Burger et al., *Blood* 96: 2655-63 (2000)). Immunizing against CXCL12 thus provides a way of treatment against chronic lymphocytic leukemia.

CXCR4 has been shown to be a coreceptor for entry of HIV into T-cells. SDF-1 inhibits infection of CD4+ cells by X4 (CXCR4-dependent) HIV strains (Oberlin et al., *Nature* 382: 833-5 (1996); Bleul et al., *Nature* 382:829-33 (1996), Rusconi et al., *Antivir. Ther.* 5:199-204 (2000)). Synthetic peptide analogs of SDF-1 have been shown to effectively inhibit HIV-1 entry and infection via the CXCR4 receptor (WO059928A1). Thus, immunization against CXCL12 provides a way to block HIV entry in T-cells, and therefore a way of treating AIDS.

SDF-1-CXCR4 interactions were also reported to play a central role in CD4+ T cell accumulation in rheumatoid arthritis synovium (Nanki et al., 2000). Immunization against SDF-1 thus provides a way of treatment against rheumatoid arthritis.

Human and murine SDF-1 are known to arise in two forms, SDF-1α and SDF-1β, by differential splicing from a single gene. They differ in four C-terminal amino acids that are present in SDF-1β (74 aa) and absent in SDF-1α (70 aa). The sequence of human SDF-1 is shown in Swissprot: SDF1_human and the sequence of mouse SDF-1 is shown inSwissprot: SDF1_mouse. SDF-1 contains four conserved cysteines that form two intra-molecular disulfide bonds. The crystal structure of SDF shows a non covalently-linked dimer (Dealwis et al., *PNAS* 95: 6941-46 (1998)). The SDF-1 structure also shows a long N-terminal extension.

Alanine-scanning mutagenesis was used to identify (part of) the receptor-binding site on SDF-1 (Ohnishi et al., *J. Interferon Cytokine Res.* 20: 691-700 (2000)) and Elisseeva et al. (*J. Biol. Chem.* 275:26799-805 (2000)) and Heveker et al. (*Curr. Biol.* 8:369-76 (1998)) described SDF-1 derived peptides inhibiting receptor binding (and HIV entry).

In the following, constructs and expression systems suitable for the generation of the compositions of the invention related to SDF-1 are described. The N- and C-terminus of SDF-1 are exposed to the solvent. In specific embodiments, an amino acid linker containing a cysteine as second attachment site is thus fused to the C-terminus of the protein sequence, while in other specific embodiments an amino acid linker containing a cysteine as second attachment site is fused to the N-terminus of the protein sequence. The amino acid linker containing a cysteine is fused to the N-terminus of the sequence corresponding to the sequence of the processed protein, or inserted at the N-terminus of the sequence of the mature form of the protein, C-terminally of the signal peptide. The genes coding for these specific constructs may be cloned in a suitable expression vector.

Expression of SDF-1 in a sendai virus system in chicken embryonic fibroblasts (Moriya et al., *FEBS Lett.* 425:105-11 (1998)) has been described as well as expression in *E.coli* (Holmes et al., *Prot. Expr. Purif.* 21: 367-77 (2001)) and chemical synthesis of SDF-1 (Dealwis et al., *PNAS* 95: 6941-46 (2001)).

In another embodiment of the invention, the antigenic determinant is B-lymphocyte chemoattractant (BLC, CXCL13). BLC is expressed in the spleen, Peyer's patches and lymph nodes (Gunn et al., 1998). Its expression is strongest in the germinal centres, where B cells undergo somatic mutation and affinity maturation. It belongs to the CXC chemokine family, and its closest homolog is GROα (Gunn et al., *Nature* 391:799-803 (1998)). Human BLC is 64% homologous to murine BLC. Its receptor is CXCR5. BLC also shares homology with IL-8. BLC recruits B-cells to follicles in secondary lymphoid organs such as the spleen and peyer's patches. BLC is also required for recruitment of B-cells to compartment of the lymph nodes rich in follicular Dendritic Cells (FDCs) (Ansel et al., *Nature* 406:309-314 (2000)). BLC also induces increased expression of Lymphotoxinα1β2 (LTα1β2) on the recruited B-cells. This provides a positive feed-back loop, since LTα1β2 promotes BLC expression (Ansel et al., *Nature* 406:309-314 (2000)). BLC has also been shown to be able to induce lymphoid neogenesis (Luther et al., *Immunity* 12:471-481(2000)). It appears that FDCs also express BLC. Thus immunization against BLC may provide a way of treatment against autoimmune diseases where lymphoid neogenesis is involved, such as Rheumatoid synovitis and Rheumatoid arthritis or Type I diabetes. A construct of BLC bearing a C-terminal His-tag has been described, and is functional (Ansel, K. M. et al., *J. Exp. Med.* 190: 1123-1134 (1999)).

In one embodiment of the present invention, the composition comprises a linker containing a cysteine residue as second attachment site and being fused at the C-terminus of the BLC sequence.

In IL-8, which is homologous to BLC, both N- and C-termini are free. Fusion of an amino acid linker containing a cysteine residue as second attachment site to the N-terminus of BLC leads to one embodiment of the invention.

In other embodiments of the present invention, the composition comprises an amino acid linker containing a cysteine and being fused to the N-terminus of the sequence corresponding to the sequence of the processed protein, or inserted at the N-terminus of the sequence of the mature form of the protein, C-terminally of the signal peptide. The genes coding for these specific constructs may be cloned in a suitable expression vector and expressed accordingly. The sequence of human BLC is shown in Accession: NP_006410. Amino acids 1-22 of the sequence are the signal peptide. The mouse sequence is shown in Accession NP_061354. Amino acids 1-21 are the signal peptide. Compositions of the invention with BLC as the antigenic determinant, in some embodiments, use the mature form of the protein for generating the compositions of the invention.

In another specific embodiment, the antigenic determinant is Eotaxin. Eotaxin is a chemokine specific for Chemokine receptor 3, present on eosinophils, basophils and Th2 cells. Eotaxin seems however to be highly specific for Eosinophils (Zimmerman et al., *J. Immunol.* 165: 5839-46 (2000)). Eosinophil migration is reduced by 70% in the eotaxin-1 knock-out mouse, which however can still develop eosinophilia (Rothenberg et al., *J. Exp. Med.* 185: 785-90 (1997)). IL-5 seems to be responsible for the migration of eosinophils from bone-marrow to blood, and eotaxin for the local migration in the tissue (Humbles et al., *J. Exp. Med.* 186: 601-12 (1997)).

The human genome contains 3 eotaxin genes, eotaxinl-3. They share 30% homology to each other. Two genes are known so far in the mouse: eotaxin 1 and eotaxin 2 (Zimmerman et al., *J. Immunol.* 165: 5839-46 (2000)). They share 38% homology. Murine eotaxin-2 shares 59% homology with human eotaxin-2. In the mouse, eotaxin-1 seems to be ubiquitously expressed in the gastro-intestinal tract, while eotaxin-2 seems to be predominantly expressed in the jejunum (Zimmerman et al., *J. Immunol.* 165: 5839-46 (2000)). Eotaxin-1 is present in broncho-alveolar fluid (Teixeira et al., *J. Clin. Invest.* 100: 1657-66 (1997)). Eotaxin has a MW of 8.3 kDa. It is in equilibrium between monomers and dimers over a wide range of conditions, with an estimated Kd of 1.3 mM at 37° C. (Crump et al., *J. Biol. Chem.* 273: 22471-9 (1998)). The monomer form is however predominant. The structure of Eotaxin has been elucidated by NMR spectroscopy. Binding site to its receptor CCR3 is at the N-terminus, and the region preceding the first cysteine is crucial (Crump et al., *J. Biol. Chem.* 273: 22471-9 (1998)). Peptides of chemokine receptors bound to Eotaxin confirmed this finding. Eotaxin has four cysteines forming two disulfide bridges. Therefore, in one embodiment, the inventive composition comprises an amino-acid linker containing a cysteine residue as second attachment site and being in one embodiment, fused to the C-terminus of the Eotaxin sequence. In further embodiments, an amino acid linker containing a cysteine is fused to the N-terminus of the sequence corresponding to the sequence of the processed protein, or inserted at the N-terminus of the sequence of the mature form of the protein, C-terminally of the signal peptide. The genes coding for these specific constructs are cloned in a suitable expression vector.

Eotaxin can be chemically synthesized (Clark-Lewis et al., *Biochemistry* 30:3128-3135 (1991)). Expression in *E. coli* has also been described for Eotaxin-1, in the cytoplasm (Crump et al., *J. Biol. Chem.* 273: 22471-9 (1998)). Expression in *E. coli* as inclusion bodies with subsequent refolding (Mayer et al., *Biochemistry* 39: 8382-95 (2000)), and Insect cell expression (Forssmann et al., *J. Exp. Med.* 185: 2171-6

(1997)) have been described for Eotaxin-2, and may, moreover, be used to arrive at the specific embodiments of the invention.

In yet another specific embodiment of the invention, the antigenic determinant is Macrophage colony-stimulating factor (M-CSF or CSF-1). M-CSF or CSF-1 is a regulator of proliferation, differentiation and survival of macrophages and their bone-marrow progenitors. The receptor for M-CSF is a cell surface tyrosine kinase receptor, encoded by the protooncogene cFMS. An elevated expression of M-CSF and its receptor has been associated with poor prognosis in several epithelial cancers such as breast, uterine and ovarian cancer. Tumor progression has been studied in a mouse strain resulting from the crossing of a transgenic mouse susceptible to mammary cancer (PyMT) with a mouse containing a recessive null mutation in the csf-1 gene. These mice show attenuated late stage invasive carcinoma and pulmonary metastasis compared to the PyMT mouse (Lin et al., *J. Exp. Med.* 193: 727-739 (2001)). The cause seems to be the absence of macrophage recruitment to neoplastic tissues. Subcutaneous growth of Lewis lung cancer is also impaired in csf.1 null mice. It is postulated that the mechanism of macrophage enhancement of tumor growth would be through angiogenic factors, growth factors and proteases produced by the macrophages.

Structural data on the soluble form of M-CSF are available (crystal structure: Pandit et al., *Science* 258:1358-62 (1992)), and show that both the N- and C-termini of the protein are accessible. However, the N-terminus is close to the site of interaction with the receptor. In addition, M-CSF is present both in a soluble and cell surface form, where the transmembrane region is at its C-terminus. Therefore certain embodiment of the present invention comprise an amino acid linker containing a cysteine and being, in one embodiment, added at the C-terminus of M-CSF or fragments thereof, at the C-terminus of the soluble form of M-CSF. In other embodiments, the amino acid linker containing a cysteine is fused to the N-terminus of the sequence corresponding to the sequence of the processed protein or of the soluble form of the protein, or inserted at the N-terminus of the sequence of the mature form of the protein or of the soluble form of the protein, C-terminally of the signal peptide. M-CSF is a dimer, where the two monomers are linked via an interchain disulfide bridge.

An expression system in *E. coli* has been described for an N-terminal 149 amino acid fragment (functional) of M-CSF (Koths et al., *Mol. Reprod. Dev.* 46:31-37 (1997)). This fragment of M-CSF, modified as outlined above, represents a one antigenic determinant in accordance with the embodiments of the invention. The human sequence is shown in Accession: NP_000748. Other antigenic determinants of the present invention comprise the N-terminal fragment consisting of residue 33-181 or 33-185 of the above sequence, corresponding to the soluble form of the receptor.

The mouse sequence is shown in Accession. NP_031804. The mature sequence starts at amino acid 33. Thus, one antigenic determinant in accordance with the present invention comprises amino-acid 33-181 or 33-185.

In one embodiment, the antigenic determinant is Resistin (Res). Passive immunization studies were performed with a rabbit polyclonal antibodies generated against a fusion protein of mouse Resistin (mRes) fused to GST, expressed in bacteria. This passive immunization lead to improved glucose uptake in an animal obesity/Type II diabetes model (Steppan et al., *Nature* 409: 307-12 (2001)).

Resistin (Res) is a 114 aa peptide hormone of approximately 12 KD. It contains 11 cysteine of which the most N-terminal one was shown to be responsible for the dimerisation of the protein and the other 10 are believed to be involved in intramolecular disulfide bonds (Banerjee and Lazar, *J. Biol. Chem.* 276: 25970-3 (2001)). Mutation of the first cysteine to alanine abolishes the dimerisation of mRes.

mRes with a FLAG tag at its C-terminus remains active in an animal model (Steppan et al., *Nature* 409: 307-12 (2001)). Similarly a C-terminally HA taged (Haemagglutinin tag) version of resistin was shown to be active in a tissue culture assay (Kim et al., *J. Biol. Chem.* 276:11252-6 (2001)). Therefore, in one embodiment, the present compositions comprise an amino-acid linker containing a cysteine residue as second attachment site and being fused at the C-terminus of the resistin sequence. In another embodiment, the amino acid linker containing a cysteine is fused to the N-terminus of the sequence corresponding to the sequence of the processed protein, or inserted at the N-terminus of the sequence of the mature form of the protein, C-terminally of the signal peptide.

In one embodiment of the present invention, MRes or huRes may also be expressed as Fc fusion molecules with a protease cleavage site inserted between Resistin and the Fc part of the construct, such as C-terminally to one or more cysteine residues of the hinge region of the Fc part of the fusion protein in a eukaryotic expression system, or such as according to the descriptions herein. Cleavage of the fusion protein releases Resistin additionally comprising either an aminoacid linker containing a cysteine residue or part or all of the hinge region of the Fc part of the fusion protein which comprises a cysteine residue at its C-terminus, which is suitable for coupling to AP205 VLP. The human Resistin sequence is shown in Accession AF323081. The mouse sequence is shown in Accession AF323080. A favored embodiment of the invention is human resistin protein fused at its C-terminus to an amino acid linker containing a cysteine residue. Human resistin construct can be generated according to the teachings disclosed herein and by comparing murine and human Resistin sequences in a protein sequence alignment to identify the part of the sequence of human Resistin to be cloned into vectors herein or in other suitable expression vectors. Example of human resistin constructs suitable for generating compositions of the inventions are human resistin-C-Xa, human resistin-C-EK and human resistin-C.

Human Resistin constructs so generated are a one embodiment of the invention. Vaccination against Resistin using the aforementioned compositions of the invention may thus provide a way of treating Type II Diabetes and obesity.

In another embodiment the antigenic determinant is Lymphotoxin-β. Immunization against lymphotoxin-β may be useful in treating Prion mediated disease. Prions are cellular proteins existing in most mammalian species. Prion proteins exist in two forms, a normally folded form that is usually present in healthy individuals (PrP$^c$) and a misfolded form that causes disease (Prp$^{Sc}$). The current prion hypotheses postulates that the misfolded prion form Prp$^{Sc}$ can catalyse the refolding of healthy prion PrP$^c$ into disease causing Prp$^{Sc}$ (A. Aguzzi, *Haematologica* 85, 3-10 (2000)). In some rare instances, this transition may also occur spontaneously, causing classical CJD in humans. Some mutations in PrP$^c$ are associated with an increase in this spontaneous transition, causing the various forms of familial CJD. However, Prp$^{Sc}$ may also be infectious and may be transmitted by blood transfusion or via the food chain. The latter form of prion mediated disease is known as Kuru and used to occur in human cannibals. However, since species that are feeding on their own individuals are not abundant, this form of orally transmitted disease was too rare to be documented for other species.

The massive feeding of cows with beef-products throughout Europe changed the situation and numbers of cows infected with a transmissible form of BSE-causing Prp$^{Sc}$, dramatically increased in recent years, afflicting hundreds of thousands of cows. This sudden appearance of massive numbers of BSE-diseased cows caused great fear in the human population that a similar disease may be induced in humans. Indeed, in 1996, the first case of a variant form of CJD was reported that could be attributed to the consumption of Prp$^{Sc}$ infected beef. Until now, this fear has further increased, since the number of infected humans has constantly increased during the following years and no cure is in sight. Moreover, since sheep succumb to a prion-mediated disease called scrapie and since other mammalian species can be infected with Prp$^{Sc}$, it is possible that BSE-like diseases may occur also in other species.

Scrapie (a prion-mediated disease) agent replication is believed to take mainly place in lymphoid tissues and was shown to depend on prion-protein expressing follicular dendritic cells (FDCs) (Brown et al., *Nature Med.* 11: 1308-1312 (1999)). The mechanism of prion transmission has been studied in great detail. It is now clear that prions first replicate in the lymphoid organs of infected mice and are subsequently transported to the central nervous system. It was shown that mice lacking functional follicular dendritic cells show an impaired prion replication in spleens and a (small) retardation of neuroinvasion (Montrasio et al., *Science* 288: 1257-1259 (2000)). This was achieved by injecting the mice with a soluble lymphotoxin-β receptor-Fc-fusion protein (LTβR-Fc). This soluble receptor construct inhibits the development of FDCs by interfering with the crucial interaction of lymphotoxin-β on T, B or NK cells with the lymphotoxin-β receptor on the FDC precursor cells. FDCs are a poorly studied cell type but it is now clear that they depend upon the production of lymphotoxin and/or TNF by B cells for their development (F. Mackay, J. L. Browning, *Nature* 395,26-27 (1998)). Indeed, mice deficient for lymphotoxin do not exhibit FDCs (M. S. Matsumoto, et al., *Science* 264, 703-707 (1996)). In addition to FDCs, antibodies may also play a role in disease progression (S. Brandner, M. A. Klein, A. Aguzzi, *Transfus Clin Biol* 6, 17-23 (1999)).

Thus, vaccination against lymphotoxin-β (also called TNFγ), LTα or LTβ receptor, thereby eliminating FDCs from lymphoid organs, may provide a vaccine for treatment or prevention of Creutzfeld-Jakob (variant form) or other prion-mediated diseases such as bovine spongioform encephalopathy (BSE) and thus prevent prion replication and neuroinvasion.

Immunization against Lymphotoxin-β may also provide a way of treating diabetes. Transgene expression of soluble LTβR-Fc fusion protein in nonobese diabetic NOD mice blocked diabetes development but not insulitis (Ettinger et al., *J. Exp. Med.* 193: 1333-40 K (2001)). Wu et al. (*J. Exp. Med.* 193: 1327-32 (2001)) also used NOD mice to study the involvement of lymphotoxin-β, but instead of transgenic animals they did inject the LTβR-Fc fusion protein. They saw a strong inhibition of diabetes development and inhibition of insulitis. Most interestingly, they could even reverse preexisting insulitis by the fusion protein treatment. In the pancreas the formation of lymphoid follicular structures could thus be reversed. Vaccination against lymphotoxin-β may thus provide a way of treatment against type-I diabetes.

In one embodiment, the inventive composition comprises an amino acid linker containing a cysteine and being added to the N-terminus of the sequence corresponding to the processed form of lymphotoxin-β, or inserted between the N-terminus of the sequence corresponding to the mature form of the protein, and the signal peptide, C-terminally to the signal peptide. In related embodiments of the invention, the extracellular part of lymphotoxin-β is expressed as a fusion protein either with glutathione-S-transferase, fused N-terminally to lymphotoxin-β, or with a 6 histidine-tag followed by a myc-tag, fused again N-terminally to the extracellular part of lymphotoxin-β. An amino acid spacer containing a protease cleavage site as well as a linker sequence containing a cysteine as attachment site, C-terminally to the protease cleavage site, are fused to the N-terminus of the sequence of the extracellular part of lymphotoxin-β. In one embodiment the extracellular part of lymphotoxin-β consists of fragments corresponding to amino acids 49-306 or 126-306 of lymphotoxin-β. These specific compositions of the invention may be cloned and expressed in the pCEP-Pu eukaryotic vector. In certain embodiments, the inventive compositions comprise an aminoacid linker containing a cysteine residue suitable as second attachment site, and being fused to the C-terminus of lymphotoxin-β or lymphotoxin-β fragments. In a particularly favored embodiment, the amino acid sequence LACGG, comprising the amino acid linker ACGG which itself contains a cysteine residue for coupling to AP205 VLP is fused to the N-terminus of the extracellular part of lymphotoxin-β or of a fragment of the extracellular part of lymphotoxin-β, yielding the proteins human C-LTβ$_{49-306}$ and human C-LTβ$_{126-306}$ after cleavage with enterokinase of the corresponding fusion proteins expressed either in vector pCEP-SP-GST-EK or vector pCP-SP-his-myc-EK.

In one embodiment, the antigen or antigenic determinant is the prion protein, fragments thereof and in particular peptides of the prion protein. In an embodiment of the invention, the antigenic determinant is the prion protein or fragments thereof. Immunization against prion protein may provide a way of treatment or prevention of Creutzfeld-Jakob (variant form) or other prion-mediated diseases. Murine peptides corresponding to fragments of the murine prion protein and of sequence CSAMSRPMIHFGNDWEDRYYRENMYR (SEQ ID NO: 17) ("cprplong") and CGNDWEDRYYREN-MYR ("cprpshort") (SEQ ID NO: 18) comprise an added N-terminal cysteine residue for chemical coupling to AP205 VLP and lead to one embodiment of the invention. In one embodiment the prion protein is the human prion protein. Guidance on how to modify human prion protein for association with the AP205 VLP is given throughout the application. Mouse prion protein constructs are disclosed, and human prion protein constructs can also be generated. Further constructs comprise the whole human prion protein sequence, and other fragments of the human prion protein, which are further compositions of the invention. Immunization against prion protein may provide a way of treatment or prevention of Creutzfeld-Jakob (variant form) or other prion-mediated diseases. Immunization using the compositions of the invention comprising the prion protein may provide a way of treatment against prion mediated diseases in other animals. The peptides of the human prion protein corresponding to the murine peptides described above and of amino acid sequence CSAM-SRPIIHFGSDYEDRYYRENMHR ("human cprplong") (SEQ ID NO: 19) and CGSDYEDRYYRENMHR ("human cprpshort") (SEQ ID NO: 20) lead to embodiments of the invention. These peptides comprise an N-terminal cysteine residue added for coupling to AP205 VLP. Corresponding bovine and sheep peptides are CSAMSRPLIHF-GNDYEDRYYRENMHR ("bovine cprplong") (SEQ ID NO: 21) and CGNDYEDRYYRENMHR ("bovine cprp-short") (SEQ ID NO: 22)

CSAMSRPLIHFGNDYEDRYYRENMYR ("sheep cprplong") (SEQ ID NO: 23) and CGNDYEDRYYREN- MYR ("sheep cprpshort") (SEQ ID NO: 24), all leading to embodiments of the invention.

In one embodiment of the invention, the antigenic determinant is tumor necrosis factor α (TNF-α), fragments thereof or peptides of TNF-α. In particular, peptides or fragments of TNF-α can be used to induce a self-specific immune response directed towards the whole protein by immunizing a human or an animal with vaccines and compositions, respectively, comprising such peptides or fragments in accordance with the invention. The following murine peptides are the murine homologs to human peptides that have been shown to be bound by antibodies neutralizing the activity of TNF-α (Yone et al. *J. Biol. Chem.* 270: 19509-19515) and were, in another embodiment of the invention, modified with cysteine residues for coupling to AP205 VLP.

MuTNFα peptide; the sequence CGG was added at the N-terminus of the epitope consisting of amino acid residues 22-32 of mature murine TNF-α, giving the sequence: CGGVEEQLEWLSQR (SEQ ID NO: 25).

3'TNF II peptide; the sequence GGC was fused at the C-terminus of the epitope consisting of amino acid residues 4-22 of mature murine TNF-α and glutamine 21 was mutated to glycine. The sequence of the resulting peptide is: SSQNSSDKPVAHVVANHGVGGC (SEQ ID NO: 26).

5'TNF II peptide: a cysteine residue was fused to the N-terminus of the epitope consisting of amino acid residues 4-22 of mature murine TNF-α and glutamine 21 was mutated to glycine. The sequence of the resulting peptide is: CSSQNSSDKPVAHVVANHGV (SEQ ID NO: 27).

The corresponding human sequence of the 4-22 epitope is SSRTPSDKPVAHVVANPQAEGQ (SEQ ID NO: 28). As for the murine sequence a cysteine is, in one embodiment, fused at the N-terminus of the epitope, or the sequence GGC is fused at the C-terminus of the epitope for covalent coupling to AP205 VLP according to the invention. It is, however, within the scope of the present invention that other cysteine containing sequences are fused at the N- or C-termini of the epitopes. In general, one or two glycine residues are, in one embodiment, inserted between the added cysteine residue and the sequence of the epitope. Other amino acids may, however, also be inserted instead of glycine residues, and these amino acid residues include small amino acids such as serine.

In a further preferred embodiment of the inventive composition, the antigen or antigenic determinant is tumor necrosis factor α (TNF-α), fragments or muteins thereof or peptides of TNF-α or fragments or muteins thereof, wherein said antigen or antigenic determinant with said second attachment site has an amino acid sequence selected from the group consisting of: a) the amino acid sequence of CSSRTPSDKPVAHVVANPQAEGQ (SEQ ID NO: 100); b) the amino acid sequence of SSRTPSDKPVAHVVANPQAEGQGGC (SEQ ID NO: 101); and c) the amino acid sequence of CGGQLQWLNRRANA (SEQ ID NO: 102).

The human sequence corresponding to amino acid residues 22-32 is QLQWLNRRANA (SEQ ID NO: 29). In one related embodiment, the sequence CGG is fused at the N-terminus of the epitope for covalent coupling to AP205 VLP according to the invention. Other TNF-α epitopes suitable for using in the present invention have been described and are disclosed for example by Yone et al. (*J. Biol. Chem.* 270: 19509-19515).

The invention further includes compositions which contain mimotopes of the antigens or antigenic determinants described herein.

One specific composition of the invention comprises an antibody or an antibody fragment presented on a virus-like particle for induction of an immune response against that antibody. In one embodiment, antibodies or antibody fragments which are produced by lymphoma cells, are selected for attachment to the virus-like particle for immunization in order to induce a protective immune response against the lymphoma.

In other further embodiments, an antibody or antibody fragment mimicking an antigen is attached to the AP205 VLP. The mimicking antibody or antibody fragment is generated by immunization and subsequent isolation of the mimicking antibody or antibody fragment, or by any known method known to the art such as e.g. hybridoma technology (Gherardi, E. et al., *J. Immunol. Methods* 126: 61-68 (1990)), phage display (Harrison et al., *Methods Enzymol.* 267: 83-109 (1996)), ribosome display (Hanes, J. et al., *Nat. Biotechnol.* 18:1287-1292 (2000)), yeast two-hybrid (Visintin, M. et al., *Proc. Natl. Acad. Sci. USA* 96: 11723-11728 (1999)), yeast surface display (Boder, E T. & Wittrup, K D. *Methods. Enzym.* 328: 430-444 (2000)), bacterial surface display (Daugherty, P S. et al., *Protein Eng.* 12: 613-621 (1999)). The mimicking antibody may also be isolated from an antibody library or a naïve antibody library using methods known to the art.

In a further embodiment, an antibody recognizing the combining site of another antibody, i.e. an anti-idiotypic antibody, further called the immunizing antibody, is used. The antibody recognized by the anti-idiotypic antibody will be further referred to as the neutralizing antibody. Thus, by immunizing against the anti-idiotypic antibody, molecules with the specificity of the neutralizing antibody are generated in situ; we will further refer to these generated antibodies as the induced antibodies. In another embodiment, the immunizing antibody is selected to interact with a ligand molecule of the target molecule against which immunization is sought. The ligand molecule may be any molecule interacting with the target molecule but will, in one embodiment, preferentially interact with the site of the target molecule against which antibodies should be generated for inhibition of its function. The ligand molecule may be a natural ligand of the target molecule, or may be any engineered, designed or isolated ligand having suitable binding properties.

The immunizing antibodies may be of human origin, such as isolated from a naïve or immune human antibody library, or may have been isolated from a library generated from another animal source, for example of murine origin.

Coupling of the antibody or antibody fragment to AP205 VLP is achieved either by limited reduction of exposed disulfide bridges (for example of the interchain disulfide bridge between CH1 and Cκ or Cλ in a Fab fragment) or, in another embodiment, by fusion of a linker containing a cysteine residue at the C-terminus of the antibody or antibody fragment. In a further embodiment, a linker containing a cysteine residue is fused to the N-terminus of the antibody or antibody fragment for attachment to a VLP or pilus protein.

A number of vaccine compositions which employ mimotopes are known in the art, as are methods for generating and identifying mimotopes of particular epitopes. For example, Arnon et al., *Immunology* 101:555-562 (2000), the entire disclosure of which is incorporated herein by reference, describe mimotope peptide-based vaccines against *Schistosoma mansoni*. The mimotopes uses in these vaccines were obtained by screening a solid-phase 8-mer random peptide library to identify mimotopes of an epitope recognized by a protective monoclonal antibody against *Schistosoma mansoni*. Similarly, Olszewska et al., *Virology* 272:98-105 (2000), the entire disclosure of which is incorporated herein by reference, describe f mice. In addition, Zuercher et al., *Eur. J. Immunol.* 30:128-135 (2000), the entire disclosure of which is incorporated herein by reference, describe compositions and methods for oral anti-IgE immunization using epitope-displaying phage. In particular, epitope-displaying M13 bacteriophages are employed as carriers for an oral anti-IgE vaccine. The vaccine compositions tested contain mimotopes and epitopes of the monoclonal anti-IgE antibody BSW17.

Embodiments of the invention include vaccine compositions which contain mimotopes that elicit immunological responses against particular antigens, as well as individual mimotope/AP205 VLP conjugates which make up these vaccine compositions, and the use of these vaccine compositions to elicit immunological responses against specific antigens or antigenic determinants. Mimotopes may also be polypeptides, such as anti-idiotypic antibodies. Therefore, in a further embodiment of the invention, the antigen or antigenic determinant is an anti-idiotypic antibody or anti-idiotypic antibody fragment.

The invention further includes compositions which contain mimotopes of the antigens or antigenic determinants described herein.

Mimotopes of particular antigens may be generated and identified by any number of means including the screening of random peptide phage display libraries (see, e.g., WO 97/31948, the entire disclosure of which is incorporated herein by reference). Screening of such libraries will often be performed to identify peptides which bind to one or more antibodies having specificity for a particular antigen.

Mimotopes suitable for use in vaccine compositions of the invention maybe linear or circular peptides. Mimotopes which are linear or circular peptides may be linked to non-natural molecular scaffolds or core particles and VLPs, respectively, by a bond which is not a peptide bond.

As suggested above, a number of human IgE mimotopes and epitopes have been identified which elicit immunological responses against human IgE molecules. (See, e.g., WO 97/31948.) Thus, in certain embodiments, vaccine compositions of the invention include compositions which elicit an immunological response against immunoglobin molecules (e.g., IgE molecules).

Peptides which can be used to elicit such immunological responses include proteins, protein subunits, domains of IgE molecules, and mimotopes which are capable of eliciting production of antibodies having specificity for IgE molecules. Generally, portions of IgE molecules used to prepare vaccine compositions will be derived from IgE molecules of the species from which the composition is to be administered. For example, a vaccine composition intended for administration to humans will often contain one or more portions of the human IgE molecule, and/or one or more mimotopes which are capable of eliciting immunological responses against human IgE molecules.

In specific embodiments, vaccine compositions of the invention intended for administration to humans will contain at least one portion of the constant region of the IgE heavy chain set out in Accession No. AAB59424. In more specific embodiments, IgE peptides used to prepare vaccine compositions of the invention comprise, or alternatively consist of, peptides having the following amino acid sequences: <u>CGG</u>VNLTWSRASG (SEQ ID NO: 30).

In additional specific embodiments, vaccine compositions of the invention will contain at least one mimotope which is capable of eliciting an immune response that results in the production of antibodies having specificity for a particular antigen. Examples of mimotopes of IgE suitable for use in the preparation of vaccine compositions of the invention include peptides having the following amino acid sequences:

| Mimotope | SEQ ID NO | Mimotope | SEQ ID NO |
|---|---|---|---|
| INHRGYWV | 31 | VKLPWRFYQV | 39 |
| RNHRGYWV | 32 | VWTACGYGRM | 40 |
| RSRSGGYWLW | 33 | GTVSTLS | 41 |
| VNLTWSRASG | 34 | LLDSRYW | 42 |
| $C_\epsilon H_3$ epitope | | QPAHSLG | 43 |
| VNLPWSRASG | 35 | LWGMQGR | 44 |
| VNLTWSFGLE | 36 | LTLSHPHWVLNHFVS | 45 |
| VNLPWSFGLE | 37 | SMGPDQTLR | 46 |
| $C_\epsilon H_3$ mimotope | | VNLTWS | 47 |
| VNRPWSFGLE | 38 | GEFCINHRGYWVCGDPA | 48 |

Preparation of Vaccines and Immunogens

VLPs of bacteriophage AP205 are useful in generating vaccine constructs, and render antigens attached to it highly immunogenic. The present invention provides methods of attachment of antigens to the AP205 VLP. In one embodiment the antigen is attached to the VLP by way of chemical cross-linking, using a heterobifunctional cross-linker. Several hetero-bifunctional cross-linkers are known to the art. In the some embodiments, the hetero-bifunctional cross-linker contains a functional group which can react with the side-chain amino group of lysine residues of the VLP, and functional group which can react with a cysteine residue naturally present, made available for reaction by reduction, or engineered on the antigen and optionally also made available for reaction by reduction. The first step of the procedure, called the derivatization, is the reaction of the VLP with the cross-linker. The product of this reaction is an activated VLP, also called activated carrier. In the second step, unreacted cross-linker is removed using usual methods such as gel filtration or dialysis. In the third step, the antigen is reacted with the activated VLP, and this step is called the coupling step. Unreacted antigen may be optionally removed in a fourth step. Several hetero-bifunctional cross-linkers are known to the art. These include the cross-linkers SMPH (Pierce), Sulfo-MBS, Sulfo-EMCS, Sulfo-GMBS, Sulfo-SLAB, Sulfo-SMPB, Sulfo-SMCC, SVSB, SIA and other cross-linkers available, for example from the Pierce Chemical Company (Rockford, Ill., USA), and having one functional group reactive towards amino groups and one functional group reactive towards cysteine residues. The above mentioned cross-linkers all lead to formation of a thioether linkage. Another class of cross-linkers suitable in the practice of the invention is characterized by the introduction of a disulfide linkage between the antigen and the VLP upon coupling. Cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength, as is well known from reaction theory in the field of organic chemistry. The degree of coupling, i.e. the amount of antigens per subunits of AP205 VLP can be adjusted by varying the experimental conditions described above to match the requirements of the vaccine. Solubility of the antigen may impose a limitation on the amount of antigen that can be coupled on each subunit, and in those cases where the obtained vaccine is insoluble, reducing the amount of antigens per subunit is beneficial.

One method of attachment of antigens to AP205 VLP, is the linking of a lysine residue on the surface of the AP205 VLP with a cysteine residue on the antigen. In some embodiments, engineering of an amino acid linker containing a cysteine residue to the antigen for coupling to AP205 VLP is required. Alternatively, a cysteine may be introduced either by insertion or mutation within the antigen.

In a preferred embodiment of the present invention, the composition comprsises an amino acid linker. Preferably, said amino acid linker is bound to the at least one antigen, antigenic determinant and organic molecule, respectively, by way of at least one covalent bond. The selection of the amino acid linker will be dependent on the nature of the antigen, on its biochemical properties, such as pI, charge distribution, or glycosylation. In general, flexible amino acid linkers are favored embodiments. Examples of amino acid linkers are the hinge region of Immunoglobulins, glycine serine linkers $(GGGGS)_n$ (SEQ ID NO: 49), and glycine linkers $(G)_n$, all further containing a cysteine residue as second attachment site and optionally further glycine residues. (The following are examples of such amino acid linkers:

```
N-terminal gamma 1:
CGDKTHTSPP                      (SEQ ID NO: 50)

C-terminal gamma 1:
DKTHTSPPCG                      (SEQ ID NO: 51)

N-terminal gamma 3:
CGGPKPSTPPGSSGGAP               (SEQ ID NO: 52)

C-terminal gamma 3:
PKPSTPPGSSGGAPGGCG              (SEQ ID NO: 53)

N-terminal glycine linker:
GCGGGG                          (SEQ ID NO: 54)

C-terminal glycine linker:
GGGGCG                          (SEQ ID NO: 55)

C-terminal glycine-lysine linker:
GGKKGC                          (SEQ ID NO: 56)

N-terminal glycine-lysine linker:
CGKKGG                          (SEQ ID NO: 57)
```

For peptides, GGCG (SEQ ID NO: 58), GGC or GGC-NH2 ("NH2" stands for amidation) linkers at the C-terminus of the peptide, or CGG at its N-terminus have shown to be useful. In some embodiments, glycine residues will be inserted between bulky amino acids and the cysteine to be used as second attachment site.

Preferred embodiments of the amino acid linker are selected from the group consisting of: (a) CGG; (b) N-terminal gamma 1-linker; (c) N-terminal gamma 3-linker; (d) Ig hinge regions; (e) N-terminal glycine linkers; (f) $(G)_kC(G)_n$ with n=0-12 and k=0-5 (SEQ ID NO: 93); (g) N-terminal glycine-serine linkers; (h) $(G)_kC(G)_m(S)_l(GGGGS)_n$ with n=0-3, k=0-5, m=0-10, l=0-2 (SEQ ID NO: 94); (i) GGC; (k) GGC-NH2; (l) C-terminal gamma 1-linker; (m) C-terminal gamma 3-linker; (n) C-terminal glycine linkers; (o) $(G)_nC(G)_k$ with n=0-12 and k=0-5 (SEQ ID NO: 95); (p) C-terminal glycine-serine linkers; (q) $(G)_m(S)_l(GGGGS)_n(G)_oC(G)_k$ with n=0-3, k=0-5, m=0-10, l=0-2, and o=0-8 (SEQ ID NO: 96).

In certain embodiments, the antigen or antigen determinant comprises a single second attachment site or a single reactive attachment site capable of association with the first attachment sites on the AP205 VLPs or VLP subunits, respectively. This ensures a defined and uniform binding and association, respectively, of the at least one, but typically more than one, preferably more than 10, 20, 40, 80, 120 antigens to the AP205 VLP. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine-(as the first attachment site) and cysteine-(as a second attachment site) interaction, it is ensured, in accordance with this preferred embodiment of the invention, that only one cysteine residue per antigen, independent whether this cysteine residue is naturally or non-naturally present on the antigen, is capable of binding and associating, respectively, with the AP205 VLP and the first attachment site of the AP205 VLP, respectively.

The cysteine residue present on the antigen has to be in its reduced state to react with the hetero-bifunctional cross-linker on the activated VLP, that is a free cysteine or a cysteine residue with a free sulfhydryl group has to be available. In the instance where the cysteine residue to function as second attachment site is in an oxidized form, for example if it is forming a disulfide bridge, reduction of this disulfide bridge with e.g. (DTT, TCEP or β-mercaptoethanol is required.

Attachment of the antigen to the AP205 VLP by using a hetero-bifunctional cross-linker according to the method described above, allows coupling of the antigen to the AP205 VLP in an oriented fashion. Other methods of binding the antigen to the AP205 VLP include methods wherein the antigen is cross-linked to the AP205 VLP using the carbodiimide EDC, and NHS. The antigen or antigen determinant may also be first thiolated through reaction, for example with SATA, SATP or iminothiolane. The antigen or antigen determinant, after deprotection if required, may then be coupled to the AP205 VLP as follows. After separation of the excess thiolation reagent, the antigen or antigen determinant is reacted with the AP205 VLP previously activated with a hetero-bifunctional cross-linker comprising a cysteine reactive moiety, and therefore displaying at least one or several functional groups reactive towards cysteine residues, to which the thiolated antigen or antigen determinant can react, such as described above. Optionally, low amounts of a reducing agent are included in the reaction mixture. In other methods, the antigen is attached to the AP205 VLP using a homo-bifunctional cross-linker such as glutaraldehyde, DSG, BM[PEO]$_4$, BS$^3$, (Pierce Chemical Company, Rockford, Ill., USA) or other known homo-bifunctional cross-linkers whith functional groups reactive towards amine groups or carboxyl groups of the AP205 VLP.

In a further embodiment, the antigen or antigen determinant is bound to the AP205 VLP through modification of the carbohydrate moieties present on glycosylated antigen or antigen determinant and subsequent reaction with the AP205 VLP. In one embodiment, the glycosylated antigen or antigen determinant is reacted with sodium periodate in a mild oxidation reaction of the carbohydrate moiety, to yield an activated antigen or antigen determinant with one or more aldehyde functional groups. The so activated antigen or antigen determinant is separated from excess sodium periodate, and further reacted with the AP205 VLP, wherein lysine residues of the AP205 VLP or of at least one AP205 VLP subunit are reacting with the previously formed aldehyde functional group on the antigen or antigen determinant, for example as described by Hermanson, G. T. in *Bioconjugate Techniques*, Academic Press Inc., San Diego, Calif., USA. Self polymerization of the activated antigen or antigen determinant may be controlled by adjusting the pH as described in the aforementioned publication. The formed Schiff base is preferably further reduced with sodium cyanoborohydride, which is subsequently removed by gel filtration or dialysis. Alternatively, carboxyl groups of the AP205 VLP or of at least one of the AP205 VLP subunit may be reacted with EDC and a dihydrazide, such as adipic acid dihydrazyde, to yield a hydrazide moiety available for reaction with the one or more aldehyde functional groups present on the activated antigen or antigen determinant. The so formed hydrazone may be further reduced with sodium cyanoborohydride. Alternatively, the activated antigen or antigen determinant with one or more aldehyde functional groups is reacted with cysteamine, resulting in the introduction of a cysteine group in the antigen or antigen determinant. Additional cross-linking methods and cross-linkers, suitable for binding an antigen or antigen determinant to a AP205 VLP, as well as guidance on performing the coupling reactions and on the use of chemical cross-linkers and chemical cross-linking procedures can be found in Hermanson, G. T. in *Bioconjugate Techniques*, Academic Press Inc., San Diego, Calif., USA.

Other methods of binding the VLP to an antigen include methods where the VLP is biotinylated, and the antigen expressed as a streptavidin-fusion protein, or methods wherein both the antigens and the VLP are biotinylated. In this case, the antigen may be first bound to streptavidin or avidin by adjusting the ratio of antigen to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the antigen, may be used as binding agents for binding the antigen to the VLP. In a preferred embodiment of the present invention, said first and/or said second attachment sites are selected from the group consisting of: (a) an antigen and an antibody or antibody fragment thereto; (b) biotin and avidin; strepavidin and biotin; (c) a receptor and its ligand; (d) a ligand-binding protein and its ligand; (e) interacting leucine zipper polypeptides; (f) an amino group and a chemical group reactive thereto; (g) a carboxyl group and a chemical group reactive thereto; (h) a sulfhydryl group and a chemical group reactive thereto; and (i) a combination thereof.

Immune Responses

The nature or type of immune response is not a limiting factor of this disclosure. The desired outcome of a therapeutic or prophylactic immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or self antigens may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

Furthermore, it may be desired to stimulate different types of immune response depending on the disease, and according to principles known in the art. It is well known, for example, that some immune responses are more appropriate for a particular antigen than other immune responses. Some immune responses are, indeed, inappropriate and can cause pathology, such as pathologic inflammation in response to infection, allergies and autoimmune disease, further described herein. While not desiring certain specific immune responses, the present invention stimulates immune responses towards therapeutic or prophylactic goals. A further particular embodiment of the invention includes the generation of an immune response able to counter the effects of a pathologic immune response.

The nature of the immune response can be affected by the nature of the antigen, route of introduction into the body, dose, dosage regimen, reptitive nature of the antigen, host background, and signalling factors of the immune system. Such knowledge is well known in the art. As such, an immune response may be tailored by the application of both art known theory and routine experimentation.

While not wishing to be bound by theory, the current invention presents particular novel and surprising advantages as a component of a pharmaceutical composition to generate an immune response, and particularly as a vaccine.

Firstly, other carriers known in the art including BSA, keyhole limpet hemocyanin, tetanus toxoid, bacterial outer-membrane proteins, cholera toxin, *Pseudomonas aeruginosa* Exotoxin A and bacterial pili maybe inappropriate for use in an individual, and in particular a human. The aforementioned carriers may induce allergic reactions, or stimulate pathologic immune responses (for example, cholera toxin, KLH, BSA). The aforementioned carriers may require the presence of adjuvants such as complete Freunds adjuvant, now considered innappropriate for use in humans. A number of the carriers may be components of current vaccines (for example, tetanus toxoid, cholera toxin, Exotoxin A), or represent antigens that are commonly encountered (for example, bacterial pili, exotoxin A, outermembrane proteins). As such an individual may possess a high level of pre-existing immunity to these carriers, such that immunization with an antigen-carrier conjugate will induce a relatively greater immune response to the carrier than to the novel antigen. For these reasons, individually or as a whole, the use of AP205 as a carrier protein may represent a useful improvement over current carrier proteins. An AP205-DerP1 conjugate composition is able to stimulate an immune response against DerP1 without the use of complete Freund's adjuvant and without evidence of pathologic immune responses.

In the use of AP205 as a carrier protein, it is possible that AP205-antigen antigens conjugated to AP205 can be taken up by antigen presenting cells and thereby stimulate T-cell help to induce immune response. Further, haptens, which are normally non immunogenic, may be coupled to AP205 thereby generating an immune response against such haptens.

A further advantageous feature of the invention is that antigens may be presented on the surface of a VLP in regular, repetitive arrays that are able to induce efficient immune responses both with and without T-cell help. This feature of the invention is particularly advantageous.

The present invention thus provides methods for improving the efficiency of vaccination, particularly against self-antigens, by increasing the degree of repetitiveness of the antigen to be used for immunization, through binding of the antigen to the AP205 VLP. Compositions, Vaccines, and the Administration Thereof, and Methods of Treatment The invention provides vaccine compositions which may be used for preventing and/or attenuating diseases or conditions. The invention further provides vaccination methods for preventing and/or attenuating diseases or conditions in individuals.

In one embodiment, the invention provides vaccines for the prevention of infectious diseases in a wide range of species, particularly mammalian species such as human, monkey, cow, dog, cat, horse, pig, etc. Vaccines may be designed to treat infections of viral etiology such as HIV, influenza, Herpes, viral hepatitis, Epstein Barr, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

In another embodiment, the invention provides vaccines for the prevention and treatment of cancer in a wide range of species, particularly mammalian species such as human, monkey, cow, dog, cat, horse, pig, etc. Vaccines may be designed to treat all types of cancer: lymphomas, carcinomas, sarcomas, melanomas, etc.

In another embodiment of the invention, conjugates, compositions and methods of the invention may be used in the design of vaccines for the treatment of allergies. Antibodies of the IgE isotype are important components in allergic reactions. Mast cells bind IgE antibodies on their surface and release histamines and other mediators of allergic response upon binding of specific antigen to the IgE molecules bound on the mast cell surface. Inhibiting production of IgE antibodies, therefore, is a promising target to protect against allergies. This should be possible by attaining a desired T helper cell response. T helper cell responses can be divided into type 1 ($T_H1$) and type 2 ($T_H2$) T helper cell responses (Romagnani, *Immunol. Today* 18:263-266 (1997)). $T_H1$ cells secrete interferon-gamma and other cytokines. In contrast, a critical cytokine produced by $T_H2$ cells is IL-4, which drived B cells to produce IgE. In many experimental systems, the development of $T_H1$ and $T_H2$ responses is mutually exclusive since $T_H1$ cells suppress the induction of $T_H2$ cells and vice versa. Thus, antigens that trigger a strong $T_H1$ response simultaneously suppress the development of $T_H2$ responses and hence the production of IgE antibodies. It is finding of the present invention that AP205 VLP induce a $T_H1$-type immune response. Thus, by using the processes of the invention, AP205 VLPs can be decorated with various allergens and used for immunization. Due to the coupling of the allergen to AP205 VLP, a $T_H1$ response will be elicited, "protective" IgG antibodies will be produced, and the production of IgE antibodies which cause allergic reactions will be prevented. Since the allergen is presented by VLPs which are recognized by a different set of helper T cells than the allergen itself, it is likely that the allergen-specific IgG antibodies will be induced even in allergic individuals harboring pre-existing $T_H2$ cells specific for the allergen. The presence of high concentrations of IgG antibodies may prevent binding of allergens to mast cell bound IgE, thereby inhibiting the release of histamine. Thus, presence of IgG antibodies may protect from IgE mediated allergic reactions. Typical substances causing allergies include but are not limited to: pollens (e.g. grass, ragweed, birch or mountain cedar pollens), house dust, mites, mammalian epidermal allergens and animal danders, mold and fungus, insect bodies and insect venom, hair, saliva, serum, feathers, food or drugs (e.g., penicillin) See Shough, H. et al., REMINGTON'S PHARMACEUTICAL SCIENCES, 19th edition, (Chap. 82), Mack Publishing Company, Mack Publishing Group, Easton, Pa. (1995), the entire contents of which is hereby incorporated by reference.

In specific embodiments, the invention provides methods for preventing and/or attenuating diseases or conditions which are caused or exacerbated by "self" gene products (e.g., tumor necrosis factors), i.e. "self antigens" as used herein. In related embodiments, the invention provides methods for inducing immunological responses in individuals which lead to the production of antibodies that prevent and/or attenuate diseases or conditions are caused or exacerbated by "self" gene products. Examples of such diseases or conditions include graft versus host disease, IgE-mediated allergic reactions, anaphylaxis, adult respiratory distress syndrome, Crohn's disease, allergic asthma, acute lyrnphoblastic leukemia (ALL), non-Hodgkin's lymphoma (NHL), Graves' disease, inflammatory autoimmune diseases, myasthenia gravis, systemic lupus erythematosus (SLE), immunoproliferative disease lymphadenopathy (IPL), angioimmunoproliferative lymphadenopathy (AIL), immunoblastive lymphadenopathy (IBL), rheumatoid arthritis, diabetes, multiple sclerosis, osteoporosis and Alzheimer's disease.

As would be understood by one of ordinary skill in the art, when compositions of the invention are administered to an individual, they may be in a composition which contains salts, buffers, adjuvants, or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1990)).

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention may be administered by various methods known in the art, but will normally be administered by injection, infusion, inhalation, oral administration, or other suitable physical methods. The compositions are, alternatively, administered intramuscularly, intravenously, transmucosally, transdermally or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Other embodiments of the invention include processes for the production of the compositions of the invention and methods of medical treatment using these compositions. It is to be understood that both the foregoing general description and the following detailed description are exemplary and explanatory only and are intended to provide further explanation of the invention as claimed.

In addition to vaccine technologies, other embodiments of the invention are drawn to methods of medical treatment for cancer and allergies, and for methods of treatment of diseases or conditions which are caused or exacerbated by "self" gene products.

All patents and publications referred to herein are expressly incorporated by reference in their entirety.

Kits

In other embodiments, the compositions of the present invention may be assembled into kits for use in detection in assays or industrial settings, in diagnosis or detection of diseases, conditions or disorders. Such kits according to the present invention may comprise at least one container containing one or more of the above-described conjugates or compositions, including AP205 conjugates and immune molecules and antibodies, respectively, directed against such conjugates. The kits of the invention may optionally further comprise at least one additional container which may contain, for example, one or more antigens, one or more haptens, one or more core particles, one or more conjugates/compositions of the invention, one or more pharmaceutically acceptable carriers or excipients, one or more buffers, one or more proteins, one or more nucleic acid molecules, and the like.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Cloning of the AP205 Coat Protein gene

The cDNA of AP205 coat protein (CP) was assembled from two cDNA fragments generated from phage AP205 RNA by using a reverse transcription-PCR technique and cloning in the commercial plasmid pCR 4-TOPO for sequencing. Reverse transcription techniques are well known to those of ordinary skill in the relevant art. The first fragment, contained in plasmid p205-246, contained 269 nucleotides upstream of the CP sequence and 74 nucleotides coding for the first 24 N-terminal amino acids of the CP. The second fragment, contained in plasmid p205-262, contained 364 nucleotides coding for amino acids 12-131 of CP and an additional 162 nucleotides downstream of the CP sequence The plasmid 283.-58 was designed by two-step PCR, in order to fuse both CP fragments from plasmids p205-246 and p205-262 in one full-length CP sequence.

An upstream primer p1.44 containing the NcoI site for cloning into plasmid pQb185, or p1.45 containing the XbaI site for cloning into plasmid pQb 10, and a downstream primer p1.46 containing the HindIII restriction site were used (recognition sequence of the restriction enzyme underlined):

```
p1.44
                                    (SEQ ID NO: 59)
5'-AACC ATG GCA AAT AAG CCA ATG CAA CCG-3' p1.45
                                    (SEQ ID NO: 60)
5'-AATCTAGAATTTTCTGCGCACCCATCCCGG-3' p1.46
                                    (SEQ ID NO: 61)
5'-AAAAGC TTA AGC AGT AGT ATC AGA CGA TAC G-3'
```

Two additional primers, p1.47, annealing at the 5' end of the fragment contained in p205-262, and p1.48, annealing at the 3' end of the fragment contained in plasmid p205-246 were used to amplify the fragments in the first PCR. Primers p1.47 and p1.48 are complementary to each other.

```
p1.47:
                                    (SEQ ID NO: 62)
5'-GAGTGATCCAACTCGTTTATCAACTACATTT-TCAGCAAGTCTG-3' p1.48:
                                    (SEQ ID NO: 63)
5'-CAGACTTGCTGAAAATGTAGTTGATAAACGA-GTTGGATCACTC-3'
```

In the first two PCR reactions, two fragments were generated. The first fragment was generated with primers p1.45 and p1.48 and template p205-246. The second fragment was generated with primers p1.47 and p1.46, and template p205-262. Both fragments were used as templates for the second PCR reaction, a splice-overlap extension, with the primer combination p1.45 and p1.46 or p1.44 and p1.46. The product of the two second-step PCR reactions were digested with XbaI or NcoI respectively, and HindIII, and cloned with the same restriction sites into pQb10 or pQb185 respectively, two pGEM-derived expression vectors under the control of E.coli tryptophan operon promoter.

Two plasmids were obtained, pAP283-58 (SEQ ID NO.2) containing the gene coding for wt AP205 CP (SEQ ID NO: 1) in pQb10, and pAP281-32 (SEQ ID NO: 4) containing the nucleotide sequence of SEQ ID NO: 125 encoding for the mutein with mutation Pro5→Thr having the amino acid sequence of SEQ ID NO: 3 in pQb185. The coat protein sequences were verified by DNA sequencing. PAP283-58 contains 49 nucleotides upstream of the ATG codon of the CP, downstream of the XbaI site, and contains the putative original ribosomal binding site of the coat protein mRNA.

Example 2

Expression and Purification of Recombinant AP205 VLP

A. Expression of Recombinant AP205 VLP

E.coli JM109 was transformed with plasmid pAP283-58. 5 ml of LB liquid medium with 20 μg/ml ampicillin were inoculated with a single colony, and incubated at 37° C. for 16-24 h without shaking.

The prepared inoculum was diluted 1:100 in 100-300 ml of LB medium, containing 20 μg/ml ampicillin and incubated at 37° C. overnight without shaking. The resulting second inoculum was diluted 1:50 in 2TY medium, containing 0.2% glucose and phosphate for buffering, and incubated at 37° C. overnight on a shaker. Cells were harvested by centrifugation and frozen at −80° C.

B. Purification of Recombinant AP205 VLP
  Solutions and Buffers:
  Lysis Buffer
  50 mM Tris-HCl pH 8.0 with 5mM EDTA, 0.1% tritonX100 and PMSF at 5 micrograms per ml.
  SAS
  Saturated ammonium sulphate in water
  Buffer NET.
  20 mM Tris-HCl, pH 7.8 with 5 mM EDTA and 150 mM NaCl.
  PEG
  40% (w/v) polyethylenglycol 6000 in NET
  Lysis:
  Frozen cells were resuspended in lysis buffer at 2 ml/g cells. The mixture was sonicated with 22 kH five times for 15 seconds, with intervals of 1 min to cool the solution on ice. The lysate was then centrifuged for 20 minutes at 12000 rpm, using a F34-6-38 rotor (Ependorf). The centrifugation steps described below were all performed using the same rotor, except otherwise stated. The supernatant was stored at 4° C., while cell debris were washed twice with lysis buffer. After centrifugation, the supernatants of the lysate and wash fractions were pooled.

Ammonium-sulphate precipitation can be further used to purify AP205 VLP. In a first step, a concentration of ammonium-sulphate at which AP205 VLP does not precipitate is chosen. The resulting pellet is discarded. In the next step, an ammonium sulphate concentration at which AP205 VLP quantitatively precipitates is selected, and AP205 VLP is isolated from the pellet of this precipitation step by centrifugation (14000 rpm, for 20 min). The obtained pellet is solubilised in NET buffer.

Chromatography:

The capsid protein from the pooled supernatants was loaded on a Sepharose 4B column (2.8×70 cm), and eluted with NET buffer, at 4 ml/hour/fraction. Fractions 28-40 were collected, and precipitated with ammonium sulphate at 60% saturation. The fractions were analyzed by SDS-PAGE and Western Blot with an antiserum specific for AP205 VLP coat protein prior to precipitation. The pellet isolated by centrifugation was resolubilized in NET buffer, and loaded on a Sepharose 2B column (2.3×65 cm), eluted at 3 ml/h/fraction. Fractions were analysed by SDS-PAGE, and fractions 44-50 were collected, pooled and precipitated with ammonium sulphate at 60% saturation. The pellet isolated by centrifugation was resolubilized in NET buffer, and purified on a Sepharose 6B column (2.5×47 cm), eluted at 3 ml/hour/fraction. The fractions were analysed by SDS-PAGE. Fractions 23-27 were collected, the salt concentration adjusted to 0.5 M, and precipitated with PEG 6000, added from a 40% stock in water and to a final concentration of 13.3%. The pellet isolated by centrifugation was resolubilized in NET buffer, and loaded on the same Sepharose 2B column as above, eluted in the same manner. Fractions were analyzed by SDS-PAGE. Fractions 43-53 were collected, and precipitated with ammonium sulphate at a saturation of 60%. The pellet isolated by centrifugation was resolubilized in water, and the obtained protein solution was extensively dialyzed against water. About 10 mg of purified protein per gram of cells could be isolated. Purification of AP 205 VLPs could be shown, which was analysed by SDS PAGE and Western-blotting. Fractions of recombinant AP205 VLP of the first Sepharose 4B chromatography step as well as of the last Sepharose 2B chromatography step could be shown on the silver-stained SDS-PAGE run under reducing conditions as well as by Western blotting with an anti-serum specific for AP205 VLP coat protein.

Figure 1A:
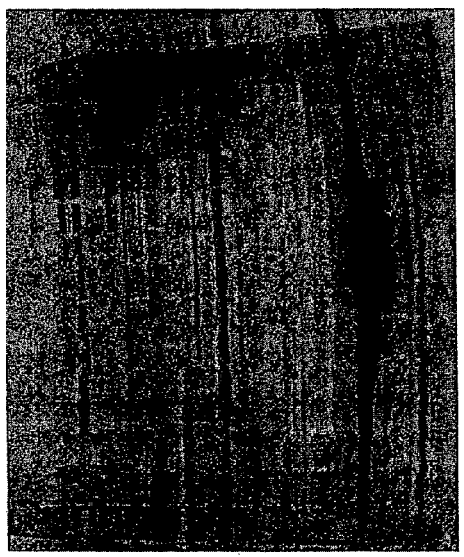
FIGS. 1A-C depict purification of AP205 proteins for use in VLPs, as analyzed by SDS PAGE and Western-blotting.
Figure 1B:
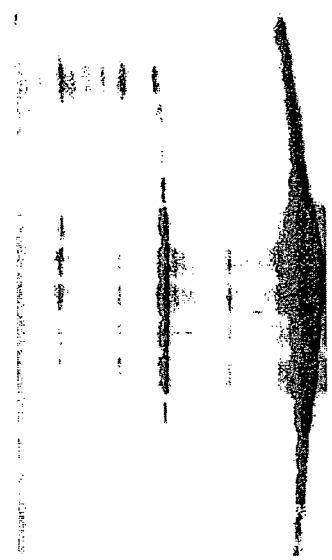
Figure 1C:
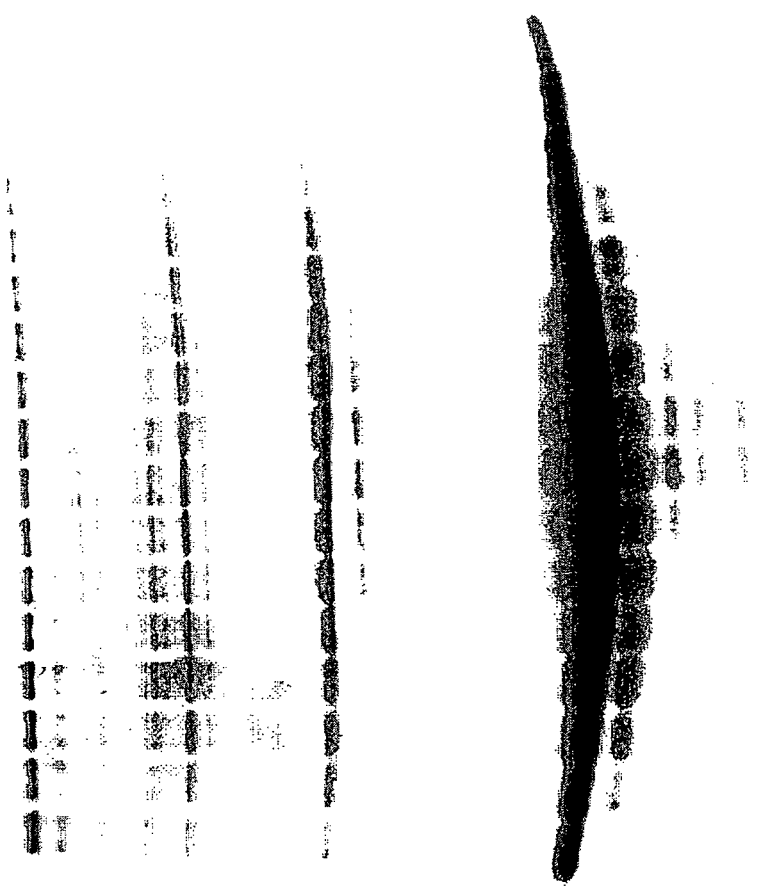
Figure 1E:
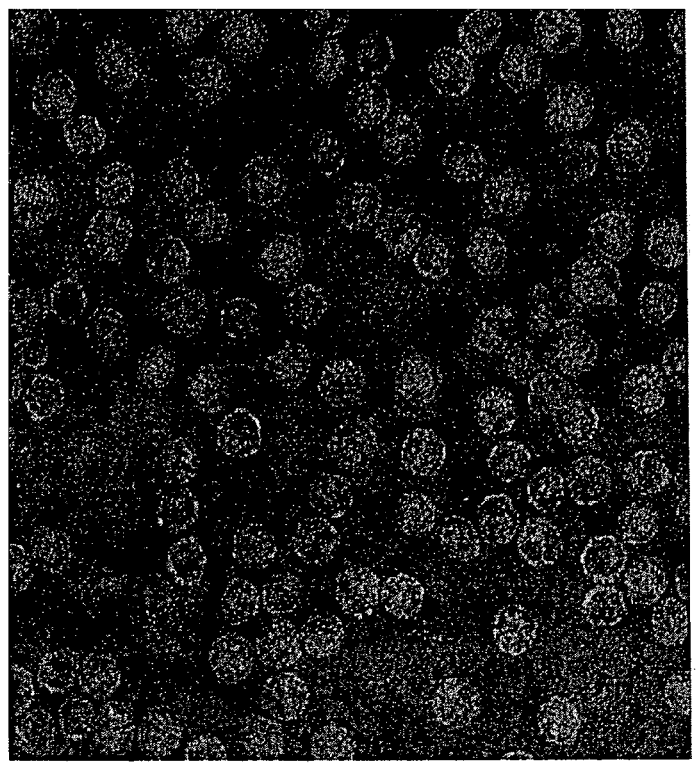
FIGS. 1D and E depict electron micrographs comparing AP205 phage particles to AP205 virus like particles spontaneously assembled from recombinant protein expressed in *E. coli* and purified.
Figure 1D:
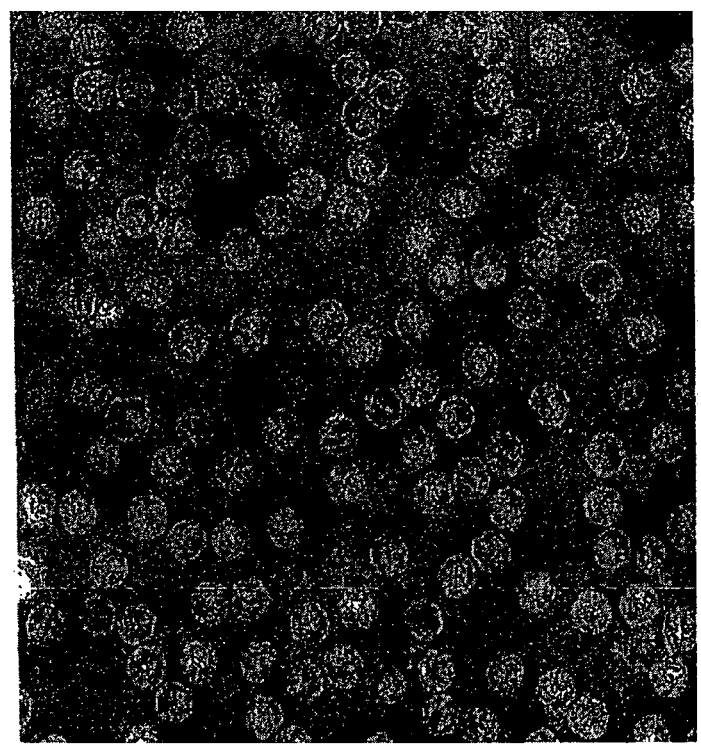

Examination of the virus-like particles in Electron microscopy showed that they were identical to the phage particles (FIGS. 1D and 1E).

FIG. 1A shows an EM picture of AP205 phage particles, while an EM picture of self assembled particles of recombinant AP205 VLP is shown in FIG. 1E.

For the sake of simplicity, the term "AP205 virus-like particle" and the term "AP205 VLP", as used within the Example Section, refers to a virus-like particle expressed and purified as described in Example 2 and composed of coat proteins having an amino acid sequence as set forth in SEQ ID NO:1.

Example 3

Coupling of Derp1.2 and Flag Peptide Antigen to AP205 VLP, and Immunization of Mice with Derp1.2 Peptide Coupled to AP205 VLP A. Coupling of Derp1.2 Peptide and Flag Peptide to Recombinant AP205 VLP The peptide Derp1.2 (sequence: CQIYPPNANKIRE-ALAQTHSA "Derp 1 p117"; aa 117-137 (SEQ ID NO: 64)) and Flag (sequence: CGGDYKDDDDK (SEQ ID NO: 65)) were chemically synthesized according to art-known methods. AP205 VLP, expressed and purified as described in example 2, was resolubilized in 20 mM Hepes, 150 mM NaCl, pH 7.4 buffer (HBS buffer). Resolubilized AP205 VLP was then reacted at a concentration of 2 mg/ml (determined in a Bradford assay), with 2.85 mM SMPH (Pierce) for 30 minutes at room temperature (RT). The reaction mixture was then dialyzed against HBS buffer, and reacted with 0.714 mM Derp1.2 or FLAG, diluted in the reaction mixture from a 50 mM stock in DMSO. The coupling reaction was left to proceed for 2 hours at 15° C., and the reaction mixture dialyzed 2×2 hours against a 1000-fold volume HBS, and flash frozen in liquid nitrogen in aliquots for storage at −80° C. until further use.

Figure 2:
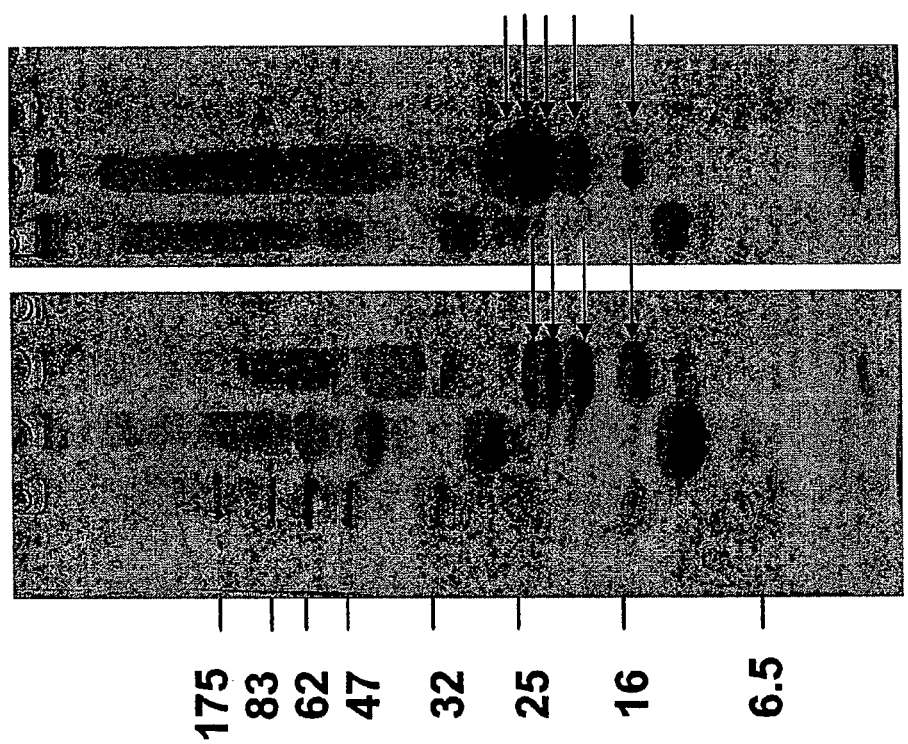
FIG. 2 shows the SDS-PAGE analysis of the coupling reaction of AP205 VLP and Qβ VLP to Derp 1.2 peptide. The samples were run under reducing conditions on a 16% Tris-glycine gel. Lane 1 is the protein marker, with corresponding molecular weights indicated on the left border of the gel; lane 2, derivatized Qβ capsid protein; lane 3, the supernatant of the coupling reaction of Qβ capsid protein to the Derp1.2 peptide; lane 4, the pellet of the coupling reaction of Qβ capsid protein to the Derp1.2 peptide; lane 5, derivatized AP205 VLP; lane 6, the supernatant of the coupling reaction of AP205 VLP to the Derp1.2 peptide; lane 7, the pellet of the coupling reaction of AP205 VLP to the Derp1.2 peptide. Coupling products corresponding to the coupling of 1, 2, 3 , 4 and respectively 5 peptides per monomer are indicated by arrows in the Figure. A higher number of epitopes could be coupled to AP205 VLP than to Qβ capsid protein.

An aliquot was thawed, and coupling of the antigen to an AP205 subunit assessed by SDS-PAGE and the protein concentration measured in a Bradford assay. The result of the coupling reaction of Derp 1.2 to AP205 VLP is shown in FIG. 2. The monomer subunit of AP205 VLP has a molecular weight of 14 kDa. Upon derivatization of AP205 VLP with the cross-linker, dimers, trimers, tetramers, pentamers and hexamers produced by cross-linking, are detected in SDS-PAGE in addition to the monomer form of the subunit.

FIG. 2 shows the SDS-PAGE analysis of the coupling reaction of AP205 VLP and Qβ VLP to Derp1.2 peptide. The samples were run under reducing conditions on a 16% Tris-glycine gel. Lane 1 is the protein marker, with corresponding molecular weights indicated on the left border of the gel; lane 2, derivatized Qβ capsid protein; lane 3, the supernatant of the coupling reaction of Qβ capsid protein to the Derp1.2 peptide; lane 4, the pellet of the coupling reaction of Qβ capsid protein to the Derp1.2 peptide; lane 5, derivatized AP205 VLP; lane 6, the supernatant of the coupling reaction of AP205 VLP to the Derp1.2 peptide; lane 7, the pellet of the coupling reaction of AP205 VLP to the Derp1.2 peptide. Coupling products corresponding to the coupling of 1, 2, 3 ,4 and respectively 5 peptides per monomer are indicated by arrows in the Figure. A higher number of epitopes could be coupled to AP205 VLP than to Qβ capsid protein.

B. Immunization of Mice with Derp1.2 Peptide Coupled to Recombinant AP205 VLP Analysis of Immune Response and IgG Subtype Determination AP205 VLP coupled to Derp1.2 peptide or Qβ VLP coupled to Derp1.2 peptide were injected s.c. in mice (3 mice each) at day 0 and 14. Derp1.2 peptide was coupled to Qβ capsid protein using the same conditions as described under A for the coupling to AP205 VLP. Each mice was immunized with 10 μg of vaccine diluted in PBS to 200 μl. Mice were retroorbitally bled on day 20, and the titer of the antibodies specific for the Derp1.2 peptide were measured in an ELISA against Derp1.2 peptide. The Der p I peptide "Der p I p52" was coupled to bovine RNAse A using the chemical cross-linker sulfo-SPDP. ELISA plates were coated with coupled RNAse preparations at a concentration of 10 μg/ml. The plates were blocked and then incubated with serially diluted mouse sera. Bound antibodies were detected with enzymatically labeled anti-mouse IgG antibodies specific for the respective subtypes. As a control, preimmune sera of the same mice were also tested (data not shown). The results are shown in FIG. 3.

Figure 3:
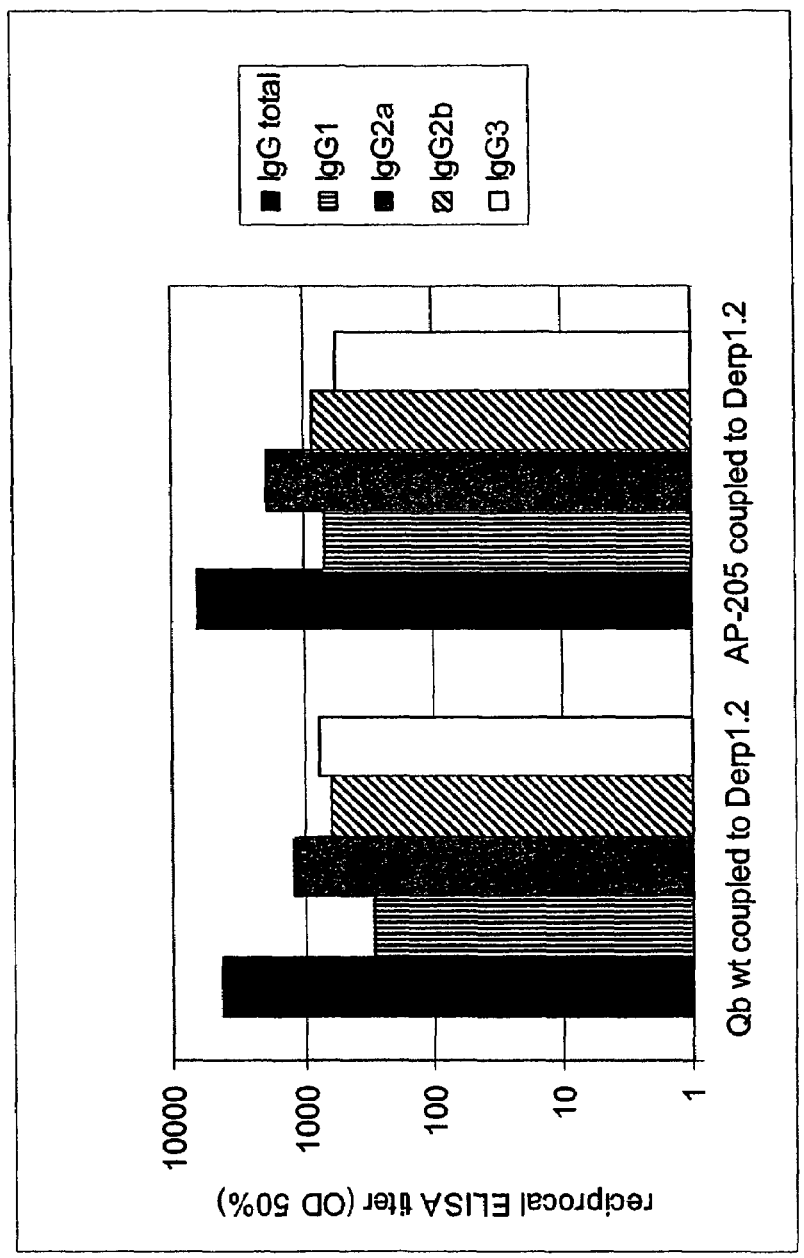
FIG. 3 shows an ELISA analysis of the IgG antibodies specific for "Derp 1.2" in sera of mice immunized against the Derp1.2 peptide coupled to AP205 VLP or Qβ capsid protein respectively. Total IgG titers, as well as IgG subtype titers were determined. No antibodies specific for Derp1.2 could be detected in any of the preimmune sera analysed for each of the IgG subtypes. The figure shows that for both AP205 and Qβ, subtypes typical of a Th1 immune response are induced, as the IgG2a titer is much higher than the IgG1 titer. A strong specific anti-peptide immune response was obtained with the peptide coupled to both VLPs. Antibodies specific for the carrier were also measured by ELISA, and these were comparable for both carriers.

FIG. 3 shows an ELISA analysis of the IgG antibodies specific for "Derp 1.2" in sera of mice immunized against the Derp1.2 peptide coupled to AP205 VLP or Qβ capsid protein respectively. Total IgG titers, as well as IgG subtype titers were determined. No antibodies specific for Derp1.2 could be detected in any of the preimmune sera analysed for each of the IgG subtypes. The figure shows that for both AP205 and Qβ, subtypes typical of a Th1 immune response are induced, as the IgG2a titer is much higher than the IgG1 titer. A strong specific anti-peptide immune response was obtained with the peptide coupled to both VLPs. Antibodies specific for the carrier were also measured by ELISA, and these were comparable for both carriers.

Example 4

Modular Eukaryotic Expression System for Coupling of Antigens to VLPs

This system was generated in order to add various amino acid linker sequences containing a cysteine residue to antigens for chemical coupling to VLPs.

A. Construction of an EBNA-derived Expression System Encoding a Cysteine-containing Amino Acid Linker and Cleavable Fc-Tag:

pCep-Pu (Wuttke et al. *J. Biol. Chem.* 276: 36839-48 (2001)) was digested with KpnI and BamHI and a new multiple cloning site was introduced with the annealed oligonucleotides PH37 and PH38 leading to pCep-MCS.

A modular system containing a free cysteine flanked by several glycines, a protease cleavage site and the constant region of the human IgG1 was generated as follows. pSec2/Hygro B (Invitrogen Cat. No. V910-20) was digested with Bsp120I and HindIII and ligated with the annealed oligonucleotides SU7 and SU8 leading to construct pSec-B-MCS. pSec-B-MCS was then digested with NheI and HindIII and ligated with the annealed oligonucleotides PH29 and PH30 leading to construct pSec 29/30. The construct pSec-FL-EK-Fc* was generated by a three fragment ligation of the following fragments; first pSec 29/30 digested with EcoRI and HindIII, the annealed oligonucleotides PH31 and PH32 and the BglI/EcoRI fragment of a plasmid (pSP-Fc*-C1) containing a modified version of the human IgG1 constant region (for details of the hu IgG1 sequence see the sequence of the final construct pCep-Xa-Fc* (FIG. 4A-4C). The resulting construct was named pSec-FL-EK-Fc*. From this plasmid the linker region and the human IgGl Fc part was excised by NheI, PmeI digestion and cloned into pCep-MCS digested with NheI and PmeI leading to construct pCep-FL-EK-Fc*. Thus a modular vector, was created where the linker sequence and the protease cleavage site, which are located between the NheI and HindIII sites, can easily be exchanged with annealed oligonucleotides. For the generation of cleavable fusion protein vectors pCep-FL-EK-Fc* was digested with NheI and HindIII and the Factor Xa cleavage site N-terminally flanked with amino acids GGGGCG (SEQ ID NO: 55) was introduced with the annealed oligonuclotides PH35 and PH36 and the enterokinase site flanked n-terminally with GGGGCG (SEQ ID NO: 55) was introduced with the annealed oligonucleotides PH39 and PH40 leading to the constructs pCep-Xa-Fc* (FIG. 4A, nucleotide sequence as set forth in SEQ ID NO: 103, amino acid sequence as set forth in SEQ ID NO: 104) and pCep-EK-Fc* (FIG. 4B, nucleotide sequence as set forth in SEQ ID NO: 105, amino acid sequence as set forth in SEQ ID NO: 106) respectively. The construct pCep-SP-EK-Fc* (FIG. 4C, nucleotide sequence as set forth in SEQ ID NO: 107, amino acid sequence as set forth in SEQ ID NO: 108) which in addition contains a eukaryotic signal peptide was generated by a three fragment ligation of pCep-EK-Fc* digested KpnI/BamHI, the annealed oligos PH41 and PH42 and the annealed oligos PH43 and PH44.

B. Large Scale Production of Fusion Proteins:

For the large scale production of the different fusion proteins 293-EBNA cells (Invitrogen) were transfected with the different pCep expression plasmids with Lipofectamine 2000 reagent (Invitrogen Corporation; Carlsabad, Calif.) according to the manufacturer's recommendation. 24-36 h post transfection the cells were split at a 1 to 3 ratio under puromycin selection (1 μg/ml) in DMEM supplemented with 10% FCS. The resistant cells were then expanded in selective medium. For the harvesting of the fusion proteins the resistant cell population were passed onto poly-L-lysine coated dishes. Once the cells had reached confluence, they were washed 2 times with PBS and serum free medium (DMEM) was added to the plates. The tissue culture supernatant were harvested every 2 to 4 days and replaced with fresh DMEM medium during a period of up to one month. The harvested supernatants were kept at 4° C.

C. Purification of the Fusion Proteins:

The recombinant Fc-fusion proteins were purified by affinity chromatography using protein A sepharose CL-4B (Amersham Pharmacia Biotech AG). Briefly chromatography columns were packed with 1-3 ml protein A resin and the tissue culture supernatants containing the recombinant proteins were applied to the column with a peristaltic pump at a flow rate of 0.5-1.5 ml/min. The column was then washed with 20-50 ml PBS. Depending on the fusion protein the protease cleavage was performed on the column or the protein was eluted as described below. Recombinant fusion proteins were eluted with a citrate/phosphate buffer (pH 3.8) supplemented with 150 mM NaCl and the fractions containing the protein were pooled and concentrated with ultrafree centrifugal filters (Millipore Corporation; Bedford, Mass.).

D. Protease Cleavage of Recombinant Fusion Proteins (Factor Xa, Enterokinase):

Eluted recombinant fusion proteins containing the enterokinase (EK) cleavage site were cleaved using the EKmax system (Invitrogen) according to the manufacturer's recommendation. The cleaved Fc part of the fusion protein was removed by incubation with protein A. The enterokinase was then removed with the EK-Away system (Invitrogen Corporation; Carlsbad, Calif.) according to the manufacturers recommendation. Similarly fusion proteins containing the factor Xa (Xa) cleavage site were cleaved using the restriction protease factor Xa cleavage and removal kit (Roche) according to the manufacturer's recommendation. The cleaved Fc part was removed by incubation with protein A and the protease was removed with the streptavidin resin provided with the kit.

The different fusion proteins were concentrated with ultrafree centrifugal filters (Millipore Corporation; Bedford, Mass.), quantitated by UV spectrophotometrie and used for subsequent coupling reactions.

FIG. 4A-4C shows partial sequences of the different eukaryotic expression vectors used. Only the modified sequences are shown.

FIG. 4A: pCep-Xa-Fc*: the sequence is shown from the BamHI site onwards and different features are shown above the translated sequence (SEQ ID NO: 103 and SEQ ID NO: 104). The arrow indicates the cleavage site of the factor Xa protease.

FIG. 4B: pCep-EK-Fc*: the sequence is shown from the BamHI site onwards and different features are shown above the translated sequence (SEQ ID NO: 105 and SEQ ID NO: 106). The arrow indicates the cleavage site of the enterokinase. The sequence downstream of the HindIII site is identical to the one shown in FIG. 4A.

FIG. 4C: pCep-SP-EK-Fc*: the sequence is shown from the beginning of the signal peptide on and different features are shown above the translated sequence (SEQ ID NO: 107 and SEQ ID NO: 108). The signal peptide sequence which is cleaved of by the signal peptidase is shown in bold The arrow indicates the cleavage site of the enterokinase. The sequence downstream of the HindIII site is identical to the one shown in FIG. 4A.

Example 5

Eukaryotic Expression and Coupling of Mouse Resistin to AP205 VLP

A. Cloning of Mouse Resistin:

Total RNA was isolated from 60 mg mouse adipose tissue using a Qiagen RNeasy kit according to the manufacturer's recommendation. The RNA was eluted in 40 µl H$_2$O. This total RNA was than used for the reverse transcription with an oligo dT primer using the ThermoScript™ RT-PCR System (Invitrogen Corporation; Carlsbad, Calif.) according to the manufacturer's recommendation. The sample was incubated at 50° C. for 1h, heated to 85° C. for 5 minutes and treated for 20 minutes at 37° C. with RNAseH.

2 µl of the RT reaction were used for the PCR amplification of mouse resistin. The PCR was performed using Platinium TAQ (Invitrogen Corporation; Carlsbad, Calif.) according to the manufacturer's recommendation using primers PH19 and PH20. Primer PH19 corresponds to positions 58-77 and primer PH20 to positions 454-435 of the mouse Resistin sequence. The PCR mix was first denatured at 94° C. for 2 minutes and than 35 cycles were performed as follows: 30 seconds 94° C., 30 seconds 56° C. and 1 minute 72° C., at the end the samples were left for 10 minutes at 72° C. The PCR fragment was purified and subcloned by TA cloning into the pGEMTeasy vector (Invitrogen Corporation; Carlsbad, Calif.) leading to pGEMT-mRes. In order to add appropriate restriction sites a second PCR was performed on pGEMT-mRes with the primers PH21 and PH22 primers using the same cycling program as described above. The forward primer PH21 contains a BamHI site and nucleotides 81-102 of the mouse Resistin sequence. The reverse primer PH22 contains an XbaI site and nucleotides 426-406 of the mouse Resistin sequence. The indicated positions refer to the mouse resistin sequence Gene Accession No. AF323080. The PCR product was purified and digested with BamHI and XbaI and subcloned into pcmv-Fc*-C1 digested with BamHI and XbaI leading to the construct pcmv-mRes-Fc*.

The Resistin open reading frame was excised from pcmv-Res-Fc* by BamHI/XbaI digestion and cloned into pCep-Xa-Fc* and pCep-EK-Fc* (see EXAMPLE 4, section B) digested with BamHI and NheI leading to the constructs pCep-mRes-Xa-Fc* and pCep-mRes-EK-Fc* respectively.

B. Production, Purification and Cleavage of Resistin pCep-mRes-Xa-Fc* and pCep-mRes-EK-Fc* constructs were then used to transfect 293-EBNA cells for the production of recombinant proteins as described in EXAMPLE 4, section B. The tissue culture supernatants were purified as described in EXAMPLE 4, section C. The purified proteins were then cleaved as described in EXAMPLE 4, section D. The resulting recombinant proteins were termed "resistin-C-Xa" or "Res-C-Xa" and "resistin-C-EK" or "Res-C-EK" according to the vector used. The purified proteins were analyzed by SDS PAGE. Bands corresponding to purified resistin-C-EK and purified resistin-C-Xa were clearly visible on the gel.

SEQ ID NO: 109, SEQ ID NO: 110, SEQ ID NO: 111, and SEQ ID NO: 112 show sequences of precursor recombinant mouse Resistin proteins used for expression. Processed recombinant mouse resistin used for coupling, i.e. Res-C-Xa and Res-C-EK, are shown in FIGS. 2A and 2B of WO 02/056905. The resistin signal sequence which is cleaved upon protein secretion by the signal peptidase is shown in italic. The amino acid sequences which result form signal peptidase and specific protease (factor Xa or enterokinase) cleavage are shown bold.

C. Coupling of Resistin-C-Xa and Resistin-C-EK to AP205 VLP

A solution of 0.2 ml of 2 mg/ml AP205 VLP in 20 mM Hepes, 150 mM NaCl pH 7.4 is reacted for 30 minutes with 5.6 µl of a solution of 100 mM SMPH (Pierce) in DMSO at 25° C. on a rocking shaker. The reaction solution is subsequently dialyzed twice for 2 hours against 1 L of 20 mM Hepes, 150 mM NaCl, pH 7.4 at 4° C. 8 µl of the dialyzed AP205 capsid protein reaction mixture is then reacted with 32 µl of resistin-C-Xa solution (resulting in a final concentration of resistin of 0.39 mg/ml) and 13 µl of the AP205 capsid protein reaction mixture is reacted with 27 pl resistin-C-EK solution (resulting in a final concentration of resistin of 0.67 mg/ml) for four hours at 25° C. on a rocking shaker. Coupling products are analysed by SDS-PAGE and Western blot under reducing conditions.

Example 6

Expression, Purification and Coupling of Murine Lymphotoxin-β, Constructs to AP205 VLP A. Introduction of Cys-containing Linkers, Expression and Purification of Mouse Lymphotoxin-β

The extracellular part of mouse lymphotoxin-β (LT-β) was recombinantly expressed with a CGG amino acid linker at its N-terminus. The linker contained one cysteine for coupling to VLP. A long (aa 49-306) and a short version (aa 126-306) of the protein were fused at their N-terminus to either glutathione S-transferase (GST) or a histidin-myc tag for purification. An enterokinase (EK) cleavage-site was inserted for cleavage of the tag.

Construction of C-LT-β49-306 and C-LT-β26-306.

Mouse LT-β49-306 was amplified by PCR with oligos 5' LT-β and 3' LT-β from a mouse spleen cDNA library inserted into pFB-LIB. For the PCR reaction, 0.5 µg of each primer and 200 ng of the template DNA was used in the 50 µl reaction mixture (1 unit of PFX Platinum polymerase, 0.3 mM dNTPs and 2 mM MgSO$_4$). The temperature cycles were as follows: 94° C. for 2 minutes, followed by 25 cycles of 94° C. (15 seconds), 68° C. (30 seconds), 68° C. (1 minute) and followed by 68° C. for 10 minutes. The PCR product was phosphorylated with T4 Kinase and ligated into pEntry1A (Life technologies) which has been cut with EcoRV and has been dephosphorylated. The resulting plasmid was named pEntry1A-LT-β49-306.

A second PCR reaction was performed with oligos 5' LT-βlong-NheI and 3' LT-βstop-NotI resp. 5' LT-βshort-NheI and 3' LT-βstop-NotI using pEntry1A-LT-β49-306 as a template. Oligos 5' LT-βlong-NheI and 5' LT-βshort-NheI had an internal NheI site and contained codons for a Cys-Gly-Gly linker and 3' LT-βstop-NotI had an internal NotI site and contained a stop codon. For the second PCR reaction, 0.5 µg of each primer and 150 ng of the template DNA was used in the 50 µl reaction mixture (1 unit of PFX Platinum polymerase, 0.3 mM dNTPs and 2 mM MgSO$_4$). The temperature cycles were as follows: 94° C. for 2 minutes, followed by 5 cycles of 94° C. (15 seconds), 50° C. (30 seconds), 68° C. (1 minute), followed by 20 cylces of 94° C. (15 seconds), 64° C. (30 seconds), 68° C. (1 minute) and followed by 68° C. for 10 minutes.

The PCR products were digested with NheI and NotI and inserted into either pCEP-SP-GST-EK or pCEP-SP-his-myc-EK (Wuttke et al. *J. Biol. Chem.* 276: 36839-48 (2001)). Resulting plasmids were named pCEP-SP-GST-EK-C-LT-β49-306, pCEP-SP-GST-EK-C-LT-β126-306, pCEP-SP-his-myc-EK-C-LT-β49-306, pCEP-SP-his-myc-EK-C-LT-β126-306, respectively. GST stands for glutathione-S-transferase, EK for enterokinase, his for a hexahistidine tag and myc for anti c-myc epitope. The C indicates the CGG linker containing the additional cysteine.

All other steps were performed by standard molecular biology protocols.

Sequence of the oligonucleotides:

```
5' LT-β:
                                        (SEQ ID NO: 66)
5'-CTT GGT GCC GCA GGA TCA G-3'

3' LT-β:
                                        (SEQ ID NO: 67)
5'-CAG ATG GCT GTC ACC CCA C-3'

5' LT-βlong-NheI:
                                        (SEQ ID NO: 68)
5'-GCC CGC TAG CCT GCG GTG GTC AGG ATC AGG GAC GTC
G-3'

5' LT-βshort-NheI:
                                        (SEQ ID NO: 69)
5'-GCC CGC TAG CCT GCG GTG GTT CTC CAG CTG CGG ATT
C-3'

3' LT-βstop-NotI
                                        (SEQ ID NO: 70)
5'-CAA TGA CTG CGG CCG CTT ACC CCA CCA TCA CCG-3'
```

B. Expression and Production of GST-EK-C-LT-β49-306, GST-EK-C-LT-β26-306, his-myc-EK-C-LT-β49-306 and his-myc-EK-C-LT-β26-306

The plasmids pCEP-SP-GST-EK-C-LT-β49-306, pCEP-SP-GST-EK-C-LT-β126-306, pCEP-SP-his-myc-EK-C-LT-β49-306 and pCEP-SP-his-myc-EK-C-LT-β126-306 were transfected into 293-EBNA cells (Invitrogen) for protein production as described in EXAMPLE 4. The resulting proteins were named GST-EK-C-LT-β49-306, GST-EK-C-LT-β126-306, his-myc-EK-C-LT-β49-306 and his-myc-EK-C-LT-β126-306.

The protein sequences of the LT-β fusion proteins were translated from the cDNA sequences:
GST-EK-C-LT-β49-306GST-EK-C-LT-β26-306
his-myc-EK-C-LT-β49-306
his-myc-EK-C-LT-β126-306

The fusion proteins were analysed on 12% SDS-PAGE gels under reducing conditions. Gels were blotted onto nitrocellulose membranes. Membranes were blocked, incubated with a monoclonal mouse anti-myc antibody or with an anti-GST antibody. Blots were subsequently incubated with horse radish peroxidase-conjugated goat anti-mouse IgG or horse radish peroxidase-conjugated rabbit anti-goat IgG. The expression of LT-β fusion proteins could be shown. LT-β fusion proteins were analysed on 12% SDS-PAGE gels under reducing conditions. Gels were blotted onto nitrocellulose membranes. Membranes were blocked, incubated either with a monoclonal mouse anti-myc antibody (dilution 1:2000) or with an anti-GST antibody (dilution 1:2000). Blots were subsequently incubated with horse radish peroxidase-conjugated goat anti-mouse IgG (dilutions 1:4000) or horse radish peroxidase-conjugated rabbit anti-goat IgG (dilutions 1:4000) .GST-EK-C-LT-β49-306 and GST-EK-C-LT-β126-306 could be detected with the anti-GST antibody at a molecular weight of 62 kDa and 48 kDa, respectively. his-myc-EK-C-LT-β49-306 and his-myc-EK-C-LT-β126-306 could be detected with the anti-myc antibody at 40-56 kDa and 33-39 kDa, respectively.

C. Purification of GST-EK-C-LT-β49-306, GST-EK-C-LT-β126-306, his-myc-EK-C-LT-β49-306 and his-myc-EK-C-LT-β126-306

GST-EK-C-LT-β49-306 and GST-EK-C-LT-β126-306 are purified on glutathione-sepharose column and his-myc-EK-C-LT-β49-306 and his-myc-EK-C-LT-β126-306 are purified on Ni-NTA sepharose column using standard purification protocols. The purified proteins are cleaved with enterokinase and analysed on a 16% SDS-PAGE gel under reducing conditions.

D. Coupling of C-LT-β49-306 and C-LT-β126-306 to AP205 VLP

A solution of 120 µM AP205 VLP in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed AP205 VLP reaction mixture is then reacted with the C-LT-β49-306 and C-LT-β126-306 solution (end concentrations: 60 µM AP205 VLP, 60 µM C-LT-β49-306 and C-LT-β126-306) for four hours at 25° C. on a rocking shaker. Coupling products are analysed by SDS-PAGE and Western blot under reducing conditions.

Example 7

Cloning, Expression, Purification and Coupling of AP205 VLP to MIF

A. Introduction of Cys-containing Linkers, Expression, Purification of Rat Macrophage Migration Inhibitory Factor MIF Rat macrophage migration inhibitory factor (rMIF) was recombinantly expressed with three different amino acid linkers C1, C2 and C3 fused at its C-terminus. Each of the linker contained one cysteine for coupling to VLP.

Construction of rMIF-C1, rMIF-C2, and rMIF-C3.

The MCS of pET22b(+) (Novagen, Inc.) was changed to GTTTAACTTT AAGAAGGAGATATACATATGGATCCG-GCTAGCGCTCGAGGGTTTAAACGGCGGC CGCATG-CACC (SEQ ID NO: 71) by replacing the original sequence from the NdeI site to XhoI site with annealed oligos primer-MCS-1F and primerMCS-1R (annealing in 15 mM TrisHCl pH 8 buffer). The resulting plasmid was termed pMod00, which had NdeI, BamHI, NheI, XhoI, PmeI and NotI restriction sites in its MCS. The annealed pair of oligos Bamnhis6-EK-Nhe-F and Bamhis6-EKNhe-R and the annealed pair of oligo1F-C-glycine-linker and oligo1R-C-glycine-linker were together ligated into BaniHI-NotI digested pMod00 plasmid to get pModEC1, which had an N terminal hexahistidine tag, an enterokinase cleavage site and a C-terminal amino acid glycine linker containing one cysteine residue. The annealed pair of oligos Bamhis6-EK-Nhe-F and Bamhi6-EKNhe R together with the annealed pair of oligo1F-C-gammal-linker and oligo1R-C-gamma1-linker were ligated into BamHI-NotI digested pMod00 plasmid to get pModEC2, which had an N terminal hexahistidine tag, an enterokinase cleavage site and a C-terminal γ1 linker, derived from the hinge region of human immunoglobulin γ1, containing one cysteine residue. The annealed pair of oligos Bamhis6-EK-Nhe-F and Bamhis6-EK-Nhe-R, the annealed pair of oligo1FA-C-gamma3-linker and oligo1RA-C-gamma3-linker, and the annealed pair of oligo1FB-C-gamma3-linker and oligo1RB-C-gamma3-linker were together ligated into BamHI-NotI digested pMod00 to get pModEC3, which had an N terminal hexahistidine tag, an enterokinase cleavage site and a C terminal γ3 linker, containing one cysteine residue, derived from the hinge region of mouse immunoglobulin γ3.

pBS-rMIF, which contains the rat MIF cDNA, was amplified by PCR with oligos rMIF-F and rMIF-Xho-R. rMIF-F had an internal NdeI site and rMIF-Xho-R had an internal XhoI site. The PCR product was digested with NdeI and XhoI and ligated into pModEC1, pModEC2 and pModEC3 digested with the same enzymes. Resulting plasmids were named pMod-rMIF-C1, pMod-rMIF-C2 and pMod-rMIF-C3, respectively.

For the PCR reaction, 15 pmol of each oligo and 1 ng of the template DNA was used in the 50 μl reaction mixture (2 units of PFX polymerase, 0.3 mM dNTPs and 2 mM MgSO$_4$). The temperature cycles were as follows: 94° C. for 2 minutes, followed by 30 cycles of 94° C. (30 seconds), 60° C. (30 seconds), 68° C. (30 seconds) and followed by 68° C. for 2 minutes.

All other steps were performed by standard molecular biology protocols.

Sequence of the oligonucleotides:

```
primerMCS-1F:
                                      (SEQ ID NO: 72)
5'-TAT GGA TCC GGC TAG CGC TCG AGG GTT AAA ACG GCG
GCC GCA T-3' primerMCS-1R:
                                      (SEQ ID NO: 73)
5'-TCG AAT GCG GCC GCC GTT AAA ACC CTC GAG CGC TAG
CCG GAT CCA-3'

Bamhis6-EK-Nhe-F:
                                      (SEQ ID NO: 74)
5'-GAT CCA CAC CAC CAC CAC CAC CAC GGT TCT GGT GAC
GAC GAT GAC AAA GCG CTA GCC C-3'

Bamhis6-EK-Nhe-R:
                                      (SEQ ID NO: 75)
5'-TCG AGG GCT AGC GCT TTG TCA TCG TCG TCA CCA GAA
CCG TGG TGG TGG TGG TGG TGT G-3' oligo1F-C-glycine-linker:
                                      (SEQ ID NO: 76)
5'-TCG AGG GTG GTG GTG GTG GTT GCG GTT AAT AAG TTT
AAA CGC-3' oligo1R-C-glycine-linker:
                                      (SEQ ID NO: 77)
5'-GGC CGC GTT AAA ACT TAT TAA CCG CAA CCA CCA CCA
CCA CCC-3' oligo1F-C-gamma1-linker:
                                      (SEQ ID NO: 78)
5'-TCG AGG ATA AAA CCC ACA CCT CTC CGC CGT GTG GTT
AAT AAG TTT AAA CGC-3' oligo1R-C-gamma1-linker:
                                      (SEQ ID NO: 79)
5'-GGC CGC GTT AAA ACT TAT TAA CCA CAC GGC GGA GAG
GTG TGG GTT TTA TCC-3' oligo1FA-C-gamma3-linker:
                                      (SEQ ID NO: 80)
5'-TCG AGC CGA AAC GTT CTA CCC CGC CGG GTT CTT
CTG-3' oligo1RA-C-gamma3-linker:
                                      (SEQ ID NO: 81)
5'-CAC CAG AAG AAC CCG GCG GGG TAG ACG GTT TCG
GC-3' oligo2FB-C-gamma3-linker:
                                      (SEQ ID NO: 82)
5'-GTG GTG CTC GGG GTG GTT GCG GTT AAT AAG TTT AAA
CGC-3' oligo2RB-C-gamma3-linker:
                                      (SEQ ID NO: 83)
5'-GGC CGC GTT AAA ACT TAT TAA CCG CAA CCA CCC GGA
G-3' rMIF-F:
                                      (SEQ ID NO: 84)
5'-GGA ATT CCA TAT GCC TAT GTT CAT CGT GAA CAC-3' rMIF-Xho-R:
                                      (SEQ ID NO: 85)
5'-CCC GCT CGA GAG CGA AGG TGG AAC CGT TC-3'
```

Expression and Purification of rMIF-Cs

Competent *E. coli* BL21 (DE3) cells were transformed with plasmids pMod-rMIF-C1, pMod-rMIF-C2 and pMod-rMIF-C3. Single colonies from ampicillin (Amp)-containing agar plates were expanded in liquid culture (SB with 150 mM MOPS, pH 7.0, 200 ug/ml Amp, 0.5% glucose) and incubated at 30° C. with 220 rpm shaking overnight. 1 l of SB (150 mM MOPS, pH 7.0, 200ug/ml Amp) was then inoculated 1:50 v/v with the overnight culture and grown to OD600=2.5 at 30° C. Expression was induced with 2 mM IPTG. Cells were harvested after overnight culture and centrifuged at 6000 rpm. Cell pellet was suspended in lysis buffer (10 mM Na$_2$HPO$_4$, 30 mM NaCl, 10 mM EDTA and 0.25% Tween-20) with 0.8 mg/ml lysozyme, sonicated and treated with benzonase. 2 ml of the lysate was then run through a 20 ml Q XL- and a 20 ml SP XL-column. The proteins rMIF-C1, rMIF-C2 and rMIF-C3 were in the flow through.

The protein sequences of the rMIF-Cs were translated from the cDNA sequences.

```
rMIF-C1
(SEQ ID NO: 114; C1 is GGGGCG
(SEQ ID NO: 55))

rMIF-C2
(SEQ ID NO: 115; C2 is PKPSTPPGSSGGAPGGCG
(SEQ ID NO: 116))

rMIF-C3
(SEQ ID NO: 117; C3 is DKTHTSPPCG
(SEQ ID NO: 118))
```

Figure 5B:
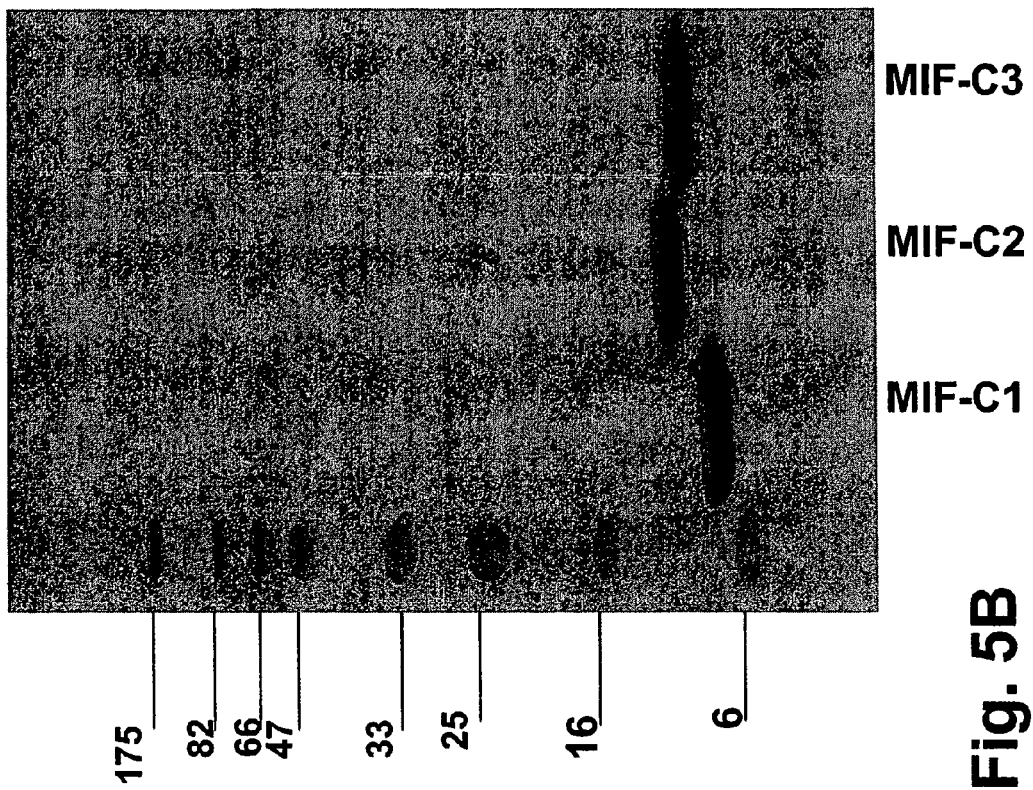
FIG. 5A-B depicts rMIF constructs, and an SDS-PAGE depicting expression and purification of rMIF constructs, for coupling to AP205 VLP.
Figure 5A:
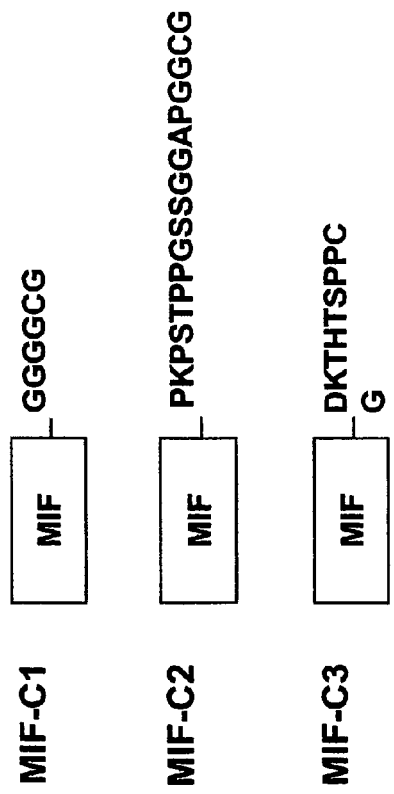

FIG. 5A shows a schematic description of the MIF constructs, with added amino acid linker containing a cysteine residue. MIF can be a protein from any mammal, including without limitation human MIF (SEQ ID NO: 119), rat MIF (SEQ ID NO: 120) or mouse MIF (SEQ ID NO: 121). The sequences of human MIF containing the C-terminal amino acid linker C1, C2 or C3 are shown in SEQ ID NOs: 122-124). FIG. 5B shows an SDS-PAGE analysis of the purified MIF constructs, run under reducing conditions and stained with Coomassie-brillant blue. Loaded on the gels are the purified rat constructs rMF-C1 (SEQ ID NO: 114); rMIF-C2 (SEQ ID NO: 115); and rMIF-C3 (SEQ ID NO: 117); described in FIG. 5A.

Example 8

Cloning, Expression, Purification and Coupling of RANKL

A. Introduction of Amino Acid Linkers Containing a Cysteine Residue, Expression and Purification of Mouse RANKL A fragment of the receptor activator of nuclear factor kappa b ligand (RANKL), which has also been termed osteoclast differentiation factor, osteoprotegerin ligand and tumor necrosis factor-related activation-induced cytokine was recombinantly expressed with an N-terminal linker containing one cysteine for coupling to VLP.

Construction of Expression Plasmids

The C-terminal coding region of the RANKL gene was amplified by PCR with oligos RANKL-UP and RANKL-DOWN. RANKL-UP had an internal ApaI site and RANKL-DOWN had an internal XhoI site. The PCR product was digested with ApaI and XhoI and ligated into pGEX-6p1 (Amersham Pharmacia). The resulting plasmid was named pGEX-RANKL. All steps were performed by standard molecular biology protocols and the sequence was verified. The plasmid pGEX-RANKL codes for a fusion protein of a glutathione S-transferase-Prescission cleavage site-cysteine-containing amino acid linker-RANKL (GST-PS-C-RANKL). The cysteine-containing amino acid linker had the sequence GCGGG. The construct also contains a hexa-histidine tag between the cysteine containing amino acid linker and the RANKL sequence.

Oligos:

```
RANKL-UP:
                                          (SEQ ID NO: 86)
5' CTGCCAGGGGCCCGGGTGCGGCGGTGGCCATCATCACCACCATCACC
AGCGCTTCTCAGGAG-3'

RANKL-down:
                                          (SEQ ID NO: 87)
5'-CCGCTCGAGTTAGTCTATGTCCTGAACTTTGAAAG-3'
Protein sequence of GST-PS-C-RANKL and cDNA
sequence of GST-PS-C-RANKL
```

Expression and Purification of C-RANKL

Competent *E. coli* BL21 (DE3) cells were transformed with the plasmid pGEX-RANKL. Single colonies from kanamycin and chloramphenicol-containing agar plates were expanded in liquid culture (LB medium, 30 µg/ml kanamycin, 50 µg/ml chloramphenicol) and incubated at 30° C. with 220 rpm shaking overnight. 1 l of LB (with 30ug/ml kanamycin) was then inoculated 1:100 v/v with the overnight culture and grown to OD600=1 at 24° C. Expression was induced with 0.4 mM IPTG. Cells were harvested after 16 h and centrifuged at 5000 rpm. Cell pellet was suspended in lysis buffer (50 mM Tris-HCl, pH=8; 25% sucrose; 1 mM EDTA, 1% NaN$_3$; 10 mM DTT; 5 mM MgCl$_2$; 1 mg/ml Lysozyme; 0.4u/ml DNAse) for 30 min. Then 2.5 volumes of buffer A (50 mM Tris-HCl, pH=8.0; 1% Triton X100; 100 mM NaCl; 0,1% NaN$_3$; 10 mM DTT;1 mM PMSF) were added and incubated at 37° C. for 15 min. The cells were sonicated and pelleted at 9000 rpm for 15 min. The supernatant was immediately used for GST-affinity chromatography.

A column GST-Trap FF of 5 ml (Amersham Pharmacia) was equilibrated in PBS, pH 7.3 (140 mM NaCl, 2.7 mM KCl, 10 mM Na$_2$HPO$_4$, 1.8 mM KH$_2$PO$_4$). The supernatant was loaded on the 5 ml GST-Trap FF column and subsequently the column was rinsed with 5 column volumes of PBS. The protein GST-PS-C-RANKL was eluted with 50 mM Tris-HCl, pH=8.0 containing GSH 10 mM.

The purified GST-PS-C-RANKL protein was digested using the protease PreScission (Amersham Pharmacia). The digestion was performed at 37° C. for 1 hour using a molar ratio of 500/1 of GST-PS-C-RANKL to PreScission.

Furthermore, the reaction of protease digestion was buffer exchanged using a HiPrep 26/10 desalting column (Amersham Pharmacia), the fractions containing the proteins were pooled and immediately used for another step of GST affinity chromatography using the same conditions reported before. Purification of C-RANKL was analysed on a SDS-PAGE gel. The gel was stained with Coomassie Brilliant Blue. The cleaved C-RANKL is present in the flow-through (unbound fraction) while the uncleaved GST-PS-C-RANKL, the cleaved GST-PS and the PreScission remain bound to the column. C-RANKL protein of the expected size of 22 kDa was obtained in high purity.

The samples loaded on a gel were the following:

Lane 1: Low molecular weight marker. Lanes 2 and 3: the supernatant of the cell lysates of the BL21/DE3 cells transformed with the empty vector pGEX6p1 and pGEX-RANKL respectively, after sixteen hours of induction with IPTG 0.4 mM. Lane 4: the purified GST-PS-C-RANKL protein after GST-Trap FF column. Lane 5: the GST-Trap FF column unbound fraction. Lane 6: the purified GST-PS-C-RANKL protein after the cleavage with the PreScission protease. Lane 7: the unbound fraction of the GST-Trap FF column loaded with the GST-RANKL digestion, which contains the purified C-RANKL. Lane 8: the bound fraction of the GST-Trap FF column loaded with the GST-PS-C-RANKL digestion and eluted with GSH.

B. Coupling of C-RANKL to AP205 VLP

A solution of 120 µM AP205 VLP in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed AP205 VLP reaction mixture is then reacted with the C-RANKL solution (end concentrations: 60 µM AP205 VLP, 60 µM C-RANKL) for four hours at 25° C. on a rocking shaker. Coupling products are analysed by SDS-PAGE and Western blot under reducing conditions.

Example 9

Cloning, Expression and Purification of IL-5 with an N-terminal Amino Acid Linker Containing a Cysteine Residue. Coupling to VLP and Elicitation of an Immune Response in Mice A. Cloning of Mouse His-C-IL-5 and Expression as Inclusion Bodies in *E. coli*

IL-5 was amplified from an ATCC clone (pmIL5-4G; ATCC number: 37562) by PCR using the following two primers: Spelinker3-Fl (SEQ ID NO: 90) and Il5StopXho-R (SEQ ID NO: 91). The product of this PCR was used as template for a second PCR with the primers SpeNlinker3-F2 (SEQ ID NO: 92) and Il5StopXho-R. The insert was digested with SpeI and NotI. This insert was ligated into a pET vector derivative (pMODEC3-8 vector), previously digested with NheI and NotI, and transformed into *E.coli* TG1 cells. The construct generated by cloning IL5 into pMODEC3-8 comprises, from its N-terminus, a hexa-histidine tag (to facilitate purification), an Enterokinase cleavage site, a gamma 3 derived amino acid linker (flanked N-terminally by the amino acids ALV and C-terminally by AS) containing a cysteine residue and the DNA encoding the mature form of IL-5 protein. Fidelity of the cloning procedure was confirmed by DNA sequencing. The protein released by cleavage with enterokinase is called "mouse C-IL-5-E".

The construct containing IL-5 described above was termed pMODC6-IL5.2 (also referred to as pMODC6-IL5) and transformed into *E.coli* strain BL21-DE3. The recombinant protein expressed in *E. coli* is termed His-C-IL5.

Clonal BL21-DE3 cells harboring pMODC6-IL5 were grown over night in 5 ml of LB containing 1 mg/L Ampicillin. A 2.0 ml aliquot of this culture was diluted into 100 ml terrific broth (TB) containing 1 mg/L Ampicillin. The culture was grown to an optical density, $OD_{600\,nm}$, of 0.7-1.0 and expression induced for 4 hours by adding 0.1 ml of a 1.0 M stock of Ispropyl β-D-Thiogalactopyranoside (IPTG) Samples were taken every 2 hours. Recombinant His-C-IL5 was expressed in an insoluble form and located in the inclusion body fraction of induced cells. Expression of His-C-IL5 was confirmed in the following manner. A 10 ml sample of culture was taken 4 hours after induction and centrifuged for 10 min at 4000×g. The pellet was suspended in 0.5 ml lysis buffer consisting of 50 mM Tris-HCl, 2 mM EDTA, 0.1% triton X-100 (pH 8.0). To the suspension was added 20 µl of Lysozyme (40 mg/ml) and after 30 min at 4° C. sonicated for 2 min. A 1.0 ml aliquot of benzonase and 100 µl aliquot of 50 mM $MgCl_2$ were added and incubated for 30 min at room temperature. After centrifugation for 15 min at 13000×g the supernatant was discarded and the pellet heated for 5 min at 98° C. in 100 µl of SDS loading buffer. Aliquots of 10 µl were then analyzed by SDS-PAGE under reducing conditions. SDS-PAGE analysis demonstrated a protein band of 17 kDa corresponding to the mass of IL-5. As control, BL21-DE2 cells containing pMODC6-IL5 were grown in the absence of IPTG and extracts prepared from the insoluble cell fraction as described above.

B. Purification and Refolding of Mouse-His-C-IL5.

A larger scale expression of IL-5 from clone pMODC6-IL5 in BL21-DE3 cells was performed in order to obtain sufficient quantities of pure IL-5 for vaccine production. Overnight cultures were grown and diluted into either 100 ml or 1 L volumes of TB medium containing 1.0 mg/L Ampicillin. A total of 3 liters of culture was thus prepared and grown at 37° C. until $OD_{600nm}$ reached 0.7 at which time IPTG was added to give a final concentration of 1.0 mM. After 4 h incubation cells were harvested by centrifugation for 30 min at 10000×g. After harvesting the pellet was resuspended in PBS (5.0 ml/g wet weight) and centrifuged for 15 minutes at 10000×g. The washed pellet was stored at −20° C. until further use.

The bacterial pellet was suspended in PBS (2.0 ml/g cell wet weight) using a Dounce homogenizer. Lysozyme (0.8 mg/ml) was added to the suspension and incubated for 30 minutes at room temperature. The suspension was sonicated for 1 minute, 3 times on ice then benzonase and $MgCl_2$ (10 mM final concentration) were added and incubated for 30 minutes at room temperature. Triton X-100 was added to a final concentration of 1% (w/v) the mixture gently stirred at room temperature for 30 minutes. The solution was centrifuged for 20 minutes at 20000×g (SS34 tubes) and the supernatant discarded. The pellet harbouring the inclusion bodies was suspended (5.0 ml/g wet weight) in washing buffer (PBS containing 2 M Urea and 1% (w/v) Triton X-100) using a Dounce homogenizer and agitated for 5 minutes. The solution was centrifuged for 20 minutes at 20000×g and the supernatant discarded. The pellet was washed and centrifuged as above 2 more times. A final wash of the inclusion bodies was performed with washing buffer in the absence of Triton X-100.

The His-C-IL-5 present in inclusion bodies of the pellet was solubilized in (5.0 ml/g cell wet weight) denaturing buffer (100 mM $NaH_2PO_4$, 10 mM Tris-HCl, 6.0 M Guanidine-hydrochloride, pH 8.0) and gently stirred for 1 h at 25° C. The suspension was centrifuged for 20 min. at 20000×g and the supernatant mixed with Ni-NTA resin (QIAgen, equilibrated with solubilization buffer). After 3 hours of gentle agitation at 4° C. the slurry was poured into a glass column (C10/10) and the resin washed with 100 ml of 100 mM $NaH_2PO_4$, 10 mM Tris, 6.0 M Guanidine-hydrochloride (pH 6.3). An additional washing step was performed with 15 ml of 100 mM $NaH_2PO_4$, 10 mM Tris, 6.0 M Guanidine-hydrochloride (pH 5.9). Mouse His-C-IL5 was eluted from the resin by applying 20 ml of 100 mM $NaH_2PO_4$, 10 mM Tris, 6.0 M Guanidine-hydrochloride (pH 4.5). Purification was anylysed by SDS-PAGE.

Fractions from the elution step containing His-C-IL-5 were pooled and dialysed against buffer comprising 8.0 M Urea 100 mM $NaH_2PO_4$, 10 mM Tris-HCl (pH 8.0) at 4° C. using a 10 kDa cut-off membrane. Following dialysis, the protein concentration was determined spectrophotometrically using the following formula; Protein (mg/ml)=$(1.55\times A_{280\ nm})-(0.76\times A_{260\ nm})$. The concentration of the protein was diluted with dialysis buffer to 0.2 mg/ml. The solution was then dialysed with a 3.5 kDa membrane for 24 hours at 4° C. against refolding buffer 1 comprising 2.0 M urea, 50 mM $NaH_2PO_4$, 5 mM reduced Glutathione, 0.5 mM oxidized Glutathione, 0.5 M Arginine, 10% (v/v) glycerol (pH 8.5) and for a further 24 h against another refolding buffer 2 comprising 50 mM $NaH_2PO_4$, 5 mM reduced Glutathione, 0.5 mM oxidized Glutathione, 0.5 M Arginine, 10% (v/v) glycerol, (pH 8.5). At the end the protein was dialysed for 24 h at 4° C. against PBS pH 8.0 then centrifuged at 10000×g for 30 min. The protein content of the supernatant was estimated by Bradford assay.

In order to further purifiy His-C-IL5, anion exchange with Hitrap Q resin (Amersham Pharmacia, Uppsala Sweeden) was performed. His-C-IL5 was concentrated to 1 mg/ml using Centrifugal Filters (Ultrafree-15 Millipore, 10 kDa cut-off) and dialyzed for 14 h against 50 mM Phosphate buffer pH 8.4. The solution was loaded onto a Hitrap Q column and washed with 50 mM Phosphate pH 8.4 buffer. His-C-IL-5 was eluted from the column by applying a NaCl gradient from 0-1 M. His-C-IL5 eluted from the column at 100 mM NaCl. Analysis of the purification was performed by SDS-PAGE and concentration measured by Bradford assay. Quartenary structure of the protein was assessed by SDS-PAGE performed under non-reducing conditions, which revealed that the His-C-IL5 is present as a dimer in the preparation.

C. Vaccine Production: Coupling His-C-IL5 to AP205 VLP

A variety of conditions may be tested to optimize the efficiency of the coupling reaction. These include the addition of reducing agent, (TCEP) to His-C-IL5 and varying the molar ratios of AP205 VLP subunit monomer and His-C-IL5 in the coupling reaction. AP205-His-C-IL-5 vaccine is produced as follows. Purified His-C-IL-5 (40 μM) is reduced for 1 h with an equimolar amount of TCEP in PBS pH 8.0. Reduced IL-5 (20 μM) is incubated for 4 hours at 22° C. with 10 pM Qβ derivatized with SMPH in a total volume of 700 μl. The reaction is dialysed 12 hours against PBS pH 8.0 using a 300 kDa cut-off dialysis membrane. The coupling reaction is analysed by SDS-PAGE and Western-Blot with anti-His and anti-AP205 antibodies (polyclonal rabbit antiserum). Protein concentration is measured by Bradford. The coupling efficiency [i.e. mol Qβ-IL5/mol Qβ monomer (total)] is measured by densitometric analysis of the corresponding bands on the Coomassie blue stained SDS-PAGE.

D. Assay of IL-5 Activity

The ability of the B cell lymphoma line BCL1 to proliferate in response to murine IL-5 was used to check the bioactivity of the re-folded recombinant His-C-IL-5 (Harriman G. R. (1991) Current Protocols in Immunology 6.5.1-6.5.5 John Wiley and Sons Inc). The proliferative activity of His-C-IL5 covalently coupled to AP205 VLP may also be assessed. Recombinant murine IL-5 (R&D systems, Minneapolis USA) was used as a control. The various forms of recombinant IL-5 were incubated in flat bottom 96 well plates with $2\times10^4$ BCL1 cells per well and incubated for 24 h at 37° C., 5% $CO_2$.1 µCi of $^3$H-Thymidine (Hartmann Analytic, Switzerland) was added to each well and the plates incubated for another 6 h at 37° C. 5% $CO_2$. The cells were harvested, washed and the incorporation of Thymidine determined by counting the β-emission with a liquid scintillation counter. The assay demonstrated that His-C-IL5 is active.

E. Immunization Protocol

In order to generate self reactive antibodies to mouse IL-5, four BalbC mice are injected subcutaneously a day 0 and day 14 with 25 µg of AP205-His-C-IL5 vaccine in 200 µl of PBS. To serve as a negative control, five mice are immunized at day 0 and 14 with a simple mixture of 6.4 µg AP205 VLP and 16 µg IL5 i.e. not covalently coupled (AP205+His-C-IL-5) in PBS. Mice are bled prior to imunisation and at day 21 of the immunisation protocol. Sera are analysed by ELISA.

F. Sera Analysis

ELISA. Maxisorp ELISA plates (Nunc) are coated with 50 µl of purified His-C-IL-5 (3 µg/ml) for 14 h at 4° C. The plates are washed 3 times with PBS and blocked with 2% BSA in PBS for 2 h at 37° C. then washed twice with PBS. Five-fold dilutions of sera are added in 2% BSA, 0.1% FCS in PBS and incubated at room temperature for 1 hour. The plates are subsequently washed 3 times with PBS and incubated with anti-mouse IgG conjugated with HRP (dilution 1:1000) at room temperature for 1 h. The plates are again washed 3 times with PBS and 100 µl/well developing solution (0.066 M Na2HPO4, 0.035 M citric acid, 0.032% $H_2O_2$, 0.4% 1,2-Phenylenediamine dihydrochloride) is added. After 5 minutes of reaction at room temperature the ELISA is stopped with 50 µl per well 5% $H_2SO_4$. Absorbance is measured at 450 nm on a Spectramax spectrophotometer (Molecular Devices).

Example 10

Cloning, Expression and Coupling of Mouse Prion Protein

A. Introduction of Amino Acid Linker Containing a Cysteine Residue, Expression and Purification of a Truncated Form of the Mouse Prion Protein A truncated form (aa 121-230) of the mouse prion protein (termed mPrP$_t$) was recombinantly expressed with a GGGGCG amino acid linker (SEQ ID NO: 55) fused at its C-terminus for coupling to AP205 VLP. The protein was fused to the N-terminus of a human Fc-fragrnent for purification. An enterokinase (EK) cleavage-site was introduced behind the EK cleavage site to cleave the Fc-part of the fusion protein after purification.

Construction of mPrP$_t$-EK-Fc*.

Mouse PrP$_t$ was amplified by PCR with the primer 5'PrP-BamHI and 3'PrP-NheI using the plasmid pBP$^{CMV}$PrP-Fc as a template. pBP$^{CMV}$PrP-Fc contained the wild-type sequence of the mouse prion protein. 5'PrP-BamHI had an internal BamHI site and contained an ATG and 3'PrP-NheI had an internal NheI site.

For the PCR reaction, 0.5 µg of each primer and 200 ng of the template DNA was used in the 50 µl reaction mixture (1 unit of PFX Platinum polymerase, 0.3 mM dNTPs and 2 mM $MgSO_4$). The temperature cycles were as follows: 94° C. for 2 minutes, followed by 5 cycles of 94° C. (15 seconds), 50° C. (30 seconds), 68° C. (45 seconds), followed by 20 cycles of 94° C. (15 seconds), 64° C. (30 seconds), 68° C. (45 seconds) and followed by 68° C. for 10 minutes.

The PCR product was digested with BamHI and NheI and inserted into pCEP-SP-EK-Fc* containing the GGGGCG linker sequence (SEQ ID NO: 55) at the 5' end of the EK cleavage sequence. The resulting plasmid was named pCEP-SP-mPrP$_t$-EK-Fc*.

All other steps were performed by standard molecular biology protocols.

Oligos:

```
Primer 5'PrP-BamHI
                                  (SEQ ID NO: 88)
5'-CGG GAT CCC ACC ATG GTG GGG GGC CTT GG-3'

Primer 3'PrP-NheI
                                  (SEQ ID NO: 89)
5'-CTA GCT AGC CTG GAT CTT CTC CCG-3'
```

Expression and Purification of mPrP$_t$-EK-Fc*

Plasmid pCEP-SP-mPrP$_t$-EK-Fc* was transfected into 293-EBNA cells (Invitrogen) and purified on a Protein A-sepharose column as described in EXAMPLE 4. mPrP$_t$ after cleavage has the sequence as identified in SEQ ID NO:324 with the GGGGCG linker at its C-terminus. The purified fusion protein mPrP$_t$-EK-Fc* was cleaved with enterokinase and analysed on a 16% SDS-PAGE gel under reducing conditions before and after enterokinase cleavage. The gel was stained with Coomassie Brilliant Blue. The mPrP$_t$-EK-Fc* fusion protein could be detected as a 50 kDa band. The cleaved mPrPt protein containing the GGGGCG amino acid linker (SEQ ID NO: 55) fused to its C-terminus could be detected as a broad band between 18 and 25 kDa. The identity of mPrP$_t$ was confirmed by western blotting (data not shown). Thus, mPrPt with a C-terminal amino acid linker containing a cysteine residue, could be expressed and purified to be used for coupling to AP205 VLP.

The samples loaded on the gel were the following.

Lane 1: Molecular weight marker. Lane 2: mPrP$_t$-EK-Fc* before cleavage. Lane 3: mPrP$_t$ after cleavage.

B. Coupling of mPrP$_t$ to AP205 VLP

A solution of 120 µM AP205 VLP in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed AP205 VLP reaction mixture is then reacted with the mPrP$_t$ solution (end concentrations: 60 µM AP205 VLP, 60 µM mPrP$_t$) for four hours at 25° C. on a rocking shaker. Coupling products are analysed by SDS-PAGE and Western blot under reducing conditions.

Example 11

Coupling of rMIF to AP205 VLP

Figure 6:
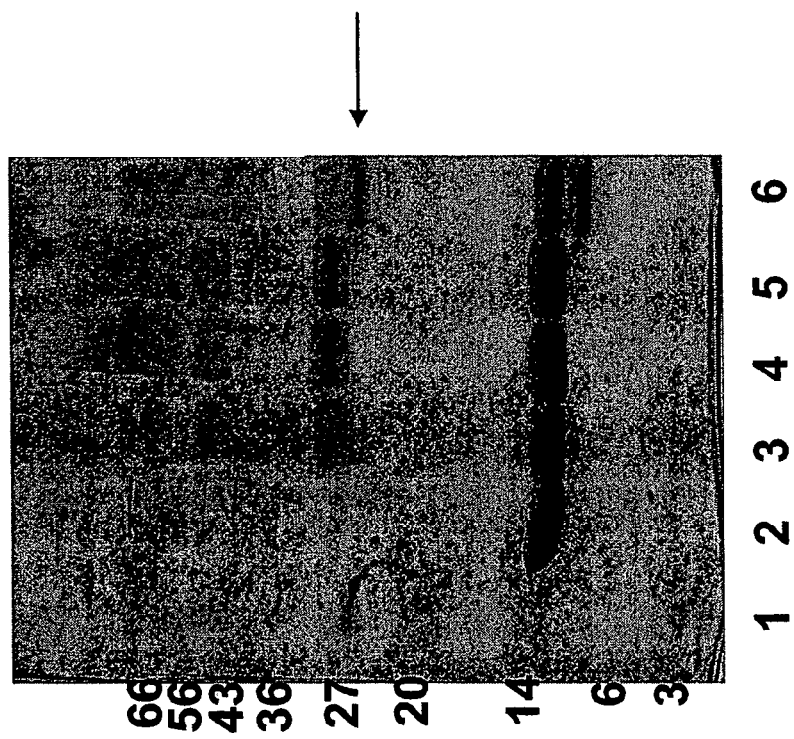
FIG. 6 shows the result of the coupling reaction of rMIF-C1 to AP205 VLP. Lane 1.

RMIF-C1 (SEQ ID NO: 114), expressed and purified as described in Example 7, in 20 mM Hepes, 150 mM NaCl pH 7.2, 0.18 mM was incubated with one molar equivalent of TCEP for 1 hour at R.T. before use in the coupling reaction. One ml of a AP205 VLP solution, 2.5 mg/ml, was reacted with a 2.3-fold molar excess of SMPH for 1 hour at R.T. The derivatized AP205 VLP was dialyzed two times 2 hours against 2 l of 20 mM Hepes, 150 mM NaCl, pH 7.2. 820 μl of the dialyzed derivatized AP205 VLP (0.18 mM) were subsequently reacted with 820 μl of a 0.18 mM rMIF-C1 solution previously treated with TCEP as described above, for 3 hours at R.T. No precipitate was observable at the end of the coupling reaction, and the samples were analyzed by SDS-PAGE under reducing conditions, and the gel stained with Coomassie Brillant Blue. The result of the coupling reaction is shown in FIG. 6. MIF has a molecular weight of, while the AP205 VLP subunit has a molecular weight of 14 kDa while rMIF-C1 has a molecular weight of 13. The coupling product is migrating as expected with an apparent molecular weight of 27, as described in FIG. 6.

Shown in FIG. 6 is the result of the coupling reaction of rMIF-C1 to AP205 VLP. Lane 1: Molecular Marker. Lane 2: AP205 VLP. Lane 3: derivatized AP205 VLP. Lane 4: dialyzed, derivatized AP205 VLP. Lane 5: dialyzed, derivatized AP205 VLP. Lane 6: Coupling reaction of rMIF-C1 to AP205 VLP. The coupling product is indicated by an arrow in the figure. The molecular weights of the marker proteins are indicated on the left border of the gel.

Example 12

Immunization of Mice and Rats with rMIF Coupled to AP205 VLP

A. Immunization of Mice with AP205 VLP Coupled to rMIF-C1

AP205 VLP coupled to rMIF-C1 (from Example 11) was injected subcutaneously in female Balb/c mice (3 mice) at day 0 and 14. Each mouse was immunized with 10 μg of vaccine diluted in PBS to 200 μl. Mice were retroorbitally bled on day 21, and the titer of the antibodies specific for rMIF-C1 were measured in an ELISA specific for rMIF-C1, as follows.

ELISA plates were coated with rMIF-C1 at a concentration of 5 μg/ml. The plates were blocked and then incubated with serially diluted mouse sera. Bound antibodies were detected with enzymatically labeled anti-mouse IgG antibody. As a control, a preimmune serum of the same mice was also tested.

Immunization with rMIF-C1 coupled to AP205 VLP led to a strong specific immune response against rMIF-C1 (FIG. 7), whereby the average titer of the three mice against rMIF-C1, defined as the dilution of the serum giving half-maximal OD was of 1:31 000. rMIF-C1 was therefore properly displayed on the AP205 VLP and accessible to the immune system for generation of a strong immune response.

Shown on FIG. 7 is the analysis by ELISA of the IgG response specific for rMIF-C1 in the sera of mice immunized with rMIF-C1 coupled to AP205 VLP. Analysis of the day 21-sera of the three mice (M1, M2 and M3) was done in duplicate. Three-fold dilutions of the sera were applied to the well. "pre imm" stands for the pre immune serum of one mouse subsequently immunized with rMIF-C1 coupled to AP205 VLP.

B. Immunization of Rats with AP205 VLP Coupled to rMIF-C1

AP205 VLP coupled to rMIF-C1 (from Example 12) is injected s.c. in rats (3 rats each) at day 0 and 28 in the absence of adjuvants. Each rat is immunized with 50 μg of vaccine diluted in PBS to 200 μl. Rats are bled on day 42, and the titer of the antibodies specific for rMIF-C1 are measured in an ELISA specific for rMIF-C1, as described above, using however an enzymatically labeled anti-Rat IgG secondary antibody.

Example 13

Coupling of the Angio I Peptide to AP205 VLP and Immunization of Mice

A. Coupling of Angio I Peptide to AP205 VLP

The Angio I peptide, having the sequence of Angiotensin II (DRVYIHPF) (SEQ ID NO: 13) fused at its N-terminus to the linker sequence CGG containing a cysteine residue for coupling to the activated VLP, was chemically synthesized. AP205 VLP, expressed and purified as described in example 2, was resolubilized in 20 mM Hepes, 150 mM NaCl, pH 7.4 buffer (HBS buffer). Resolubilized AP205 VLP was then reacted at a concentration of 2 mg/ml (determined in a Bradford assay), with 1.43 mM SMPH (Pierce) for 30 minutes at room temperature (RT). The reaction mixture was then dialyzed twice against HBS buffer for 2 hours at 4° C., and reacted with 1.144 mM Angio I peptide (sequence: CGGDRVYIHPF (SEQ ID NO: 12), free amine and free acid), diluted in the reaction mixture from a 50 mM stock in DMSO. The coupling reaction was left to proceed for 2 hours at 15° C., and the reaction mixture dialyzed 2×2 hours against a 1000-fold volume HBS, and flash frozen in liquid nitrogen in aliquots for storage at −80° C. until further use.

An aliquot was thawed, and coupling of the antigen to an AP205 subunit assessed by SDS-PAGE and the protein concentration measured in a Bradford assay. Coupling efficiency of the peptide to AP205 VLP, as defined by the sum of the intensities of the bands corresponding to 1, 2 or 3 peptides coupled per monomer subunit, divided by the sum of the intensities of coupled and uncoupled AP205 monomer subunits, was of 88%. Epitope density was measured similarly as coupling efficiency, with the modification that the intensity of the coupling bands are multiplied by the number of coupled peptide per subunit in the respective band, in the numerator. Epitope density was of 1.6 Angio I peptides per AP205 VLP subunit.

B. Immunization of Mice with AP205 VLP Coupled to Angio I Peptide

AP205 VLP coupled to Angio I peptide produced as described in part A was injected s.c. in three mice at day 0 and 14 in the absence of adjuvants. Each mouse was immunized with 25 μg of vaccine diluted in PBS to 200 μl. Mice were retro-orbitally bled on day 21, and the titer of the antibodies specific for Angio I peptide were measured by ELISA. The Angio I peptide was coupled to bovine RNAse A using the chemical cross-linker sulfo-SPDP. ELISA plates were coated with Angio I-coupled RNAse at a concentration of 10 μg/ml. The plates were blocked and then incubated with serially diluted mouse sera. Bound antibodies were detected with enzymatically labeled anti-mouse IgG antibodies. As a control preimmune sera of the same mice were also tested. The results are shown in FIG. 8.

FIG. 8 shows an ELISA analysis of the IgG antibodies specific for Angio I peptide in the sera of the three mice (1-3) immunized on day 0 and 14 against the Angio I peptide coupled to AP205 VLP. Total IgG titers were determined in the day 21 sera. No antibodies specific for Angio I could be detected in the preimmune serum analysed. A very high specific titer against Angio I of 1:69 000 in average (given as the dilution giving half maximal OD at 450 nm) was obtained, demonstrating that self-tolerance against Angio I (a selfpeptide in the mouse) had been broken. The data demonstrate that vaccines with very high display of peptides are obtained upon coupling antigens to AP205 VLP. The data also demonstrate that very high titers against self-antigens are obtained upon coupling of these self-antigens to AP205 VLP and subsequent immunization with the resulting vaccine in the absence of adjuvant.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising:
   (a) a core particle selected from the group consisting of
      (i) an AP205 virus-like particle comprising at least one protein comprising amino acids 2-131 of SEQ ID NO:1;
      (ii) an AP205 virus-like particle comprising at least one protein comprising amino acids 2-131 of SEQ ID NO:3; and
      (iii) an AP205 virus-like particle comprising a mutein of SEQ ID NO:1, wherein said mutein consists of an addition, deletion or substitution of one to three amino acids from amino acids 1-131 of SEQ ID NO:1; and
   (b) an organic molecule, wherein said organic molecule is an influenza antigen, and wherein said organic molecule is bound to said core particle.

2. The composition of claim 1, wherein said organic molecule forms an ordered and repetitive array on the surface of said core particle.

3. The composition of claim 1, wherein said organic molecule is bound to said core particle via a third molecule.

4. The composition of claim 1, wherein said organic molecule is bound to said core particle by at least one covalent bond.

5. The composition of claim 1, wherein said organic molecule is bound to said core particle by at least one peptide covalent bond.

6. The composition of claim 1, wherein said organic molecule is bound to said core particle by at least one non-peptide covalent bond.

7. The composition of claim 1, wherein said core particle comprises at least one first attachment site, said organic molecule comprises at least one second attachment site, such that said second attachment site associates with said first attachment site to form an ordered and repetitive array via at least one covalent bond.

8. The composition of claim 7, wherein said first attachment site is an amino group, and wherein said second attachment site is a sulfhydryl group.

9. The composition of claim 7, wherein said first attachment site comprises a lysine residue, and wherein said second attachment site comprises a cysteine residue.

10. The composition of claim 7, wherein said second attachment site does not naturally occur within said organic molecule.

11. The composition of claim 1, wherein said composition comprises an amino acid linker.

12. The composition of claim 11, wherein said amino acid linker is bound to said organic molecule by way of at least one covalent bond.

13. The composition of 11, wherein said amino acid linker comprises said second attachment site.

14. The composition of claim 11, wherein said amino acid linker is selected from the group consisting of:
   (a) CGG;
   (b) an N-terminal gamma 1-linker;
   (c) an N-terminal gamma 3-linker;
   (d) an Ig hinge region;
   (e) an N-terminal glycine linker;
   (f) $(G)_k C(G)_n$ with n=0-12 and k=0-5 (SEQ ID NO: 93);
   (g) an N-terminal glycine-serine linker;
   (h) $(G)_k C(G)_m (S)_l (GGGGS)_n$ with n=0-3, k=0-5, m=0-10, l=0-2 (SEQ ID NO: 94);
   (i) GGC;
   (j) GGC-NH2;
   (k) a C-terminal gamma 1-linker;
   (l) a C-terminal gamma 3-linker;
   (m) a C-terminal glycine linker;
   (n) $(G)_n C(G)_k$ with n=0-12 and k=0-5 (SEQ ID NO: 95);
   (o) a C-terminal glycine-serine linker; and
   (p) $(G)_m (S)_l (GGGGS)_n (G)_o C(G)_k$ with n=0-3, k=0-5, m=0-10, l=0-2, and o=0-8 (SEQ ID NO: 96).

15. The composition of claim 1, wherein said organic molecule is an antigen or an antigenic determinant.

16. The composition of claim 1, wherein said organic molecule is an antigen of
   a polypeptide of Influenza virus
   and
   or any fragment thereof.

17. The composition of claim 15, wherein said antigen or antigenic determinant is a peptide, a protein, or a fragment of an Influenza M2 protein.

18. The composition of claim 7, wherein said covalent bond is a peptide covalent bond.

19. The composition of claim 7, wherein said covalent bond is a non-peptide covalent bond.

20. A pharmaceutical composition comprising the composition of claim 1 and a pharmaceutically acceptable carrier.

21. A composition comprising the composition of claim 1 and an adjuvant.

22. A method of immunization of an animal comprising administering the composition of claim 1 to said animal, whereby an immune response against said organic molecule is produced in said animal.

23. A process for producing a non-naturally occurring, ordered and repetitive array comprising:
   (a) providing a molecular scaffold comprising a virus-like particle selected from the group consisting of:
      (i) a protein comprising amino acids 2-131 of SEQ ID NO:1;

(ii) a protein comprising amino acids 2-131 of SEQ ID NO:3; and (iii) a mutein of SEQ ID NO:1, wherein said mutein consists of an addition, deletion or substitution of one to three amino acids from amino acids 1-131 of SEQ ID NO:1;

(b) providing an organic molecule suitable for inducing an immune response, wherein said organic molecule is an influenza antigen;

(c) providing a means of associating (a) and (b), said means optionally contained within (a) and/or (b), or as a separate molecule; and (d) combining the elements of (a) through (c), such that said organic molecule associates with said scaffold to form said ordered and repetitive array.

24. A method of treating or preventing a disease, disorder or physiologic condition in an animal, comprising administering the composition of claim 1 to an animal, whereby an immune response against said organic molecule is produced in said animal, and wherein said immune response results in treatment or prevention of said disease, disorder or physiologic condition.

25. A method of treating or preventing a disease, disorder or physiologic condition in an animal, said method comprising administering the composition of claim 21 to an animal, whereby an immune response against said organic molecule is produced in said animal, and wherein said immune response results in treatment or prevention of said disease, disorder or physiologic condition.

26. The composition of claim 1, wherein said core particle is an AP205 virus-like particle comprising at least one protein comprising amino acids 2-131 of SEQ ID NO:1.

27. The composition of claim 1, wherein said core particle is an AP205 virus-like particle comprising at least one protein comprising amino acids 2-131 of SEQ ID NO:3.

28. The composition of claim 1, wherein said core particle is an AP205 virus-like particle comprising a mutein of SEQ ID NO:1, wherein said mutein consists of an addition, deletion or substitution of one to three amino acids from amino acids 1-131 of SEQ ID NO:1.

29. The composition of claim 15, wherein said antigen or antigenic determinant is an Influenza M2 protein.

30. The composition of claim 15, wherein said antigen or antigenic determinant is an Influenza M2 protein having the amino acid sequence as set forth in SEQ ID NO:126 or SEQ ID NO:127.

31. The composition of claim 15, wherein said antigen or antigenic determinant is a fragment of an Influenza M2 protein being at least 6 amino acids in length.

32. The composition of claim 31, wherein said Influenza M2 protein has the amino acid sequence as set forth in SEQ ID NO:126 or SEQ ID NO:127.

33. The composition of claim 31, wherein said fragment of said Influenza M2 protein consists of the amino acids 2 to 24 of said M2 protein.

34. The composition of claim 33, wherein said Influenza M2 protein has the amino acid sequence as set forth in SEQ ID NO:126.

35. The composition of claim 33, wherein said Influenza M2 protein has the amino acid sequence as set forth in SEQ ID NO:127.

36. The composition of claim 34, wherein said core particle is an AP205 virus-like particle comprising at least one protein comprising amino acids 2-131 of SEQ ID NO:1.

37. The composition of claim 34, wherein said core particle is an AP205 virus-like particle comprising at least one protein comprising amino acids 2-131 of SEQ ID NO:3.

38. The composition of claim 34, wherein said core particle is an AP205 virus-like particle comprising a mutein of SEQ ID NO:1, wherein said mutein consists of an addition, deletion or substitution of one to three amino acids from amino acids 1-131 of SEQ ID NO:1.

39. The composition of claim 8, wherein said covalent bond is a non-peptide covalent bond.

40. The composition of claim 35, wherein said core particle is an AP205 virus-like particle comprising at least one protein comprising amino acids 2-131 of SEQ ID NO:1.

41. The composition of claim 35, wherein said core particle is an AP205 virus-like particle comprising at least one protein comprising amino acids 2-131 of SEQ ID NO:3.

42. The composition of claim 35, wherein said core particle is an AP205 virus-like particle comprising a mutein of SEQ ID NO:1, wherein said mutein consists of an addition, deletion or substitution of one to three amino acids from amino acids 1-131 of SEQ ID NO:1.

43. The composition of claim 36, wherein said organic molecule is bound to said core particle by at least one covalent bond.

44. The composition of claim 43, wherein said covalent bond is a peptide covalent bond.

45. The composition of claim 43, wherein said covalent bond is a non-peptide covalent bond.

46. The composition of claim 1, wherein said influenza antigen is hemagglutinin.

47. The composition of claim 46, wherein said organic molecule is bound to said core particle by at least one peptide covalent bond.

48. The composition of claim 46, wherein said organic molecule is bound to said core particle by at least one non-peptide covalent bond.

49. The composition of claim 1, wherein said influenza antigen is neuraminidase.

50. The composition of claim 49, wherein said organic molecule is bound to said core particle by at least one peptide covalent bond.

51. The composition of claim 49, wherein said organic molecule is bound to said core particle by at least one non-peptide covalent bond.

* * * * *

SEQUENCE LISTING

```
<160> NUMBER OF SEQ ID NOS: 125

<210> SEQ ID NO 1
<211> LENGTH: 131
<212> TYPE: PRT
<213> ORGANISM: Bacteriophage AP205

<400> SEQUENCE: 1

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 2
<211> LENGTH: 3635
<212> TYPE: DNA
<213> ORGANISM: Artificial Sequence
<220> FEATURE:
<223> OTHER INFORMATION: Plasmid, pAP283-58, encoding RNA phage AP205
      coat protein

<400> SEQUENCE: 2
cgagctcgcc cctggcttat cgaaattaat acgactcact atagggagac cggaattcga      60
gctcgcccgg ggatcctcta gaattttctg cgcacccatc ccgggtggcg cccaaagtga     120
ggaaaatcac atggcaaata agccaatgca accgatcaca tctacagcaa ataaaattgt     180
gtggtcggat ccaactcgtt tatcaactac attttcagca agtctgttac gccaacgtgt     240
taaagttggt atagccgaac tgaataatgt ttcaggtcaa tatgtatctg tttataagcg     300
tcctgcacct aaaccggaag gttgtgcaga tgcctgtgtc attatgccga atgaaaacca     360
atccattcgc acagtgattt cagggtcagc cgaaaacttg gctaccttaa aagcagaatg     420
```

-continued

| | |
|---|---|
| ggaaactcac aaacgtaacg ttgacacact cttcgcgagc ggcaacgccg gtttgggttt | 480 |
| ccttgaccct actgcggcta tcgtatcgtc tgatactact gcttaagctt gtattctata | 540 |
| gtgtcaccta atcgtatgt gtatgataca taaggttatg tattaattgt agccgcgttc | 600 |
| taacgacaat atgtacaagc ctaattgtgt agcatctggc ttactgaagc agaccctatc | 660 |
| atctctctcg taaactgccg tcagagtcgg tttggttgga cgaaccttct gagtttctgg | 720 |
| taacgccgtt ccgcaccccg gaaatggtca ccgaaccaat cagcagggtc atcgctagcc | 780 |
| agatcctcta cgccggacgc atcgtggccg gcatcaccgg cgccacaggt gcggttgctg | 840 |
| gcgcctatat cgccgacatc accgatgggg aagatcgggc tcgccacttc gggctcatga | 900 |
| gcgcttgttt cggcgtgggt atggtggcag gccccgtggc cggggactg ttgggcgcca | 960 |
| tctccttgca tgcaccattc cttgcggcgg cggtgctcaa cggcctcaac ctactactgg | 1020 |
| gctgcttcct aatgcaggag tcgcataagg gagagcgtcg atatggtgca ctctcagtac | 1080 |
| aatctgctct gatgccgcat agttaagcca actccgctat cgctacgtga ctgggtcatg | 1140 |
| gctgcgcccc gacacccgcc aacaccgct gacgcgccct gacgggcttg tctgctcccg | 1200 |
| gcatccgctt acagacaagc tgtgaccgtc tccgggagct gcatgtgtca gaggtttca | 1260 |
| ccgtcatcac cgaaacgcgc gaggcagctt gaagacgaaa gggcctcgtg atacgcctat | 1320 |
| ttttataggt taatgtcatg ataataatgg tttcttagac gtcaggtggc acttttcggg | 1380 |
| gaaatgtgcg cggaacccct atttgtttat ttttctaaat acattcaaat atgtatccgc | 1440 |
| tcatgagaca ataaccctga taaatgcttc aataatattg aaaaggaag agtatgagta | 1500 |
| ttcaacattt ccgtgtcgcc cttattccct tttttgcggc attttgcctt cctgttttg | 1560 |
| ctcacccaga aacgctggtg aaagtaaaag atgctgaaga tcagttgggt gcacgagtgg | 1620 |
| gttacatcga actggatctc aacagcggta agatccttga gagttttcgc cccgaagaac | 1680 |
| gttttccaat gatgagcact tttaaagttc tgctatgtgg cgcggtatta tcccgtattg | 1740 |
| acgccgggca agagcaactc ggtcgccgca tacactattc tcagaatgac ttggttgagt | 1800 |
| actcaccagt cacagaaaag catcttacgg atggcatgac agtaagagaa ttatgcagtg | 1860 |
| ctgccataac catgagtgat aacactgcgg ccaacttact tctgacaacg atcggaggac | 1920 |
| cgaaggagct aaccgctttt ttgcacaaca tgggggatca tgtaactcgc cttgatcgtt | 1980 |
| gggaaccgga gctgaatgaa gccataccaa acgacgagcg tgacaccacg atgcctgtag | 2040 |
| caatggcaac aacgttgcgc aaactattaa ctggcgaact acttactcta gcttcccggc | 2100 |
| aacaattaat agactggatg gaggcggata agttgcagg accacttctg cgctcggccc | 2160 |
| ttccggctgg ctggtttatt gctgataaat ctggagccgg tgagcgtggg tctcgcggta | 2220 |
| tcattgcagc actggggcca gatggtaagc cctcccgtat cgtagttatc tacacgacgg | 2280 |
| ggagtcaggc aactatggat gaacgaaata gacagatcgc tgagataggt gcctcactga | 2340 |
| ttaagcattg gtaactgtca gaccaagttt actcatatat actttagatt gatttaaaac | 2400 |
| ttcattttta atttaaaagg atctaggtga agatcctttt tgataatctc atgaccaaaa | 2460 |
| tcccttaacg tgagttttcg ttccactgag cgtcagaccc cgtagaaaag atcaaggat | 2520 |
| cttcttgaga tccttttttt ctgcgcgtaa tctgctgctt gcaaacaaaa aaaccaccgc | 2580 |
| taccagcggt ggtttgtttg ccggatcaag agctaccaac tctttttccg aaggtaactg | 2640 |
| gcttcagcag agcgcagata ccaaatactg tccttctagt gtagccgtag ttaggccacc | 2700 |
| acttcaagaa ctctgtagca ccgcctacat acctcgctct gctaatcctg ttaccagtgg | 2760 |

```
ctgctgccag tggcgataag tcgtgtctta ccggggttgga ctcaagacga tagttaccgg    2820
ataaggcgca gcggtcgggc tgaacggggg gttcgtgcac acagcccagc ttggagcgaa    2880
cgacctacac cgaactgaga tacctacagc gcgagcattg agaaagcgcc acgcttcccg    2940
aagggagaaa ggcggacagg tatccggtaa gcggcagggt cggaacagga gagcgcacga    3000
gggagcttcc aggggaaac gcctggtatc tttatagtcc tgtcgggttt cgccacctct     3060
gacttgagcg tcgattttg tgatgctcgt caggggggcg gagcctatgg aaaaacgcca     3120
gcaacgcggc cttttacgg ttcctggcct tttgctggcc ttttgctcac atgttctttc     3180
ctgcgttatc ccctgattct gtggataacc gtattaccgc ctttgagtga gctgataccg    3240
ctcgccgcag ccgaacgacc gagcgcagcg agtcagtgag cgaggaagcg gaagagcgcc    3300
caatacgcaa accgcctctc cccgcgcgtt ggccgattca ttaatgcagc tgtggtgtca    3360
tggtcggtga tcgccagggt gccgacgcgc atctcgactg catggtgcac caatgcttct    3420
ggcgtcaggc agccatcgga agctgtggta tggccgtgca ggtcgtaaat cactgcataa    3480
ttcgtgtcgc tcaaggcgca ctcccgttct ggataatgtt ttttgcgccg acatcataac    3540
ggttctggca aatattctga aatgagctgt tgacaattaa tcatcgaact agttaactag    3600
tacgcaagtt cacgtaaaaa gggtatcgcg gaatt                               3635

<210> SEQ ID NO 3
<211> LENGTH: 131
<212> TYPE: PRT
<213> ORGANISM: Artificial Sequence
<220> FEATURE:
<223> OTHER INFORMATION: Bacteriophage AP205 mutant

<400> SEQUENCE: 3

Met Ala Asn Lys Thr Met Gln Pro Ile Thr Ser Thr Ala Asn Lys Ile
1               5                  10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 4
<211> LENGTH: 3613
<212> TYPE: DNA
<213> ORGANISM: Artificial Sequence
<220> FEATURE:
<223> OTHER INFORMATION: Plasmid pAP281-32

<400> SEQUENCE: 4
cgagctcgcc cctggcttat cgaaattaat acgactcact atagggagac cggaattcga      60
```

```
gctcgcccgg ggatcctcta gattaaccca acgcgtagga gtcaggccat ggcaaataag      120
acaatgcaac cgatcacatc tacagcaaat aaaattgtgt ggtcggatcc aactcgttta      180
tcaactacat tttcagcaag tctgttacgc caacgtgtta agttggtat agccgaactg       240 aataatgttt caggtcaata tgtatctgtt tataagcgtc ctgcacctaa accggaaggt      300
tgtgcagatg cctgtgtcat tatgccgaat gaaaaccaat ccattcgcac agtgatttca      360
gggtcagccg aaaacttggc taccttaaaa gcagaatggg aaactcacaa acgtaacgtt      420
gacacactct tcgcgagcgg caacgccggt ttgggtttcc ttgaccctac tgcggctatc      480
gtatcgtctg atactactgc ttaagcttgt attctatagt gtcacctaaa tcgtatgtgt      540
atgatacata aggttatgta ttaattgtag ccgcgttcta acgacaatat gtacaagcct      600
aattgtgtag catctggctt actgaagcag accctatcat ctctctcgta aactgccgtc      660
agagtcggtt tggttggacg aaccttctga gtttctggta acgccgttcc gcaccccgga      720
aatggtcacc gaaccaatca gcagggtcat cgctagccag atcctctacg ccggacgcat      780
cgtggccggc atcaccggcg ccacaggtgc ggttgctggc gcctatatcg ccgacatcac      840
cgatggggaa gatcgggctc gccacttcgg gctcatgagc gcttgttctcg gcgtgggtat    900 ggtggcaggc cccgtggccg ggggactgtt gggcgccatc tccttgcatg caccattcct      960
tgcggcggcg gtgctcaacg gcctcaacct actactgggc tgcttcctaa tgcaggagtc      1020
gcataaggga gagcgtcgat atggtgcact ctcagtacaa tctgctctga tgccgcatag      1080
ttaagccaac tccgctatcg ctacgtgact gggtcatggc tgcgcccga cacccgccaa       1140 cacccgctga cgcgccctga cgggcttgtc tgctcccggc atccgcttac agacaagctg      1200
tgaccgtctc cgggagctgc atgtgtcaga ggttttcacc gtcatcaccg aaacgcgcga      1260
ggcagcttga agacgaaagg gcctcgtgat acgcctattt ttataggtta atgtcatgat      1320
aataatggtt tcttagacgt caggtggcac ttttcgggga aatgtgcgcg gaaccccctat   1380 ttgtttattt ttctaaatac attcaaatat gtatccgctc atgagacaat aaccctgata      1440
aatgcttcaa taatattgaa aaaggaagag tatgagtatt caacatttcc gtgtcgccct     1500
tattcccttt tttgcggcat tttgccttcc tgttttgct cacccagaaa cgctggtgaa       1560
agtaaaagat gctgaagatc agttgggtgc acgagtgggt tacatcgaac tggatctcaa     1620
cagcggtaag atccttgaga gttttcgccc cgaagaacgt tttccaatga tgagcacttt     1680
taaagttctg ctatgtggcg cggtattatc ccgtattgac gccgggcaag agcaactcgg     1740
tcgccgcata cactattctc agaatgactt ggttgagtac tcaccagtca cagaaaagca    1800
tcttacggat ggcatgacag taagagaatt atgcagtgct gccataacca tgagtgataa   1860
cactgcggcc aacttacttc tgacaacgat cggaggaccg aaggagctaa ccgcttttt    1920 gcacaacatg ggggatcatg taactcgcct tgatcgttgg gaaccggagc tgaatgaagc   1980
cataccaaac gacgagcgtg acaccacgat gcctgtagca atggcaacaa cgttgcgcaa   2040
actattaact ggcgaactac ttactctagc ttcccggcaa caattaatag actggatgga   2100
ggcggataaa gttgcaggac cacttctgcg ctcggccctt ccggctggct ggtttattgc    2160
tgataaatct ggagccggtg agcgtgggtc tcgcggtatc attgcagcac tggggccaga   2220
tggtaagccc tcccgtatcg tagttatcta cacgacgggg agtcaggcaa ctatggatga   2280
acgaaataga cagatcgctg agataggtgc ctcactgatt aagcattggt aactgtcaga    2340
ccaagtttac tcatatatac tttagattga tttaaaactt catttttaat ttaaaaggat    2400
ctaggtgaag atccttttg ataatctcat gaccaaaatc ccttaacgtg agttttcgtt     2460
```

```
ccactgagcg tcagaccccg tagaaaagat caaaggatct tcttgagatc ctttttttct    2520
gcgcgtaatc tgctgcttgc aaacaaaaaa accaccgcta ccagcggtgg tttgtttgcc    2580
ggatcaagag ctaccaactc ttttccgaa ggtaactggc ttcagcagag cgcagatacc     2640
aaatactgtc cttctagtgt agccgtagtt aggccaccac ttcaagaact ctgtagcacc    2700
gcctacatac ctcgctctgc taatcctgtt accagtggct gctgccagtg gcgataagtc    2760
gtgtcttacc gggttggact caagacgata gttaccggat aaggcgcagc ggtcgggctg    2820 aacgggggt tcgtgcacac agcccagctt ggagcgaacg acctacaccg aactgagata     2880
cctacagcgc gagcattgag aaagcgccac gcttcccgaa gggagaaagg cggacaggta    2940
tccggtaagc ggcagggtcg aacaggaga gcgcacgagg gagcttccag ggggaaacgc     3000
ctggtatctt tatagtcctg tcgggtttcg ccacctctga cttgagcgtc gatttttgtg    3060
atgctcgtca gggggcgga gcctatgaa aaacgccagc aacgcggcct ttttacggtt      3120
cctggccttt tgctggcctt tgctcacat gttctttcct gcgttatccc ctgattctgt     3180
ggataaccgt attaccgcct ttgagtgagc tgataccgct cgccgcagcc gaacgaccga    3240
gcgcagcgag tcagtgagcg aggaagcgga agagcgccca atacgcaaac cgcctctccc    3300
cgcgcgttgg ccgattcatt aatgcagctg tggtgtcatg gtcggtgatc gccagggtgc    3360
cgacgcgcat ctcgactgca tggtgcacca atgcttctgg cgtcaggcag ccatcggaag    3420
ctgtggtatg gccgtgcagg tcgtaaatca ctgcataatt cgtgtcgctc aaggcgcact    3480
cccgttctgg ataatgtttt ttgcgccgac atcataacgg ttctggcaaa tattctgaaa    3540
tgagctgttg acaattaatc atcgaactag ttaactagta cgcaagttca cgtaaaaagg    3600
gtatcgcgga att                                                      3613

<210> SEQ ID NO 5
<211> LENGTH: 57
<212> TYPE: DNA
<213> ORGANISM: Artificial Sequence
<220> FEATURE:
<223> OTHER INFORMATION: sequence containing putative AP205 ribosomal
      binding site

<400> SEQUENCE: 5
tctagaattt tctgcgcacc catcccgggt ggcgcccaaa gtgaggaaaa tcacatg      57

<210> SEQ ID NO 6
<211> LENGTH: 35
<212> TYPE: DNA
<213> ORGANISM: Artificial Sequence
<220> FEATURE:
<223> OTHER INFORMATION: Shine-Dalgarno sequence of vector pQb185

<400> SEQUENCE: 6
tctagattaa cccaacgcgt aggagtcagg ccatg                             35

<210> SEQ ID NO 7
<211> LENGTH: 42
<212> TYPE: PRT
<213> ORGANISM: Homo sapiens

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

-continued

```
Gly Leu Met Val Gly Gly Val Val Ile Ala
        35                  40

<210> SEQ ID NO 8
<211> LENGTH: 18
<212> TYPE: PRT
<213> ORGANISM: Artificial Sequence
<220> FEATURE:
<223> OTHER INFORMATION: Abeta 1-15 GGC

<400> SEQUENCE: 8

Asp Ala Glu Phe Arg His Asp Ser Gly Tyr Glu Val His His Gln Gly
1               5                   10                  15

Gly Cys

<210> SEQ ID NO 9
<211> LENGTH: 30
<212> TYPE: PRT
<213> ORGANISM: Artificial Sequence
<220> FEATURE:
<223> OTHER INFORMATION: Abeta 1-27 GGC

<400> SEQUENCE: 9

Asp Ala Glu Phe Arg His Asp Ser Gly Tyr Glu Val His His Gln Lys
1               5                   10                  15

Leu Val Phe Phe Ala Glu Asp Val Gly Ser Asn Gly Gly Cys
            20                  25                  30

<210> SEQ ID NO 10
<211> LENGTH: 17
<212> TYPE: PRT
<213> ORGANISM: Artificial Sequence
<220> FEATURE:
<223> OTHER INFORMATION: Abeta 33-42 mutant

<400> SEQUENCE: 10

Cys Gly His Gly Asn Lys Ser Gly Leu Met Val Gly Gly Val Val Ile
1               5                   10                  15

Ala

<210> SEQ ID NO 11
<211> LENGTH: 14
<212> TYPE: PRT
<213> ORGANISM: Homo sapiens

<400> SEQUENCE: 11

Asp Arg Val Tyr Ile His Pro Phe His Leu Val Ile His Asn
1               5                   10

<210> SEQ ID NO 12
<211> LENGTH: 10
<212> TYPE: PRT
<213> ORGANISM: Homo sapiens

<400> SEQUENCE: 12

Asp Arg Val Tyr Ile His Pro Phe His Leu
1               5                   10

<210> SEQ ID NO 13
<211> LENGTH: 8
<212> TYPE: PRT
<213> ORGANISM: Homo sapiens

<400> SEQUENCE: 13
```

```
Asp Arg Val Tyr Ile His Pro Phe
1               5

<210> SEQ ID NO 14
<211> LENGTH: 11
<212> TYPE: PRT
<213> ORGANISM: Artificial Sequence
<220> FEATURE:
<223> OTHER INFORMATION: CGG-angiotensin I

<400> SEQUENCE: 14

Cys Gly Gly Asp Arg Val Tyr Ile His Pro Phe
1               5                   10

<210> SEQ ID NO 15
<211> LENGTH: 13
<212> TYPE: PRT
<213> ORGANISM: Artificial Sequence
<220> FEATURE:
<223> OTHER INFORMATION: CGG-Angiotensin I peptide

<400> SEQUENCE: 15

Cys Gly Gly Asp Arg Val Tyr Ile His Pro Phe His Leu
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Angiotensin-I GGC peptide

<400> SEQUENCE: 16

Asp Arg Val Tyr Ile His Pro Phe His Leu Gly Gly Cys
1               5                   10

<210> SEQ ID NO 17
<211> LENGTH: 26
<212> TYPE: PRT
<213> ORGANISM: Artificial Sequence
<220> FEATURE:
<223> OTHER INFORMATION: prion peptide "cprplong"

<400> SEQUENCE: 17

Cys Ser Ala Met Ser Arg Pro Met Ile His Phe Gly Asn Asp Trp Glu
1               5                   10                  15

Asp Arg Tyr Tyr Arg Glu Asn Met Tyr Arg
            20                  25

<210> SEQ ID NO 18
<211> LENGTH: 16
<212> TYPE: PRT
<213> ORGANISM: Artificial Sequence
<220> FEATURE:
<223> OTHER INFORMATION: prion peptide "cprpshort"

<400> SEQUENCE: 18

Cys Gly Asn Asp Trp Glu Asp Arg Tyr Tyr Arg Glu Asn Met Tyr Arg
1               5                   10                  15

<210> SEQ ID NO 19
<211> LENGTH: 26
<212> TYPE: PRT
<213> ORGANISM: Artificial Sequence
<220> FEATURE:
<223> OTHER INFORMATION: prion protein "human cprplong"
```

```
<400> SEQUENCE: 19

Cys Ser Ala Met Ser Arg Pro Ile Ile His Phe Gly Ser Asp Tyr Glu
1               5                   10                  15

Asp Arg Tyr Tyr Arg Glu Asn Met His Arg
            20                  25

<210> SEQ ID NO 20
<211> LENGTH: 16
<212> TYPE: PRT
<213> ORGANISM: Artificial Sequence
<220> FEATURE:
<223> OTHER INFORMATION: prion peptide "human cprpshort"

<400> SEQUENCE: 20

Cys Gly Ser Asp Tyr Glu Asp Arg Tyr Tyr Arg Glu Asn Met His Arg
1               5                   10                  15

<210> SEQ ID NO 21
<211> LENGTH: 26
<212> TYPE: PRT
<213> ORGANISM: Artificial Sequence
<220> FEATURE:
<223> OTHER INFORMATION: prion peptide "bovine cprplong"

<400> SEQUENCE: 21

Cys Ser Ala Met Ser Arg Pro Leu Ile His Phe Gly Asn Asp Tyr Glu
1               5                   10                  15

Asp Arg Tyr Tyr Arg Glu Asn Met His Arg
            20                  25

<210> SEQ ID NO 22
<211> LENGTH: 16
<212> TYPE: PRT
<213> ORGANISM: Artificial Sequence
<220> FEATURE:
<223> OTHER INFORMATION: prion peptide "bovine cprpshort"

<400> SEQUENCE: 22

Cys Gly Asn Asp Tyr Glu Asp Arg Tyr Tyr Arg Glu Asn Met His Arg
1               5                   10                  15

<210> SEQ ID NO 23
<211> LENGTH: 26
<212> TYPE: PRT
<213> ORGANISM: Artificial Sequence
<220> FEATURE:
<223> OTHER INFORMATION: prion peptide "sheep cprplong"

<400> SEQUENCE: 23

Cys Ser Ala Met Ser Arg Pro Leu Ile His Phe Gly Asn Asp Tyr Glu
1               5                   10                  15

Asp Arg Tyr Tyr Arg Glu Asn Met Tyr Arg
            20                  25

<210> SEQ ID NO 24
<211> LENGTH: 16
<212> TYPE: PRT
<213> ORGANISM: Artificial Sequence
<220> FEATURE:
<223> OTHER INFORMATION: prion peptide "sheep cprpshort"

<400> SEQUENCE: 24

Cys Gly Asn Asp Tyr Glu Asp Arg Tyr Tyr Arg Glu Asn Met Tyr Arg
1               5                   10                  15
```

<210> SEQ ID NO 25
<211> LENGTH: 14
<212> TYPE: PRT
<213> ORGANISM: Artificial Sequence
<220> FEATURE:
<223> OTHER INFORMATION: murine TNF- a mutant

<400> SEQUENCE: 25

Cys Gly Gly Val Glu Glu Gln Leu Glu Trp Leu Ser Gln Arg
1               5                   10

<210> SEQ ID NO 26
<211> LENGTH: 22
<212> TYPE: PRT
<213> ORGANISM: Artificial Sequence
<220> FEATURE:
<223> OTHER INFORMATION: murine TNF- a mutant

<400> SEQUENCE: 26

Ser Ser Gln Asn Ser Ser Asp Lys Pro Val Ala His Val Val Ala Asn
1               5                   10                  15

His Gly Val Gly Gly Cys
            20

<210> SEQ ID NO 27
<211> LENGTH: 20
<212> TYPE: PRT
<213> ORGANISM: Artificial Sequence
<220> FEATURE:
<223> OTHER INFORMATION: murine TNF-a mutant peptide

<400> SEQUENCE: 27

Cys Ser Ser Gln Asn Ser Ser Asp Lys Pro Val Ala His Val Val Ala
1               5                   10                  15

Asn His Gly Val
            20

<210> SEQ ID NO 28
<211> LENGTH: 22
<212> TYPE: PRT
<213> ORGANISM: Artificial Sequence
<220> FEATURE:
<223> OTHER INFORMATION: human TNF-a peptide mutant

<400> SEQUENCE: 28

Ser Ser Arg Thr Pro Ser Asp Lys Pro Val Ala His Val Val Ala Asn
1               5                   10                  15

Pro Gln Ala Glu Gly Gln
            20

<210> SEQ ID NO 29
<211> LENGTH: 11
<212> TYPE: PRT
<213> ORGANISM: Homo sapiens

<400> SEQUENCE: 29

Gln Leu Gln Trp Leu Asn Arg Arg Ala Asn Ala
1               5                   10

<210> SEQ ID NO 30
<211> LENGTH: 13
<212> TYPE: PRT
<213> ORGANISM: Artificial Sequence
<220> FEATURE:

```
<223> OTHER INFORMATION: CGG-IgE peptide mutant

<400> SEQUENCE: 30

Cys Gly Gly Val Asn Leu Thr Trp Ser Arg Ala Ser Gly
1               5                   10

<210> SEQ ID NO 31
<211> LENGTH: 8
<212> TYPE: PRT
<213> ORGANISM: Artificial Sequence
<220> FEATURE:
<223> OTHER INFORMATION: IgE mimotope

<400> SEQUENCE: 31

Ile Asn His Arg Gly Tyr Trp Val
1               5

<210> SEQ ID NO 32
<211> LENGTH: 8
<212> TYPE: PRT
<213> ORGANISM: Artificial Sequence
<220> FEATURE:
<223> OTHER INFORMATION: IgE mimotope

<400> SEQUENCE: 32

Arg Asn His Arg Gly Tyr Trp Val
1               5

<210> SEQ ID NO 33
<211> LENGTH: 10
<212> TYPE: PRT
<213> ORGANISM: Artificial Sequence
<220> FEATURE:
<223> OTHER INFORMATION: IgE mimotope

<400> SEQUENCE: 33

Arg Ser Arg Ser Gly Gly Tyr Trp Leu Trp
1               5                   10

<210> SEQ ID NO 34
<211> LENGTH: 10
<212> TYPE: PRT
<213> ORGANISM: Artificial Sequence
<220> FEATURE:
<223> OTHER INFORMATION: IgE mimotope

<400> SEQUENCE: 34

Val Asn Leu Thr Trp Ser Arg Ala Ser Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: CeH3 epitope

<400> SEQUENCE: 35

Val Asn Leu Pro Trp Ser Arg Ala Ser Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: CeH3 epitope
```

```
<400> SEQUENCE: 36

Val Asn Leu Thr Trp Ser Phe Gly Leu Glu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: CeH3 epitope

<400> SEQUENCE: 37

Val Asn Leu Pro Trp Ser Phe Gly Leu Glu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: CeH3 mimotope

<400> SEQUENCE: 38

Val Asn Arg Pro Trp Ser Phe Gly Leu Glu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: CeH3 mimotope

<400> SEQUENCE: 39

Val Lys Leu Pro Trp Arg Phe Tyr Gln Val
1               5                   10

<210> SEQ ID NO 40
<211> LENGTH: 10
<212> TYPE: PRT
<213> ORGANISM: Artificial Sequence
<220> FEATURE:
<223> OTHER INFORMATION: CeH3 mimotope

<400> SEQUENCE: 40

Val Trp Thr Ala Cys Gly Tyr Gly Arg Met
1               5                   10

<210> SEQ ID NO 41
<211> LENGTH: 7
<212> TYPE: PRT
<213> ORGANISM: Artificial Sequence
<220> FEATURE:
<223> OTHER INFORMATION: CeH3 mimotope

<400> SEQUENCE: 41

Gly Thr Val Ser Thr Leu Ser
1               5

<210> SEQ ID NO 42
<211> LENGTH: 7
<212> TYPE: PRT
<213> ORGANISM: Artificial Sequence
<220> FEATURE:
<223> OTHER INFORMATION: CeH3 mimotope
```

```
<400> SEQUENCE: 42

Leu Leu Asp Ser Arg Tyr Trp
1               5

<210> SEQ ID NO 43
<211> LENGTH: 7
<212> TYPE: PRT
<213> ORGANISM: Artificial Sequence
<220> FEATURE:
<223> OTHER INFORMATION: CeH3 mimotope

<400> SEQUENCE: 43

Gln Pro Ala His Ser Leu Gly
1               5

<210> SEQ ID NO 44
<211> LENGTH: 7
<212> TYPE: PRT
<213> ORGANISM: Artificial Sequence
<220> FEATURE:
<223> OTHER INFORMATION: CeH3 mimotope

<400> SEQUENCE: 44

Leu Trp Gly Met Gln Gly Arg
1               5

<210> SEQ ID NO 45
<211> LENGTH: 15
<212> TYPE: PRT
<213> ORGANISM: Artificial Sequence
<220> FEATURE:
<223> OTHER INFORMATION: CeH3 mimotope

<400> SEQUENCE: 45

Leu Thr Leu Ser His Pro His Trp Val Leu Asn His Phe Val Ser
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: CeH3 mimotope

<400> SEQUENCE: 46

Ser Met Gly Pro Asp Gln Thr Leu Arg
1               5

<210> SEQ ID NO 47
<211> LENGTH: 6
<212> TYPE: PRT
<213> ORGANISM: Artificial Sequence
<220> FEATURE:
<223> OTHER INFORMATION: CeH3 mimotope

<400> SEQUENCE: 47

Val Asn Leu Thr Trp Ser
1               5

<210> SEQ ID NO 48
<211> LENGTH: 17
<212> TYPE: PRT
<213> ORGANISM: Artificial Sequence
<220> FEATURE:
<223> OTHER INFORMATION: CeH3 mimotope

<400> SEQUENCE: 48
```

```
Gly Glu Phe Cys Ile Asn His Arg Gly Tyr Trp Val Cys Gly Asp Pro
1               5                   10                  15

Ala

<210> SEQ ID NO 49
<211> LENGTH: 5
<212> TYPE: PRT
<213> ORGANISM: Artificial Sequence
<220> FEATURE:
<223> OTHER INFORMATION: glycine serine linker
<220> FEATURE:
<221> NAME/KEY: REPEAT
<222> LOCATION: (1)..(5)
<223> OTHER INFORMATION: These residues can be repeated from zero to any
      times as a group

<400> SEQUENCE: 49

Gly Gly Gly Gly Ser
1               5

<210> SEQ ID NO 50
<211> LENGTH: 10
<212> TYPE: PRT
<213> ORGANISM: Artificial Sequence
<220> FEATURE:
<223> OTHER INFORMATION: N-terminal gamma1 linker

<400> SEQUENCE: 50

Cys Gly Asp Lys Thr His Thr Ser Pro Pro
1               5                   10

<210> SEQ ID NO 51
<211> LENGTH: 9
<212> TYPE: PRT
<213> ORGANISM: Artificial Sequence
<220> FEATURE:
<223> OTHER INFORMATION: C-terminal gamma 1 linker

<400> SEQUENCE: 51

Asp Lys Thr His Thr Ser Pro Pro Cys
1               5

<210> SEQ ID NO 52
<211> LENGTH: 17
<212> TYPE: PRT
<213> ORGANISM: Artificial Sequence
<220> FEATURE:
<223> OTHER INFORMATION: N-terminal gamma 3 linker

<400> SEQUENCE: 52

Cys Gly Gly Pro Lys Pro Ser Thr Pro Pro Gly Ser Ser Gly Gly Ala
1               5                   10                  15

Pro

<210> SEQ ID NO 53
<211> LENGTH: 18
<212> TYPE: PRT
<213> ORGANISM: Artificial Sequence
<220> FEATURE:
<223> OTHER INFORMATION: C-terminal gamma 3 linker

<400> SEQUENCE: 53

Pro Lys Pro Ser Thr Pro Pro Gly Ser Ser Gly Gly Ala Pro Gly Gly
1               5                   10                  15

Cys Gly
```

```
<210> SEQ ID NO 54
<211> LENGTH: 6
<212> TYPE: PRT
<213> ORGANISM: Artificial Sequence
<220> FEATURE:
<223> OTHER INFORMATION: N-terminal glycine linker

<400> SEQUENCE: 54

Gly Cys Gly Gly Gly Gly
1               5

<210> SEQ ID NO 55
<211> LENGTH: 6
<212> TYPE: PRT
<213> ORGANISM: Artificial Sequence
<220> FEATURE:
<223> OTHER INFORMATION: C-terminal glycine linker

<400> SEQUENCE: 55

Gly Gly Gly Gly Cys Gly
1               5

<210> SEQ ID NO 56
<211> LENGTH: 6
<212> TYPE: PRT
<213> ORGANISM: Artificial Sequence
<220> FEATURE:
<223> OTHER INFORMATION: C-terminal glycine-lysine linker

<400> SEQUENCE: 56

Gly Gly Lys Lys Gly Cys
1               5

<210> SEQ ID NO 57
<211> LENGTH: 6
<212> TYPE: PRT
<213> ORGANISM: Artificial Sequence
<220> FEATURE:
<223> OTHER INFORMATION: N-terminal glycine-lysine linker

<400> SEQUENCE: 57

Cys Gly Lys Lys Gly Gly
1               5

<210> SEQ ID NO 58
<211> LENGTH: 4
<212> TYPE: PRT
<213> ORGANISM: Artificial Sequence
<220> FEATURE:
<223> OTHER INFORMATION: C-terminal linker

<400> SEQUENCE: 58

Gly Gly Cys Gly
1

<210> SEQ ID NO 59
<211> LENGTH: 25
<212> TYPE: DNA
<213> ORGANISM: Artificial Sequence
<220> FEATURE:
<223> OTHER INFORMATION: p1.44 primer

<400> SEQUENCE: 59
aaccatggca aataagccaa tgcaa                                    25
```

```
<210> SEQ ID NO 60
<211> LENGTH: 30
<212> TYPE: DNA
<213> ORGANISM: Artificial Sequence
<220> FEATURE:
<223> OTHER INFORMATION: p1.45 primer

<400> SEQUENCE: 60
aatctagaat tttctgcgca cccatcccgg                                    30

<210> SEQ ID NO 61
<211> LENGTH: 31
<212> TYPE: DNA
<213> ORGANISM: Artificial Sequence
<220> FEATURE:
<223> OTHER INFORMATION: p1.46 primer

<400> SEQUENCE: 61
aaaagcttaa gcagtagtat cagacgatac g                                  31

<210> SEQ ID NO 62
<211> LENGTH: 43
<212> TYPE: DNA
<213> ORGANISM: Artificial Sequence
<220> FEATURE:
<223> OTHER INFORMATION: p1.47 primer

<400> SEQUENCE: 62
gagtgatcca actcgtttat caactacatt ttcagcaagt ctg                     43

<210> SEQ ID NO 63
<211> LENGTH: 43
<212> TYPE: DNA
<213> ORGANISM: Artificial Sequence
<220> FEATURE:
<223> OTHER INFORMATION: p1.48 primer

<400> SEQUENCE: 63
cagacttgct gaaaatgtag ttgataaacg agttggatca ctc                     43

<210> SEQ ID NO 64
<211> LENGTH: 21
<212> TYPE: PRT
<213> ORGANISM: Artificial Sequence
<220> FEATURE:
<223> OTHER INFORMATION: Derp1 117-137 peptide mutant

<400> SEQUENCE: 64

Cys Gln Ile Tyr Pro Pro Asn Ala Asn Lys Ile Arg Glu Ala Leu Ala
1               5                   10                  15
Gln Thr His Ser Ala
            20

<210> SEQ ID NO 65
<211> LENGTH: 11
<212> TYPE: PRT
<213> ORGANISM: Artificial Sequence
<220> FEATURE:
<223> OTHER INFORMATION: Flag

<400> SEQUENCE: 65

Cys Gly Gly Asp Tyr Lys Asp Asp Asp Asp Lys
1               5                   10

<210> SEQ ID NO 66
<211> LENGTH: 19
```

<212> TYPE: DNA
<213> ORGANISM: Artificial Sequence
<220> FEATURE:
<223> OTHER INFORMATION: 5' LT- b primer

<400> SEQUENCE: 66
cttggtgccg caggatcag                                          19

<210> SEQ ID NO 67
<211> LENGTH: 19
<212> TYPE: DNA
<213> ORGANISM: Artificial Sequence
<220> FEATURE:
<223> OTHER INFORMATION: 3' LT-b primer

<400> SEQUENCE: 67
cagatggctg tcaccccac                                          19

<210> SEQ ID NO 68
<211> LENGTH: 37
<212> TYPE: DNA
<213> ORGANISM: Artificial Sequence
<220> FEATURE:
<223> OTHER INFORMATION: 5' LT- blong-NheI primer

<400> SEQUENCE: 68
gcccgctagc ctgcggtggt caggatcagg gacgtcg                      37

<210> SEQ ID NO 69
<211> LENGTH: 37
<212> TYPE: DNA
<213> ORGANISM: Artificial Sequence
<220> FEATURE:
<223> OTHER INFORMATION: 5' LT- sbhort-NheI primer

<400> SEQUENCE: 69
gcccgctagc ctgcggtggt tctccagctg cggattc                      37

<210> SEQ ID NO 70
<211> LENGTH: 33
<212> TYPE: DNA
<213> ORGANISM: Artificial Sequence
<220> FEATURE:
<223> OTHER INFORMATION: 3' LT- bstop-NotI primer

<400> SEQUENCE: 70
caatgactgc ggccgcttac cccaccatca ccg                          33

<210> SEQ ID NO 71
<211> LENGTH: 74
<212> TYPE: DNA
<213> ORGANISM: Artificial Sequence
<220> FEATURE:
<223> OTHER INFORMATION: MCS of vector pET22b(+)

<400> SEQUENCE: 71
gtttaacttt aagaaggaga tatacatatg gatccggcta gcgctcgagg gtttaaacgg     60
cggccgcatg cacc                                                      74

<210> SEQ ID NO 72
<211> LENGTH: 43
<212> TYPE: DNA
<213> ORGANISM: Artificial Sequence
<220> FEATURE:
<223> OTHER INFORMATION: primerMCS-1F

```
<400> SEQUENCE: 72
tatggatccg gctagcgctc gagggtttaa acggcggccg cat        43

<210> SEQ ID NO 73
<211> LENGTH: 45
<212> TYPE: DNA
<213> ORGANISM: Artificial Sequence
<220> FEATURE:
<223> OTHER INFORMATION: primerMCS-1R

<400> SEQUENCE: 73
tcgaatgcgg ccgccgttta aaccctcgag cgctagccgg atcca      45

<210> SEQ ID NO 74
<211> LENGTH: 58
<212> TYPE: DNA
<213> ORGANISM: Artificial Sequence
<220> FEATURE:
<223> OTHER INFORMATION: Bamhis6-EK-Nhe-F primer

<400> SEQUENCE: 74
gatccacacc accaccacca ccacggttct ggtgacgacg atgacaaagc gctagccc    58

<210> SEQ ID NO 75
<211> LENGTH: 58
<212> TYPE: DNA
<213> ORGANISM: Artificial Sequence
<220> FEATURE:
<223> OTHER INFORMATION: Bamhis6-EK-Nhe-R

<400> SEQUENCE: 75
tcgagggcta gcgctttgtc atcgtcgtca ccagaaccgt ggtggtggtg gtggtgtg    58

<210> SEQ ID NO 76
<211> LENGTH: 42
<212> TYPE: DNA
<213> ORGANISM: Artificial Sequence
<220> FEATURE:
<223> OTHER INFORMATION: oligo1F-C-glycine-linker

<400> SEQUENCE: 76
tcgagggtgg tggtggtggt tgcggttaat aagtttaaac gc         42

<210> SEQ ID NO 77
<211> LENGTH: 42
<212> TYPE: DNA
<213> ORGANISM: Artificial Sequence
<220> FEATURE:
<223> OTHER INFORMATION: oligo1R-C-glycine-linker

<400> SEQUENCE: 77
ggccgcgttt aaacttatta accgcaacca ccaccaccac cc         42

<210> SEQ ID NO 78
<211> LENGTH: 51
<212> TYPE: DNA
<213> ORGANISM: Artificial Sequence
<220> FEATURE:
<223> OTHER INFORMATION: oligo1F-C-gamma1-linker

<400> SEQUENCE: 78
tcgaggataa aacccacacc tctccgccgt gtggttaata agtttaaacg c           51

<210> SEQ ID NO 79
<211> LENGTH: 51
```

<212> TYPE: DNA
<213> ORGANISM: Artificial Sequence
<220> FEATURE:
<223> OTHER INFORMATION: oligo1R-C-gamma1-linker

<400> SEQUENCE: 79
ggccgcgttt aaacttatta accacacggc ggagaggtgt gggttttatc c                51

<210> SEQ ID NO 80
<211> LENGTH: 36
<212> TYPE: DNA
<213> ORGANISM: Artificial Sequence
<220> FEATURE:
<223> OTHER INFORMATION: oligo1FA-C-gamma3-linker

<400> SEQUENCE: 80
tcgagccgaa accgtctacc ccgccgggtt cttctg                                 36

<210> SEQ ID NO 81
<211> LENGTH: 38
<212> TYPE: DNA
<213> ORGANISM: Artificial Sequence
<220> FEATURE:
<223> OTHER INFORMATION: oligo1RA-C-gamma3-linker

<400> SEQUENCE: 81
caccaccaga agaacccggc ggggtagacg gtttcggc                               38

<210> SEQ ID NO 82
<211> LENGTH: 39
<212> TYPE: DNA
<213> ORGANISM: Artificial Sequence
<220> FEATURE:
<223> OTHER INFORMATION: oligo2FB-C-gamma3-linker

<400> SEQUENCE: 82
gtggtgctcc gggtggttgc ggttaataag tttaaacgc                              39

<210> SEQ ID NO 83
<211> LENGTH: 37
<212> TYPE: DNA
<213> ORGANISM: Artificial Sequence
<220> FEATURE:
<223> OTHER INFORMATION: oligo2RB-C-gamma3-linker

<400> SEQUENCE: 83
ggccgcgttt aaacttatta accgcaacca cccggag                                37

<210> SEQ ID NO 84
<211> LENGTH: 33
<212> TYPE: DNA
<213> ORGANISM: Artificial Sequence
<220> FEATURE:
<223> OTHER INFORMATION: rMIF-F

<400> SEQUENCE: 84
ggaattccat atgcctatgt tcatcgtgaa cac                                    33

<210> SEQ ID NO 85
<211> LENGTH: 29
<212> TYPE: DNA
<213> ORGANISM: Artificial Sequence
<220> FEATURE:
<223> OTHER INFORMATION: rMIF-Xho-R

<400> SEQUENCE: 85
cccgctcgag agcgaaggtg gaaccgttc 29

<210> SEQ ID NO 86
<211> LENGTH: 62
<212> TYPE: DNA
<213> ORGANISM: Artificial Sequence
<220> FEATURE:
<223> OTHER INFORMATION: RANKL-UP oligonucleotide

<400> SEQUENCE: 86
ctgccagggg cccgggtgcg gcggtggcca tcatcaccac catcaccagc gcttctcagg 60
ag 62

<210> SEQ ID NO 87
<211> LENGTH: 35
<212> TYPE: DNA
<213> ORGANISM: Artificial Sequence
<220> FEATURE:
<223> OTHER INFORMATION: RANKL-DOWN oligonucleotide

<400> SEQUENCE: 87
ccgctcgagt tagtctatgt cctgaacttt gaaag 35

<210> SEQ ID NO 88
<211> LENGTH: 29
<212> TYPE: DNA
<213> ORGANISM: Artificial Sequence
<220> FEATURE:
<223> OTHER INFORMATION: Primer 5'PrP-BamHI

<400> SEQUENCE: 88
cgggatccca ccatggtggg gggccttgg 29

<210> SEQ ID NO 89
<211> LENGTH: 24
<212> TYPE: DNA
<213> ORGANISM: Artificial Sequence
<220> FEATURE:
<223> OTHER INFORMATION: Primer 3'PrP-NheI

<400> SEQUENCE: 89
ctagctagcc tggatcttct cccg 24

<210> SEQ ID NO 90
<211> LENGTH: 55
<212> TYPE: DNA
<213> ORGANISM: Artificial Sequence
<220> FEATURE:
<223> OTHER INFORMATION: primer Spelinker3-F1

<400> SEQUENCE: 90
ccccgccggg ttcttctggc ggtgctccgg ctagcatgga gattcccatg agcac 55

<210> SEQ ID NO 91
<211> LENGTH: 49
<212> TYPE: DNA
<213> ORGANISM: Artificial Sequence
<220> FEATURE:
<223> OTHER INFORMATION: Primer IL5StopXho-R

<400> SEQUENCE: 91
ttttgcggcc gcgtttaaac tcgagttatt agccttccat tgcccactc 49

<210> SEQ ID NO 92
<211> LENGTH: 52

```
<212> TYPE: DNA
<213> ORGANISM: Artificial Sequence
<220> FEATURE:
<223> OTHER INFORMATION: Primer SpeNlinker3-F2

<400> SEQUENCE: 92
ttttactagt tggttgcggc ggcccgaaac cgagcacccc gccgggttct tc          52

<210> SEQ ID NO 93
<211> LENGTH: 3
<212> TYPE: PRT
<213> ORGANISM: Artificial Sequence
<220> FEATURE:
<223> OTHER INFORMATION: N-terminal glycine linker
<220> FEATURE:
<221> NAME/KEY: REPEAT
<222> LOCATION: (1)..(1)
<223> OTHER INFORMATION: Glycine can be repeated from zero to five times
<220> FEATURE:
<221> NAME/KEY: REPEAT
<222> LOCATION: (3)..(3)
<223> OTHER INFORMATION: Glycine can be repeated from zero to twelve
      times

<400> SEQUENCE: 93

Gly Cys Gly
1

<210> SEQ ID NO 94
<211> LENGTH: 9
<212> TYPE: PRT
<213> ORGANISM: Artificial Sequence
<220> FEATURE:
<223> OTHER INFORMATION: N-terminal glycine-serine linker
<220> FEATURE:
<221> NAME/KEY: REPEAT
<222> LOCATION: (1)..(1)
<223> OTHER INFORMATION: Glycine can be repeated from zero to five times
<220> FEATURE:
<221> NAME/KEY: REPEAT
<222> LOCATION: (3)..(3)
<223> OTHER INFORMATION: Glycine can be repeated from zero to ten times
<220> FEATURE:
<221> NAME/KEY: REPEAT
<222> LOCATION: (4)..(4)
<223> OTHER INFORMATION: Serine can be repeated from zero to two times
<220> FEATURE:
<221> NAME/KEY: REPEAT
<222> LOCATION: (5)..(9)
<223> OTHER INFORMATION: These residues can be repeated from zero to
      three times as a group

<400> SEQUENCE: 94

Gly Cys Gly Ser Gly Gly Gly Gly Ser
1               5

<210> SEQ ID NO 95
<211> LENGTH: 3
<212> TYPE: PRT
<213> ORGANISM: Artificial Sequence
<220> FEATURE:
<223> OTHER INFORMATION: C-terminal glycine linker
<220> FEATURE:
<221> NAME/KEY: REPEAT
<222> LOCATION: (1)..(1)
<223> OTHER INFORMATION: Glycine can be repeated from zero to twelve
      times
<220> FEATURE:
<221> NAME/KEY: REPEAT
<222> LOCATION: (3)..(3)
<223> OTHER INFORMATION: Glycine can be repeated from zero to five times

<400> SEQUENCE: 95
```

```
Gly Cys Gly
1

<210> SEQ ID NO 96
<211> LENGTH: 10
<212> TYPE: PRT
<213> ORGANISM: Artificial Sequence
<220> FEATURE:
<223> OTHER INFORMATION: C-terminal glycine-serine linker
<220> FEATURE:
<221> NAME/KEY: REPEAT
<222> LOCATION: (1)..(1)
<223> OTHER INFORMATION: Glycine can be repeated from zero to ten times
<220> FEATURE:
<221> NAME/KEY: REPEAT
<222> LOCATION: (2)..(2)
<223> OTHER INFORMATION: Serine can be repeated from zero to two times
<220> FEATURE:
<221> NAME/KEY: REPEAT
<222> LOCATION: (3)..(7)
<223> OTHER INFORMATION: These residues can be repeated from zero to
      three times as a group
<220> FEATURE:
<221> NAME/KEY: REPEAT
<222> LOCATION: (8)..(8)
<223> OTHER INFORMATION: Glycine can be repeated from zero to eight
      times
<220> FEATURE:
<221> NAME/KEY: REPEAT
<222> LOCATION: (10)..(10)
<223> OTHER INFORMATION: Glycine can be repeated from zero to five times

<400> SEQUENCE: 96

Gly Ser Gly Gly Gly Gly Ser Gly Cys Gly
1               5                   10

<210> SEQ ID NO 97
<211> LENGTH: 23
<212> TYPE: PRT
<213> ORGANISM: Artificial Sequence
<220> FEATURE:
<223> OTHER INFORMATION: C-Der p1 peptide mutant

<400> SEQUENCE: 97

Cys Gly Asn Gln Ser Leu Asp Leu Ala Glu Gln Glu Leu Val Asp Cys
1               5                   10                  15

Ala Ser Gln His Gly Cys His
            20

<210> SEQ ID NO 98
<211> LENGTH: 10
<212> TYPE: PRT
<213> ORGANISM: Artificial Sequence
<220> FEATURE:
<223> OTHER INFORMATION: C-Angiotensin I peptide

<400> SEQUENCE: 98

Cys Asp Arg Val Tyr Ile His Pro Phe His
1               5                   10

<210> SEQ ID NO 99
<211> LENGTH: 26
<212> TYPE: PRT
<213> ORGANISM: Homo sapiens

<400> SEQUENCE: 99

Cys Thr Ala Arg Thr Glu Leu Asn Val Gly Ile Asp Phe Asn Trp Glu
1               5                   10                  15
```

```
<210> SEQ ID NO 100
<211> LENGTH: 23
<212> TYPE: PRT
<213> ORGANISM: Artificial Sequence
<220> FEATURE:
<223> OTHER INFORMATION: C TNF-a peptide mutant

<400> SEQUENCE: 100

Cys Ser Ser Arg Thr Pro Ser Asp Lys Pro Val Ala His Val Val Ala
1               5                   10                  15

Asn Pro Gln Ala Glu Gly Gln
            20

<210> SEQ ID NO 101
<211> LENGTH: 25
<212> TYPE: PRT
<213> ORGANISM: Artificial Sequence
<220> FEATUR

```
ggc gtg gag gtg cat aat gcc aag aca aag ccg cgg gag gag cag tac      288
Gly Val Glu Val His Asn Ala Lys Thr Lys Pro Arg Glu Glu Gln Tyr
                85                  90                  95 aac agc acg tac cgt gtg gtc agc gtc ctc acc gtc ctg cac cag gac      336
Asn Ser Thr Tyr Arg Val Val Ser Val Leu Thr Val Leu His Gln Asp
            100                 105                 110 tgg ctg aat ggc aag gag tac aag tgc aag gtc tcc aac aaa gcc ctc      384
Trp Leu Asn Gly Lys Glu Tyr Lys Cys Lys Val Ser Asn Lys Ala Leu
        115                 120                 125 cca gcc tcc atc gag aaa acc atc tcc aaa gcc aaa ggg cag ccc cga      432
Pro Ala Ser Ile Glu Lys Thr Ile Ser Lys Ala Lys Gly Gln Pro Arg
    130                 135                 140 gaa cca cag gtg tac acc ctg ccc cca tcc cgg gat gag ctg acc aag      480
Glu Pro Gln Val Tyr Thr Leu Pro Pro Ser Arg Asp Glu Leu Thr Lys
145                 150                 155                 160 aac cag gtc agc ctg acc tgc ctg gtc aaa ggc ttc tat ccc agc gac      528
Asn Gln Val Ser Leu Thr Cys Leu Val Lys Gly Phe Tyr Pro Ser Asp
                165                 170                 175 atc gcc gtg gag tgg gag agc aat ggg cag ccg gag aac aac tac aag      576
Ile Ala Val Glu Trp Glu Ser Asn Gly Gln Pro Glu Asn Asn Tyr Lys
            180                 185                 190 acc acg cct ccc gtg ttg gac tcc gac ggc tcc ttc ttc ctc tac agc      624
Thr Thr Pro Pro Val Leu Asp Ser Asp Gly Ser Phe Phe Leu Tyr Ser
        195                 200                 205 aag ctc acc gtg gac aag agc agg tgg cag cag ggg aac gtc ttc tca      672
Lys Leu Thr Val Asp Lys Ser Arg Trp Gln Gln Gly Asn Val Phe Ser
    210                 215                 220 tgc tcc gtg atg cat gag gct ctg cac aac cac tac acg cag aag agc      720
Cys Ser Val Met His Glu Ala Leu His Asn His Tyr Thr Gln Lys Ser
225                 230                 235                 240 ctc tcc ctg tct ccg ggt aaa tgac                                     745
Leu Ser Leu Ser Pro Gly Lys
                245
```

<210> SEQ ID NO 104
<211> LENGTH: 247
<212> TYPE: PRT
<213> ORGANISM: Artificial Sequence
<220> FEATURE:
<223> OTHER INFORMATION: pCep-Xa-Fc*

<400> SEQUENCE: 104

```
Asp Pro Ala Ala Gly Leu Glu Val Leu Ala Gly Gly Gly Gly Cys Gly
1               5                   10                  15

Ile Glu Gly Arg Lys Leu Thr His Thr Cys Pro Pro Cys Pro Ala Pro
            20                  25                  30

Glu Ala Glu Gly Ala Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125
```

```
Pro Ala Ser Ile Glu Lys Thr Ile Ser Lys Ala Lys Gly Gln Pro Arg
        130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 105
<211> LENGTH: 96
<212> TYPE: DNA
<213> ORGANISM: Artificial Sequence
<220> FEATURE:
<223> OTHER INFORMATION: pCep-EK-Fc*
<220> FEATURE:
<221> NAME/KEY: CDS
<222> LOCATION: (1)..(96)

<400> SEQUENCE: 105 gat cca gca gct ggg ctc gag gtg cta gcg gga ggg ggt gga tgt ggg     48
Asp Pro Ala Ala Gly Leu Glu Val Leu Ala Gly Gly Gly Gly Cys Gly
1               5                   10                  15 gac gat gac gac aag ctt act cac aca tgc cca ccg tgc cca gca cct     96
Asp Asp Asp Asp Lys Leu Thr His Thr Cys Pro Pro Cys Pro Ala Pro
            20                  25                  30

<210> SEQ ID NO 106
<211> LENGTH: 32
<212> TYPE: PRT
<213> ORGANISM: Artificial Sequence
<220> FEATURE:
<223> OTHER INFORMATION: pCep-EK-Fc*

<400> SEQUENCE: 106

Asp Pro Ala Ala Gly Leu Glu Val Leu Ala Gly Gly Gly Gly Cys Gly
1               5                   10                  15

Asp Asp Asp Asp Lys Leu Thr His Thr Cys Pro Pro Cys Pro Ala Pro
            20                  25                  30

<210> SEQ ID NO 107
<211> LENGTH: 144
<212> TYPE: DNA
<213> ORGANISM: Artificial Sequence
<220> FEATURE:
<223> OTHER INFORMATION: pCep-SP-EK-Fc*
<220> FEATURE:
<221> NAME/KEY: CDS
<222> LOCATION: (1)..(141)

<400> SEQUENCE: 107 atg gag aca gac aca ctc ctg cta tgg gta ctg ctg ctc tgg gtt cca     48
Met Glu Thr Asp Thr Leu Leu Leu Trp Val Leu Leu Leu Trp Val Pro
1               5                   10                  15
```

| | |
|---|---|
| ggt tcc act ggt gac gcg gat cca gca gct ggg ctc gag gtg cta gcg<br>Gly Ser Thr Gly Asp Ala Asp Pro Ala Ala Gly Leu Glu Val Leu Ala<br>        20                   25                  30 | 96 |
| gga ggg ggt gga tgt ggg gac gat gac gac aag ctt act cac aca tgc<br>Gly Gly Gly Gly Cys Gly Asp Asp Asp Asp Lys Leu Thr His Thr<br>    35                   40                   45 | 144 |

<210> SEQ ID NO 108
<211> LENGTH: 47
<212> TYPE: PRT
<213> ORGANISM: Artificial Sequence
<220> FEATURE:
<223> OTHER INFORMATION: pCep-SP-EK-Fc*

<400> SEQUENCE: 108

Met Glu Thr Asp Thr Leu Leu Leu Trp Val Leu Leu Leu Trp Val Pro
1               5                   10                  15

Gly Ser Thr Gly Asp Ala Asp Pro Ala Ala Gly Leu Glu Val Leu Ala
            20                  25                  30

Gly Gly Gly Gly Cys Gly Asp Asp Asp Asp Lys Leu Thr His Thr
        35                  40                  45

<210> SEQ ID NO 109
<211> LENGTH: 399
<212> TYPE: DNA
<213> ORGANISM: Artificial Sequence
<220> FEATURE:
<223> OTHER INFORMATION: Res-C-Xa
<220> FEATURE:
<221> NAME/KEY: CDS
<222> LOCATION: (10)..(399)

<400> SEQUENCE: 109

| | |
|---|---|
| ggatccggg atg aag aac ctt tca ttt ccc ctc ctt ttc ctt ttc ttc ctt<br>           Met Lys Asn Leu Ser Phe Pro Leu Leu Phe Leu Phe Phe Leu<br>            1            5                    10 | 51 |
| gtc cct gaa ctg ctg ggc tcc agc atg cca ctg tgt ccc atc gat gaa<br>Val Pro Glu Leu Leu Gly Ser Ser Met Pro Leu Cys Pro Ile Asp Glu<br>15                    20                   25                  30 | 99 |
| gcc atc gac aag aag atc aaa caa gac ttc aac tcc ctg ttt cca aat<br>Ala Ile Asp Lys Lys Ile Lys Gln Asp Phe Asn Ser Leu Phe Pro Asn<br>               35                  40                   45 | 147 |
| gca ata aag aac att ggc tta aat tgc tgg aca gtc tcc tcc aga ggg<br>Ala Ile Lys Asn Ile Gly Leu Asn Cys Trp Thr Val Ser Ser Arg Gly<br>           50                   55                   60 | 195 |
| aag ttg gcc tcc tgc cca gaa ggc aca gca gtc ttg agc tgc tcc tgt<br>Lys Leu Ala Ser Cys Pro Glu Gly Thr Ala Val Leu Ser Cys Ser Cys<br>        65                   70                  75 | 243 |
| ggc tct gcc tgt ggc tcg tgg gac att cgt gaa gaa aaa gtg tgt cac<br>Gly Ser Ala Cys Gly Ser Trp Asp Ile Arg Glu Glu Lys Val Cys His<br>        80                   85                   90 | 291 |
| tgc cag tgt gca agg ata gac tgg aca gca gcc cgc tgc tgt aag ctg<br>Cys Gln Cys Ala Arg Ile Asp Trp Thr Ala Ala Arg Cys Cys Lys Leu<br>95                100               105             110 | 339 |
| cag gtc gct tcc tct cta gcg gga ggg ggt gga tgt ggg atc gaa ggt<br>Gln Val Ala Ser Ser Leu Ala Gly Gly Gly Gly Cys Gly Ile Glu Gly<br>             115                  120               125 | 387 |
| cgc aag ctt act<br>Arg Lys Leu Thr<br>            130 | 399 |

<210> SEQ ID NO 110
<211> LENGTH: 130

<212> TYPE: PRT
<213> ORGANISM: Artificial Sequence
<220> FEATURE:
<223> OTHER INFORMATION: Res-C-Xa

<400> SEQUENCE: 110

```
Met Lys Asn Leu Ser Phe Pro Leu Leu Phe Leu Phe Phe Leu Val Pro
1               5                   10                  15

Glu Leu Leu Gly Ser Ser Met Pro Leu Cys Pro Ile Asp Glu Ala Ile
            20                  25                  30

Asp Lys Lys Ile Lys Gln Asp Phe Asn Ser Leu Phe Pro Asn Ala Ile
            35                  40                  45

Lys Asn Ile Gly Leu Asn Cys Trp Thr Val Ser Ser Arg Gly Lys Leu
        50                  55                  60

Ala Ser Cys Pro Glu Gly Thr Ala Val Leu Ser Cys Ser Cys Gly Ser
65                  70                  75                  80

Ala Cys Gly Ser Trp Asp Ile Arg Glu Glu Lys Val Cys His Cys Gln
                85                  90                  95

Cys Ala Arg Ile Asp Trp Thr Ala Ala Arg Cys Cys Lys Leu Gln Val
            100                 105                 110

Ala Ser Ser Leu Ala Gly Gly Gly Gly Cys Gly Ile Glu Gly Arg Lys
            115                 120                 125

Leu Thr
    130
```

<210> SEQ ID NO 111
<211> LENGTH: 399
<212> TYPE: DNA
<213> ORGANISM: Artificial Sequence
<220> FEATURE:
<223> OTHER INFORMATION: Res-C-EK
<220> FEATURE:
<221> NAME/KEY: CDS
<222> LOCATION: (10)..(399)

<400> SEQUENCE: 111

```
ggatccggg atg aag aac ctt tca ttt ccc ctc ctt ttc ctt ttc ttc ctt        51
          Met Lys Asn Leu Ser Phe Pro Leu Leu Phe Leu Phe Phe Leu
          1               5                   10 gtc cct gaa ctg ctg ggc tcc agc atg cca ctg tgt ccc atc gat gaa         99
Val Pro Glu Leu Leu Gly Ser Ser Met Pro Leu Cys Pro Ile Asp Glu
15                  20                  25                  30 gcc atc gac aag aag atc aaa caa gac ttc aac tcc ctg ttt cca aat        147
Ala Ile Asp Lys Lys Ile Lys Gln Asp Phe Asn Ser Leu Phe Pro Asn
                35                  40                  45 gca ata aag aac att ggc tta aat tgc tgg aca gtc tcc tcc aga ggg        195
Ala Ile Lys Asn Ile Gly Leu Asn Cys Trp Thr Val Ser Ser Arg Gly
            50                  55                  60 aag ttg gcc tcc tgc cca gaa ggc aca gca gtc ttg agc tgc tcc tgt        243
Lys Leu Ala Ser Cys Pro Glu Gly Thr Ala Val Leu Ser Cys Ser Cys
65                  70                  75 ggc tct gcc tgt ggc tcg tgg gac att cgt gaa gaa aaa gtg tgt cac        291
Gly Ser Ala Cys Gly Ser Trp Asp Ile Arg Glu Glu Lys Val Cys His
80                  85                  90 tgc cag tgt gca agg ata gac tgg aca gca gcc cgc tgc tgt aag ctg        339
Cys Gln Cys Ala Arg Ile Asp Trp Thr Ala Ala Arg Cys Cys Lys Leu
95                  100                 105                 110 cag gtc gct tcc tct cta gcg gga ggg ggt gga tgt ggg gac gat gac        387
Gln Val Ala Ser Ser Leu Ala Gly Gly Gly Gly Cys Gly Asp Asp Asp
                115                 120                 125
```

```
gac aag ctt act                                                          399
Asp Lys Leu Thr
        130

<210> SEQ ID NO 112
<211> LENGTH: 130
<212> TYPE: PRT
<213> ORGANISM: Artificial Sequence
<220> FEATURE:
<223> OTHER INFORMATION: Res-C-EK

<400> SEQUENCE: 112

Met Lys Asn Leu Ser Phe Pro Leu Leu Phe Leu Phe Phe Leu Val Pro
1               5                   10                  15

Glu Leu Leu Gly Ser Ser Met Pro Leu Cys Pro Ile Asp Glu Ala Ile
            20                  25                  30

Asp Lys Lys Ile Lys Gln Asp Phe Asn Ser Leu Phe Pro Asn Ala Ile
        35                  40                  45

Lys Asn Ile Gly Leu Asn Cys Trp Thr Val Ser Ser Arg Gly Lys Leu
    50                  55                  60

Ala Ser Cys Pro Glu Gly Thr Ala Val Leu Ser Cys Ser Cys Gly Ser
65                  70                  75                  80

Ala Cys Gly Ser Trp Asp Ile Arg Glu Glu Lys Val Cys His Cys Gln
                85                  90                  95

Cys Ala Arg Ile Asp Trp Thr Ala Ala Arg Cys Cys Lys Leu Gln Val
            100                 105                 110

Ala Ser Ser Leu Ala Gly Gly Gly Cys Gly Asp Asp Asp Lys
        115                 120                 125

Leu Thr
    130

<210> SEQ ID NO 113
<211> LENGTH: 26
<212> TYPE: PRT
<213> ORGANISM: Mus musculus

<400> SEQUENCE: 113

Cys Thr Ala Arg Thr Glu Leu Asn Val Gly Leu Asp Phe Thr Trp His
1               5                   10                  15

Ser Pro Pro Ser Lys Ser His His Lys Lys
            20                  25

<210> SEQ ID NO 114
<211> LENGTH: 120
<212> TYPE: PRT
<213> ORGANISM: Artificial Sequence
<220> FEATURE:
<223> OTHER INFORMATION: rat MIF-C1

<400> SEQUENCE: 114

Pro Met Phe Ile Val Asn Thr Asn Val Pro Arg Ala Ser Val Pro Glu
1               5                   10                  15

Gly Phe Leu Ser Glu Leu Thr Gln Gln Leu Ala Gln Ala Thr Gly Lys
            20                  25                  30

Pro Ala Gln Tyr Ile Ala Val His Val Val Pro Asp Gln Leu Met Thr
        35                  40                  45

Phe Ser Gly Thr Ser Asp Pro Cys Ala Leu Cys Ser Leu His Ser Ile
    50                  55                  60

Gly Lys Ile Gly Gly Ala Gln Asn Arg Asn Tyr Ser Lys Leu Leu Cys
65                  70                  75                  80
```

```
Gly Leu Leu Ser Asp Arg Leu His Ile Ser Pro Asp Arg Val Tyr Ile
                85                  90                  95

Asn Tyr Tyr Asp Met Asn Ala Ala Asn Val Gly Trp Asn Gly Ser Thr
            100                 105                 110

Phe Ala Gly Gly Gly Gly Cys Gly
        115                 120

<210> SEQ ID NO 115
<211> LENGTH: 132
<212> TYPE: PRT
<213> ORGANISM: Artificial Sequence
<220> FEATURE:
<223> OTHER INFORMATION: rat MIF-C2

<400> SEQUENCE: 115

Pro Met Phe Ile Val Asn Thr Asn Val Pro Arg Ala Ser Val Pro Glu
1               5                   10                  15

Gly Phe Leu Ser Glu Leu Thr Gln Gln Leu Ala Gln Ala Thr Gly Lys
            20                  25                  30

Pro Ala Gln Tyr Ile Ala Val His Val Val Pro Asp Gln Leu Met Thr
        35                  40                  45

Phe Ser Gly Thr Ser Asp Pro Cys Ala Leu Cys Ser Leu His Ser Ile
    50                  55                  60

Gly Lys Ile Gly Gly Ala Gln Asn Arg Asn Tyr Ser Lys Leu Leu Cys
65                  70                  75                  80

Gly Leu Leu Ser Asp Arg Leu His Ile Ser Pro Asp Arg Val Tyr Ile
                85                  90                  95

Asn Tyr Tyr Asp Met Asn Ala Ala Asn Val Gly Trp Asn Gly Ser Thr
            100                 105                 110

Phe Ala Pro Lys Pro Ser Thr Pro Pro Gly Ser Ser Gly Gly Ala Pro
        115                 120                 125

Gly Gly Cys Gly
    130

<210> SEQ ID NO 116
<211> LENGTH: 18
<212> TYPE: PRT
<213> ORGANISM: Artificial Sequence
<220> FEATURE:
<223> OTHER INFORMATION: amino acid linker C2

<400> SEQUENCE: 116

Pro Lys Pro Ser Thr Pro Pro Gly Ser Ser Gly Gly Ala Pro Gly Gly
1               5                   10                  15

Cys Gly

<210> SEQ ID NO 117
<211> LENGTH: 124
<212> TYPE: PRT
<213> ORGANISM: Artificial Sequence
<220> FEATURE:
<223> OTHER INFORMATION: rat MIF-C3

<400> SEQUENCE: 117

Pro Met Phe Ile Val Asn Thr Asn Val Pro Arg Ala Ser Val Pro Glu
1               5                   10                  15

Gly Phe Leu Ser Glu Leu Thr Gln Gln Leu Ala Gln Ala Thr Gly Lys
            20                  25                  30

Pro Ala Gln Tyr Ile Ala Val His Val Val Pro Asp Gln Leu Met Thr
```

-continued

```
                35                  40                  45
Phe Ser Gly Thr Ser Asp Pro Cys Ala Leu Cys Ser Leu His Ser Ile
 50                  55                  60

Gly Lys Ile Gly Gly Ala Gln Asn Arg Asn Tyr Ser Lys Leu Leu Cys
 65                  70                  75                  80

Gly Leu Leu Ser Asp Arg Leu His Ile Ser Pro Asp Arg Val Tyr Ile
                 85                  90                  95

Asn Tyr Tyr Asp Met Asn Ala Ala Asn Val Gly Trp Asn Gly Ser Thr
                100                 105                 110

Phe Ala Asp Lys Thr His Thr Ser Pro Pro Cys Gly
            115                 120

<210> SEQ ID NO 118
<211> LENGTH: 10
<212> TYPE: PRT
<213> ORGANISM: Artificial Sequence
<220> FEATURE:
<223> OTHER INFORMATION: amino acid linker C3

<400> SEQUENCE: 118

Asp Lys Thr His Thr Ser Pro Pro Cys Gly
 1               5                  10

<210> SEQ ID NO 119
<211> LENGTH: 114
<212> TYPE: PRT
<213> ORGANISM: Homo sapiens

<400> SEQUENCE: 119

Pro Met Phe Ile Val Asn Thr Asn Val Pro Arg Ala Ser Val Pro Asp
 1               5                  10                  15

Gly Phe Leu Ser Glu Leu Thr Gln Gln Leu Ala Gln Ala Thr Gly Lys
                20                  25                  30

Pro Pro Gln Tyr Ile Ala Val His Val Val Pro Asp Gln Leu Met Ala
            35                  40                  45

Phe Gly Gly Ser Ser Glu Pro Cys Ala Leu Cys Ser Leu His Ser Ile
 50                  55                  60

Gly Lys Ile Gly Gly Ala Gln Asn Arg Ser Tyr Ser Lys Leu Leu Cys
 65                  70                  75                  80

Gly Leu Leu Ala Glu Arg Leu Arg Ile Ser Pro Asp Arg Val Tyr Ile
                 85                  90                  95

Asn Tyr Tyr Asp Met Asn Ala Ala Asn Val Gly Trp Asn Asn Ser Thr
                100                 105                 110

Phe Ala

<210> SEQ ID NO 120
<211> LENGTH: 114
<212> TYPE: PRT
<213> ORGANISM: Rattus norvegicus

<400> SEQUENCE: 120

Pro Met Phe Ile Val Asn Thr Asn Val Pro Arg Ala Ser Val Pro Glu
 1               5                  10                  15

Gly Phe Leu Ser Glu Leu Thr Gln Gln Leu Ala Gln Ala Thr Gly Lys
                20                  25                  30

Pro Ala Gln Tyr Ile Ala Val His Val Val Pro Asp Gln Leu Met Thr
            35                  40                  45

Phe Ser Gly Thr Ser Asp Pro Cys Ala Leu Cys Ser Leu His Ser Ile
```

```
                50                  55                  60
Gly Lys Ile Gly Gly Ala Gln Asn Arg Asn Tyr Ser Lys Leu Leu Cys
 65                  70                  75                  80

Gly Leu Leu Ser Asp Arg Leu His Ile Ser Pro Asp Arg Val Tyr Ile
                 85                  90                  95

Asn Tyr Tyr Asp Met Asn Ala Ala Asn Val Gly Trp Asn Gly Ser Thr
                100                 105                 110

Phe Ala

<210> SEQ ID NO 121
<211> LENGTH: 114
<212> TYPE: PRT
<213> ORGANISM: Mus musculus

<400> SEQUENCE: 121

Pro Met Phe Ile Val Asn Thr Asn Val Pro Arg Ala Ser Val Pro Glu
 1               5                  10                  15

Gly Phe Leu Ser Glu Leu Thr Gln Gln Leu Ala Gln Ala Thr Gly Lys
                 20                  25                  30

Pro Ala Gln Tyr Ile Ala Val His Val Val Pro Asp Gln Leu Met Thr
                 35                  40                  45

Phe Ser Gly Thr Asn Asp Pro Cys Ala Leu Cys Ser Leu His Ser Ile
 50                  55                  60

Gly Lys Ile Gly Gly Ala Gln Asn Arg Asn Tyr Ser Lys Leu Leu Cys
 65                  70                  75                  80

Gly Leu Leu Ser Asp Arg Leu His Ile Ser Pro Asp Arg Val Tyr Ile
                 85                  90                  95

Asn Tyr Tyr Asp Met Asn Ala Ala Asn Val Gly Trp Asn Gly Ser Thr
                100                 105                 110

Phe Ala

<210> SEQ ID NO 122
<211> LENGTH: 120
<212> TYPE: PRT
<213> ORGANISM: Artificial Sequence
<220> FEATURE:
<223> OTHER INFORMATION: human MIF-C1

<400> SEQUENCE: 122

Pro Met Phe Ile Val Asn Thr Asn Val Pro Arg Ala Ser Val Pro Asp
 1               5                  10                  15

Gly Phe Leu Ser Glu Leu Thr Gln Gln Leu Ala Gln Ala Thr Gly Lys
                 20                  25                  30

Pro Pro Gln Tyr Ile Ala Val His Val Val Pro Asp Gln Leu Met Ala
                 35                  40                  45

Phe Gly Gly Ser Ser Glu Pro Cys Ala Leu Cys Ser Leu His Ser Ile
 50                  55                  60

Gly Lys Ile Gly Gly Ala Gln Asn Arg Ser Tyr Ser Lys Leu Leu Cys
 65                  70                  75                  80

Gly Leu Leu Ala Glu Arg Leu Arg Ile Ser Pro Asp Arg Val Tyr Ile
                 85                  90                  95

Asn Tyr Tyr Asp Met Asn Ala Ala Asn Val Gly Trp Asn Asn Ser Thr
                100                 105                 110

Phe Ala Gly Gly Gly Gly Cys Gly
                115                 120
```

<210> SEQ ID NO 123
<211> LENGTH: 132
<212> TYPE: PRT
<213> ORGANISM: Artificial Sequence
<220> FEATURE:
<223> OTHER INFORMATION: human MIF-C2

<400> SEQUENCE: 123

```
Pro Met Phe Ile Val Asn Thr Asn Val Pro Arg Ala Ser Val Pro Asp
1               5                   10                  15

Gly Phe Leu Ser Glu Leu Thr Gln Gln Leu Ala Gln Ala Thr Gly Lys
            20                  25                  30

Pro Pro Gln Tyr Ile Ala Val His Val Val Pro Asp Gln Leu Met Ala
        35                  40                  45

Phe Gly Gly Ser Ser Glu Pro Cys Ala Leu Cys Ser Leu His Ser Ile
    50                  55                  60

Gly Lys Ile Gly Gly Ala Gln Asn Arg Ser Tyr Ser Lys Leu Leu Cys
65                  70                  75                  80

Gly Leu Leu Ala Glu Arg Leu Arg Ile Ser Pro Asp Arg Val Tyr Ile
                85                  90                  95

Asn Tyr Tyr Asp Met Asn Ala Ala Asn Val Gly Trp Asn Asn Ser Thr
            100                 105                 110

Phe Ala Pro Lys Pro Ser Thr Pro Pro Gly Ser Ser Gly Gly Ala Pro
        115                 120                 125

Gly Gly Cys Gly
        130
```

<210> SEQ ID NO 124
<211> LENGTH: 124
<212> TYPE: PRT
<213> ORGANISM: Artificial Sequence
<220> FEATURE:
<223> OTHER INFORMATION: human MIF-C3

<400> SEQUENCE: 124

```
Pro Met Phe Ile Val Asn Thr Asn Val Pro Arg Ala Ser Val Pro Asp
1               5                   10                  15

Gly Phe Leu Ser Glu Leu Thr Gln Gln Leu Ala Gln Ala Thr Gly Lys
            20                  25                  30

Pro Pro Gln Tyr Ile Ala Val His Val Val Pro Asp Gln Leu Met Ala
        35                  40                  45

Phe Gly Gly Ser Ser Glu Pro Cys Ala Leu Cys Ser Leu His Ser Ile
    50                  55                  60

Gly Lys Ile Gly Gly Ala Gln Asn Arg Ser Tyr Ser Lys Leu Leu Cys
65                  70                  75                  80

Gly Leu Leu Ala Glu Arg Leu Arg Ile Ser Pro Asp Arg Val Tyr Ile
                85                  90                  95

Asn Tyr Tyr Asp Met Asn Ala Ala Asn Val Gly Trp Asn Asn Ser Thr
            100                 105                 110

Phe Ala Asp Lys Thr His Thr Ser Pro Pro Cys Gly
        115                 120
```

<210> SEQ ID NO 125
<211> LENGTH: 396
<212> TYPE: DNA
<213> ORGANISM: Artificial Sequence
<220> FEATURE:
<223> OTHER INFORMATION: AP205 P5T mutant

<400> SEQUENCE: 125

-continued

```
atggcaaata agacaatgca accgatcaca tctacagcaa ataaaattgt gtggtcggat        60
ccaactcgtt tatcaactac attttcagca agtctgttac gccaacgtgt taaagttggt       120
atagccgaac tgaataatgt ttcaggtcaa tatgtatctg tttataagcg tcctgcacct       180
aaaccggaag gttgtgcaga tgcctgtgtc attatgccga atgaaaacca atccattcgc       240
acagtgattt cagggtcagc cgaaaacttg gctaccttaa aagcagaatg ggaaactcac       300
aaacgtaacg ttgacacact cttcgcgagc ggcaacgccg gtttgggttt ccttgaccct       360
actgcggcta tcgtatcgtc tgatactact gcttaa                                 396
```